US007579173B2

(12) United States Patent
DeAngelis et al.

(10) Patent No.: US 7,579,173 B2
(45) **Date of Patent: *Aug. 25, 2009**

(54) TARGETED GLYCOSAMINOGLYCAN POLYMERS BY POLYMER GRAFTING AND METHODS OF MAKING AND USING THE SAME

(75) Inventors: Paul L. DeAngelis, Edmond, OK (US); Wei Jing, Edmond, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/651,379

(22) Filed: Jan. 9, 2007

(65) Prior Publication Data

US 2007/0128703 A1 Jun. 7, 2007

Related U.S. Application Data

(63) Continuation of application No. 10/642,248, filed on Aug. 15, 2003, now Pat. No. 7,223,571, which is a continuation-in-part of application No. 10/195,908, filed on Jul. 15, 2002, now abandoned, which is a continuation-in-part of application No. 10/142,143, filed on May 8, 2002, now Pat. No. 7,307,159, and a continuation-in-part of application No. 09/842,484, filed on Apr. 25, 2001, now abandoned, and a continuation-in-part of application No. 09/437,277, filed on Nov. 10, 1999, now Pat. No. 6,444,447, and a continuation-in-part of application No. 09/283,402, filed on Apr. 1, 1999, now abandoned.

(60) Provisional application No. 60/404,356, filed on Aug. 16, 2002, provisional application No. 60/479,432, filed on Jun. 18, 2003, provisional application No. 60/491,362, filed on Jul. 31, 2003, provisional application No. 60/107,929, filed on Nov. 11, 1998, provisional application No. 60/080,414, filed on Apr. 2, 1998, provisional application No. 60/199,538, filed on Apr. 25, 2000, provisional application No. 60/289,554, filed on May 8, 2001.

(51) Int. Cl.
*C12P 19/18* (2006.01)
*C12P 19/00* (2006.01)
*C12P 19/04* (2006.01)

(52) U.S. Cl. ........................................ 435/97; 435/101

(58) Field of Classification Search ...................... None
See application file for complete search history.

(56) References Cited

U.S. PATENT DOCUMENTS 4,224,179 A 9/1980 Schneider
4,235,871 A 11/1980 Papahadjopoulos et al.
4,511,478 A 4/1985 Nowinski et al.
4,517,295 A 5/1985 Bracke et al.
4,585,754 A 4/1986 Meisner et al.
4,615,697 A 10/1986 Robinson
4,708,861 A 11/1987 Popescu et al.
4,780,414 A 10/1988 Nimrod et al.
4,782,046 A 11/1988 Brown et al.
4,784,990 A 11/1988 Nimrod et al.
4,801,539 A 1/1989 Akasaka et al.
4,822,867 A 4/1989 Erhan
4,983,392 A 1/1991 Robinson
4,990,601 A 2/1991 Skjak-Braek et al.
5,008,253 A 4/1991 Casu et al.
5,015,577 A 5/1991 Weigel et al.
5,023,175 A 6/1991 Hosoya et al.
5,071,751 A 12/1991 Morita et al.
5,171,689 A 12/1992 Kawaguri et al.
5,217,743 A 6/1993 Farah
5,314,876 A 5/1994 Lormeau et al.
5,337,747 A 8/1994 Neftel
5,384,398 A 1/1995 Lormeau et al.
5,472,704 A 12/1995 Santus et al.
5,473,034 A 12/1995 Yasui et al.
5,607,694 A 3/1997 Marx
5,610,241 A 3/1997 Lee et al.
5,622,850 A 4/1997 Sloma et al.
5,631,019 A 5/1997 Marx
5,651,982 A 7/1997 Marx
5,876,433 A 3/1999 Lunn
5,948,900 A 9/1999 Yother et al.
5,958,899 A 9/1999 Zoppetti et al.
6,120,536 A 9/2000 Ding et al.
6,156,373 A 12/2000 Zhong et al.
6,162,797 A 12/2000 Zoppetti et al.
RE37,336 E 8/2001 Weigel et al.
6,423,514 B1 7/2002 Briskin
2003/0100534 A1 5/2003 Zoppetti et al.

FOREIGN PATENT DOCUMENTS

EP 0195303 11/1989

(Continued)

OTHER PUBLICATIONS

"The Combinations of Haemoglobin With Oxygen and with Carbon Monoxide.", Hill, J. Biochem., 7:471-480 (1913).
"Die Kinetik Der Invertinwirkung", Michaelis and Menten, Biochem. Z., 49: 333-338 (1913) (No translation available).
"The Role of the Mucoid Polysaccharide (Hyaluronic Acid) in the Virulence of Group a Hemolytic Streptococci", Kass et al., J. Of Exp. Med., 79:319-330 (1944).
"The Production of Capsules, Hyaluronic Acid and Hyaluronidase by Group A and Group C Streptocooci", MacLennan, J. Gen. Microbiol., 14:134-142 (1956).

(Continued)

*Primary Examiner*—Nashaat T Nashed
*Assistant Examiner*—Md. Younus Meah
(74) *Attorney, Agent, or Firm*—Dunlap Codding, P.C.

(57) ABSTRACT

The present invention relates to methodology for polymer grafting by a polysaccharide synthase and, more particularly, polymer grafting using the hyaluronate or chondroitin or heparin/heparosan synthases from *Pasteurella,* in order to create a variety of glycosaminoglycan oligosaccharides having a natural or chimeric or hybrid sugar structure with a targeted size that are substantially monodisperse in size.

28 Claims, 41 Drawing Sheets

FOREIGN PATENT DOCUMENTS

| | | |
|---|---|---|
| EP | 0144019 | 6/1990 |
| EP | 0266578 | 7/1993 |
| EP | 0244757 | 11/1994 |
| EP | 00300035 | 5/1995 |
| EP | 0036776 | 5/1998 |
| EP | 01304338 | 4/2003 |
| GB | 2249315 | 5/1992 |
| JP | 61-257169 | 11/1986 |
| JP | 62032893 | 2/1987 |
| JP | 63094988 | 4/1988 |
| JP | 4-80202 | 3/1992 |
| JP | 4-124854 | 4/1992 |
| JP | 4-134854 | 5/1992 |
| JP | 4-158796 | 6/1992 |
| JP | 8-38336 | 2/1996 |
| WO | 91/03559 | 3/1991 |
| WO | 94/00463 | 1/1994 |
| WO | 95/24497 | 9/1995 |
| WO | 95/33067 | 12/1995 |
| WO | 97/20061 | 6/1997 |
| WO | 00/27437 | 5/2000 |
| WO | 01/02597 | 1/2001 |
| WO | PCT/US01/13395 | 11/2001 |
| WO | PCT/JP02/07859 | 2/2003 |

OTHER PUBLICATIONS

"The Isolation and Characterization of a Hyaluronidase Produced by a Capsulated Strain of Group C *Streptococcus*", MacLennan, J. Gen. Microbiol., 14:143-152 (1956).

"The Biosynthesis of Hyaluronic Acid by Group A *Streptococcus*", Markovitz et al., J. Biol. Chem., 234 (9):2343-2350 (1959).

"The Biosynthesis of Hyaluronic Acid by *Streptococcus*," Stoolmiller, et al., Journal of Biological Chemistry, vol. 244, No. 2, pp. 236-246 (1969).

"Cleavage of Structural Proteins During the Assembly of the Head of Bacteriophage T4", Laemmli, Nature, 227:680-685 (1970).

"The Isolation and Characterization of Hyaluronic Acid From *Pasteurella Multocida*", Cifonelli, et al., Carbohydrate Research, 14, 272-276, (1970).

"A Rapid and Sensitive Method for the Quantitation of Microgram Quantities of Protein Utilizing the Principle of Protein-Dye Binding", Bradford, Analytical Biochemistry, 72:248-254 (1976).

"Genetic Mapping of the K1 and K4 Antigens (L) of *Escherichia coli*. Non-Allelism of K(L) Antigens With K Antigens of O8:K27(A), O8:K8 (L) and O9:K57 (B)", Orskov et al., Acta Pathol Microbiol Scand B, 84:125-131 (1976).

"Synthesis and Assembly of the Membrane Proteins in *E. coli*", Ito et al., Cell, 11:551-559 (1977).

"Electrophoretic Transfer of Proteins From Polyacrylamide Gels to Nitrocellulose Sheets: Procedure and Some Applications", Biochemistry, 76: 4350-4354 (1979).

"Biosynthesis of Hyaluronic Acid by *Streptococcus*", Sugahara et al., J. Biol. Chem., 254:6252-6261 (1979).

"Modern Genetics", Ayala, et al., Benjamin/Cummings Publishing Col., Mento Park CA, p. 45 (1980).

"Hyaluronidase Production by Type B *Pasteurella Multocida* From Cases of Hemorrhagic Septicemia", Carter, et al., Journal of Clinical Microbiology, p. 94-96, (1980).

"Hyaluronate Capsule Prevents Attachment of Group A *Streptococci* to Mouse Peritoneal Macrophages", Whitnack et al., Infection and Immunity, 31(3):985-991 (1981).

"Strains of *Escherichia coli* Carrying the Structural Gene for Histidyl-tRNA Synthetase on a High Copy-Number Plasmid", Eisenbeis, et al., Mol. Gen. Genet. 183:115-122 (1981).

"The Structure of the Capsular Polysaccharide (K5 Antigen) of Urinary-Tract-Infective *Escherichia coli* 010:K5:H4", Vann et al., Biochem J. 116:359-364 (1981).

"Synthesis of Hyaluronate in Differentiated Teratocarcinoma Cells," Prehm, et al., J. Biochem, vol. 211, pp. 181-189 (1983).

"Streptococcal Hyaluronic Acid: Proposed Mechanisms of Degradation and Loss of Synthesis During Stationary Phase", Van de Rijn, J. Bacteriol., 156(3):1059-1065 (1983).

"Differences in the Effects of pH on the Hydrolytic and Transgalactosylic Reactions of Beta-Galactosidase (*Escherichia coli*)", Huber et al., Can. J. Biochem. Cell Biol., 61:198-206 (1983).

"Hyaluronate is Synthesized at Plasma Membranes", Prehm, Biochem. J., 220:597-600 (1984).

"Subcellular Locations of Hyaluronate Synthase in Oligodendroglioma Cells", Philipson et al., J. Biol. Chem., 259(8):5017-5023 (1984).

"Binding and Reactivity at the 'Glucose' Site of Galactosyl-Beta-Galactosidase (*Escherichia coli*)", Huber et al., Arch Biochem Biophys., 234: 151-160 (1984).

"Heparin, Its Fractions, Fragments and Derivatives. Some Newer Perspectives", Fareed, Seminars in Thrombosis and Hemostasis. 11(1):1-9 (1985).

"Solubilization of Hyaluronic Acid Synthetic Activity From *Streptococci* and its Activation With Phospholipids", Triscott et al., J. Biol. Chem., 261(13):6004-6009 (1986).

"Isolation of Streptococcal Hyaluronate Synthase", Prehm et al., Biochem. J., 235:887-889 (1986).

"Effect of Replacing Uridine 33 in Yeast tRNAPhe on the Reaction With Ribosomes", Dix et al., J. Biol. Chem., 261(22):10112-8 (1986).

"Molecular Cloning and Analysis of Genes for Production of K5, K7, K12, and K92 Capsular Polysaccharides in *Escherichia coli*", Roberts et al., J. Bacteriology. 168(3):1228-1233 (1986).

"Isolation, Structure and Expression of Mammalian Genes for Histidyl-tRNA Synthetase," Tsui, et al., Nucleic Acids Research, vol. 15, No. 8, pp. 3349-3367, (1987).

"Role of Cysteine in Glutathione Synthase From *Escherichia coli* B", Kato et al., J. Biol. Chem., 263(24):11646-11651 (1988).

"Structure and Serological Characteristics of the Capsular K4 Antigen of *Escherichia coli* O5:K4:H4, A Fructose-Containing Polysaccharide With a Chondroitin Backbone", Rodriguez et al., Eur. J. Biochem., 177:117-124 (1988).

"The Carboxy-Terminal Domain of the LexA Repressor Oligomerises Essentially as the Entire Protein", Schnarr et al., FEBS Lett., 234:56-60 (1988).

"Common Organization of Gene Clusters for Production of Different Capsular Polysaccharides (K Antigens) in *Escherichia coli*", Roberts, J. Bacteriology. 170(3):1305-1310 (1988).

"The Biology of Hyaluronan", Evered and Whelan Eds., CIBA Foundation Symposium 143 (1989).

"A Cryptic Fimbrial Gene in *Serratia marcescens*", Moriya et al., J. Bacteriol., 171(12): 6629-36 (1989).

"Monoclonal Antibodies Specific for K88ab, K88ac and K88ad Antigens of *Escherichia coli*", Li et al., Wei Sheng Wu Xue Bao, 29:348-353 (1989). (Abstract only).

"Kinetic Characterization of the Unisite Catalytic Pathway of Seven Beta-Subunit Mutant F1-ATPases From *Escherichia coli*", al-Shawi et al., J. Biol. Chem., 264(26): 15376-83 (1989).

"The Role of Bacterial Polysaccharide Capsules as Virulence Factors", Moxon et al., Current Topics in Microbiology and Immunology, 150:65-85 (1990).

"Slow-Binding Inhibition of the *Escherichia coli* Pyruvate Dehydrogenase Multienzyme Complex by Acetylphosphinate", Schonbrunn-Hanebeck et al., Biochemistry, 29(20): 4880-5 (1990).

"Molecular Cloning and Expression of the Genes Encoding the *Escherichia coli* K4 Capsular Polysaccharide, A Fructose-Substituted Chondroitin", Drake et al., FEMS Microbiol. Lett., 54(1-3):227-30 (1990).

"Expression of the *Escherichia coli* K5 Capsular Antigen: Immunoelectron Microscopic and Biochemical Studies with Recombinant *E. coli*", Kroncke et al., J. Bacteriology. 172(2):1085-1091 (1990).

"Molecular analysis of the *Escherichia coli* K5 kps locus: identification and characterization of an inner-membrane capsular polysaccharide transport system", Smith et al., Molecular Microbiology. 4(11):1863-1869 (1990).

"Shuttle Vectors Containing a Multiple Cloning Site and a Lacza Gena for Conjugal Transfer of DNA From *Escherichia coli* to Gram-Positive Bacteria," Trieu-Cout, et al., Gene, vol. 102, pp. 99-104, (1991).
"Hyaluronic Acid Capsule is a Virulence Factor for Mucoid Group A *Streptococci*", Wessels et al., Microbiology, 88:8317-8321 (1991).
"Electron Microscopic Study of Coexpression of Adhesive Protein Capsules and Polysaccharide Capsules in *Escherichia coli*", Kronke et al., Infect. Immunity, 58:2710-4 (1991).
"Transport and Utilization of Ferrioxamine-E-Bound Iron in *Erwinia herbicola* (*Pantoea agglomerans*)", Matzanke et al., Biol. Met., 181-185 (1991).
"Modulation of the Tight Binding of Carboxyarabinitol 1, 5-Biphosphate to the Large Subunit of Ribulose 1,5-Bisphosphate Carboxylase/Oxygenase", Smrcka et al., Arch. Biochem. Biophys., 286: 14-9 (1991).
"Biosynthesis of heparin. Use of *Escherichia coli* K5 capsular polysaccharide as a model substrate in enzymic polymer-modification reactions", Kusche et al., Biochem J. 275(pt1):151-8 (1991).
"Experimental and Clinical Pharmacology of Glycosaminoglycans (GAGs)". Soldani et al., Drugs Exptl. Clin. Res. XVII(1):81-85 (1991).
"Analysis of the Streptococcal Hyaluronic Acid Synthase Complex Using the Photoaffinity Probe 5-Azido-UDP-Glucuronic Acid," Van de Rijn, et al., J. Biol., Chem., vol. 267, No. 34, pp. 24302-24306, (1992).
"Molecular Characterization of a Locus Required for Hyaluronic Acid Capsule Production in Group A *Streptococci*," Dougherty, et al., J. Exp. Med., vol. 175, pp. 1291-1299, (1992).
"Hyaluronan," Laurent, et al., FASEB Journal, vol. 6, pp. 2397-2404, (1992).
"Role of Cysteins 640, 656, and 661 in Steroid Binding to Rat Glucocorticoid Receptors", Chakraborti et al., J. Biol. Chem., 267(16):11366-11373 (1992).
"Slow-Onset Inhibition of Ribosomal Peptidyltransferase by Lincomycin", Kallia-Raftopoulos et al., Arch. Biochem. Biophys., 298: 332-339 (1992).
"Enhanced Catalysis by Active-Site Mutagenesis at Aspartic Acid 153 in *Escherichia coli* Alkaline Phosphatase", Matlin et al., Biochemistry, 31(35): 8196-8200 (1992).
"A Study of Vitamin Inhibition of the Mutagenicity of the Antineoplastic Drugs", Zhao and Huang, Zhonghua Yu Fang Yi Xue Za Zhi, 26:291-293 (1992). (Abstract only).
"Biosynthesis of heparin. The D-glucuronosyl- and N-acetyl-D-glucosaminyltransferase reactions and their relation to polymer modification", Lidholt et al., Biochem J. 287(pt 1):21-9 (1992).
"Hyaluronic Acid and a (1-4)-B-D-Xylan, Extracellular Polysaccharides of *Pasteurella multocida* (Carter Type A) Strain 880", Rosner, et al., Carbohydrate Research, 223, 329-333 (1992).
"Localization of Hyaluronan in Mouse Embryos During Implantation, Gastrulation and Organogenesis", Fenderson et al., Differentiation, 54:85-98 (1993).
"Hyaluronan-Binding Proteins in Development, Tissue Homeostasis, and Disease", Knudson et al., FASEB, 7:1233-1241 (1993).
"Molecular Cloning, Identification, and Sequence of the Hyaluronan Synthase Gene From Group A *Streptococcus pyogenes*", DeAngelis et al., J. Biol. Chem., 268(26):19181-19184 (1993).
"Isolation of a *Streptococcus pyogenes* Gene Locus That Directs Hyaluronan Biosynthesis in Acapsular Mutants and in Heterologous Bacteria," DeAngelis, et al., J. Biol. Chem., vol. 268, No. 20, pp. 14568-14571, (1993).
"Hyaluronate Synthase: Cloning and Sequencing of the Gene From *Streptococcus* sp.," Lansing, et al., J. Biochem., vol. 289, pp. 179-184, (1993).
"Molecular Characterization of HASB From an Operon Required for Hyaluronic Acid Synthesis in Group A *Streptococci*," Dougherty, et al., J. Biol. Chem., vol. 268, No. 10, pp. 7118-7124, (1993).
"Preliminary Study of Test Methods to Assess the Virucidal Activity of Skin Disinfectants Using Poliovirus and Bacteriophages", Davies et al., Journal of Hospital Infection, 25(2): 125-131 (1993).
"The *Escherichia coli* serA-Linked Capsule Locus and its Flanking Sequences are Polymorphic, Genetic Evidence for the Existence of More Than Two Groups of Capsule Gene Clusters", Drake et al., J. Gen. Microbiol., 139 (Pt. 8): 1707-1714 (1993).
"Reaction of Modified and Unmodified tRNA (Tyr) Substrates With Tyrosyl-tRNA Synthetase (*Bacillus stearothermophilus*)", Avis et al., Biochemistry, 32(20): 5312-5320 (1993).
"Effect of pH on Solubility and Ionic State of Lipopolysaccharide Obtained From the Deep Rough Mutant of *Escherichia coli*", Din et al., Biochemistry, 32(17): 4579-4586 (1993).
"Synthesis of the K5 (group II) capsular polysaccharide in transport-deficient recombinant *Escherichia coli*", Bronner et al., FEMS Microbiology Letters 113:273-284 (1993).
"Biosynthesis of Heparin/Heparan Sulfate", Lind et al., The Journal of Biological Chemistry. 268(28):20705-20708 (1993).
"Capsular hyaluronic acid in *Pasteurella multocida* type A and its counterpart in type D", Pandit et al., Research in Veterinary Science. 54:20-24 (1993).
"Effects on Virulence of Mutations in a Locus Essential for Hyaluronic Acid Capsule Expression in Group A *Streptococci*", Wessels et al., Infection and Immunity, 62(2):433-441 (1994).
"A Hyaluronidase Activity of the Sperm Plasma Membrane Protein PH-20 Enables Sperm to Penetrate the Cumulus Cell Layer Surrounding the Egg", Lin et al., The Journal of Cell Biology, 125(5): 1157-1163 (1994).
"Dynamics of Lactose Permease of *Escherichia coli* Determined by Site-Directed Fluorescense Labeling", Jung et al., Biochemistry, 33:3980-3985 (1994).
"Cysteine 148 in the Lactose Permease of *Escherichia coli* is a Component of a Substrate Binding Site", Wu et al., Biochemistry, 33:12166-12171 (1994).
"Molecular Characterization of HASA From an Operon Required for Hyaluronic Acid Synthesis in Group A *Streptococci*," Dougherty, et al., J. Biol. Chem., vol. 269, No. 1, pp. 169-175, (1994).
"The *Streptococcus pyogenes* Hyaluronan Sytnhase: Sequence Comparison and Conservation Among Various Group A Strains," DeAngelis, et al., Biochem. and Biophy. Res. Comm., vol. 199, No. 1, pp. 1-10, (1994).
"Molecular Fingerprinting of *Pasteurella multocida* Associated With Progressive Atrophic Rhinitis in Swine Herds". Gardner et al. Database Medline on Diaolog, US Nat'l. Library of Medicine (Bethesda, MD, USA) No. 95161494, Abstract, J. Vet. Diagn. Invest. Oct. 1994. vol. 6, No. 4 pp. 442-447, see entire abstract.
"Amino Acid Residues of the Kringle-4 and Kringle-5 Domains of Human Plasminogen That Stabilize Their Interactions With Omega-Amino Acid Ligands", McCance et al., J. Biol. Chem., 269(51):32405-32410 (1994).
"Heparin-like compounds prepared by chemical modification of capsular polysaccharide from *E. coli*", Casu et al., Elsevier Science. 263:271-284 (1994).
"Substrate specificities of glycosyltransferases involved in formation of heparin precursor and *E. coli* K5 capsular polysaccharides", Lidholt et al., Carbohydrate Research. 255:87-101 (1994).
"Presumptive Identification of *Pasteurella multocida* serogroups A, D and F by capsule depolymerisation with mucopolysaccharidases", Rimler, Veterinary Record.134:191-192 (1994).
"Hyaluronidase and Chondroitinase Activity of *Pasteurella multocida* Serotype B:2 Involved in Haemorrhagic Septicaemia", Rimler, et al., Veterinary Record 134, 67-68 (1994).
The Elucidation of Novel Capsular Genotypes of *Haemophilus influenzae* Type B With the Polymerase Chain Reaction. Leaves et al. J. Medical Microbiology. 1995, vol. 43, pp. 120-124, entire document.
"Kinetic Mechanism of Kinesin Motor Domain", Ma and Taylor, Biochemistry, 34(40): 13233-13241 (1995).
"Cloning of the putative tumor suppressor gene for hereditary multiple exostoses (EXT1)", Ahn et al., Nat. Genet. 11(2):137-43 (1995).
"Region 2 of the *Escherichia coli* K5 capsule gene cluster encoding proteins for the biosynthesis of the K5 polysaccharide", Petit et al., Molecular Microbiology. 17(4):611-620 (1995).
"Structural and functional properties of heparin analogues obtained by chemical sulphation of *Escherichia coli* K5 capsular polysaccharide", Razi et al., Biochem J. 309 (pt2):465-72 (1995).

"Influence of chondroitinase on direct hemagglutination titers and phagocytosis of *Pasteurella multocida* serogroups A, D and F", Rimler et al., Veterinary Microbiology. 47:287-294 (1995).
"Homologs of the *Xenopus* Developmental Gene DG42 are Present in Zebrafish and Mouse and are Involved in the Synthesis of Nod-Like Chitin Oligosaccharides During Early Embryogenesis", Semino et al., Proc. Natl Acad. Sci. USA, 93:4548-4553 (1996).
"Enzymological Characterization of the *Pasteurella multocida* Hyaluronic Acid Synthase", DeAngelis, Biochemistry, 35 (30): 9768-9771 (1996).
"Construction and Characterization of a Potential Live Oral Carrier-Based Vaccine Against Vibrio Chlolerae". Favre et al. Infection and Immunity. Sep. 1996. vol. 64, No. 9 pp. 3565-3570, entire document.
"Functional Cloning of the cDNA for a Human Hyaluronan Synthase", Shyjan et al., J. Biol. Chem., 271(38):23395-23399 (1996).
"Coating the Surface: A Model for Expression of Capsular Polysialic Acid in *Escherchia coli* K1", Bliss et al., Molecular Microbiology, 21(2):221-231 (1996).
"Molecular Cloning and Characterization of a Putative Mouse Hyaluronan Synthase", Spicer et al., J. Biol. Chem., 271(38):23400-23406 (1996).
"Expression Cloning and Molecular Characterization of HAS Protein, A Eukaryotic Hyaluronan Synthase", Itano et al., J. Biol. Chem., 271(17):9875-9878 (1996).
"Molecular Identification of a Putative Human Hyaluronan Synthase", Wantanabe et al., J. Biol. Chem., 271(38):22945-22948 (1996).
"Molecular Cloning of a Human Hyaluronan Synthase", Itano et al., Biochemical and Biophysical Research Communications, 222:816-820 (1996).
"Production and Purification of an Extracellularly Produced K4 Polysachharide From *Escherichia coli*", Manzoni et al., Biotechnol. Lett., 18(4): 383-386 (1996).
"A Novel Family of Phospholipase D Homologues That Includes Phospholipid Synthases and Putative Endonucleases: Identification of Duplicated Repeats and Potential Active Site Residues", Ponting and Kerr, Protein Science, 914-922 (May 1996).
"Biosynthesis of Dermatan Sulphate. Defructosylated *Escherichia coli* K4 Capsular Polysaccharide as a Substrate for the D-Glucuronyl C-5 Epimerase, and an Indication of a Two-Base Reaction Mechanism", Hannesson et al., Biochem. J., 313(Pt. 2): 589-596 (1996).
"The EXT2 multiple exostoses gene defines a family of putative tumor suppressor genes", Stickens et al., Nat. Genet. 14(1):25-32 (1996).
"Construction and Characterization of a Potential Live Oral Carrier-Based Vaccine Against *Vibrio chlolerae*". Favre et al. Infection and Immunity. Sep. 1996. vol. 64, No. 9 pp. 3565-3570, entire document.
"Capsular Hyaluronic Acid-Mediated Adhesion of *Pasteurella multocida* to Turkey Air Sac Macrophages", Pruimboom, et al., Avian Diseases 40:887-893, (1996).
"Hyaluronan Synthases", Weigel et al., J. Biol. Chem., 272 (22): 13997-14000 (1997).
"Identification of Sulfhydryl-Modified Cysteine Residues in the Ligand Binding Pocket of Retinoic Acid Receptor β", Wolfgang et al., J. Biol. Chem., 272(2):746-753 (1997).
"Hyaluronan in Morphogenesis", B.P. Toole, Journal of Internal Medicine, 242:35-40 (1997).
"Hyaluronan Synthase of Chlorella Virus PBCV-1", DeAngelis et al, Science, 278:1800-1803 (1997).
"Molecular Cloning, Expression, and Characterization of the Authentic Hyaluronan Synthase From Group C *Streptococcus equisimilis*", Kumari and Weigel, J. Biol. Chem., 272(51):32539-32546 (1997).
"Site-Directed Spin Labeling of Transmembrane Domain VII and the 4B1 Antibody Epitope in the Lactose Permease of *Escherichia coli*", Voss et al., Biochemistry, 36:15055-15061 (1997).
"Reactive Cysteines of the Yeast Plasma-Membrane H -ATPase (PMA1)", Petrov et al., J. Biol. Chem., 272(3):1688-1693 (1997).
"Biosynthesis of the *Escherichia coli* K4 Capsule Polysaccharide: A Parallel System for Studies of Glycosyltransferases in Chondroitin Formation", Lidholt et al., J. Biol. Chem., 272(5):2682-2687 (1997).
"Kinetic Mechanism of Monomeric Non-Claret Disjunctional Protein (Ncd) ATPase", Pechatnikova et al., J. Biol. Chem., 272(49): 30735-30740 (1997).
"A Two-Site Mechanism for ATP Hydrolysis by the Asymmetric Rep Dimer P2S as Revealed by Site-Specific Inhibition With ADP-A1F4", Wong and Lohman, Biochemistry, 36(11): 3115-3125 (1997).
"The Structure of the Human Multiple Exostoses 2 Gene and Characterization of Homologs in Mouse and *Caenorhabditis elegans*", Clines et al., Cold Spring Harbor Laboratory Press. 7:359-367 (1997).
"Identification and Localization of the Gene for EXTL, a Third Member of the Multiple Exostoses Gene Family", Wise et al., Cold Spring Harbor Laboratory Press. 7:10-16 (1997).
"Identification and Molecular Cloning of a Unique Hyaluronan Synthase From *Pasteurella multocida*", DeAngelis et al., J. Biol. Chem., 273(14): 8454-8458 (1998).
The Capsule Biosynthetic Locus of *Pasteurella multocida* A:1. Chung, et al. FEMS Microbiol. Lett. Sep. 15, 1998, vol. 166, No. 2, pp. 289-296, entire document.
"CYS-Scanning Mutagenesis: A Novel Approach to Structure-Function Relationships in Polytopic Membrane Proteins", Frillingos et al., FASEB, 12:1281-1299 (Oct. 1998).
"Characterization and Molecular Evolution of a Vertebrate Hyaluronan Synthase Gene Family", Spicer et al., J. Biol. Chem., 273(4):1923-1932 (1998).
"Eukaryotic Hyaluronan Synthases", Spicer and McDonald, Glycoforum, Sep. 15, 1998.
"The Active Streptococcal Hyaluronan Synthases (HASs) Contain a Single has Monomer and Multiple Cardiolipin Molecules", Tlapak-Simmons et al., J. Biol. Chem., 273(40):26100-26109 (1998).
"Role of Fimbriae-Mediated Adherence for Neutrophil Migration Across *Escherichia coli*-Infected Epithelial Cell Layers", Godaly et al., Molecular Microbiology, 30(4): 725-735 (1998).
"Complete Kinetic Mechanism of Elongation Factor Tu-Dependent Binding of Aminoacyl-tRNA to the a Site of the *E. coli* Ribosome", Pape et al., EMBO J., 17(24): 7490-7497 (1998).
Wyatt Technology Corporation: Heparin Characterization. 4/5; www.tigc.org.
Griffiths, G., et al.: Characterization of the Glycosyltransferase Enzyme from the *Escherichia coli* K5 Capsule Gene Cluster and Identification and Characterization of the Glucuronyl Active Site. The Journal of Biological Chemistry, 273(19):11752-11757 (1998).
"Expression and functional analysis of mouse EXT1, a homolog exostoses type 1 gene", Lin et al., Biochem Biophys Res Commun.; 248(3):738-43 (1998).
"The Putative Tumor Suppressors EXT1 and EXT2 Are Glycosyltransferases Required for the Biosynthesis of Heparan Sulfate", Lind et al., The Journal of Biological Chemistry, 273(41):26265-26268 (1998).
"The putative tumor suppressor EXT1 alters the expression of cell-curface heparan sulfate", McCormick et al., Nat. Genet. 19(2):158-61 (1998).
"The localization of KpsC, S and T, and KfiA, C and D Proteins Involved in the biosynthesis of the *Escherichia coli* K5 capsular polysaccharide: evidence for a membrane-bound complex", Rigg et al., Microbiology 144, 2905-2914 (1998).
"Identification of a Third EXT-like Gene (EXTL3) Belonging to the EXT Gene Family", Van Hul et al., Genomics. 47(2):230-7 (1998).
"Transposon Tn916 Insertional Mutagenesis of *Pasteurella multocida* and Direct Sequencing of Disruption Site", Paul L. DeAngelis, Microbial Pathogenesis, 24: 203-209 (1998).
"Hyaluronan Synthase Expression in Bovine Eyes", Usui et al., Investigative Ophythamology & Visual Science, 40(3):563-567 (Mar. 1999).
"Three Isoforms of Mammalian Hyaluronan Synthases Have Distinct Enzymatic Properties", Itano et al., J. Biol. Chem., 274(35):25085-25092 (1999).
"Hyaluronan Synthases: Fascinating Glycosyltransferases From Vertebrates, Bacterial Pathogens and Algal Viruses", P.L. DeAngelis, CMLS, 56:670-682 (1999).

"Membrane Protein Folding and Stability: Physical Principles", White and Wimley, Annu. Rev. Biophys. Biomol. Struc., 28:319-365 (1999).
"Location of Helix III in the Lactose Permease of *Escherichia coli* as Determined by Site-Directed Thiol Cross-Linking", Wang and Kaback, Biochemistry, 38:16777-16782 (1999).
"Kinetic Characterization of the Recombinant Hyaluronan Synthases From *Streptococcus pyogenes* and *Streptococcus equisimilis*", Tlapak-Simmons, J. Biol. Chem., 274(7):4246-4253 (1999).
"Purification and Lipid Dependence of the Recombinant Hyaluronan Synthases From *Streptococcus pyogenes* and *Streptococcus equisimilis*", Tlapak-Simmons, J. Biol. Chem., 274(7):4239-4245 (1999).
"Structure/Function Studies of Glycoslytransferases", Breton and Imberty, Current Opinion in Structural Biology, 9:563-571 (1999).
"Transfer RNA Identity Contributes to Transition State Stabilization During Aminoacyl-tRNA Synthesis", Ibba et al., Nucleic Acids Research, 27(18):3631-3637 (1999).
"Contractile Function and Myoplasmic Free Ca2+ (Cam) in Coronary and Mesenteric Arteries of Endotoxemic Guinea Pigs", Jones et al., Shock, 11: 64-71 (1999).
"Biosynthesis of the *Escherichia coli* K5 Polysaccharide, a Representative of Group II Polysaccharides: Polymerization In Vitro and Characterization of the Product", Finke et al., Journal of Bacteriology. 4088-4094 (1999).
"The Tumor Suppressor EXT-like Gene EXTL2 Encodes an 1, 4-N-Acety1hexosaminyltransferase That Transfers N-Acetylgalactosamine and N-Acetylglucosamine to the Common Glycosaminoglycan-Protein Linkage Region", Kitigawa et al., The Journal of Biological Chemistry. 273(20):13933-13937 (1999).
"Production and Chemical Processing of Low Molecular Weight Heparins", Linhardt et al., Thieme Medical Publishers, Inc. 25(3):5-16 (1999).
"New insights on the specificity of heparin and haparan sulfate lyases from *Flavobacterium* heparinum revealed by the use of synthetic derivatives of K5 polysaccharide from *E. coli* and 2-O-desulfated heparin", Nader et al., Glycoconj J. 16(6):265-70 (1999).
"A director interaction between EXT proteins and glycosyltransferases is defective in hereditary multple exostoses", Simmons et al., Hum. Mol. Genet. ; 8(12):2155-64 (1999).
"Identification of mutations in the human EXT1 and EXT2 genes", Song et al., Chin J. Med. Genet., 16(4):208-10 (1999).
Paul L. DeAngelis, "Molecular Directionality of Polysaccharide Polymerization by the *Pasteurella multocida* Hyaluronan Synthase", J. Biological Chemistry, vol. 274: 26557-26562 (1999).
"New Frontiers in Medical Sciences: Redefining Hyaluronan", Abatangelo and Weigel Eds., (2000).
C. Heldermon, K. Kumari, V. Tlapak-Simons & P. Weigel, "Streptococcal hyaluronan synthase and the synthesis of 'designer' hyaluronan", Elsevier Science, 41-50 (2000).
"In Vitro Synthesis of Hyaluronan by a Single Protein Derived From Mouse HAS1 Gene and Characterization of Amino Acid Residues Essential for the Activity", Yoshida et al., J. Biol. Chem., 275(1):497-506 (2000).
"Regulation of Plasminogen Activator Inhibitor-1 and Urokinase by Hyaluronan Fragments in Mouse Macrophages", Horton et al., Am. J. Physiol. Lung Cell Mol. Physiol., 279:L707-L715 (2000).
Identification and Molecular Cloning of a Chondroitin Synthase From *Pasteurella multocida* Type F, Paul DeAngelis, et al., Journal of Biological Chemistry, vol. 275, No. 31, pp. 24124-24129, Apr. 2000.
"Kinetic Studies on the Interaction Between a Ribosomal Complex Active in Peptide Bond Formation and the Macrolide Antibiotics Tylosin and Erythromycin", Dinos et al., Biochemistry, 39(38): 11621-11628 (2000).
"Structure-Function Relationships in Novel Peptide Dodecamers With Broad-Spectrum Bactericidal and Endotoxin-Neutralizing Activities", Mayo et al., Biochemical Journal, 349(3): 717-728 (2000).
"*Pasteurella multocida* capsule: composition, function and genetics", Boyce et al., Journal of Biotechnology 83:153-160 (2000).
"Biosynthesis of heparin/heparan sulfate: kinetic studies of the glucuronyl C5-epimerase with N-sulfated derivatives of the *Escherichia coli* K5 capsular polysaccharide as substrates", Hagner-McWhirter et al., Glycobiology. 10(2):159-71 (2000).
"Identification That KfiA, a Protein Essential for the Biosynthesis of the *Escherichia coli* K5 Capsular Polysaccharide, Is a UDP-GlcNAc Glycosyltransferase", Hodson et al., The Journal of Biological Chemistry, 275(35):27311-27315 (2000).
"EXT 1 Gene Mutation Induces Chondrocyte Cytoskeletal Abnormalities and Defective Collagen Expression in the Exostoses", Legeai-Mallet et al., J Bone Miner Res. 15(8):1489-500 (2000).
"Disruption of gastrulation and heparan sulfate biosynthesis in EXT1-Deficient Mice", Lin et al., Dev. Biol. 224(2):299-311 (2000).
"The putative tumor suppressors EXT1 And EXT2 form a stable complex that accumulates in the Golgi apparatus and catalyzes the synthesis of heparan sulfate", McCormick et al., PNAS, 97(2):668-673 (2000).
"Heparan/Chondroitin Sulfate Biosynthesis", Pedersen et al., The Journal of Biological Chemistry, 275(44):34580-34585 (2000).
"Heparin and heparan sulfate: biosynthesis, structure and function", Sasisekharan et al., Elsevier Science, Ltd. 1367-5931:626-631 (2000).
"The EXT1/EXT2 tumor suppressors: catalytic activities and role in heparan sulfate biosynthesis", Senay et al., EMBO Reports 1(3):282-286 (2000).
"Structural Analysis of Glycosaminoglycans in *Drosophila* and *Caenorhabditis elegans* and Demonstrations That tout-velu, a *Drosophila* Gene Related to EXT Tumor Suppressors, Affects Heparan Sulfate in Vivo", Toyoda et al., The Journal of Biological Chemistry, 275( 4):2269-2275 (2000).
"Location of the Glucuronosyltransferase Domain in the Heparan Sulfate Copolymerase EXT1 by Analysis of Chinese Hamster Ovary Cell Mutants", Wei et al., The Journal of Biological Chemistry, 275(36):27733-27740 (2000).
"Complete Cysteine-Scanning Mutagenesis and Site Directed Chemical Modification of the Tn10-Encoded Metal-Tetracycline/H Antiporter", Tamura et al., J. Biol. Chem., 276(23):20330-20339 (2001).
"Identification and Disruption of Two Discrete Loci Encoding Hyaluronic Acid Capsule Biosynthesis Genes hasA, hasB, and hasC in *Streptococcus uberis*", Ward et al., Infection and Immunity, 69(1):392-399 (2001).
"Topological Organization of the Hyaluronan Synthase From *Streptococcus pyogenes*", Heldermon et al., J. Biol. Chem., 276(3):2037-2046 (2001).
"Site-Directed Mutation of Conserved Cysteine Residues Does Not Inactivate the *Streptococcus pyogenes* Hyaluronan Synthase", Heldermon et al., Glycobiology, 11(12):1017-1024 (2001).
"Molecular Cloning of Rabbit Hyaluronic Acid Synthases and Their Expression Patterns in Synovial Membrane and Articular Cartilage", Ohno et al., Biochimica et Biophysics Acta, 1520 (71-78) (2001).
Molecular Cloning and Expression of a Human Chondroitin Synthase, Hiroshi Kitagawa, et al., Journal of Biological Chemistry, vol. 276, No. 42, pp. 38721-38726, Aug. 2001.
Utility of Molecularly Dissected Synthases for Chemoenzymatic Synthesis of Glycosaminoglycan Oligosaccharides, Paul DeAngelis, Glycobiology, vol. 11, No. 10, pp. 934, Oct. 2001.
"Ring Opening is Not Rate-Limiting in the GTP Cyclohydrolase I Reaction", Bacher et al., J. Biol. Chem., 276(4): 2622-2626 (2001).
"Subunit Communication in Tetrameric Class 2 Human Liver Aldehyde Dehydrogenase as the Basis for Half-of-the-Site Reactivity and the Dominance of the Oriental Subunit in a Heterotetramer", Weiner et al., Chemico-Biological Interactions, 130-132(1-3):47-56 (2001).
Bio Tie Therapies; BioHeparin—Prospectus; Jun. 2001. (Finland).
"Etiological Point Mutations in the Hereditary Multiple Exostoses Gene EXT1: A Functional Analysis of Heparan Sulfate Polymerase Activity", Cheung et al., Am. J. Hum. Genet. 69:55-66, (2001).
"The link between heparan sulfate and hereditary bone disease: finding a function for the EXT family of putative tumor suppressor proteins", Duncan et al., The Journal of Clinical Investigation, 108(4):511-516 (2001).
"Human tumor suppressor EXT gene family members EXTL1 and EXTL3 encode alpha 1,4-N-acetylglucosaminyltransferases that likely are involved in heparan sulfate/heparin biosynthesis", Kim et al., Proc. Natl. Acad. Sci. U.S.A. 1998(13):7176-81 (2001).
"Rib-2, a *Caenorhabditis elegans* Homolog of the Human Tumor Suppressor EXT Genes Encodes a Novel 1,4-N-Acetylglucosaminyltransferase Involved in the Biosynthetic Initiation and Elongation of Heparan Sulfate", Kitigawa et al., The Journal of Biological Chemistry, 276(7):4834-4838 (2001).
"Fibroblast Growth Factor-2 Antagonist Activity and Angiostatic Capacity of Sulfated *Escherichia coli* K5 Polysaccharide Derivatives", Leali et al., The Journal of Biological Chemistry, 276(41):37900-37908 (2001).
"Complete genomic sequence of *Pasteurella multocida*, Pm70", May et al., Proc. Natl. Acad. Sci. 98(6):3460-3465 (2001).
"Toward a Biotechnological Heparin through Combined Chemical and Enzymatic Modification of the *Escherichia coli* K5 Polysaccharide", Naggi et al., Seminars in Thrombosis and Hemostasis, 27(5):437-443 (2001).
"Genetic organization of *Pasteurella multocida* cap loci and development of a multiplex capsular typing system", Townsend et al., J. Clin. Microbiol. 39(3):924-929 (2001).
"Anticoagulation: The Present and Future" Van Aken et al., Clin. Appl. Thrombosis/Hemostasis, 7(3):195-204, (2001).
"The Streptococcal Hyaluronan Synthases are Inhibited by Sulfhydryl-Modifying Reagents, but Conserved Cysteine Residues are Not Essential for Enzyme Function", Kumari et al., J. Biol. Chem., 277(16):13943-13952 (2002).
Biosynthesis of Chondroitin/Dermatan Sulfate, Jeremiah Silbert, et al., IUBMB Life, vol. 54, pp. 177-186, Oct. 2002.
Functional Characteristics and Catalytic Mechanisms of the Bacterial Hyaluronan Synthases, Paul Weigel, IUBMB Life, vol. 54, pp. 201-211, Oct. 2002.
Keratan Sulfate Biosynthesis, James Funderburgh, IUBMB Life, vol. 54, pp. 187-194, 2002.
Mammalian Hyaluronan Synthases, Naoki Itano, et al., IUBMB Life, vol. 54, pp. 195-199, 2002.
"Identification of the capsular polysaccharides of Type D and F *Pasteurella multocida* as unmodified heparin and chondroitin, respectively", DeAngelis et al., Carbohydrate Research 337:1547-1552 (2002).
"Identification and Molecular Cloning of a Heparosan Synthase from *Pasteurella multocida* Type D", DeAngelis et al., The Journal of Biological Chemistry. 277(9):7209-7213 (2002).
"Identification of the *Xenopus laevis* cDNA for EXT1: A Phylogenetic Perspective", Hill et al., DNA Sequence, 13(2):85-92 (2002).
"cDNA cloning and distribution of XEXT1, the *Xenopus* homologue of EXT1", Katada et al., Dev Genese Evol. 212:248-250 (2002).
"Demonstration of a Novel Gene DEXT3 of *Drosophila melanogaster* as the Essential N-Acetylglucosamine Transferase in the Heparan Sulfate Biosynthesis", Kim et al., The Journal of Biological Chemistry, 277(16):13659-13665 (2002).
"Inhibition of B16-BL6 melanoma lung colonies by semisynthetic sulfaminoheparosan sulfates from *E. coli* K5 polysaccharide", Poggi et al., Semin Thromb Hemost. 28(4):383-92 (2002).
"Heparin and Heparan Sulfate Biosynthesis", Sugahara et al., Life, 54:163-175 (2002).
"Hereditary multiple exostoses and heparan sulfate polymerization", Zak et al., Biochimica et Biophysica Acta 1573:346-355 (2002).
Molecular Cloning and Expression of Human Chondroitin N-Acetylgalactosaminyltransferase, Toru Uyama, et al. Journal of Biological Chemistry, vol. 277, No. 11, pp. 8841-8846, Jan. 2002.
Molecular Cloning and Characterization of Chondroitin Polymerase From *Escherichia coli* Strain K4, Toshio Ninomiya, et al., Journal of Biological Chemistry, vol. 277, No. 24, pp. 21567-21575, Apr. 2002.
Molecular Cloning and Characterization of a Novel Chondroitin Sulfate Glucuronyltransferase That Transfers Glucuronic Acid to N-Acetylgalactosamine, Masanori Gotoh, et al., Journal of Biological Chemistry, vol. 277, No. 41, pp. 38179-38188, Jul. 2002.
Structure Function Analysis of *Pasteurella* Glycosaminoglycan Synthesis, Wei Jing, et al., Glycobiology, vol. 12, No. 10, pp. 705, Oct. 2002.
"Detection of Submicrogram Quantities of Glycosaminoglycans on Agarose Gels by Sequential Staining With Toluidine Blue and Stains-All", Volpi and Maccari, Electrophoresis, 23(24):4060-4066 (2002).
"Structural/Functional Characterization of the Alpha 2-Plasmin Inhibitor C-Terminal Peptide", Frank et al., Biochemistry, 42:1078-1085 (2003).
"Trp-999 of Beta-Galactosidase (*Escherichia coli*) is a Key Residue for Binding, Catalysis, and Synthesis of Allolactose, the Natural LAC Operon Inducer", Huber et al., Biochemistry, 42(6): 1796-1803 (2003).
"Separation of Capsular Polysaccharide K4 and Defructosylated K4 Derived Disaccharides by High-Performance Capillary Electrophoresis and High-Performance Liquid Chromatography", Volpi, Electrophoresis, 24(6): 1063-1068 (2003).
"Milligram-Scale Preparation and Purification of Oligosaccharides of Defined Length Possessing the Structure of Chondroitin From Defructosylated Capsular Polysaccharide K4", Volpi, Glycobiology, 13(9):635-640 (2003).
"Broad spectrum inhibition of HIV-1 infection by sulfated K5 *Escherichia coli* polysaccharide derivatives", Vicenzi et al., AIDS. 17(2):177-81 (2003).
W. Jing & P. DeAngelis, "Synchronized Chemoenzymatic Synthesis of Monodisperse Hyaluronan Polymers", J. Biological Chemistry, vol. 279: 42345-42349 (2004).

A

B

A1 SIIVTTFNRPAILSITLACLVNQKTHYPFEVIVTD
A2 SIYIPAYNCANYIQRCVDSALNQ-TTVDLEVCICN

A1 DGSQEDLSPIIRQYENKLDIRYVRQKDNGFQASAAR
A2 DGSTDNTLEVINKLYGNNPRVRIMSKPNGGIASAS-

D247/249
* *

A1 NMGLRLAKYDFIGLLDCDMAPNPLWVHSYVAELLED
A2 NAAVSFAKGYYIGQLDSDDYLEPDAVELCLKEFLKD

```
       1                                                      50
pmCS   MNTLSQAIKA YNSNDYELAL KLFEKSAETY GRKIVEFQII KGKEKLSTNS
pmHAS  ---------- ------Q--- --------I- ---------T -------AHP

       51                                                    100
pmCS   YVS------- EDKKNSVCDS SLDIATQLLL SNVKKLTLSE SEKNSLKNKW
pmHAS  S-NSAHLSVN KEE-VN---- P--------- ------V--D ----T-----

       101                                                   150
pmCS   KSITGKKSEN AEIRKVELVP KDFPKDLVLA PLPDHVNDFT WYKNRKKSLG
pmHAS  -LL-E----- --V-A-A--- ---------- ---------- ---K---R--

       151                                                   200
pmCS   IKPVNKNIGL SIIIPTFNRS RILDITLACL VNQKTNYPFE VVVADDGSKE
pmHAS  ---EHQHV-- ---VT----P A--S------ -----H---- -I-T----Q-

       201                                                   250
pmCS   NLLTIVQKYE QKLDIKYVRQ KDYGYQLCAV RNLGLRTAKY DFVSILDCDM
pmHAS  D-SP-IRQ-- N----R---- --N-F-AS-A --M---L--- --IGL-----

       251                                                   300
pmCS   APQQLWVHSY LTELLEDNDI VLIGPRKYVD THNITAEQFL NDPYLIESLP
pmHAS  --NP------ VA-----D-L TI------I- -QH-DPKD-- -NAS-L----

       301                                                   350
pmCS   ETATNNNPSI TSKGNISLDW RLEHFKKTDN LRLCDSPFRY FVAGNVAFSK
pmHAS  -VK---SVAA KGE-TV---- ---Q-E--E- ---S-----F -A------A-

       351                                                   400
pmCS   EWLNKVGWFD EEFNHWGGED VEFGYRLFAK GCFFRVIDGG MAIHQEPPGK
pmHAS  K----S-F-- ---------- --------R- -S--KT---I --Y-------

       401                                                   450
pmCS   ENETEREAGK SITLKIVKEK VPYIYRKLLP IEDSHIHRIP LVSIYIPAYN
pmHAS  ----D----- N---D-MR-- ---------- ------N-V- ----------

       451                                                   500
pmCS   CANYIQRCVD SALNQTVVDL EVCICNDGST DNTLEVINKL YGNNPRVRIM
pmHAS  ---------- ---------- ---------- ---------- ----------

       501                                                   550
pmCS   SKPNGGIASA SNAAVSFAKG YYIGQLDSDD YLEPDAVELC LKEFLKDKTL
pmHAS  ---------- ---------- ---------- ---------- ----------

       551                                                   600
pmCS   ACVYTTNRNV NPDGSLIANG YNWPEFSREK LTTAMIAHHF RMFTIRAWHL
pmHAS  ---------- ---------- ---------- ---------- ----------

       601                                                   650
pmCS   TDGFNENIEN AVDYDMFLKL SEVGKFKHLN KICYNRVLHG DNTSIKKLGI
pmHAS  ------K--- ---------- ---------- ---------- ----------

       651                                                   700
pmCS   QKKNHFVVVN QSLNRQGINY YNYDKFDDLD ESRKYIFNKT AEYQEEMDKL
pmHAS  ---------- --------T- ----E----- ---------- ------I-I-

       701                                                   750
pmCS   KDLKLIQNKD AKIAVSIFYP NTLNGLVKKL NNIIEYNKNI FVIILHVDKN
pmHAS  --I-I----- ---------- ---------- ---------- ---V------

       751                                                   800
pmCS   HLTPDIKKEI LAFYHKHQVN ILLNNDISYY TSNRLIKTEA HLSNINKLSQ
pmHAS  ---------- ---------- ---------- ---------- ----------

       801                                                   850
pmCS   LNLNCEYIIF DNHDSLFVKN DSYAYMKKYD VGMNFSALTH DWIEKINAHP
pmHAS  ---------- ---------- ---------- ---------- ----------

       851                                                   900
pmCS   PFKKLIKTYF NDNDLRSMNV KGASQGMFMK YALPHELLTI IKEVITSCQS
pmHAS  ---------- -----K---- ---------T ---A------ ----------

       901                                                   950
pmCS   IDSVPEYNTE DIWFQFALLI LEKKTGHVFN KTSTLTYMPW ERKLQWTNEQ
pmHAS  ---------- ---------- ---------- ---------- ----------

       951                  972
pmCS   IQSAKKGENI PVNKFIINSI TL
pmHAS  -E---R---- ---------- --
```

Figure 14

```
          91                                                 140
HS1       APPLVSIIMTSHNTEKFIEASINSLLLQTYNNLEVIVVDDYSTDKTFQIA
KfiC      GKDLVSIIMSVFNSEDTIAYSLHSLLNQTYENIEILVCDDCSSDKSLEII
con       ...LVSIIM*..N*E..I..S..SLL.QTY#N.E!.V.DD.S*DK*.#I.

          141                                                190
HS1       SRIANSTSKVKTFRLNSNLGTYFAKNTGILKSKGDIIFFQDSDDVCHHER
KfiC      KSIAYSSSRVKVYSSRKNQGPYNIRNELIKKAHGNFITFQDADDLSHPER
con       ..IA.S*S*VK.%....N.G.Y...N..I.K..G#.I.FQD.DD..H.ER

          191                                                240
HS1       IERCVNALLSNKDNIAVRCAYSRINLETQNIIKVNDNKYKLGLITLGVYR
KfiC      IQRQVEVLRNNKAVICM.ANWIRVASNGKIQFFYDDKATRMSVVSSMIKK
con       I#R.V#.L..NK..I.......R!..#.......#D...*$..!*..!.*

          441                                                490
HS2       YITCDDDIRYPADYINTMIKKINKYND.KAAIGLHGVIFPSRVNKYFSSD
KfiA      IVLTDDDIIYPPDYVEKMLNFYNSFAIFNCIVGIHGCIYIDAFDGD.QSK
con       .!..DDDI.YP.DY!#.M....N.%......!G.HG.I%....#....S.

          491                                                540
HS2       RIVYNFQKTFRKDTAVNILGTGTVAFRVSIFNKFSLSDFEHPGMVDIYFS
KfiA      RKVFSFTQGLLRPRVVNQLGTGTVFLKADQLPSLKYMDGSQR.FVDVRFS
con       R.V%.F.....*...VN.LGTGTV..*.........D......VD!.FS
```

Figure 15A

```
           1       10        20        30        40        50        60        70
           |--------+---------+---------+---------+---------+---------+---------|
KfiC       GKDLVSIIMSVFNSEDTIAYSLHSLLNQTYENIEILVCDDCSSDKSLEIIKSIAYSSSRVKVYSSRKNQG
HSA1       APPLVSIIMTSHNTEKFIEASINSLLLQTYNNLEVIVVDDYSTDKTFQIASRIANSTSKVKTFRLNSNLG
kfiA         MIVANMSSYPPRKKELVHSIQSLHAQV-DKINLCLNEFEEIPEELDGFSKLNPVI----PDKDYKDVG
HSA2        IPVYINICSIPSRIKQLQYTIGVLKNQC-DHFHIYLDGYPEVPDFIKKLGNKATVINCQNKNESIRDNG
Consensus  ..p.v.ni.s.p.r.k.l.ysi.sL.nQ..#.i.i.l....e.p..l...s..a.vi........s.k#.G

           71      80        90        100       110       120       130      140
           |--------+---------+---------+---------+---------+---------+---------|
KfiC       PYNIRNELIKKAHGNFITFQDADDLSHPERIQRQVEVLRNNKAVICM-ANWIRVASNGKIQFFYDDKATR
HSA1       TYFAKNTGILKSKGDIIFFQDSDDVCHHERIERCVNALLSNKDNIAVRCAYSRINLETQNIIKVNDNKYK
kfiA       KFIF------PCAKNDMIVLTDDDIIYPPDYVEKMLNFYNSFAIFNCIVGIHGCIYIDAFDGD-QSKRKV-
HSA2       KFILLEKLIKENKDGYYITCDDDIRYPADYINTMIKKINKYND-KAAIGLHGVIFPSRVNKYFSSDRIV-
Consensus  k%i....lik.ak.d.i...DdDi.ypp#y!#.n.n..ns..d..a..g.hg.!.....n..f.sdrkv.

           141    150       160       170       180       190       200      210
           |--------+---------+---------+---------+---------+---------+---------|
KfiC       MSVYSSMIKKDIFATVGGYRQSLIGADTEFYETVIMRYGRESIVRLLQPLILGLWGDSGLTRNKGTEALP
HSA1       LGLITLGVYRKVFNEIGFFNCTTKASDDEFYHRIIKYYGKNRINNLFLPLYYNTMREDSLFSDM-VEHVD
kfiA       FSFTQGLLRPRVVNQLG--TGTVFLKADQLPSLKYMDGSQR-FVDVRFSRYMLENEIGMICVPREKNHLR
HSA2       YNFQKTFRKDTAVNILG--TGTVAFRVSIFNKFSLSDFEHPGMVDIYFSILCKKNNILQVCISRPSNHLT
Consensus  .sf.....k..vvn.lG..tgtv....d.f.....nd......vd..fs.y...n.i...c..r..#wl.

           211    220       230       240       250       260263
           |--------+---------+---------+---------+---------+--|
KfiC       DGYISQSRREYSDIAARQRVLGKSIVSDKDVRGLLSRYGLFKDVSGIIEQ
HSA1       ENNIKQKTSDARQNYLHEFQKIHNERKFNELKEIFS-FPRIHDALPISKEMSK
kfiA       EVS-SGSMEGLWNIFTKKWPLDI-IKETQAIAGYSKLNLELVYNVEG
HSA2       EDN-KNT-ETLFHEFQNRDEIQSKLIISNNPWGYSSIYPLLNNNANYSELIPC
Consensus  #.n.k.s.e.l...f.....l...i...n...gyss.ypll..n...se....
```

Figure 15B

```
           1         10        20        30        40        50        60        70
           |---------+---------+---------+---------+---------+---------+---------|
pnHS                                 MSLFKRATELFKSGNYKDALTLYENIAKIYG----SESLVKYNIDI
pglA       MKRKKEMTQKQMTKNPPQHEKENELNTFQNKIDSLKTTLNKDIISQQTLLAKQDSKHPLSASLENENKLL
DcbF                                 MSLFKRATELFKSGNYKDALTLYENIAKIYG----SESLVKYNIDI
Consensus  .........................$slFkrat#lfKsgnyKDaltlyeniAKiyg....SeSLvkyNidi

           71        80        90        100       110       120       130       140
           |---------+---------+---------+---------+---------+---------+---------|
pnHS       CKK-NITQSKSNKIEEDNISGENKF-----SVSIKDLYNEISNSELGITKERLGAPPLVSIIMTSHNTEK
pglA       LKQLQLVLQEFEKIYTYNQALEAKLEKDKQTTSITDLYNEVAKSDLGLVKETNSVNPLVSIIMTSHNTAQ
DcbF       CKK-NITQSKSNKIEEDNISGENEF-----SVSIKDLYNEISNSELGITKERLGAPPLVSIIMTSHNTEK
Consensus  cKk.#itqsks#KIeedNisgEnkf.....svSIkDLYNE!snS@LGitKErlgapPLVSIIMTSHNTek

           141       150       160       170       180       190       200       210
           |---------+---------+---------+---------+---------+---------+---------|
pnHS       FIEASINSLLLQTYNNLEVIVVDDYSTDKTFQIASRIANSTSKVKTFRLNSNLGTYFAKNTGILKSKGDI
pglA       FIEASINSLLLQTYKNIEIIIVDDDSSDNTFEIASRIANTTSKVRVFRLNSNLGTYFAKNTGILKSKGDI
DcbF       FIEASINSLLLQTYNNLEVIVVDDYSTDKTFQIASRIANSTSKVKTFRLNSNLGTYFAKNTGILKSKGDI
Consensus  FIEASINSLLLQTYnNlE!I!VDDySt DkTF#IASRIANsTSKVktFRLNSNLGTYFAKNTGILKSKGDI

           211       220       230       240       250       260       270       280
           |---------+---------+---------+---------+---------+---------+---------|
pnHS       IFFQDSDDVCHHERIERCVNALLSNKDNIAVRCAYSRINLETQNIIKVNDNKYKLGLITLGVYRKVFNEI
pglA       IFFQDSDDVCHHERIERCVNILLANKETIAVRCAYSRLAPETQHIIKVNNHDYRLGFITLGMHRKVFQEI
DcbF       IFFQDSDDVCHHERIERCVNALLSNKDNIAVRCAYSRINLETQNIIKVNDNKYKLGLITLGVYRKVFNEI
Consensus  IFFQDSDDVCHHERIERCVNaLLsNK#nIAVRCAYSRinlETQnIIKVN#nkYkLGlITLGvyRKVF%EI

           281       290       300       310       320       330       340       350
           |---------+---------+---------+---------+---------+---------+---------|
pnHS       GFFNCTTKASDDEFYHRIIKYYGKNRINNLFLPLYYNTMREDSLFSDMVEHVDENNIKQKTSDARQNYLH
pglA       GFFNCTTKGSDDEFFHRIAKYYGKEKIKMLLLPLYYNTMREHSLFTDMVEHIDMHNIIQKMSDTRQHYAT
DcbF       GFFNCTTKASDDEFYHRIIKYYGKNRINNLFLPLYYNTMREDSLFSDMVEHVDENNIKQKTSDARQNYLH
Consensus  GFFNCTTKaSDDEF%HRIiKYYGK#rInNLfLPLYYNTMRE#SLFsDMVEH!D#hNIkQKtSDaRQnYlh

           351       360       370       380       390       400       410       420
           |---------+---------+---------+---------+---------+---------+---------|
pnHS       EFQKIHNERKLNELKEIFSFPRIHDALPISKEMSKLSNPKIPVYINICSIPSRIKQLQYTIGVLKNQCDH
pglA       LFQAMHNETASHDFKNLFQFPRIYDALPVPQEMSKLSNPKIPVYINICSIPSRIAQLRRIIGILKNQCDH
DcbF       EFQKIHNERKFNELKEIFSFPRIHDALPISKEMSKLSNPKIPVYINICSIPSRIKQLQYTIGVLKNQCDH
Consensus  eFQkiHNErk.n#lK#iFsFPRIhDALP!skEMSKLSNPKIPVYINICSIPSRIkQLqytIG!LKNQCDH

           421       430       440       450       460       470       480       490
           |---------+---------+---------+---------+---------+---------+---------|
pnHS       FHIYLDGYPEVPDFIKKLGNKATVINCQNKNESIRDNGKFILLEKLIKENKDGYYITCDDDIRYPADYTN
pglA       FHIYLDGYVEIPDFIKNLGNKATVVHCKDKDNSIRDNGKFILLEELIEKNQDGYYITCDDDIIYPSDYIN
DcbF       FHIYLDGYPEVPDFIKKLGNKATVINCQNKNESIRDNGKFILLEKLIKENKDGYYITCDDDIRYPADYIN
Consensus  FHIYLDGYpE!PDFIKkLGNKATV!nCq#K##SIRDNGKFILLEkLIkeNkDGYYITCDDDIr-YPaDYiN

           491       500       510       520       530       540       550       560
           |---------+---------+---------+---------+---------+---------+---------|
pnHS       TMIKKINKYNDKAAIGLHGVIFPSRVNKYFSSDRIVYNFQKPLENDTAVNILGTGTVAFRVSIFNKFSLS
pglA       TMIKKLNEYDDKAVIGLHGILFPSRMTKYFSADRLVYSFYKPLEKDKAVNVLGTGTVSFRVSLFNQFSLS
DcbF       TMIKKINKYNDKAAIGLHGVIFPSRVNKYFSSDRIVYNFQKTFRK
Consensus  TMIKKiNkY#DKAaIGLHG!iFPSRvnKYFSsDRiVYnFqKplekd.avn.lgtgtv.frvs.fn.fsls

           561       570       580       590       600       610       620       630
           |---------+---------+---------+---------+---------+---------+---------|
pnHS       DFEHPGMVDIYFSILCKKNNILQVCISRPSNWLTEDNKNTETLFHEFQNRDEIQSKLIISNNPWGYSSIY
pglA       DFTHSGMADIYFSLLCKKNNILQICISRPANWLTEDNRDSETLYHQYRDNDEQQTQLIHENGPWGYSSIY
DcbF
Consensus  df.h.gn.diyfs.lckknnilq.cisrp.nwltedn...etl.h.....de.q..li..n.pwgyssiy

           631       640       651
           |---------+---------|
pnHS       PLLNNNANYSELIPCLSFYNE
pglA       PLVKNHPKFTDLIPCLPFYFL
DcbF
Consensus  pl..n......lipcl.fy..
```

Figure 15C

```
Multalin version 5.4.1
Copyright I.N.R.A. France 1989, 1991, 1994, 1996
Published research using this software should cite
Multiple sequence alignment with hierarchical clustering
F. CORPET, 1988, Nucl. Acids Res., 16 (22), 10881-10890
Symbol comparison table: blosum62
Gap weight: 12
Gap length weight: 2
Consensus levels: high=90% low=50%
Consensus symbols:
 ! is anyone of IV
 $ is anyone of LM
 % is anyone of FY
 # is anyone of NDQEBZ

 MSF:    651    Check:   0        ..
 Name: A              Len:   651  Check:  612  Weight:  0.58
 Name: B              Len:   651  Check:  249  Weight:  0.58
 Name: pglA           Len:   651  Check: 7677  Weight:  1.08
 Name: DcbF           Len:   651  Check: 7537  Weight:  1.76
 Name: Consensus      Len:   651  Check: 5816  Weight:  0.00

//

              1                                                   50
       A2     .......... .......... ....MSLFKR ATELFKSGNY KDALTLYENI
      B10     .......... .......... ....MSLFKR ATELFKSGNY KDALTLYENI
     pglA     MKRKKEMTQK QMTKNPPQHE KENELNTFQN KIDSLKTTLN KDIISQQTLL
     DcbF     .......... .......... ....MSLFKR ATELFKSGNY KDALTLYENI
   sensus     .......... .......... ....$slFkr at#lfKsgny KDaltlyeni

              51                                                 100
       A2     AKIYG....S ESLVKYNIDI CKK.NITQSK SNKIEEDNIS GENKF.....
      B10     AKIYG....S ESLVKYNIDI CKK.NITQSK SNKIEEDNIS GENKF.....
     pglA     AKQDSKHPLS ASLENENKLL LKQLQLVLQE FEKIYTYNQA LEAKLEKDKQ
     DcbF     AKIYG....S ESLVKYNIDI CKK.NITQSK SNKIEEDNIS GENEF.....
Consensus     AKiyg....S eSLvkyNidi cKk.#itqsk s#KIeedNis gEnkf.....

              101                                                150
       A2     SVSIKDLYNE ISNSELGITK ERLGAPPLVS IIMTSHNTEK FIEASINSLL
      B10     SVSIKDLYNE ISNSELGITK ERLGAPPLVS IIMTSHNTEK FIEASINSLL
     pglA     TTSITDLYNE VAKSDLGLVK ETNSVNPLVS IIMTSHNTAQ FIEASINSLL
     DcbF     SVSIKDLYNE ISNSELGITK ERLGAPPLVS IIMTSHNTEK FIEASINSLL
Consensus     svSIkDLYNE !snS#LGitK ErlgapPLVS IIMTSHNTek FIEASINSLL

              151                                                200
       A2     LQTYNNLEVI VVDDYSTDKT FQIASRIANS TSKVKTFRLN SNLGTYFAKN
      B10     LQTYNNLEVI VVDDYSTDKT FQIASRIANS TSKVKTFRLN SNLGTYFAKN
     pglA     LQTYKNIEII IVDDDSSDNT FEIASRIANT TSKVRVFRLN SNLGTYFAKN
     DcbF     LQTYNNLEVI VVDDYSTDKT FQIASRIANS TSKVKTFRLN SNLGTYFAKN
Consensus     LQTYnNlE!I !VDDyStDkT F#IASRIANs TSKVktFRLN SNLGTYFAKN
```

Fig. 15C cont'd

```
           201                                                    250
A2         TGILKSKGDI IFFQDSDDVC HHERIERCVN ALLSNKDNIA VRCAYSRINL
B10        TGILKSKGDI IFFQDSDDVC HHERIERCVN ALLSNKDNIA VRCAYSRINL
pglA       TGILKSKGDI IFFQDSDDVC HHERIERCVN ILLANKETIA VRCAYSRLAP
DcbF       TGILKSKGDI IFFQDSDDVC HHERIERCVN ALLSNKDNIA VRCAYSRINL
Consensus  TGILKSKGDI IFFQDSDDVC HHERIERCVN aLLsNK#nIA VRCAYSRinl

           251                                                    300
A2         ETQNIIKVND NKYKLGLITL GVYRKVFNEI GFFNCTTKAS DDEFYHRIIK
B10        ETQNIIKVND NKYKLGLITL GVYRKVFNEI GFFNCTTKAS DDEFYHRIIK
pglA       ETQHIIKVNN MDYRLGFITL GMHRKVFQEI GFFNCTTKGS DDEFFHRIAK
DcbF       ETQNIIKVND NKYKLGLITL GVYRKVFNEI GFFNCTTKAS DDEFYHRIIK
Consensus  ETQnIIKVN# nkYkLGlITL GvyRKVF#EI GFFNCTTKaS DDEF%HRIiK

           301                                                    350
A2         YYGKNRINNL FLPLYYNTMR EDSLFSDMVE WVDENNIKQK TSDARQNYLH
B10        YYGKNRINNL FLPLYYNTMR EDSLFSDMVE WVDENNIKQK TSDARQNYLH
pglA       YYGKEKIKNL LLPLYYNTMR ENSLFTDMVE WIDNHNIIQK MSDTRQHYAT
DcbF       YYGKNRINNL FLPLYYNTMR EDSLFSDMVE WVDENNIKQK TSDARQNYLH
Consensus  YYGK#rInNL fLPLYYNTMR E#SLFsDMVE W!D#nNIkQK tSDaRQnYlh

           351                                                    400
A2         EFQKIHNERK LNELKEIFSF PRIHDALPIS KEMSKLSNPK IPVYINICSI
B10        EFQKIHNERK LNELKEIFSF PRIHDALPIS KEMSKLSNPK IPVYINICSI
pglA       LFQAMHNETA SHDFKNLFQF PRIYDALPVP QEMSKLSNPK IPVYINICSI
DcbF       EFQKIHNERK FNELKEIFSF PRIHDALPIS KEMSKLSNPK IPVYINICSI
Consensus  eFQkiHNErk .n#lK#iFsF PRIhDALP!s kEMSKLSNPK IPVYINICSI

           401                                                    450
A2         PSRIKQLQYT IGVLKNQCDH FHIYLDGYPE VPDFIKKLGN KATVINCQNK
B10        PSRIKQLQYT IGVLKNQCDH FHIYLDGYPE VPDFIKKLGN KATVINCQNK
pglA       PSRIAQLRRI IGILKNQCDH FHIYLDGYVE IPDFIKNLGN KATVVHCKDK
DcbF       PSRIKQLQYT IGVLKNQCDH FHIYLDGYPE VPDFIKKLGN KATVINCQNK
Consensus  PSRIkQLqyt IG!LKNQCDH FHIYLDGYpE !PDFIKkLGN KATV!nCq#K

           451                                                    500
A2         NESIRDNGKF ILLEKLIKEN KDGYYITCDD DIRYPADYTN TMIKKINKYN
B10        NESIRDNGKF ILLEKLIKEN KDGYYITCDD DIRYPADYIN TMIKKINKYN
pglA       DNSIRDNGKF ILLEELIEKN QDGYYITCDD DIIYPSDYIN TMIKKLNEYD
DcbF       NESIRDNGKF ILLEKLIKEN KDGYYITCDD DIRYPADYIN TMIKKINKYN
Consensus  ##SIRDNGKF ILLEkLIkeN kDGYYITCDD DIrYPaDYiN TMIKKiNkY#

           501                                                    550
A2         DKAAIGLHGV IFPSRVNKYF SSDRIVYNFQ KPLENDTAVN ILGTGTVAFR
B10        DKAAIGLHGV IFPSRVNKYF SSDRIVYNFQ KPLENDTAVN ILGTGTVAFR
pglA       DKAVIGLHGI LFPSRMTKYF SADRLVYSFY KPLEKDKAVN VLGTGTVSFR
DcbF       DKAAIGLHGV IFPSRVNKYF SSDRIVYNFQ KTFRK..... ..........
Consensus  DKAaIGLHG! iFPSRvnKYF SsDRiVYnFq Kplekd.avn .lgtgtv.fr

           551                                                    600
A2         VSIFNKFSLS DFEHPGMVDI YFSILCKKNN ILQVCISRPS NWLTEDNKNT
B10        VSIFNKFSLS DFEHPGMVDI YFSILCKKNN ILQVCISRPS NWLTEDNKNT
pglA       VSLFNQFSLS DFTHSGMADI YFSLLCKKNN ILQICISRPA NWLTEDNRDS
DcbF       .......... .......... .......... .......... ..........
Consensus  vs.fn.fsls df.h.gm.di yfs.lckknn ilq.cisrp. nwltedn...
```

Fig. 15C cont'd

```
           601                                                650
       A2  ETLFHEFQNR DEIQSKLIIS NNPWGYSSIY PLLNNNANYS ELIPCLSFYN
      B10  ETLFHEFQNR DEIQSKLIIS NNPWGYSSIY PLLNNNANYS ELIPCLSFYN
     pglA  ETLYHQYRDN DEQQTQLIME NGPWGYSSIY PLVKNHPKFT DLIPCLPFYF
     DcbF  .......... .......... .......... .......... ..........
Consensus  etl.h..... de.q..li.. n.pwgyssiy pl..n..... .lipcl.fy.

           651
       A2  E
      B10  E
     pglA  L
     DcbF  .
Consensus  .
```

Figure 15D

```
Multalin version 5.4.1
Copyright I.N.R.A. France 1989, 1991, 1994, 1996
Published research using this software should cite
Multiple sequence alignment with hierarchical clustering
F. CORPET, 1988, Nucl. Acids Res., 16 (22), 10881-10890
Symbol comparison table: blosum62
Gap weight: 12
Gap length weight: 2
Consensus levels: high=90% low=50%
Consensus symbols:
 ! is anyone of IV
 $ is anyone of LM
 % is anyone of FY
 # is anyone of NDQEBZ

 MSF:    651    Check:   0          ..
 Name: pmHS          Len:    651  Check:  612  Weight:  0.75
 Name: pglA          Len:    651  Check: 7677  Weight:  0.75
 Name: DcbF          Len:    651  Check: 7537  Weight:  1.49
 Name: Consensus     Len:    651  Check: 5816  Weight:  0.00

//

                1                                                  50
     pmHS   .......... .......... ....MSLFKR ATELFKSGNY KDALTLYENI
     pglA   MKRKKEMTQK QMTKNPPQHE KENELNTFQN KIDSLKTTLN KDIISQQTLL
     DcbF   .......... .......... ....MSLFKR ATELFKSGNY KDALTLYENI
Consensus   .......... .......... ....$slFkr at#lfKsgny KDaltlyeni

                51                                                100
     pmHS   AKIYG....S ESLVKYNIDI CKK.NITQSK SNKIEEDNIS GENKF.....
     pglA   AKQDSKHPLS ASLENENKLL LKQLQLVLQE FEKIYTYNQA LEAKLEKDKQ
     DcbF   AKIYG....S ESLVKYNIDI CKK.NITQSK SNKIEEDNIS GENEF.....
Consensus   AKiyg....S eSLvkyNidi cKk.#itqsk s#KIeedNis gEnkf.....

                101                                               150
     pmHS   SVSIKDLYNE ISNSELGITK ERLGAPPLVS IIMTSHNTEK FIEASINSLL
     pglA   TTSITDLYNE VAKSDLGLVK ETNSVNPLVS IIMTSHNTAQ FIEASINSLL
     DcbF   SVSIKDLYNE ISNSELGITK ERLGAPPLVS IIMTSHNTEK FIEASINSLL
Consensus   svSIkDLYNE !snS#LGitK ErlgapPLVS IIMTSHNTek FIEASINSLL

                151                                               200
     pmHS   LQTYNNLEVI VVDDYSTDKT FQIASRIANS TSKVKTFRLN SNLGTYFAKN
     pglA   LQTYKNIEII IVDDDSSDNT FEIASRIANT TSKVRVFRLN SNLGTYFAKN
     DcbF   LQTYNNLEVI VVDDYSTDKT FQIASRIANS TSKVKTFRLN SNLGTYFAKN
Consensus   LQTYnNlE!I !VDDyStDkT F#IASRIANs TSKVktFRLN SNLGTYFAKN

                201                                               250
     pmHS   TGILKSKGDI IFFQDSDDVC HHERIERCVN ALLSNKDNIA VRCAYSRINL
     pglA   TGILKSKGDI IFFQDSDDVC HHERIERCVN ILLANKETIA VRCAYSRLAP
     DcbF   TGILKSKGDI IFFQDSDDVC HHERIERCVN ALLSNKDNIA VRCAYSRINL
Consensus   TGILKSKGDI IFFQDSDDVC HHERIERCVN aLLsNK#nIA VRCAYSRinl

                251                                               300
     pmHS   ETQNIIKVND NKYKLGLITL GVYRKVFNEI GFFNCTTKAS DDEFYHRIIK
     pglA   ETQHIIKVNN MDYRLGFITL GMHRKVFQEI GFFNCTTKGS DDEFFHRIAK
     DcbF   ETQNIIKVND NKYKLGLITL GVYRKVFNEI GFFNCTTKAS DDEFYHRIIK
Consensus   ETQnIIKVN# nkYkLGlITL GvyRKVF#EI GFFNCTTKaS DDEF%HRIiK
```

Figure 15D

```
           301                                                    350
     pmHS  YYGKNRINNL FLPLYYNTMR EDSLFSDMVE WVDENNIKQK TSDARQNYLH
     pglA  YYGKEKIKNL LLPLYYNTMR ENSLFTDMVE WIDNHNIIQK MSDTRQHYAT
     DcbF  YYGKNRINNL FLPLYYNTMR EDSLFSDMVE WVDENNIKQK TSDARQNYLH
Consensus  YYGK#rInNL fLPLYYNTMR E#SLFsDMVE W!D#nNIkQK tSDaRQnYlh

           351                                                    400
     pmHS  EFQKIHNERK LNELKEIFSF PRIHDALPIS KEMSKLSNPK IPVYINICSI
     pglA  LFQAMHNETA SHDFKNLFQF PRIYDALPVP QEMSKLSNPK IPVYINICSI
     DcbF  EFQKIHNERK FNELKEIFSF PRIHDALPIS KEMSKLSNPK IPVYINICSI
Consensus  eFQkiHNErk .n#lK#iFsF PRIhDALP!s kEMSKLSNPK IPVYINICSI

           401                                                    450
     pmHS  PSRIKQLQYT IGVLKNQCDH FHIYLDGYPE VPDFIKKLGN KATVINCQNK
     pglA  PSRIAQLRRI IGILKNQCDH FHIYLDGYVE IPDFIKNLGN KATVVHCKDK
     DcbF  PSRIKQLQYT IGVLKNQCDH FHIYLDGYPE VPDFIKKLGN KATVINCQNK
Consensus  PSRIkQLqyt IG!LKNQCDH FHIYLDGYpE !PDFIKkLGN KATV!nCq#K

           451                                                    500
     pmHS  NESIRDNGKF ILLEKLIKEN KDGYYITCDD DIRYPADYTN TMIKKINKYN
     pglA  DNSIRDNGKF ILLEELIEKN QDGYYITCDD DIIYPSDYIN TMIKKLNEYD
     DcbF  NESIRDNGKF ILLEKLIKEN KDGYYITCDD DIRYPADYIN TMIKKINKYN
Consensus  ##SIRDNGKF ILLEkLIkeN kDGYYITCDD DIrYPaDYiN TMIKKiNkY#

           501                                                    550
     pmHS  DKAAIGLHGV IFPSRVNKYF SSDRIVYNFQ KPLENDTAVN ILGTGTVAFR
     pglA  DKAVIGLHGI LFPSRMTKYF SADRLVYSFY KPLEKDKAVN VLGTGTVSFR
     DcbF  DKAAIGLHGV IFPSRVNKYF SSDRIVYNFQ KTFRK..... ..........
Consensus  DKAaIGLHG! iFPSRvnKYF SsDRiVYnFq Kplekd.avn .lgtgtv.fr

           551                                                    600
     pmHS  VSIFNKFSLS DFEHPGMVDI YFSILCKKNN ILQVCISRPS NWLTEDNKNT
     pglA  VSLFNQFSLS DFTHSGMADI YFSLLCKKNN ILQICISRPA NWLTEDNRDS
     DcbF  .......... .......... .......... .......... ..........
Consensus  vs.fn.fsls df.h.gm.di yfs.lckknn ilq.cisrp. nwltedn...

           601                                                    650
     pmHS  ETLFHEFQNR DEIQSKLIIS NNPWGYSSIY PLLNNNANYS ELIPCLSFYN
     pglA  ETLYHQYRQN DEQQTQLIME NGPWGYSSIY PLVKNHPKFT DLIPCLPFYF
     DcbF  .......... .......... .......... .......... ..........
Consensus  etl.h..... de.q..li.. n.pwgyssiy pl..n..... .lipcl.fy.

           651
     pmHS  E
     pglA  L
     DcbF  .
Consensus  .
```

| enzyme | activity |
|---|---|
| pmHAS $^{1-703}$ | HAS |
| pmCS $^{1-704}$ | CS |
| pm-EG | GlcUA-Tase |
| pm-FH | CS |
| pm-IK | GlcUA-Tase |
| pm-JL | HAS |

| enzyme | activity HAS | activity CS | activity GlcUA-Tase |
|---|---|---|---|
| pm-BD | - | + | + (boxed) |
| + | | | |
| pm-AC | + | - | + (boxed) |
| + | | | |
| pm-FH | - | + | + |
| pm-EG | - | - | + |
| Pm-JL | + | - | + |
| pm-IK | - | - | + |
| pmCHC | + | + | + |
| pmHCH | not expressed | | |

Model of *Pasteurella* Symthase Polymerization

Model of Reaction Synchronization

Model of Stoichiometric Control of Polymer Size

Lane: M 1 2 3 4 5

HA4 (ug) 4 3 2.4 2 1.5

10kb
5kb
1kb

| Sample No | *Mn* | *Mw* | polydispersity |
|---|---|---|---|
| #1 | 283400 | 283800 | 1.001 |
| #2 | 346400 | 347000 | 1.002 |
| #3 | 422200 | 423700 | 1.004 |
| #4 | 490000 | 493100 | 1.006 |
| #5 | 569700 | 575200 | 1.010 |

| | 1 | 2 | 3 | 4 | 5 | 6 | 7 | 8 | 9 | 10 | 11 | 12 |
|---|---|---|---|---|---|---|---|---|---|---|---|---|
| 572kDa HA (μg) | | | 5 | 10 | 15 | | | | | | | |
| 970kDa HA (μg) | | | | | | | 5 | 10 | 15 | | | |
| Genzyme HA (μg) | | | | | | | | | | 8 | | |

1 2 3 4 5 6 7 8 9 10 11 12

FIGURE 29.
Agarose Gels of Ladders and Migration
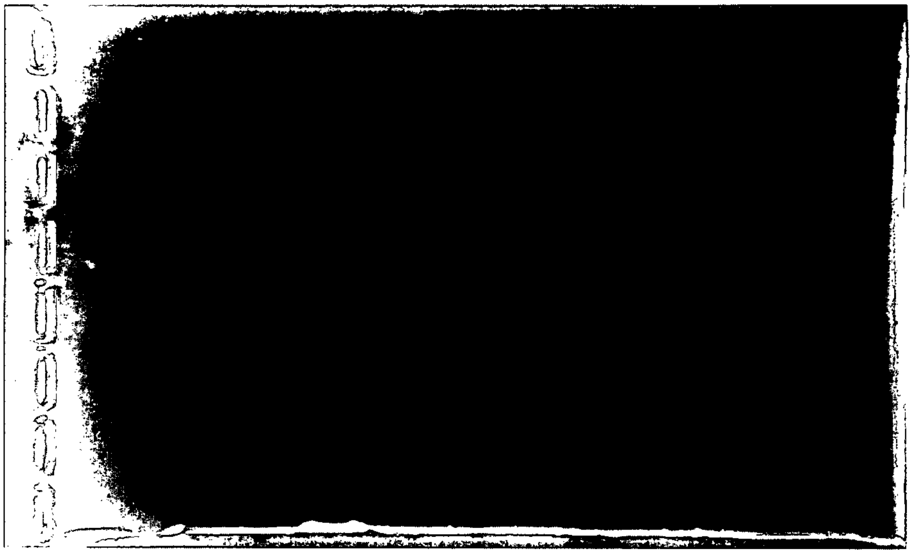
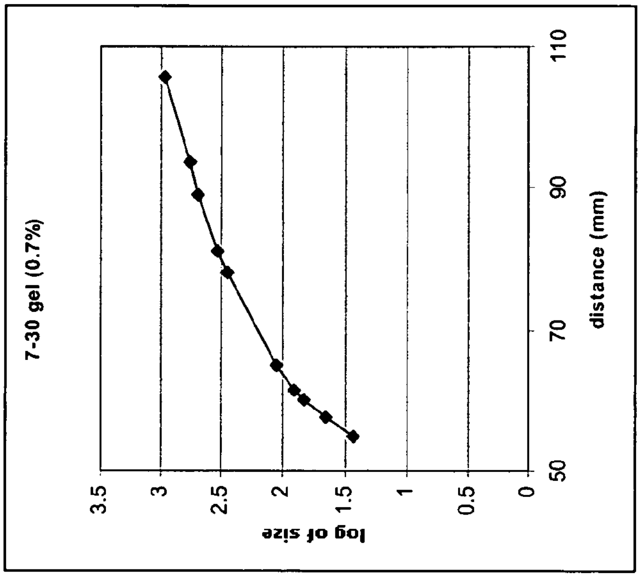

FIGURE 33
A.
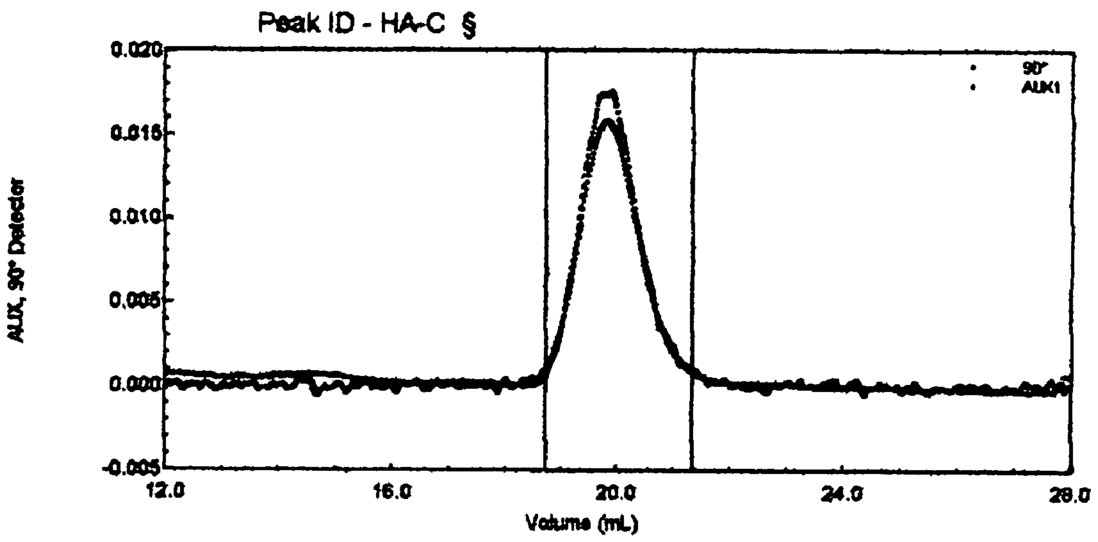
B.
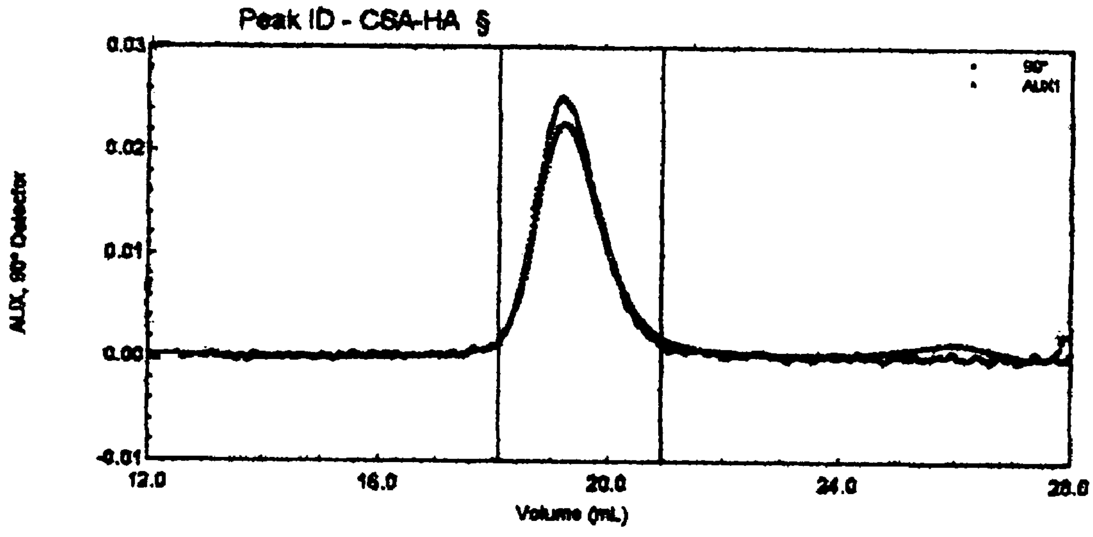

TARGETED GLYCOSAMINOGLYCAN POLYMERS BY POLYMER GRAFTING AND METHODS OF MAKING AND USING THE SAME

CROSS-REFERENCE TO RELATED APPLICATIONS

This application is a continuation of U.S. Ser. No. 10/642,248, filed Aug. 15, 2003; now U.S. Pat. No.7,223,571which claims benefit under 35 U.S.C. 119(e) of provisional applications U.S. Ser. No. 60/404,356, filed Aug. 16, 2002; U.S. Ser. No. 60/479,432, filed Jun. 18, 2003; and U.S. Ser. No. 60/491,362, filed Jul. 31, 2003.

Said U.S. Ser. No. 10/642,248 is also a continuation-in-part of U.S. Ser. No. 10/195,908, filed Jul. 15, 2002; now abandoned which is a continuation-in-part of U.S. Ser. No. 09/437,277, filed Nov. 10, 1999, now U.S. Pat. No. 6,444,447, issued Sep. 3, 2002; which claims benefit under 35 U.S.C. 119(e) of U.S. Provisional No. 60/107,929, filed Nov. 11, 1998.

Said U.S. Ser. No. 10/195,908 is also a continuation-in-part of U.S. Ser. No. 09/283,402, filed Apr. 1, 1999, now abandoned; which claims benefit under 35 U.S.C. 119(e) of U.S. Provisional No. 60/080,414, filed Apr. 2, 1998.

Said U.S. Ser. No. 10/195,908 is also a continuation-in-part of U.S. Ser. No. 09/842,484, filed Apr. 25, 2001; now abandoned which claims benefit under 35 U.S.C. 119(e) of U.S. Ser. No. 60/199,538, filed Apr. 25, 2000.

Said U.S. Ser. No. 10/195,908 is also a continuation-in-part of U.S. Ser. No. 10/142,143, filed May 8, 2002; now U.S. Pat. No. 7,307,159 which claims benefit under 35 U.S.C. 119(e) of U.S. Ser. No. 60/289,554, filed May 8, 2001.

The contents of each of the above-referenced patents and patent applications are hereby expressly incorporated herein in their entirety by reference.

STATEMENT REGARDING FEDERALLY SPONSORED RESEARCH OR DEVELOPMENT

This application was supported in part by National Research Grant C2163601 from the National Science Foundation. The United States Government may have rights in and to this application by virtue of this funding.

BACKGROUND

1. Field of the Invention

The present invention relates to methodology for the production of polymers, such as polysachharides or oligosaccharides, by a glycosaminoglycan synthase and, more particularly, polymer production utilizing glycosaminoglycan synthases from *Pasteurella multocida.*

Various glycosaminoglycans show potential as non-toxic therapeutic agents to modulate blood coagulation, cancer metastasis, or cell growth. Complex sugars cause biological effects by binding to target proteins including enzymes and receptors. Methodologies to synthesize many compounds, however, and to test for potency and selectivity are limiting steps in drug discovery. Moreover, glycosaminoglycans of different sizes can have dramatically different biological effects. As such, the presently claimed and disclosed invention also relates to a chemoenzymatic synthesis methodology to create both pure, chimeric, and hybrid polymers composed of hyaluronan, chondroitin, keratan, dermatan, heparin units, and combinations thereof (e.g., chimeric or hybrid polymers), wherein the pure, chimeric and hybrid polymers are substantially monodisperse in size.

2. Description of the Related Art

Polysaccharides are large carbohydrate molecules comprising from about 25 sugar units to thousands of sugar units. Oligosaccharides are smaller carbohydrate molecules comprising less than about 25 sugar units. Animals, plants, fungi and bacteria produce an enormous variety of polysaccharide structures that are involved in numerous important biological functions such as structural elements, energy storage, and cellular interaction mediation. Often, the polysaccharide s biological function is due to the interaction of the polysaccharide with proteins such as receptors and growth factors. The glycosaminoglycan class of polysaccharides and oligosaccharides, which includes heparin, chondroitin, dermatan, keratan, and hyaluronic acid, plays major roles in determining cellular behavior (e.g., migration, adhesion) as well as the rate of cell proliferation in mammals. These polysaccharides and oligosaccharides are, therefore, essential for the correct formation and maintenance of the organs of the human body.

Several species of pathogenic bacteria and fungi also take advantage of the polysaccharide s role in cellular communication. These pathogenic microbes form polysaccharide surface coatings or capsules that are identical or chemically similar to host molecules. For instance, Group A & C *Streptococcus* and Type A *Pasteurella multocida* produce authentic hyaluronic acid capsules, and other *Pasteurella multocida* (Type F and D) and pathogenic *Escherichia coli* (K4 and K5) are known to make capsules composed of polymers very similar to chondroitin and heparin. The pathogenic microbes form the polysaccharide surface coatings or capsules because such a coating is nonimmunogenic and protects the bacteria from host defenses, thereby providing the equivalent of molecular camouflage.

Enzymes alternatively called synthases, synthetases, or transferases, catalyze the polymerization of polysaccharides found in living organisms. Many of the known enzymes also polymerize activated sugar nucleotides. The most prevalent sugar donors contain UDP, but ADP, GDP, and CMP are also used depending on (1) the particular sugar to be transferred and (2) the organism. Many types of polysaccharides are found at, or outside of, the cell surface. Accordingly, most of the synthase activity is typically associated with either the plasma membrane on the cell periphery or the Golgi apparatus membranes that are involved in secretion. In general, these membrane-bound synthase proteins are difficult to manipulate by typical procedures, and only a few enzymes have been identified after biochemical purification.

A larger number of synthases have been cloned and sequenced at the nucleotide level using reverse genetic approaches in which the gene or the complementary DNA (cDNA) was obtained before the protein was characterized. Despite this sequence information, the molecular details concerning the three-dimensional native structures, the active sites, and the mechanisms of catalytic action of the polysaccharide synthases, in general, are very limited or absent. For example, the catalytic mechanism for glycogen synthesis is not yet known in detail even though the enzyme was discovered decades ago. In another example, it is still a matter of debate whether most of the enzymes that produce heteropolysaccharides utilize one UDP-sugar binding site to transfer both precursors, or alternatively, if there exists two dedicated regions for each substrate.

A wide variety of polysaccharides are commercially harvested from many sources, such as xanthan from bacteria, carrageenans from seaweed, and gums from trees. This substantial industry supplies thousands of tons of these raw materials for a multitude of consumer products ranging from ice cream desserts to skin cream cosmetics. Vertebrate tissues and pathogenic bacteria are the sources of more exotic polysaccharides utilized in the medical field e.g., as surgical aids, vaccines, and anticoagulants. For example, two glycosaminoglycan polysaccharides, heparin from pig intestinal mucosa and hyaluronic acid from rooster combs, are employed in several applications including clot prevention and eye surgery, respectively. Polysaccharides extracted from bacterial capsules (e.g., various *Streptococcus pneumoniae* strains) are utilized to vaccinate both children and adults against disease with varying levels of success. However, for the most part, one must use the existing structures found in the raw materials as obtained from nature. In many of the older industrial processes, chemical modification (e.g., hydrolysis, sulfation, deacetylation) is used to alter the structure and properties of the native polysaccharide. However, the synthetic control and the reproducibility of large-scale reactions are not always successful. Additionally, such polysaccharides are only available having a large molecular weight distribution, and oligosaccharides of the same repeat units are not available.

Some of the current methods for designing and constructing carbohydrate polymers in vitro utilize: (i) difficult, multistep sugar chemistry, or (ii) reactions driven by transferase enzymes involved in biosynthesis, or (iii) reactions harnessing carbohydrate degrading enzymes catalyzing transglycosylation or hydrolysis. The latter two methods are often restricted by the specificity and the properties of the available naturally occurring enzymes. Many of these enzymes are neither particularly abundant nor stable but are almost always expensive. Overall, the procedures currently employed yield polymers containing between 2 and about 12 sugars. Unfortunately, many of the physical and biological properties of polysaccharides do not become apparent until the polymer contains 25, 100, or even thousands of monomers.

As stated above, polysaccharides are the most abundant biomaterials on earth, yet many of the molecular details of their biosynthesis and function are not clear. Hyaluronic acid or HA is a linear polysaccharide of the glycosaminoglycan class and is composed of up to thousands of β(1,4)GlcUA-β(1,3)GlcNAc repeats. In vertebrates, HA is a major structural element of the extracellular matrix and plays roles in adhesion and recognition. HA has a high negative charge density and numerous hydroxyl groups, therefore, the molecule assumes an extended and hydrated conformation in solution. The viscoelastic properties of cartilage and synovial fluid are, in part, the result of the physical properties of the HA polysaccharide. HA also interacts with proteins such as CD44, RHAMM, and fibrinogen thereby influencing many natural processes such as angiogenesis, cancer, cell motility, wound healing, and cell adhesion.

There are numerous medical applications of HA. For example, HA has been widely used as a viscoelastic replacement for the vitreous humor of the eye in ophthalmic surgery during implantation of intraocular lenses in cataract patients. HA injection directly into joints is also used to alleviate pain associated with arthritis. Chemically cross-linked gels and films are also utilized to prevent deleterious adhesions after abdominal surgery. Other researchers using other methods have demonstrated that adsorbed HA coatings also improve the biocompatibility of medical devices such as catheters and sensors by reducing fouling and tissue abrasion.

HA is also made by certain microbes that cause disease in humans and animals. Some bacterial pathogens, namely Gram-negative *Pasteurella multocida* Type A and Gram-positive *Streptococcus* Group A and C, produce an extracellular HA capsule which protects the microbes from host defenses such as phagocytosis. Mutant bacteria that do not produce HA capsules are $10^2$- and $10^3$-fold less virulent in comparison to the encapsulated strains. Furthermore, the *Paramecium bursaria Chlorella* virus (PBCV-1) directs the algal host cells to produce a HA surface coating early in infection.

The various HA synthases (HAS), the enzymes that polymerize HA, utilize UDP-GlcUA and UDP-GlcNAc sugar nucleotide precursors in the presence of a divalent Mn, Mg, or Co ion to polymerize long chains of HA. The HA chains can be quite large ($n=10^2$ to $10^4$). In particular, the HASs are membrane proteins localized to the lipid bilayer at the cell surface. During HA biosynthesis, the HA polymer is transported across the bilayer into the extracellular space. In all HASs, a single species of polypeptide catalyzes the transfer of two distinct sugars. In contrast, the vast majority of other known glycosyltransferases transfer only one monosaccharide.

HasA (or spHAS) from Group A *Streptococcus pyogenes* was the first HA synthase to be described at the molecular level. The various vertebrate homologs (*Xenopus* DG42 or XlHAS1; murine and human HAS1, HAS2, and HAS3) and the viral enzyme, A98R, are quite similar at the amino acid level to certain regions of the HasA polypeptide chain (~30% identity overall) and were discovered only after the sequence of spHAS was disclosed in 1994. At least 7 short motifs (5-9 residues) interspersed throughout these Class I enzymes are identical or quite conserved. The evolutionary relationship among these HA synthases from such dissimilar sources is not clear at present. The enzymes are predicted to have a similar overall topology in the bilayer: membrane-associated regions at the amino and the carboxyl termini flank a large cytoplasmic central domain (~200 amino acids). The amino terminal region appears to contain two transmembrane segments, while the carboxyl terminal region appears to contain three to five membrane-associated or transmembrane segments, depending on the species. Very little of these HAS polypeptide chains are expected to be exposed to the outside of the cell.

With respect to the reaction pathway utilized by this group of enzymes, mixed findings have been reported from indirect experiments. The Group A streptococcal enzyme was reported to add sugars to the nonreducing terminus of the growing chain as determined by selective labeling and degradation studies. Using a similar approach, however, two laboratories working with the enzyme preparations from mammalian cells concluded that the new sugars were added to the reducing end of the nascent chain. In comparing these various studies, the analysis of the enzymatically-released sugars from the streptococcal system added more rigorous support for their interpretation. In another type of experiment, HA made in mammalian cells was reported to have a covalently attached UDP group as measured by an incorporation of low amounts of radioactivity derived from $^{32}P$-labeled UDP-sugar into an anionic polymer. This data implied that the last sugar was transferred to the reducing end of the polymer. Thus, it remains unclear if these rather similar HAS polypeptides from vertebrates and streptococci actually utilize different reaction pathways.

On the other hand, the Class II HAS, pmHAS, has many useful catalytic properties including the ability to elongate exogenous acceptors at the non-reducing end with HA chains. The homologous chondroitin synthase, pmCS, also is useful, but it adds chondroitin chains to the acceptor s non-reducing terminus.

To facilitate the development of biotechnological medical improvements, the present invention provides a method for the production of glycosaminoglycans of HA, chondroitin, and chimeric or hybrid molecules incorporating both HA and chondroitin, wherein the glycosaminoglycans are substantially monodisperse and thus have a defined size distribution.

The present invention also encompasses the use of one or more modified synthases that have the ability to produce non-natural polymers. An advantage of these mutant enzymes is that their altered specificity allows new useful groups or units to be added to the polymer.

The present invention also encompasses the methodology of polysaccharide or oligosaccharide polymer grafting, i.e., HA, heparosan or chondroitin, using either a hyaluronan synthase (pmHAS) or a chondroitin synthase (pmCS) or a heparin synthase (pmHS, also referred to as pmHS1, and PglA, also referred to as pmHS2), respectively, from various types of *P. multocida*. Modified versions of the pmHAS or pmCS or pmHS1, or pmHS2 enzymes (whether genetically or chemically modified) can also be utilized to graft on polysaccharides of various size and composition. Thus, the present invention results in (1) the targeting of specific, desirable size distributions or size ranges and (2) the synthesis of monodisperse (narrow size distribution) polymers.

SUMMARY OF THE INVENTION

A unique HA synthase, pmHAS, from the fowl cholera pathogen, Type A *P. multocida*, has been identified and cloned and is disclosed and claimed in co-pending U.S. Ser. No. 10/217,613, filed Aug. 12, 2002, and entitled DNA Encoding Hyaluronan Synthase From *Pasteurella Multocida* and Methods, the contents of which are hereby expressly incorporated herein in their entirety. Expression of this single, 972-residue protein allows *Escherichia coli* host cells to produce HA capsules in vivo; normally *E. coli* does not make HA. Extracts of recombinant *E. coli*, when supplied with the appropriate UDP-sugars, make HA in vitro. Thus, the pmHAS is an authentic HA synthase.

A unique chondroitin synthase, pmCS, from Type F *P. multocida*, has been identified and cloned and is disclosed and claimed in co-pending U.S. Ser. No. 09/842,484, filed Apr. 25, 2002, and entitled Chondroitin Synthase Gene and Methods of Making and Using Same, the contents of which are hereby expressly incorporated herein in their entirety. Expression of the catalytically active portion (residues 1-704) of this single, 965-residue protein allows *E. coli* host cells to produce an enzyme that will polymerize chondroitin chains. Laboratory strains of *E. coli* normally do not make chondroitin. Extracts of recombinant *E. coli*, when supplied with the appropriate UDP-sugars, make chondroitin in vitro. Thus, the pmCS is an authentic chondroitin synthase.

Two unique heparin synthases, PglA (now referred to as pmHS2) and pmHS (now referred to as pmHS1), from Type A, D, and F *P. multocida* and Type D *P. multocida*, respectively, have been identified and cloned and are disclosed and claimed in co-pending U.S. Ser. No. 10/142,143, filed May 8, 2002, and entitled Heparin/Heparosan Synthase from *P. multocida* and Methods of Making and Using Same, the contents of which are hereby expressly incorporated herein in their entirety. Expression of these single 652-residue and 617-residue, respectively, proteins allows *E. coli* host cells to produce enzymes that polymerize heparosan chains. Laboratory strains of *E. coli* normally do not make heparin. Extracts of recombinant *E. coli*, when supplied with the appropriate UDP-sugars, make heparin in vitro. Thus, the pmHS2 and the pmHS1 are authentic heparin synthases.

It has also been determined that the recombinant pmHAS, pmHS1, pmHS2, and pmCS synthases add sugars to the non-reducing end of a growing polymer chain. The correct monosaccharides are added sequentially in a stepwise fashion to the nascent chain or a suitable exogenous HA or chondroitin oligosaccharide acceptor molecule. The pmHAS sequence, however, is significantly different from the other known HA synthases. There appears to be only two short potential sequence motifs ([D/N]DGS[S/T]; DSD[D/T]Y) in common between pmHAS and the Group A HAS spHAS. Instead, a portion of the central region of the pmHAS is more homologous to the amino termini of other bacterial glycosyltransferases that produce different capsular polysaccharides or lipopolysaccharides. Furthermore, pmHAS is about twice as long as any other HAS enzyme.

When the pmHAS is given long elongation reaction times, HA polymers of at least 400 sugars long are formed. Unlike the Class I HA synthases, recombinant versions of pmHAS and pmCS produced in certain foreign hosts also have the ability to extend exogenously supplied HA or chondroitin oligosaccharides with long HA and chondroitin polymers in vitro, respectively. The recombinant pmHS1 and pmHS2 enzymes produced in a foreign host have the ability to extend HA, chondroitin, or heparin oligosaccharides with long heparosan chains in vitro. See e.g., U.S. Ser. No. 10/195,908, filed Jul. 15, 2002, the contents of which are expressly incorporated herein by reference in their entirety. If recombinant versions of pmHAS or pmCS or pmHS1 or pmHS2 are supplied with functional acceptor oligosaccharides, total HA, chondroitin and heparin biosynthesis is increased up to 50-fold over reactions without the exogenous oligosaccharide. The native versions of the pmHAS, pmCS, pmHS1, and PmHS2 enzymes isolated from *P. multocida* do not perform such elongation reactions with exogenous acceptor (or perform with very low efficiency) due to the presence of a nascent HA, chondroitin, or heparin chain in the natural host. The nature of the polymer retention mechanism of the pmHAS, pmCS, pmHS1, and PmHS2 polypeptide might be the causative factor for this activity: i.e. a HA- or chondroitin- or heparin-binding site may exist that holds onto the HA or chondroitin or heparin chain during polymerization. Small HA or chondroitin or heparin oligosaccharides supplied by the hand of man are also capable of occupying this site of the recombinant enzyme and thereafter be extended into longer polysaccharide chains.

Most membrane proteins are relatively difficult to study due to their insolubility in aqueous solution, and the native HASs, CSs, HSs, and PmHS2s are no exception. The HAS enzyme from Group A and C *Streptococcus* bacteria has been detergent-solubilized and purified in an active state in small quantities. Once isolated in a relatively pure state, the streptococcal enzyme has very limited stability. A soluble recombinant form of the HAS enzyme from *P. multocida* called $pmHAS^{1-703}$ comprises residues 1-703 of the 972 residues of the native pmHAS enzyme. $pmHAS^{1-703}$ can be mass-produced in *E. coli* and purified by chromatography. The $pmHAS^{1-703}$ enzyme retains the ability of the parent enzyme to add onto either a long HA polymer, a short HA primer, a long chondroitin polymer, a short chondroitin primer, a short chondroitin polymer, as well as other exogenous acceptors. The chondroitin chain may also be sulfated. Furthermore, the purified $pmHAS^{1-703}$ enzyme is stable in an optimized buffer for days on ice and for hours at normal reaction temperatures. One formulation of the optimal buffer consists of 1M ethylene glycol, 0.1-0.2 M ammonium sulfate, 50 mM Tris, pH 7.2, and protease inhibitors which also allow the stability and specificity at typical reaction conditions for sugar transfer. For the reaction UDP-sugars and divalent manganese (10-20 mM) are added. $pmHAS^{1-703}$ will also add a HA polymer onto plastic beads with an immobilized short HA primer or any other substrate capable of having an acceptor molecule or acceptor group thereon.

pmCS, pmHAS, pnHS, and PmHS2 possess two separate glycosyltransferase sites. Protein truncation studies demonstrated that residues 1-117 of pmHAS can be deleted without affecting catalytic activity; similar truncation of the homologous pmCS, pmHS1, and PmHS2 enzymes may also be preferred. The carboxyl-terminal boundary of the GlcUA-transferase of pmHAS resides within residues 686-703 and within residues 686-704 of pmCS. These sites each contain a DGS and DXD motif; all aspartate residues of these motifs are essential for HA synthase activity. D196, D247 and D249 mutants possessed only GlcUA-transferase activity while D477, D527 and D529 mutants possessed only GlcNAc-transferase activity. These results further confirm our previous assignment of the active sites within the synthase polypeptide. The WGGED sequence motif appears to be involved in GlcNAc-transferase activity because E396 mutants and D370 mutants possessed only GlcUA-transferase activity. The highly homologous (90% identical) pmCS can also be mutated in the same fashion. For example, mutating the homologous DXD motif in the GlcUA site of pmCS results in an enzyme with only GalNAc-transferase activity.

Type F *P. multocida* synthesizes an unsulfated chondroitin (β3N-acetylgalactosamine [GalNAc]-β4GlcUA) capsule. Domain swapping between pmHAS and the homologous chondroitin synthase, pmCS, has been performed. A chimeric or hybrid enzyme consisting of residues 1-427 of pmHAS and residues 421-704 of pmCS was an active HA synthase. On the other hand, the converse chimeric or hybrid enzyme consisting of residues 1-420 of pmCS and residues 428-703 of pmHAS was an active chondroitin synthase. Overall, these findings support the model of two independent transferase sites within a single polypeptide as well as further delineate the site boundaries of both enzymes. The hexosamine-transferase site resides in the N-terminal domain while the GlcUA-transferase site resides in the COOH-terminal domain of these GAG synthases.

The present invention encompasses methods of producing a variety of unique biocompatible molecules and coatings based on polysaccharides. Polysaccharides, especially those of the glycosaminoglycan class, serve numerous roles in the body as structural elements and signaling molecules. By grafting or making hybrid molecules composed of more than one polymer backbone, it is possible to meld distinct physical and biological properties into a single molecule without resorting to unnatural chemical reactions or residues. The present invention also incorporates the propensity of certain recombinant enzymes, when prepared in a virgin state, to utilize various acceptor molecules as the seed for further polymer growth: naturally occurring forms of the enzyme or existing living wild-type host organisms do not display this ability. Thus, the present invention results in (a) the production of hybrid oligosaccharides or polysaccharides and (b) the formation of polysaccharide coatings. Such hybrid polymers can serve as "molecular glue"—i.e., when two cell types or other biomaterials interact with each half of a hybrid molecule, then each of the two phases are bridged.

Such polysaccharide coatings are useful for integrating a foreign object within a surrounding tissue matrix. For example, a prosthetic device is more firmly attached to the body when the device is coated with a naturally adhesive polysaccharide. Additionally, the device's artificial components could be masked by the biocompatible coating to reduce immunoreactivity or inflammation. Another aspect of the present invention is the coating or grafting of GAGs onto various drug delivery matrices or bioadhesives or suitable medicaments to improve and/or alter delivery, half-life, persistence, targeting and/or toxicity.

Recombinant pmHAS, pmCS, pmHS1, and PmHS2 elongate exogenous functional oligosaccharide acceptors to form long or short polymers in vitro; thus far no other Class I HA synthase has displayed this capability. The directionality of synthesis was established definitively by testing the ability of pmHAS and pmCS and pmHS1 and PmHS2 to elongate defined oligosaccharide derivatives. The non-reducing end sugar addition allows the reducing end to be modified for other purposes; the addition of GAG chains to small molecules, polymers, or surfaces is thus readily performed. Analysis of the initial stages of synthesis demonstrated that pmHAS and pmCS and pmHS1 and PmHS2 added single monosaccharide units sequentially. Apparently the fidelity of the individual sugar transfer reactions is sufficient to generate the authentic repeating structure of HA or chondroitin or heparin. Therefore, simultaneous addition of disaccharide block units is not required as hypothesized in some recent models of polysaccharide biosynthesis. pmHAS and pmCS and pmHS1 and PmHS2 appear distinct from most other known HA and chondroitin and heparin synthases based on differences in sequence, topology in the membrane, and/or putative reaction mechanism.

As mentioned previously, pmHAS, the 972-residue membrane-associated hyaluronan synthase, catalyzes the transfer of both GlcNAc and GlcUA to form an HA polymer. In order to define the catalytic and membrane-associated domains, pmHAS and pmCS mutants have been analyzed. $pmHAS^{1-703}$ is a soluble, active HA synthase suggesting that the carboxyl-terminus is involved in membrane association of the native enzyme. $pmHAS^{1-650}$ is inactive as a HA synthase, but retains GlcNAc-transferase activity. Within the pmHAS sequence, there is a duplicated domain containing a short motif, DGS or Asp-Gly-Ser, that is conserved among many glycosyltransferases. Changing this aspartate in either domain to asparagine, glutamate, or lysine reduced the HA synthase activity to low levels. The mutants substituted at residue 196 possessed GlcUA-transferase activity while those substituted at residue 477 possessed GlcNAc-transferase activity. The Michaelis constants of the functional transferase activity of the various mutants, a measure of the apparent affinity of the enzymes for the precursors, were similar to wild-type values. Furthermore, mixing D196N and D477K mutant proteins in the same reaction allowed HA polymerization at levels similar to the wild-type enzyme. These results provide the first direct evidence that the synthase polypeptide utilizes two separate glycosyltransferase sites. Likewise, pmCS mutants were made and tested having the same functionality and sequence similarity to the mutants created for pmHAS.

*Pasteurella multocida* Type F, the minor fowl cholera pathogen, produces an extracellular polysaccharide capsule that is a putative virulence factor. As outlined in U.S. Ser. No. 09/842,484, filed Apr. 25, 2002, and entitled Chondroitin Synthase Gene and Methods of Making and Using Same, the contents of which are hereby expressly incorporated herein in their entirety, the capsule of Pasteurella multocida Type F was removed by treating microbes with chondroitin AC lyase. It was found by acid hydrolysis that the polysaccharide contained galactosamine and glucuronic acid. A Type F polysaccharide synthase was molecularly cloned and its enzymatic activity was characterized. The 965-residue enzyme, called pmCS, is 90% identical at the nucleotide and the amino acid level to the hyaluronan synthase, pmHAS, from *P. multocida*

Type A. A recombinant *Escherichia coli*-derived, truncated, soluble version of pmCS (residues 1-704) was shown to catalyze the repetitive addition of sugars from UDP-GalNAc and UDP-GlcUA to chondroitin oligosaccharide acceptors in vitro. Other structurally related sugar nucleotide precursors did not substitute in the elongation reaction. Polymer molecules composed of ~$10^3$ sugar residues were produced as measured by gel filtration chromatography. The polysaccharide synthesized in vitro was sensitive to the action of chondroitin AC lyase but resistant to the action of hyaluronan lyase. This was the first report identifying a glycosyltransferase that forms a polysaccharide composed of chondroitin disaccharide repeats, $[\beta(1,4)GlcUA\text{-}\beta(1,3)GalNAc]_n$. In analogy to known hyaluronan synthases, a single polypeptide species, pmCS, possesses both transferase activities. The heparin synthases, pmHS1 and PmHS2, from *P. multocida*, also are a single polypeptide specie that possess both transferase activities to catalyze heparin/heparosan.

Promising initial target polymers for a variety of therpaeutic uses are glycosaminoglycan chains composed of about 5 kDa to about 4 MDa. The two current competing state-of-the-art techniques for creating the desired smaller size glycosaminoglycan [GAG] polymers are extremely limited and will not allow the medical potential of the sugars to be achieved. Small GAG molecules are presently made either by: (1) partially depolymerizing costly large polymers with degradative enzymes or with chemical means (e.g., heat, acid, sonication), or (2) highly demanding organic chemistry-based carbohydrate synthesis. The former method is difficult to control, inefficient, costly, and is in a relatively stagnant development stage. For example, the enzyme wants to degrade the polymer to the 2 or 4 sugar end stage product, but this sugar is inactive for many therapeutic treatments. The use of acid hydrolysis also removes a fraction of the acetyl groups from the GlcNAc or GalNAc groups thereby introducing a positive charge into an otherwise anionic molecule. The latter method, chemical synthesis, involves steps with low to moderate repetitive yield and has never been reported for a HA-oligosaccharide longer than 6 to 8 sugars in length. Also racemization (e.g., production of the wrong isomer) during chemical synthesis creates inactive or harmful molecules; the inclusion of the wrong isomer in a therapeutic preparation in the past has had tragic consequences as evidenced by the birth defects spawned by the drug Thalidomide. As sugars contain many similar reactive hydroxyl groups, in order to effect proper coupling between two sugars in a chemical synthesis, most hydroxyl groups must be blocked or protected. At the conclusion of the reaction, all of the protecting groups must be removed, but this process is not perfect; as a result, a fraction of the product molecules retain these unnatural moieties. The issues of racemization and side-products from chemical synthesis are not problems for the high-fidelity enzyme catalysts of the presently claimed and disclosed invention.

The partial depolymerization method only yields fragments of the original GAG polymer and is essentially useless for creating novel sugars beyond simple derivatizations (e.g., esterifying some fraction of GlcUA residues in an indiscriminate fashion). Chemical synthesis may suffice in theory to make novel sugars, but the strategy needs to be customized for adding a new sugar, plus the problems with side-reactions/isomerization and the ultimate oligosaccharide size still pose the same trouble as described earlier. Another distinct method using the degradative enzymes to generate small molecules by running in reverse on mixtures of two polymers (e.g., HA and chondroitin) has some potential for novel GAG polysaccharide synthesis. See e.g. J Biochem (Tokyo). April 2000; 127(4):695-702, Chimeric glycosaminoglycan oligosaccharides synthesized by enzymatic reconstruction and their use in substrate specificity determination of *Streptococcus hyaluronidase*, Takagaki K, Munakata H, Majima M, Kakizaki I, Endo M.; and J Biol Chem. Feb. 24, 1995;270(8):3741-7, Enzymic reconstruction of glycosaminoglycan oligosaccharide chains using the transglycosylation reaction of bovine testicular hyaluronidase, Saitoh H, Takagaki K, Majima M, Nakamura T, Matsuki A, Kasai M, Narita H, Endo M. However, this technology can make only a very limited scope of products with a block pattern (no single or specifically spaced substitutions possible) using slow reactions that cannot easily be customized or controlled. No other technology is as versatile as the presently claimed and disclosed biocatalytic system with respect to flexibility of final polysaccharide structure in the about 5 kDa to about 4 MDa size range. Novel, designer molecules can be prepared with minimal re-tooling by use of the appropriate hyaluronic acid or chondroitin or heparin enzyme catalysts and substrates.

The size of the HA polysaccharide dictates its biological effect in many cellular and tissue systems based on many reports in the literature. However, no source of very defined, uniform HA polymers with sizes greater than 5 kDa is currently available. This situation is complicated by the observation that long and short HA polymers appear to have antagonistic or inverse effects on some biological systems. Therefore, HA preparations containing a mixture of both size populations may yield contradictory or paradoxical results. Thus, one of the objects of the present invention is to provide a method to produce HA with very narrow, substantially monodisperse size distributions that overcomes the disadvantages and defects of the prior art.

The methods for enzymatically producing defined glycosaminoglycan polymers of the present invention involves providing at least one functional acceptor and at least one recombinant glycosaminoglycan transferase capable of elongating the functional acceptor in a controlled or repetitive fashion to form extended glycosaminoglycan-like molecules. At least one of UDP-GlcUA, UDP-GalUA UDP-GlcNAc, UDP-Glc, UDP-GalNAc, UDP-GlcN, UDP-GalN and a structural variant or derivative thereof is added in a stoichiometric ratio to the functional acceptor to provide glycosaminoglycan polymers that are substantially monodisperse in size.

The term "substantially monodisperse in size" as used herein will be understood to refer to defined glycoasminoglycan polymers that have a very narrow size distribution. For example, substantially monodisperse glycosaminoglycan polymers having a molecular weight in a range of from about 3.5 kDa to about 0.5 MDa will have a polydispersity value (i.e., Mw/Mn, where Mw is the average molecular weight and Mn is the number average molecular weight) in a range of from about 1.0 to about 1.1, and preferably in a range from about 1.0 to about 1.05. In yet another example, substantially monodisperse glycosaminoglycan polymers having a molecular weight in a range of from about 0.5 MDa to about 4.5 MDa will have a polydispersity value in a range of from about 1.0 to about 1.5, and preferably in a range from about 1.0 to about 1.2.

The functional acceptor utilized in accordance with the present invention will have at least two sugar units of uronic acid and/or hexosamine, wherein the uronic acid may be GlcUA, IdoUA or GalUA, and the hexosamine may be GlcNAc, GalNAc, GlcN or GalN. In one embodiment, the functional acceptor may be an HA oligosaccharide of about 3 sugar units to about 4.2 kDa, or an HA polymer having a mass of about 3.5 kDa to about 2 MDa. In another embodiment, the functional acceptor may be a chondroitin oligosaccharide or polymer, a chondroitin sulfate oligosaccharide or polymer, or a heparosan-like polymer. In yet another embodiment, the functional acceptor may be an extended acceptor such as HA chains, chondroitin chains, heparosan chains, mixed glycosaminoglycan chains, analog containing chains or any combination thereof.

Any recombinant glycosaminoglycan transferase described or incorporated by reference herein may be utilized in the methods of the present invention. For example, the recombinant glycosaminoglycan transferase utilized in accordance with the present invention may be a recombinant hyaluronan synthase, a recombinant chondroitin synthase, a recombinant heparosan synthase, or any active fragment or mutant thereof. The recombinant glycosaminglycan transferase may be capable of adding only one UDP-sugar described herein above or may be capable of adding two or more UDP-sugars described herein above.

BRIEF DESCRIPTION OF THE SEVERAL VIEWS OF THE DRAWINGS

FIG. 12 is a sequence alignment of pmCS and pmHAS. The two *Pasteurella* GAG synthases are highly homologous. Identical residues are denoted with the hyphen. The numbering scheme corresponds to the slightly longer pmHAS sequence. The putative A1 (residues 161-267) and A2 (residues 443-547) domains correspond to regions important for hexosamine transferase or for glucuronic acid transferase activity, respectively (33). Most sequence differences are found in the amino-terminal half of the polypeptides.

FIG. 15(A-D) graphically depicts the alignment of the pmHS1 (two clones: A2, B10) with PmHS2, KfiA, KfiC, and DcbF. pmHS1 is shown in various forms: HSA1 and HSA2 are the two putative domains of pmHS1; pORF=partial open reading frame which was obtained before complete sequence determined; recon=reconstructed open reading frame with sequence from multiple sources.

FIG. 29 is an electrophoresis gel that illustrates the migration of a ladder constructed of HA of defined size distribution for use as a standard.

FIG. 33. Size exclusion (or gel filtration) chromatography analysis coupled with multi-angle laser light scattering detection confirms the monodisperse nature of polymers created by the present invention. In A, HA (starting MW 81 kDa) extended with chondroitin chains using pmCS (same sample used in FIG. 32 lane #7, overnight [O/N] extension) was analyzed; the material was 280,000 Mw and polydispersity (Mw/Mn) was 1.003±0.024. Chondroitin sulfate extended with HA chains using pmHAS (same sample used in FIG. 31, lane #23) was analyzed and shown in the bottom chromatogram; the material was 427,000 Mw and polydispersity (Mw/Mn) was 1.006±0.024.

DETAILED DESCRIPTION OF THE INVENTION

Figure 1:
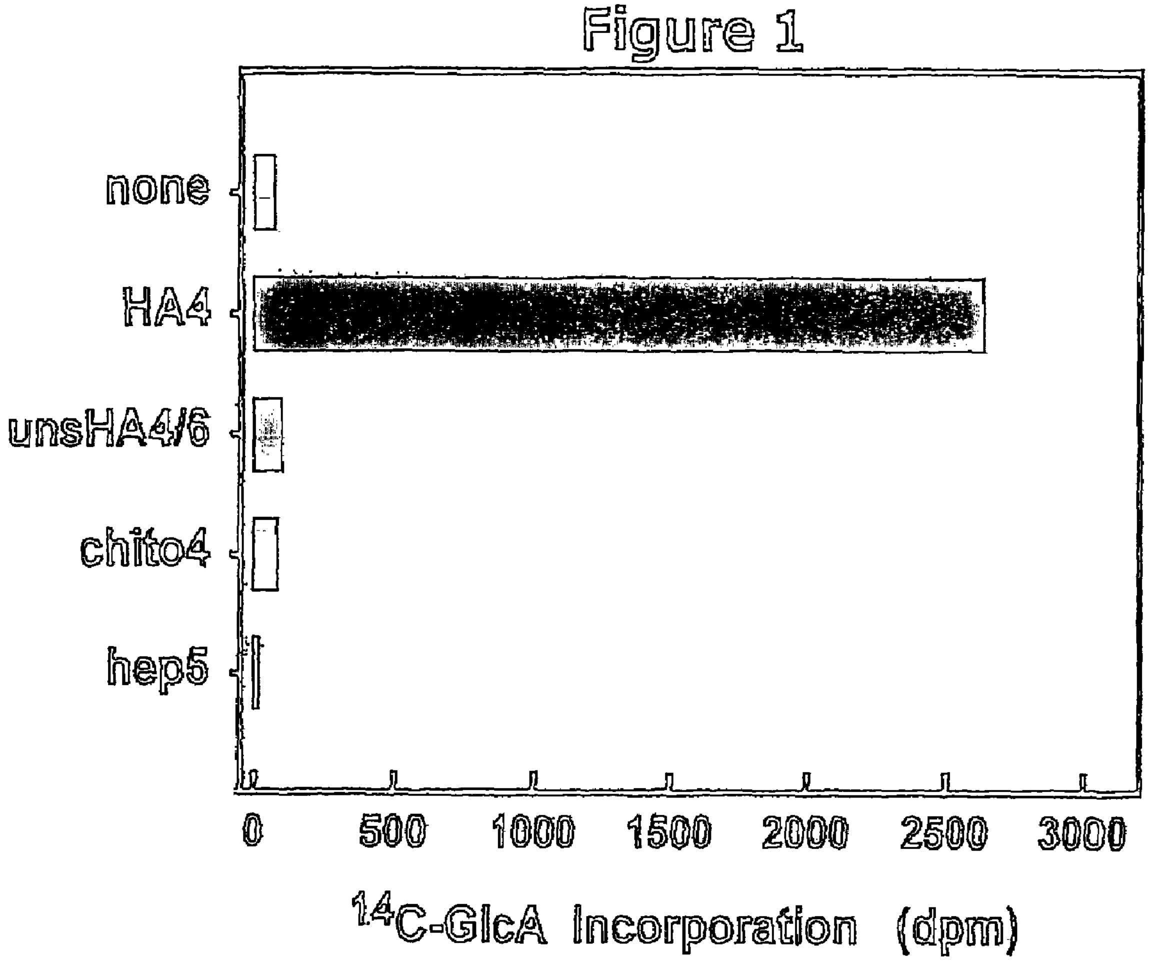
FIG. 1 is a graphical representation showing that an HA tetramer stimulates pmHAS polymerization.

Before explaining at least one embodiment of the invention in detail, it is to be understood that the invention is not limited in its application to the details of construction and the arrangements of the components set forth in the following description or illustrated in the drawings. The invention is capable of other embodiments or of being practiced or carried out in various ways. Also, it is to be understood that the phraseology and terminology employed herein is for purpose of description and should not be regarded as limiting.

Glycosaminoglycans (GAGs) are linear polysaccharides composed of repeating disaccharide units containing a derivative of an amino sugar (either glucosamine or galactosamine). Hyaluronan [HA], chondroitin, and heparan sulfate/heparin contain a uronic acid as the other component of the disaccharide repeat while keratan contains a galactose. The GAGs are summarized in Table I.

TABLE I

| | | Post-Polymerization Modifications | |
|---|---|---|---|
| Polymer | Disaccharide Repeat | Vertebrates | Bacteria |
| Hyaluronan | β3GlcNAc β4GlcUA | none | none |
| Chondroitin | β3GalNAc β4GlcUA | O-sulfated/epimerized | none |
| Heparin/heparan | α4GlcNAc β4GlcUA | O,N-sulfated/epimerized | none |
| Keratan | β4GlcNAc β3Gal | O-sulfated | not reported |

Vertebrates may contain all four types of GAGs, but the polysaccharide chain is often further modified after sugar polymerization. One or more modifications including O-sulfation of certain hydroxyls, deacetylation and subsequent N-sulfation, or epimerization of glucuronic acid to iduronic acid are found in most GAGs except HA. An amazing variety of distinct structures have been reported for chondroitin sulfate and heparan sulfate/heparin even within a single polymer chain. A few clever pathogenic microbes also produce unmodified GAG chains; the bacteria use extracellular polysaccharide coatings as molecular camouflage to avoid host defenses. The chondroitin and heparan sulfate/heparin chains in vertebrates are initially synthesized by elongation of a xylose-containing linkage tetrasaccharide attached to a variety of proteins. Keratan is either O-linked or N-linked to certain proteins depending on the particular molecule. HA and all of the known bacterial GAGs are not part of the classification of proteins known as glycoproteins. All GAGs except HA are found covalently linked to a core protein, and such combination is referred to as a proteoglycan. Glycoproteins are usually much smaller than proteoglycans and only contain from 1-60% carbohydrate by weight in the form of numerous relatively short, branched oligosaccharide chains, whereas a proteoglycan can contain as much as 95% carbohydrate by weight. The core protein in a proteoglycan is also usually a glycoprotein, therefore usually contains other oligosaccharide chains besides the GAGs.

GAGs and their derivatives are currently used in the medical field as ophthalmic and viscoelastic supplements, adhesion surgical aids to prevent post-operative adhesions, catheter and device coatings, and anticoagulants. Other current or promising future applications include anti-cancer medications, tissue engineering matrices, immune and neural cell modulators, and drug targeting agents.

Complex carbohydrates, such as GAGs, are information rich molecules. A major purpose of the sugars that make up GAGs is to allow communication between cells and extracellular components of multicellular organisms. Typically, certain proteins bind to particular sugar chains in a very selective fashion. A protein may simply adhere to the sugar, but quite often the protein s intrinsic activity may be altered and/or the protein transmits a signal to the cell to modulate its behavior. For example, in the blood coagulation cascade, heparin binding to inhibitory proteins helps shuts down the clotting response. In another case, HA binds to cells via the CD44 receptor that stimulates the cells to migrate and to proliferate. Even though long GAG polymers (i.e., >$10^2$ Da) are found naturally in the body, typically the protein's binding site interacts with a stretch of 4 to 10 monosaccharides. Therefore, oligosaccharides can be used to either (a) substitute for the polymer, or (b) to inhibit the polymer s action depending on the particular system.

HA polysaccharide plays structural roles in the eye, skin, and joint synovium. Large HA polymers (~$10^6$ Da) also stimulate cell motility and proliferation. On the other hand, shorter HA polymers (~$10^4$ Da) often have the opposite effect. HA-oligosaccharides composed of 10 to 14 sugars [$HA_{10-14}$] have promise for inhibition of cancer cell growth and metastasis. In an in vivo assay, mice injected with various invasive and virulent tumor cell lines (melanoma, glioma, carcinomas from lung, breast and ovary) develop a number of large tumors and die within weeks. Treatment with HA oligosaccharides greatly reduced the number and the size of tumors. Metastasis, the escape of cancer cells throughout the body, is one of the biggest fears of both the ailing patient and the physician. HA or HA-like oligosaccharides appear to serve as a supplemental treatment to inhibit cancer growth and metatasis.

The preliminary mode of action of the HA-oligosaccharide sugars is thought to be mediated by binding or interacting with one of several important HA-binding proteins (probably CD44 or RHAM) in the mammalian body. One proposed scenario for the anticancer action of HA-oligosaccharides is that multiple CD44 protein molecules in a cancer cell can bind simultaneously to a long HA polymer. This multivalent HA binding causes CD44 activation (perhaps mediated by dimerization or a receptor patching event) that triggers cancer cell activation and migration. However, if the cancer cell is flooded with small HA-oligosaccharides, then each CD44 molecule individually binds a different HA molecule in a monovalent manner such that no dimerization/patching event occurs. Thus no activation signal is transmitted to the cell. Currently, it is believed that the optimal HA-sugar size is 10 to 14 sugars. Although this size may be based more upon the size of HA currently available for testing rather than biological functionality—i.e., now that HA molecules and HA-like derivatives <10 sugars are available according to the methodologies of the present invention, the optimal HA size or oligosaccharide composition may be found to be different.

It has also been shown that treatment with certain anti-CD44 antibodies or CD44-antisense nucleic acid prevents the growth and metastasis of cancer cells in a fashion similar to HA-oligosaccharides; in comparison to the sugars, however, these protein-based and nucleic acid-based reagents are somewhat difficult to deliver in the body and/or may have long-term negative effects. A very desirable attribute of HA-oligosaccharides for therapeutics is that these sugar molecules are natural by-products that can occur in small amounts in the healthy human body during the degradation of HA polymer; no untoward innate toxicity, antigenicity, or allergenic concerns are obvious.

Other emerging areas for the potential therapeutic use of HA oligosaccharides are the stimulation of blood vessel formation and the stimulation of dendritic cell maturation. Enhancement of wound-healing and resupplying cardiac oxygenation may be additional applications that harness the ability of HA oligosaccharides to cause endothelial cells to form tubes and sprout new vessels. Dendritic cells possess adjuvant activity in stimulating specific CD4 and CD8 T cell responses. Therefore, dendritic cells are targets in vaccine development strategies for the prevention and treatment of infections, allograft reactions, allergic and autoimmune diseases, and cancer.

Heparin interacts with many proteins in the body, but two extremely interesting classes are coagulation cascade proteins and growth factors. Antithrombin III [ATIII] and certain other hemostasis proteins are 100,000-fold more potent inhibitors of blood clotting when complexed with heparin. Indeed, heparin is so potent it must be used in a hospital setting and requires careful monitoring in order to avoid hemorrhage. Newer, processed lower molecular weight forms of heparin are safer, but this material is still a complex mixture. It has been shown that a particular pentasaccharide (5 sugars long) found in heparin is responsible for the ATIII-anticoagulant effect. But since heparin is a very heterogeneous polymer, it is difficult to isolate the pentasaccharide (5 sugars long) in a pure state. The pentasaccharide can also be prepared in a conventional chemical synthesis involving ~50 to 60 steps. However, altering the synthesis or preparing an assortment of analogs in parallel is not always feasible—either chemically or financially.

Many growth factors, including VEGF (vascular endothelial growth factor), HBEGF (heparin-binding epidermal growth factor), and FGF (fibroblast growth factor), bind to cells by interacting simultaneously with the growth factor receptor and a cell-surface heparin proteoglycan; without the heparin moiety, the potency of the growth factor plummets. Cell proliferation is modulated in part by heparin; therefore, diseases such as cancer and atherosclerosis are potential targets. Abnormal or unwanted proliferation would be curtailed if the growth factor was prevented from stimulating target disease-state cells by interacting with a heparin-like oligosaccharide analog instead of a surface-bound receptor. Alternatively, in certain cases, the heparin oligosaccharides alone have been shown to have stimulatory effects.

Chondroitin is the most abundant GAG in the human body, but all of its specific biological roles are not yet clear. Phenomenon such as neural cell outgrowth appears to be modulated by chondroitin. Both stimulatory and inhibitory effects have been noted depending on the chondroitin form and the cell type. Therefore, chondroitin or similar molecules are of utility in re-wiring synaptic connections after degenerative diseases (e.g., Alzheimer's) or paralytic trauma. The epimerized form of chondroitin (GlcUA converted to the C5 isomer, iduronic acid or IdoUA), dermatan, selectively inhibits certain coagulation proteins such as heparin cofactor II. By modulating this protein in the coagulation pathway instead of ATIII, dermatan appears to allow for a larger safety margin than heparin treatment for reduction of thrombi or clots that provoke strokes and heart attacks.

Many details of GAG/protein interactions are not yet clear due to (a) the heterogeneity of GAGs (in part due to their biosynthesis pathway), and (b) the difficulty in analyzing long polysaccharides and membrane receptor proteins at the molecular level. Fortunately, many short oligosaccharides have biological activities that serve to assist research pursuits as well as to treat disease in the near future. Conventional chemical synthesis of short GAG oligosaccharides is possible, but the list of roadblocks includes: (i) difficult multistep syntheses that employ toxic catalysts, (ii) very low yield or high failure rates with products longer than ~6 monosaccharides, (iii) imperfect control of stereoselectivity (e.g., wrong anomer) and regioselectivity (e.g., wrong attachment site), and (iv) the possibility for residual protection groups (non-carbohydrate moieties) in the final product.

Chemoenzymatic synthesis, however, employing catalytic glycosyltransferases with exquisite control and superb efficiency is currently being developed by several universities and companies. A major obstacle is the production of useful catalyst because the vast majority of glycosyltransferases are rare membrane proteins that are not particularly robust. In the copending applications referenced herein and in the presently claimed and disclosed invention, several practical catalysts from Pasteurella bacteria that allow for the synthesis of the three most important human GAGs (i.e., the three known acidic GAGs) are described and enabled (e.g. HA, chondroitin, and heparin).

All of the known HA, chondroitin and heparan sulfate/heparin glycosyltransferase enzymes that synthesize the alternating sugar repeat backbones in microbes and in vertebrates utilize UDP-sugar precursors and divalent metal cofactors (e.g., magnesium, cobalt, and/or manganese ion) near neutral pH according to the overall reaction:

$$nUDP\text{-}GlcUA+nUDP\text{-}HexNAc\ \mathbf{2}nUDP+[GlcUA\text{-}HexNAc]_n$$

where HexNAc=GlcNAc or GalNAc. Depending on the specific GAG and the particular organism or tissue examined, and the degree of polymerization, n, ranges from about 25 to about 10,000. If the GAG is polymerized by a single polypeptide, the enzyme is called a synthase or co-polymerase.

As outlined in and incorporated by reference in the "Cross-Reference" section of this application hereinabove, the present applicant(s) have discovered four new dual-action enzyme catalysts from distinct isolates of the Gram-negative bacterium *Pasteurella multocida* using various molecular biology strategies. *P. multocida* infects fowl, swine, and cattle as well as many wildlife species. The enzymes are: a HA synthase, or (pmHAS); a chondroitin synthase, or (pmCS); and two heparosan synthases, or (pmHS1 and PmHS2). To date, no keratan synthase from any source has been identified or reported in the literature.

In U.S. Ser. No. 10/217,613, filed Aug. 12, 2002, the contents of which are hereby expressly incorporated herein by reference in their entirety, the molecular directionality of pmHAS synthesis was disclosed and claimed. pmHAS is unique in comparison to all other existing HA synthases of *Streptococcus* bacteria, humans and an algal virus. Specifically, recombinant pmHAS can elongate exogeneously-supplied short HA chains (e.g., 24 sugars) into longer HA chains (e.g., 3 to 150 sugars). The pmHAS synthase has been shown to add monosaccharides one at a time in a step-wise fashion to the growing chain. The pmHAS enzyme's exquisite sugar transfer specificity results in the repeating sugar backbone of the GAG chain. The pmCS enzyme, which is about 90% identical at the amino acid level to pmHAS, performs the same synthesis reactions but transfers GalNAc instead of GlcNAc. The pmCS enzyme was described and enabled in U.S. Ser. No. 09/842,484. The pmHS1 and PmHS2 enzymes are not very similar at the amino acid level to pmHAS, but perform the similar synthesis reactions; the composition of sugars is identical but the linkages differ because heparosan is Beta4GlcUA-alpha4GlcNAc. The pmHS1 and PmHS2 enzymes were described and enabled in copending U.S. Ser. No. 10/142,143.

The explanation for the step-wise addition of sugars to the GAG chain during biosynthesis was determined by analyzing mutants of the pmHAS enzyme. pmHAS possesses two independent catalytic sites in one polypeptide. Mutants were created that transferred only GlcUA, and distinct mutants were also created that transferred only GlcNAc. These mutants cannot polymerize HA chains individually, but if the two types of mutants are mixed together in the same reaction with an acceptor molecule, then polymerization was rescued. The chondroitin synthase, pmCS, has a similar sequence and similar two-domain structure. The heparosan synthases, pmHS1 and PmHS2, also contain regions for the two active sites. Single action mutants have also been created for the chondroitin synthase, pmCS, and are described hereinafter in detail.

The naturally occurring *Pasteurella* GAG synthases are very specific glycosyltransferases with respect to the sugar transfer reaction; only the correct monosaccharide from the authentic UDP-sugar is added onto acceptors. The epimers or other closely structurally related precursor molecules (e.g., UDP-glucose) are not utilized. The GAG synthases do, however, utilize certain heterologous acceptor sugars. For example, pmHAS will elongate short chondroitin acceptors with long HA chains. pmHS1 will also add long heparosan chains onto HA acceptor oligosaccharides as well as heparin oligosaccharides (see hereinbelow). Therefore, the presently claimed and disclosed invention encompasses a wide range of hybrid or chimeric GAG oligosaccharides prepared utilizing these *P. multocida* GAG catalysts.

As used herein, the term "nucleic acid segment" and "DNA segment" are used interchangeably and refer to a DNA molecule which has been isolated free of total genomic DNA of a particular species. Therefore, a "purified" DNA or nucleic acid segment as used herein, refers to a DNA segment which contains a Hyaluronate Synthase ("HAS") coding sequence or Chondroitin Synthase (CS) coding sequence or Heparin/Heparosan Synthase (HS) coding sequence yet is isolated away from, or purified free from, unrelated genomic DNA, for example, total *Pasteurella multocida*. Included within the term "DNA segment", are DNA segments and smaller fragments of such segments, and also recombinant vectors, including, for example, plasmids, cosmids, phage, viruses, and the like.

Similarly, a DNA segment comprising an isolated or purified pmHAS or pmCS or pmHS1 or PmHS2 gene refers to a DNA segment including HAS or CS or HS coding sequences isolated substantially away from other naturally occurring genes or protein encoding sequences. In this respect, the term "gene" is used for simplicity to refer to a functional protein-, polypeptide- or peptide-encoding unit. As will be understood by those in the art, this functional term includes genomic sequences, cDNA sequences or combinations thereof. "Isolated substantially away from other coding sequences" means that the gene of interest, in this case pmHAS or pmCS or pmHS1 or PmHS2 forms the significant part of the coding region of the DNA segment, and that the DNA segment does not contain other non-relevant large portions of naturally-occurring coding DNA, such as large chromosomal fragments or other functional genes or DNA coding regions. Of course, this refers to the DNA segment as originally isolated, and does not exclude genes or coding regions later added to, or intentionally left in, the segment by the hand of man.

Due to certain advantages associated with the use of prokaryotic sources, one will likely realize the most advantages upon isolation of the HAS or CS or HS gene from the prokaryote *P. multocida*. One such advantage is that, typically, eukaryotic genes may require significant post-transcriptional modifications that can only be achieved in a eukaryotic host. This will tend to limit the applicability of any eukaryotic HAS or CS or HS gene that is obtained. Moreover, those of ordinary skill in the art will likely realize additional advantages in terms of time and ease of genetic manipulation where a prokaryotic enzyme gene is sought to be employed. These additional advantages include (a) the ease of isolation of a prokaryotic gene because of the relatively small size of the genome and, therefore, the reduced amount of screening of the corresponding genomic library, and (b) the ease of manipulation because the overall size of the coding region of a prokaryotic gene is significantly smaller due to the absence of introns. Furthermore, if the product of the pmHAS or pmCS or pmHS1 or PmHS2 gene (i.e., the enzyme) requires posttranslational modifications, these would best be achieved in a similar prokaryotic cellular environment (host) from which the gene was derived.

Preferably, DNA sequences in accordance with the present invention will further include genetic control regions which allow the expression of the sequence in a selected recombinant host. The genetic control region may be native to the cell from which the gene was isolated, or may be native to the recombinant host cell, or may be an exaggerous segment that is compatible with and recognized by the transcriptional machinery of the selected recbominant host cell. Of course, the nature of the control region employed will generally vary depending on the particular use (e.g., cloning host) envisioned.

In particular embodiments, the invention concerns isolated DNA segments and recombinant vectors incorporating DNA sequences which encode a pmHAS or pmCS or pmHS1 or PmHS2 gene, that includes within its amino acid sequence an amino acid sequence in accordance with SEQ ID NO:2, 4, 6, 8, 9, or 70, respectively. Moreover, in other particular embodiments, the invention concerns isolated DNA segments and recombinant vectors incorporating DNA sequences which encode a gene that includes within its nucleic acid sequence an amino acid sequence encoding HAS or CS or HS peptides or peptide fragment thereof, and in particular to a HAS or CS or HS peptide or peptide fragment thereof, corresponding to *Pasteurella multocida* HAS or CS or HS. For example, where the DNA segment or vector encodes a full length HAS or CS or HS protein, or is intended for use in expressing the HAS or CS or HS protein, preferred sequences are those which are essentially as set forth in SEQ ID NO:1, 3, 5, 7, 69, or 71, respectively.

Truncated pmHAS gene (such as, but not limited to, $pmHAS^{1-703}$, SEQ ID NO:71) also falls within the definition of preferred sequences as set forth above. For instance, at the carboxyl terminus, approximately 270-272 amino acids may be removed from the sequence and still have a functioning HAS. Those of ordinary skill in the art would appreciate that simple amino acid removal from either end of the pmHAS sequence can be accomplished. The truncated versions of the sequence (as disclosed hereinafter) simply have to be checked for HAS activity in order to determine if such a truncated sequence is still capable of producing HAS. The other GAG synthases disclosed and claimed herein are also amenable to truncation or alteration with preservation of activity and such truncated or alternated GAG synthases also fall within the scope of the present invention.

Nucleic acid segments having HAS or CS or HS activity may be isolated by the methods described herein. The term "a sequence essentially as set forth in SEQ ID NO:X means that the sequence substantially corresponds to a portion of SEQ ID NO:X and has relatively few amino acids or codons encoding amino acids which are not identical to, or a biologically functional equivalent of, the amino acids or codons encoding amino acids of SEQ ID NO:X. The term "biologically functional equivalent" is well understood in the art and is further defined in detail herein, as a gene having a sequence essentially as set forth in SEQ ID NO:X, and that is associated with the ability of prokaryotes to produce HA or a hyaluronic acid or chondroitin or heparin polymer in vitro or in vivo. In the above examples X refers to either SEQ ID NO:1, 2, 3, 4, 5, 6, 7, 8, 9, 69, 70 or 71 or any additional sequences set forth herein, such as the truncated or mutated versions of $pmHAS^{1-703}$ that are contained generally in SEQ ID NOS: 10-60.

The art is replete with examples of practitioner's ability to make structural changes to a nucleic acid segment (i.e. encoding conserved or semi-conserved amino acid substitutions) and still preserve its enzymatic or functional activity when expressed. See for special example of literature attesting to such: (1) Risler et al. Amino Acid Substitutions in Structurally Related Proteins. A Pattern Recognition Approach. J. Mol. Biol. 204:1019-1029 (1988) [ . . . according to the observed exchangeability of amino acid side chains, only four groups could be delineated; (i) Ile and Val; (ii) Leu and Met, (iii) Lys, Arg, and Gln, and (iv) Tyr and Phe.]; (2) Niefind et al. Amino Acid Similarity Coefficients for Protein Modeling and Sequence Alignment Derived from Main-Chain Folding Anoles. J. Mol. Biol. 219:481-497 (1991) [similarity parameters allow amino acid substitutions to be designed]; and (3) Overington et al. Environment-Specific Amino Acid Substitution Tables: Tertiary Templates and Prediction of Protein Folds, Protein Science 1:216-226 (1992) [Analysis of the pattern of observed substitutions as a function of local environment shows that there are distinct patterns . . . Compatible changes can be made.]

These references and countless others, indicate that one of ordinary skill in the art, given a nucleic acid sequence or an amino acid, could make substitutions and changes to the nucleic acid sequence without changing its functionality (specific examples of such changes are given hereinafter and are generally set forth in SEQ ID NOS:10-60). Also, a substituted nucleic acid segment may be highly identical and retain its enzymatic activity with regard to its unadulterated parent, and yet still fail to hybridize thereto. Additionally, the present application discloses 4 enzymes and numerous mutants of these enzymes that still retain at least 50% of the enzymatic activity of the unmutated parent enzyme—i.e., ½ of the dual action transferase activity of the unadulterated parent. As such, variations of the sequences and enzymes that fall within the above-defined functional limitations have been disclosed and enabled. One of ordinary skill in the art, given the present specification, would be able to identify, isolate, create, and test DNA sequences and/or enzymes that produce natural or chimeric or hybrid GAG molecules. As such, the presently claimed and disclosed invention should not be regarded as being solely limited to the specific sequences disclosed herein.

The invention discloses nucleic acid segments encoding an enzymatically active HAS or CS or HS from *P. multocida*—pmHAS, pmCS, pmHS1, and PmHS2, respectively. One of ordinary skill in the art would appreciate that substitutions can be made to the pmHAS or pmCS or pmHS1 or PmHS2 nucleic acid segments listed in SEQ ID NO:1, 3, 5, 7, 69, and 71, respectively, without deviating outside the scope and claims of the present invention. Indeed, such changes have been made and are described hereinafter with respect to the mutants produced. Standardized and accepted functionally equivalent amino acid substitutions are presented in Table II. In addition, other analogous or homologous enzymes that are functionally equivalent to the disclosed synthase sequences would also be appreciated by those skilled in the art to be similarly useful in the methods of the present invention, that is, a new method to control precisely the size distribution of polysaccharides, namely glycosaminoglycans.

TABLE II

| Amino Acid Group | Conservative and Semi-Conservative Substitutions |
|---|---|
| NonPolar R Groups | Alanine, Valine, Leucine, Isoleucine, Proline, Methionine, Phenylalanine, Tryptophan |
| Polar, but uncharged, R Groups | Glycine, Serine, Threonine, Cysteine, Asparagine, Glutamine |
| Negatively Charged R Groups | Aspartic Acid, Glutamic Acid |
| Positively Charged R Groups | Lysine, Arginine, Histidine |

Another preferred embodiment of the present invention is a purified nucleic acid segment that encodes a protein in accordance with SEQ ID NO:1 or 3 or 5 or 7 or 71, respectively, further defined as a recombinant vector. As used herein, the term "recombinant vector" refers to a vector that has been modified to contain a nucleic acid segment that encodes an HAS or CS or HS protein, or fragment thereof. The recombinant vector may be further defined as an expression vector comprising a promoter operatively linked to said HAS- or CS- or HS-encoding nucleic acid segment.

A further preferred embodiment of the present invention is a host cell, made recombinant with a recombinant vector comprising an HAS or CS or HS gene. The preferred recombinant host cell may be a prokaryotic cell. In another embodiment, the recombinant host cell is an eukaryotic cell. As used herein, the term "engineered" or "recombinant" cell is intended to refer to a cell into which a recombinant gene, such as a gene encoding HAS or CS or HS, has been introduced mechanically or by the hand of man. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene, a copy of a genomic gene, or will include genes positioned adjacent to a promoter associated or not naturally associated with the particular introduced gene.

In preferred embodiments, the HAS- or CS- or HS-encoding DNA segments further include DNA sequences, known in the art functionally as origins of replication or "replicons", which allow replication of contiguous sequences by the particular host. Such origins allow the preparation of extrachromosomally localized and replicating chimeric or hybrid segments or plasmids, to which HAS- or CS- or HS-encoding DNA sequences are ligated. In more preferred instances, the employed origin is one capable of replication in bacterial hosts suitable for biotechnology applications. However, for more versatility of cloned DNA segments, it may be desirable to alternatively or even additionally employ origins recognized by other host systems whose use is contemplated (such as in a shuttle vector).

The isolation and use of other replication origins such as the SV40, polyoma or bovine papilloma virus origins, which may be employed for cloning or expression in a number of higher organisms, are well known to those of ordinary skill in the art. In certain embodiments, the invention may thus be defined in terms of a recombinant transformation vector which includes the HAS- or CS- or HS-coding gene sequence together with an appropriate replication origin and under the control of selected control regions.

Thus, it will be appreciated by those of skill in the art that other means may be used to obtain the HAS or CS or HS gene or cDNA, in light of the present disclosure. For example, polymerase chain reaction or RT-PCR produced DNA fragments may be obtained which contain full complements of genes or cDNAs from a number of sources, including other strains of *Pasteurella* or from a prokaryot with similar glycosyltransferases or from eukaryotic sources, such as cDNA libraries. Virtually any molecular cloning approach may be employed for the generation of DNA fragments in accordance with the present invention. Thus, the only limitation generally on the particular method employed for DNA isolation is that the isolated nucleic acids should encode a biologically functional equivalent HAS or CS or HS.

Once the DNA has been isolated, it is ligated together with a selected vector. Virtually any cloning vector can be employed to realize advantages in accordance with the invention. Typical useful vectors include plasmids and phages for use in prokaryotic organisms and even viral vectors for use in eukaryotic organisms. Examples include pKK223-3, pSA3, recombinant lambda, SV40, polyoma, adenovirus, bovine papilloma virus and retroviruses. However, it is believed that particular advantages will ultimately be realized where vectors capable of replication in both biotechnologically useful Gram-positive or Gram-negative bacteria (e.g., *Bacillus, Lactococcus*, or *E. coli*) are employed.

Vectors such as these, exemplified by the pSA3 vector of Dao and Ferretti or the pAT19 vector of Trieu-Cuot, et al., allow one to perform clonal colony selection in an easily manipulated host such as *E. coli*, followed by subsequent transfer back into a food grade *Lactococcus* or *Bacillus* strain for production of hyaluronan or chondroitin or heparin polymer. In another embodiment, the recombinant vector is employed to make the functional GAG synthase for in vitro use. These are benign and well studied organisms used in the production of certain foods and biotechnology products and are recognized as GRAS (generally recognized as safe) organisms. These are advantageous in that one can augment the *Lactococcus* or *Bacillus* strain's ability to synthesize HA or chondroitin or heparin through gene dosaging (i.e., providing extra copies of the HAS or CS or HS gene by amplification) and/or inclusion of additional genes to increase the availability of HA or chondroitin or heparin precursors. The inherent ability of a bacterium to synthesize HA or chondroitin or heparin can also be augmented through the formation of extra copies, or amplification, of the plasmid that carries the HAS or CS or HS gene. This amplification can account for up to a 10-fold increase in plasmid copy number and, therefore, the HAS or CS or HS gene copy number.

Another procedure to further augment HAS or CS or HS gene copy number is the insertion of multiple copies of the gene into the plasmid. Another technique would include integrating at least one copy of the HAS or CS or HS gene into chromosomal DNA. This extra amplification would be especially feasible, since the bacterial HAS or CS or HS gene size is small. In some scenarios, the chromosomal DNA-ligated vector is employed to transfect the host that is selected for clonal screening purposes such as *E. coli*, through the use of a vector that is capable of expressing the inserted DNA in the chosen host.

In certain other embodiments, the invention concerns isolated DNA segments and recombinant vectors that include within their sequence a nucleic acid sequence essentially as set forth in SEQ ID NO:1,3,5,7,69, or 71. The term "essentially as set forth in SEQ ID NO:1,3,5,7,69, or 71 is used in the same sense as described above and means that the nucleic acid sequence substantially corresponds to a portion of SEQ ID NO:1,3,5,7,69, or 71 and has relatively few codons which are not identical, or functionally equivalent, to the codons of SEQ ID NO:1,3,5,7,69, or 71. The term "functionally equivalent codon" is used herein to refer to codons that encode the same amino acid, such as the six codons for arginine or serine, and also refers to codons that encode biologically equivalent amino acids, as set forth in Table II.

It will also be understood that amino acid and nucleic acid sequences may include additional residues, such as additional N— or C-terminal amino acids or 5' or 3' nucleic acid sequences, and yet still be essentially as set forth in one of the sequences disclosed herein, so long as the sequence meets the criteria set forth above, including the maintenance of biological protein activity where protein expression and enzyme activity is concerned. The addition of terminal sequences particularly applies to nucleic acid sequences which may, for example, include various non-coding sequences flanking either of the 5' or 3' portions of the coding region or may include various internal sequences, which are known to occur within genes. Furthermore, residues may be removed from the N— or C-terminal amino acids and yet still be essentially as set forth in one of the sequences disclosed herein, so long as the sequence meets the criteria set forth above, as well.

Allowing for the degeneracy of the genetic code as well as conserved and semi-conserved substitutions, sequences which have between about 40% and about 99%; or more preferably, between about 80% and about 90%; or even more preferably, between about 90% and about 99% identity to the nucleotides of SEQ ID NO:1,3,5,7,69, or 71 will be sequences which are "essentially as set forth in SEQ ID NO:1,3,5,7,69, or 71. Sequences which are essentially the same as those set forth in SEQ ID NO:1,3,5,7,69, or 71 may also be functionally defined as sequences which are capable of hybridizing to a nucleic acid segment containing the complement of SEQ ID NO:1,3,5,7,69, or 71 under standard stringent hybridization conditions, moderately stringent hybridization conditions," "less stringent hybridization conditions," or "low stringency hybridization conditions." Suitable standard or less stringent hybridization conditions will be well known to those of skill in the art and are clearly set forth hereinbelow. In a preferred embodiment, standard stringent hybridization conditions or less stringent hybridization conditions are utilized.

The terms "standard stringent hybridization conditions," "moderately stringent conditions," and less stringent hybridization conditions or "low stringency hybridization conditions" are used herein, describe those conditions under which substantially complementary nucleic acid segments will form standard Watson-Crick base-pairing and thus "hybridize" to one another. A number of factors are known that determine the specificity of binding or hybridization, such as pH; temperature; salt concentration; the presence of agents, such as formamide and dimethyl sulfoxide; the length of the segments that are hybridizing; and the like. There are various protocols for standard hybridization experiments. Depending on the relative similarity of the target DNA and the probe or query DNA, then the hybridization is performed under stringent, moderate, or under low or less stringent conditions.

The hybridizing portion of the hybridizing nucleic acids is typically at least about 14 nucleotides in length, and preferably between about 14 and about 100 nucleotides in length. The hybridizing portion of the hybridizing nucleic acid is at least about 60%, e.g., at least about 80% or at least about 90%, identical to a portion or all of a nucleic acid sequence encoding a HAS or chondroitin or heparin synthase or its complement, such as SEQ ID NO:1,3,5,7,69, or 71 or the complement thereof. Hybridization of the oligonucleotide probe to a nucleic acid sample typically is performed under standard or stringent hybridization conditions. Nucleic acid duplex or hybrid stability is expressed as the melting temperature or $T_m$, which is the temperature at which a probe nucleic acid sequence dissociates from a target DNA. This melting temperature is used to define the required stringency conditions. If sequences are to be identified that are related and substantially identical to the probe, rather than identical, then it is useful to first establish the lowest temperature at which only homologous hybridization occurs with a particular concentration of salt (e.g., SSC, SSPE, or HPB). Then, assuming that 1% mismatching results in a 1C decrease in the $T_m$, the temperature of the final wash in the hybridization reaction is reduced accordingly (for example, if sequences having >95% identity with the probe are sought, the final wash temperature is decreased by about 5 C). In practice, the change in $T_m$ can be between about 0.5° and about 1.5° per 1% mismatch. Examples of standard stringent hybridization conditions include hybridizing at about 68 C in 5×SSC/5× Denhardt's solution/1.0% SDS, followed with washing in 0.2×SSC/0.1% SDS at room temperature or hybridizing in 1.8×HPB at about 30 C to about 45 C followed by washing a 0.2-0.5×HPB at about 45°. Moderately stringent conditions include hybridizing as described above in 5×SSC†5×Denhardt's solution 1% SDS washing in 3×SSC at 42 C. The parameters of salt concentration and temperature can be varied to achieve the optimal level of identity between the probe and the target nucleic acid. Additional guidance regarding such conditions is readily available in the art, for example, by Sambrook et al., 1989, Molecular Cloning, A Laboratory Manual, (Cold Spring Harbor Press, N.Y.); and Ausubel et al. (eds.), 1995, Current Protocols in Molecular Biology, (John Wiley & Sons, N.Y.). Several examples of low stringency protocols include: (A) hybridizing in 5×SSC, 5× Denhardts reagent, 30% formamide at about 30 C for about 20 hours followed by washing twice in 2×SSC,0.1% SDS at about 30 C for about 15 min followed by 0.5×SSC, 0.1% SDS at about 30 C for about 30 min (FEMS Microbiology Letters, 2000, vol. 193, p. 99-103); (B) hybridizing in 5×SSC at about 45 C overnight followed by washing with 2×SSC, then by 0.7×SSC at about 55°. (J. Viological Methods, 1990, vol. 30, p. 141-150); or (C) hybridizing in 1.8×HPB at about 30° to about 45°; followed by washing in 1× HPB at 23°.

Naturally, the present invention also encompasses DNA segments which are complementary, or essentially complementary, to the sequences set forth in SEQ ID NO:1 or 3 or 5 or 7 or 69 or 71. Nucleic acid sequences which are "complementary" are those which are capable of base-pairing according to the standard Watson-Crick complementarity rules. For example, the sequence 5'-ATAGCG-3' is complementary to the sequence 5'-CGCTAT-3" because when the two sequences are aligned, each "T" is able to base-pair with an "A", which each "G" is able to base pair with a "C". As used herein, the term "complementary sequences" means nucleic acid sequences which are substantially complementary, as may be assessed by the nucleotide comparison set forth above, or as defined as being capable of hybridizing to the nucleic acid segment of SEQ ID NO:1,3,5,7, or 69, or 71 under standard stringent, moderately stringent, or less stringent hybridizing conditions.

The nucleic acid segments of the present invention, regardless of the length of the coding sequence itself, may be combined with other DNA sequences, such as promoters, polyadenylation signals, additional restriction enzyme sites, multiple cloning sites, epitope tags, polyhistidine regions, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

Naturally, it will also be understood that this invention is not limited to the particular amino acid and nucleic acid sequences of SEQ ID NO:1, 2, 3, 4, 5, 6, 7, 8, 9, 69, 70, or 71. Recombinant vectors and isolated DNA segments may therefore variously include the HAS or CS or HS coding regions themselves, coding regions bearing selected alterations or modifications in the basic coding region, or they may encode larger polypeptides which nevertheless include HAS or CS or HS coding regions or may encode biologically functional equivalent proteins or peptides which have variant amino acid sequences.

The DNA segments of the present invention encompass DNA segments encoding biologically functional equivalent HAS or CS or HS proteins and peptides. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the enzyme activity or to antigenicity of the HAS or CS or HS protein or to test HAS or CS or HS mutants in order to examine HAS or CS or HS activity at the molecular level or to produce HAS or CS or HS mutants having changed or novel enzymatic activity and/or sugar substrate specificity.

Traditionally, chemical or physical treatments of polysaccharides were required to join two dissimilar materials. For example, a reactive nucleophile group of one polymer or surface was exposed to an activated acceptor group of the other material. Two main problems exist with this approach, however. First, the control of the chemical reaction cannot be refined, and differences in temperature and level of activation often result in a distribution of several final products that vary from lot to lot preparation. For instance, several chains may be cross-linked in a few random, ill-defined areas, and the resulting sample is not homogenous. Second, the use of chemical reactions to join molecules often leaves an unnatural or nonbiological residue at the junction of biomaterials. For example, the use of an amine and an activated carboxyl group would result in an amide linkage. This inappropriate residue buried in a carbohydrate may pose problems with biological systems such as the subsequent production of degradation products which accumulate to toxic levels or the triggering of an immune response.

Use of pmHAS for Polymer Grafting and Polysaccharide Production

Most polysaccharide polymers must be of a certain length before their physical or biological properties become apparent. Often the polysaccharide must comprise at least 20-100 sugar units. Certain enzymes that react with exogenous polymers have been previously available, but typically add only one sugar unit. The unique enzymes described in the present invention, (e.g., pmHAS, pmCS, pmHS1, and PmHS2) form polymers of at least 100-400 sugar units in length. Thus, one embodiment of the presently claimed and disclosed invention, results in long, defined linear polymers composed of only natural glycosidic linkages.

The four known glycosaminoglycan synthesizing enzymes from *Pasteurella multocida* bacteria normally make polymers similar to or identical to vertebrate polymers. These bacteria employ the polysaccharide, either HA (Type A bacteria), chondroitin (Type F bacteria), or heparosan (unsulfated, unepimerized heparin Type D bacteria) as an extracellular coating to serve as molecular camouflage. Native enzymes normally make polymer chains of a single type of sugar repeat. If a recombinant HAS or CS or HS enzyme is employed, however, the enzyme can be forced to work on an exogenous functional acceptor molecule. For instance, the recombinant enzyme may be incubated with a polymer acceptor, and the recombinant enzyme will then elongate the acceptor with UDP-sugar precursors. The known native enzymes do not perform this reaction since they already contain a growing polymer chain that was formed in the living cell; enzyme preparations from native cells retain the polymer following isolation.

pmHAS (SEQ ID NO:2), a 972 amino acid residue protein from *Pasteurella multocida*, is made in a functional state in recombinant *Escherichia coli*. The pmHAS gene is given in SEQ ID NO:1. Other functional derivatives of pmHAS, for example an enzyme called pmHAS$^{1-703}$ (SEQ ID NO:9) and the pmHAS$^{1-703}$ gene (SEQ ID NO:71), have been produced which are soluble. The soluble form can be prepared in larger quantities and in a purer state than the naturally occurring full-length enzyme. The preferred *E. coli* strains do not have an UDP-Glc dehydrogenase and therefore the recombinant enzyme does not make HA chain in the foreign host. Therefore, the enzyme is in a virgin state since the empty acceptor site can be occupied with foreign polymers. For example, the recombinant enzyme may be incubated in a mixture comprising from about 10 to about 50 mM Tris pH 7.2, from 0.5 to about 20 mM $MnCl_2$, from about 0.1 to about 30 mM UDP-GlcUA, from about 0.1 to about 30 mM UDP-GlcNAc, and a suitable acceptor at about 20-37° for from about 1 to about 600 minutes. Suitable acceptors can be any functional acceptor, such as a glycosaminoglycan acceptor or sugar acceptor, for example, but not by limitation, short HA chains (two or more sugar units such as $HA_4$) or short chondroitin sulfate chains (5 sugar units) or long chondroitin sulfate chains (~$10^2$ sugar units). In the case of the latter acceptors, pmHAS (or its derivatives), then elongates the foreign acceptors (i.e., long or short chondroitin polymers) at their nonreducing termini with authentic HA chains. The length of the HA chain added onto the acceptor is controlled by altering the concentration of UDP-sugars (thus changing the stoichiometry of UDP-sugar to acceptor) and/or the reaction time. Immobilized acceptors, such as beads or other solid objects with bound acceptor oligosaccharides, can also be extended by the pmHAS enzyme using UDP-sugars. In this manner, the pmHAS enzyme (or its derivatives) can be used to attach polysaccharide chains to any suitable acceptor molecule.

Type A *P. multocida* produces HA capsule [GlcUA-GlcNAc repeats] and possesses the pmHAS enzyme. On the other hand, Type F *P. multocida* produces a chondroitin or chondroitin-like polymer capsule [GlcUA-GalNAc repeats]. The DNA encoding an open reading frame (GenBank accession #AF195517) that is 90% identical to pmHAS at the protein level has been cloned; this enzyme is called PmCS, the *P. multocida* chondroitin synthase. The amino acid sequence of pmCS is set forth in SEQ ID NO:4 and the pmCS gene sequence is set forth in SEQ ID NO:3. As the PmCS enzyme s sequence is so similar to pmHAS, one of ordinary skill in the art, given the present specification, is able to manipulate the pmCS in the same manner as that for pmHAS and any manipulation that is successful with regard to the pmHAS would be performable with the pmCS, with the exception that chondroitin chains would be grafted instead of HA. Either HA or chondroitin or heparin chains can serve as acceptors for pmCS as both acceptors serve well for pmHAS.

Such hybrid polysaccharide materials composed of HA, chondroitin and heparin cannot be formed in a controlled fashion (targeted size and monodisperse) especially with regard to medium to large size polymers (i.e., greater than 15 KDa) by any other existing process without (1) leaving unnatural residues, and/or (2) producing undesirable crosslinking reactions. The testicular hyaluronidase method gives a variety of small products derived from quasi-random linkage of GAGs, HA and chondroitin. Very large polymers are not major or significant products. The chimeric or hybrid polysaccharide materials can serve as biocompatible molecular glue for cell/cell interactions in artificial tissues or organs and the HA/chondroitin/heparin hybrid mimics natural proteoglycans that normally contain an additional protein intermediate between polymer chains. The present invention, therefore, obviates the requirement for a protein intermediary. A recombinant HA/chondroitin/heparin chimeric or hybrid polysaccharide, devoid of such an intermediary protein, is desirous since molecules from animal sources are potentially immunogenic—the chimeric or hybrid polysaccharide, however, would not appear as foreign to the host, thus no immune response is generated. Also, the recombinant polymers can be made free of adventitious agents (e.g., prions, viruses etc.)

An intrinsic and essential feature of polysaccharide synthesis is the repetitive addition-of sugar monomer units to the growing polymer. The glycosyltransferase remains in association with the nascent chain. This feature is particularly relevant for HA biosynthesis as the HA polysaccharide product, in all known cases, is transported out of the cell; if the polymer was released, then the HAS would not have another chance to elongate that particular molecule. Three possible mechanisms for maintaining the growing polymer chain at the active site of the enzyme are immediately obvious. First, the enzyme possesses a carbohydrate polymer binding pocket or cleft. Second, the nascent chain is covalently attached to the enzyme during its synthesis. Third, the enzyme binds to the nucleotide base or the lipid moiety of the precursor while the nascent polymer chain is still covalently attached.

The HAS activity of the native pmHAS enzyme found in *P. multocida* membrane preparations is not stimulated by the addition of HA oligosaccharides; theoretically, the endogenous nascent HA chain initiated in vivo renders the exogenously supplied acceptor unnecessary. However, recombinant pmHAS produced in an *E. coli* strain that lacks the UDP-GlcUA precursor, and thus lacks a nascent HA chain, is able to bind and to elongate exogenous HA oligosaccharides. As mentioned above, there are three likely means for a nascent HA chain to be held at or near the active site. In the case of pmHAS, it appears that a HA-binding site exists near or at the sugar transferase catalytic site.

Defined oligosaccharides that vary in size and composition are used to discern the nature of the interaction between pmHAS and the sugar chain. For example, it appears that the putative HA-polymer binding pocket of. pmHAS will bind and elongate at least an intact HA disaccharide with increased efficiency occurring when a trisaccharide is used (reduced tetramer or a synthetic trisaccharide). Oligosaccharide binding to pmHAS appears to be somewhat selective because the heparosan pentamer, which only differs in the glycosidic linkages from HA-derived oligosaccharides, does not serve as an acceptor. However, chondroitin [GlcUA-GalNAc repeat] does serve as an acceptor for pmHAS.

To date, no other HA synthase besides pmHAS has been shown to utilize an exogenous acceptor or primer sugar. In an early study of a cell-free HA synthesis system, preparations of native Group A Streptococcal HAS were neither inhibited nor stimulated by the addition of various HA oligosaccharides including the HA tetramer derived from testicular hyaluronidase digests. These membrane preparations were isolated from cultures that were producing copious amounts of HA polysaccharide. The cells were hyaluronidase-treated to facilitate handling. Therefore, it is quite likely that the native streptococcal enzyme was isolated with a small nascent HA chain attached to or bound to the protein much as suspected in the case of the native pmHAS. Theoretically, the existing nascent chain formed in vivo would block the entry and subsequent utilization of an exogenous acceptor by the isolated enzyme in vitro. With the advent of molecularly cloned HAS genes, it is possible to prepare virgin enzymes lacking a nascent HA chain if the proper host is utilized for expression. In these tests, recombinant yeast with spHAS did not use HA acceptors proving that the Class I enzyme intrinsically cannot elongate such acceptors.

Both heparin and chondroitin, in mammalian systems, are synthesized by the addition of sugar units to the nonreducing end of the polymer chain. In vivo, the glycosyltransferases initiate chain elongation on at least primer monosachharides [more preferably tetrasaccharides such as xylose-galactose-galactose-GlcUA] that are attached to serine residues of proteoglycan core molecules. In vitro, enzyme extracts transfer a single sugar to exogenously added heparin or chondroitin oligosaccharides; unfortunately, the subsequent sugar of the disaccharide unit is usually not added and processive elongation to longer polymers does not occur. Therefore it is likely that some component is altered or missing in the in vitro system. In the case of heparin biosynthesis, a single enzyme transfers both GlcUA and GlcNAc sugars to the glycosaminoglycan chain based on co-purification or expression studies.

Recent work with the *E. coli* K5 KfiA and KfiC enzymes, which polymerize heparosan, indicates that a pair of proteins can transfer both sugars to the nonreducing end of acceptor molecules in vitro. Processive elongation, however, was not demonstrated in these experiments; crude cell lysates transferred a single sugar to defined even- or odd-numbered oligosaccharides.

Recombinant pmHAS adds single monosaccharides in a sequential fashion to the nonreducing termini of the nascent HA chain. Elongation of HA polymers containing hundreds of sugars has been demonstrated in vitro. The simultaneous formation of the disaccharide repeat unit is not necessary for generating the alternating structure of the HA molecule. The intrinsic specificity and fidelity of each half-reaction (e.g., GlcUA added to a GlcNAc residue or vice versa) apparently is sufficient to synthesize authentic HA chains.

A great technical benefit resulting from the alternating disaccharide structure of HA is that the reaction can be dissected by controlling the availability of UDP-sugar nucleotides. By omitting or supplying precursors in a reaction mixture, the glycosyltransferase may be stopped and started at different stages of synthesis of the heteropolysaccharide. In contrast, there is no facile way to control in a step-wise fashion the glycosyltransferase enzymes that produce important homopolysaccharides such as chitin, cellulose, starch, and glycogen.

An alternative method for controlling polymerization has been accomplished by creating mutants that only add one sugar linkage onto a short HA oligosaccharide. For example, $pmHAS^{1-650}$ (SEQ. ID NO:10) can only add single GlcNAc sugars onto the non-reducing end (i.e., HA tetrasaccharide [GlcNAc-GlcUA-GlcNAc-GlcUA]) of an acceptor (i.e., forms the HA pentamer). On the other hand, a mutant has been created and called $pmHAS^{1-703}$-D477N (SEQ. ID NO:11) [pmHAS residues 1-703 with an asparagine substituted for the asparatate at position 477], that transfers only a single GlcNAc residue onto the non-reducing terminal GlcUa group of the short HA oligosaccharide. If extracts of two such single-action point mutants (e.g. D477N, SEQ ID NO:11 and D196N [i.e., pmHAS residues 1-703 with an asparagine substituted for the aspartate at position 196], SEQ ID NO:12) are mixed together with an acceptor in the presence of UDP-GlcNAc and UDP-GlcUA, then significant polymerization is achieved. It is also obvious that by carrying out the steps of GlcNAc or GlcUA transfer separately and sequentially, almost any HA chain length is possible. The same is also true with regard to PmCS either alone or in combination with pmHAS as well as pmHS1 or PmHS2 either alone or in combination with pmCS and pmHAS, individually or as a group.

As stated above, membrane preparations from recombinant *E. coli* containing a pmHAS protein had HA synthase activity as judged by incorporation of radiolabel from UDP-[$^{14}$C]GlcUA into polymer when co-incubated with both UDP-GlcNAc and Mn ion. Due to the similarity at the amino acid level of pmHAS to several lipopolysaccharide transferases, it was hypothesized that HA oligosaccharides serve as acceptors for GlcUA and GlcNAc transfer. Addition of unlabeled even-numbered HA tetramer (from testicular hyaluronidase digests) to reaction mixtures with recombinant $pmHAS^{1-703}$ stimulates incorporation of radiolabel from UDP-[$^{14}$C]GlcUA into HA polymer by ~20- to 60-fold in comparison to reactions without oligosaccharides as shown in FIG. 1. The acceleration of incorporation by acceptor was not predicted or expected. The mechanism of action is probably the bypassing of a slow polymer initiation step; the synthase with acceptor proceeds rapidly to the fast elongation step. The present invention builds on these kinetic observations in reactions set up by the hand of man with recombinant versions of the pmHAS.

In FIG. 1, a series of reactions containing $pmHAS^{1-703}$ (30 g total membrane protein) were incubated with UDP-[$^{14}$C]GlcUA ($2\times10^4$ dpm, 120 M) and UDP-GlcNAc (450 M) in assay buffer (50 I reaction vol.) in the presence of no added sugar (none) or various oligosaccharides (HA4, 4 g HA tetramer; unsHA4/6, 4 g unsaturated HA tetramer and hexamer; chito4, 50 g chitotetraose; hep5, 20 g heparosan pentamer). After 1 hour, the reactions were analyzed by descending paper chromatography. Incorporation of radiolabel from UDP-[$^{14}$C]GlcUA into high molecular weight HA is shown. The intact tetramer (HA4) served as a functional acceptor. Reactions with heparosan and chitooligosaccharides, as well as GlcNAc and/or GlcUA (not shown), incorporated as much radiolabel as parallel reactions with no acceptor. The free monosaccharides GlcUA and GlcNAc, either singly or in combination at concentrations of up to 100 M, do not serve as acceptors; likewise, the beta-methyl glycosides of these sugars do not stimulate HAS activity.

In the same manner, $pmHAS^{1-703}$ has been shown to add sugars onto a chondroitin pentamer acceptor. The $pmHAS^{1-703}$ and reagents were prepared in the same manner as shown in FIG. 1, except that a chondroitin pentamer was used as the acceptor molecule. The results of this experiment are shown in TABLE III.

TABLE III

| Sugar | Mass | Incorporation of $^{14}$C-GlcUA dpm |
|---|---|---|
| None | Not Applicable. | 60 |
| HA | 5 μg | 2,390 |
| Chondroitin Pentamer | 20 μg | 6,690 |

Thus, it can be seen that the pmHAS$^{1-703}$ can utilize molecules other than the naturally occurring acceptors or primer molecules as the basis for forming a polysaccharide polymer chain.

Figure 2:
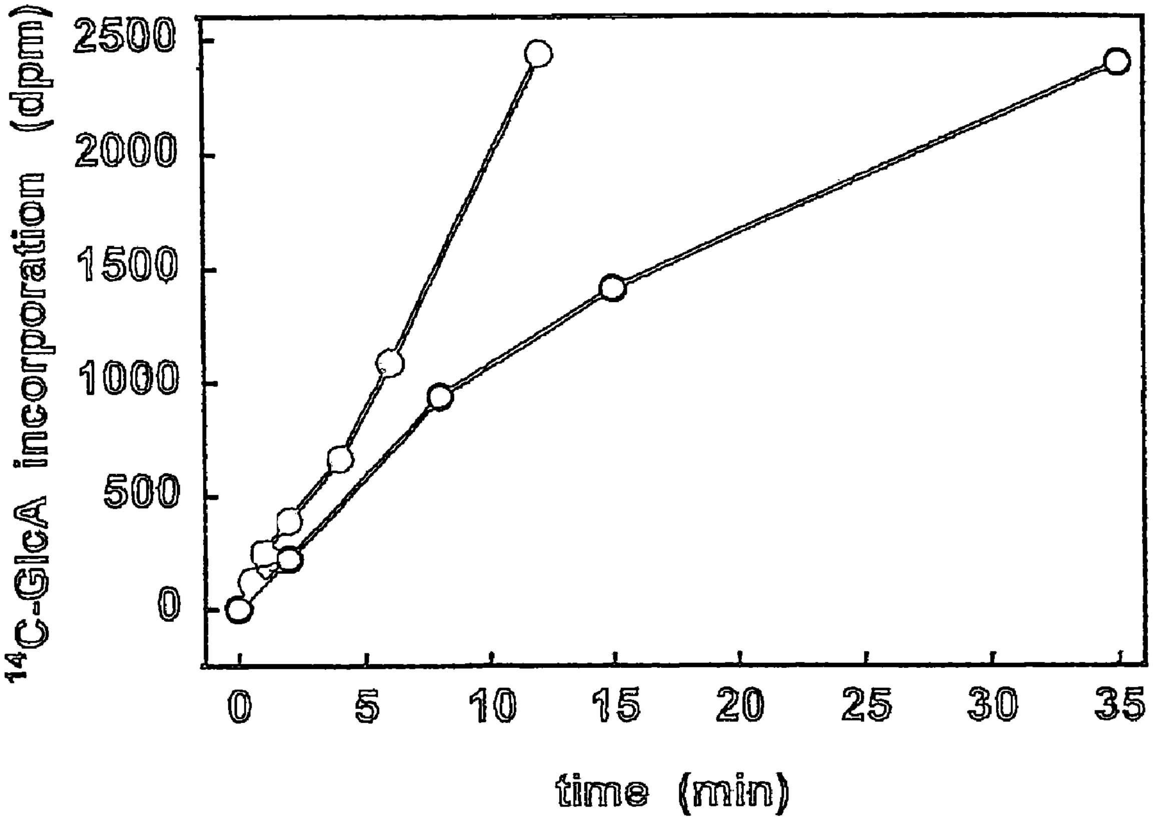
FIG. 2 is a graphical plot showing that HA polymerization is effected by HA oligosaccharides.

The HA polymerizing activity of recombinant pmHAS$^{1-703}$ is dependent on the simultaneous incubation with both UDP-sugar precursors and a $Mn^{2+}$ ion. The level of incorporation is dependent on protein concentration, on HA oligosaccharide concentration, and on incubation time as shown in FIG. 2. In FIG. 2, two parallel reactions containing pmHAS$^{1-703}$ with even-numbered HA oligosaccharides (105 g membrane protein/point with a mixture of HA hexamer, octamer, and decamer, 4.4. g total; solid circles) or six-fold more pmHAS$^{1-703}$ without oligosaccharide acceptor (630 g protein/point; open circles) were compared. The enzyme preparations were added to prewarmed reaction mixtures containing UDP-[$^{14}$C]GlcUA (240 M $6\times10^4$ dpm/point) and UDP-GlcNAc (600 M) in assay buffer. At various times, 50 I aliquots were withdrawn, terminated, and analyzed by paper chromatography. The exogenously supplied acceptor accelerated the bulk incorporation of sugar precursor into polymer product by pmHAS$^{1-703}$, but the acceptor was not absolutely required.

HA synthesized in the presence or the absence of HA oligosaccharides is sensitive to HA lyase (>95% destroyed) and has a molecular weight of ~$1\text{-}5\times10^4$ Da (~50-250 monosaccharides). No requirement for a lipid-linked intermediate was observed as neither bacitracin (0.5 mg/ml) nor tunicamycin (0.2 mg/ml) alter the level of incorporation in comparison to parallel reactions with no inhibitor.

Figure 3:
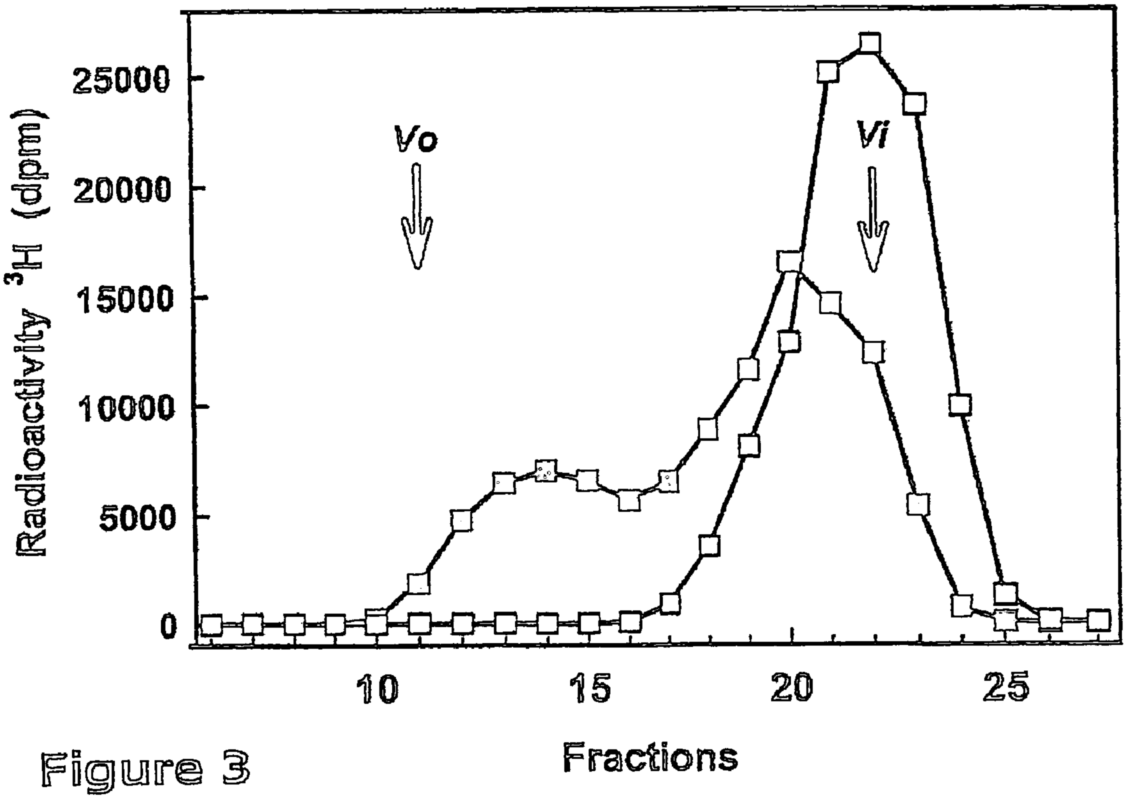
FIG. 3 is a graphical plot showing HA tetramer elongation into larger polymers by pmHAS.

Gel filtration chromatography analysis of reactions containing recombinant pmHAS$^{1-703}$, $^3$H-HA tetramer, UDP-GlcNAc and UDP-GlcUA show that labeled polymers from ~0.5 to $5\times10^4$ Da (25-250 monosaccharides) are made as shown in FIG. 3. In FIG. 3, gel filtration analysis on Sephacryl S-200 (20 ml column, 0.7 ml fractions) shows that pmHAS$^{1-703}$ makes HA polysaccharide using HA tetramer acceptor and UDP-sugars. Dextrans of greater than or equal to 80 kDa (~400 monosaccharides) elute in the void volume (Vo arrow). The starting tetramer elutes in the included volume (Vi arrow). Membranes (190 g total protein), UDP-GlcUA (200 M), UDP-GlcNAc (600 M), and radiolabeled $^3$H-HA tetramer ($1.1\times10^5$ dpm) were incubated for 3 hours before gel filtration (solid squares). As a negative control, a parallel reaction containing all the components except for UDP-GlcNAc was analyzed (open squares). The small primer was elongated into higher molecular weight product if both precursors were supplied. In a parallel reaction without UDP-GlcNAc, the elution profile of the labeled tetramer is not altered.

The activity of the native pmHAS$^{1-703}$ from *P. multocida* membranes, however, is not stimulated by the addition of HA oligosaccharides under similar conditions. The native pmHAS$^{1-703}$ enzyme has an attached or bound nascent HA chain that is initiated in the bacterium prior to membrane isolation. The recombinant enzyme, on the other hand, lacks such a nascent HA chain since the *E. coli* host does not produce the UDP-GlcUA precursor needed to make HA polysaccharide. Therefore, the exogenous HA-derived oligosaccharide has access to the active site of pmHAS$^{1-703}$ and can be elongated.

The tetramer from bovine testicular hyaluronidase digests of HA terminates at the nonreducing end with a GlcUA residue and this molecule served as an acceptor for HA elongation by pmHAS$^{1-703}$. On the other hand, the tetramer and hexamer oligosaccharides produced by the action of *Streptomyces* HA lyase did not stimulate HA polymerization as shown in FIG. 1; unsHA4/6". As a result of the lyase eliminative cleavage, the terminal unsaturated sugar is missing the C4 hydroxyl of GlcUA which would normally be extended by the HA synthase. The lack of subsequent polymerization onto this terminal unsaturated sugar is analogous to the case of dideoxynucleotides causing chain termination if present during DNA synthesis. A closed pyranose ring at the reducing terminus was not required by pmHAS$^{1-703}$ since reduction with borohydride did not affect the HA tetramer s ability to serve as an acceptor thus allowing the use of borotritide labeling to monitor the fate of oligosaccharides.

Neither Yeast-derived recombinant Group A HasA (spHAS) nor recombinant DG42 produced elongated HA-derived oligosaccharides into larger polymers. First, the addition of HA tetramer (or a series of longer oligosaccharides) did not significantly stimulate nor inhibit the incorporation of radiolabeled UDP-sugar precursors into HA (<5% of control value) by these Class I HA synthases. In parallel experiments, the HAS activity of HasA or DG42 was not affected by the addition of chitin-derived oligosaccharides. Second, the recombinant Class I enzymes did not elongate the radiolabeled HA tetramer in the presence of UDP-sugars (Table IV). These same preparations of enzymes, however, were highly active in the conventional HAS assay in which radiolabeled UDP-sugars were polymerized into HA.

TABLE IV

| Enzyme | Units[a] | EDTA | Incorporation of HA4 into polymer (pmoles) |
|---|---|---|---|
| PmHAS$^{1-703}$ | 6[b] | — | 240 |
| | | † | 1.7 |
| HasA | 9,800 | — | ≦0.2 |
| | | † | ≦0.2 |
| DG42 | 11,500 | — | ≦0.1 |
| | | † | ≦0.3 |

[a]pmoles of GlcUA transfer/hr in the conventional HAS assay
[b]measured without HA tetramer; 360 units with 100 M HA tetramer.

As shown in Table IV, the various recombinant enzymes were tested for their ability to convert HA tetramer into molecular weight products. The reactions contained radiolabeled HA tetramer ($5\text{-}8\times10^5$ dpm), 750 M UDP-GlcNAc, 360 M UDP-GlcUA, 20 mM $XCl_2$, 50 mM Tris, pH 7-7.6 (the respective X cation and pH values used for each enzyme were: pmHAS$^{1-703}$, Mn/7.2; *Xenopous* DG42, Mg/7.6; Group A streptococcal HasA, Mg/7.0), and enzyme (units/reaction listed). As a control, parallel reactions in which the metal ion was chelated (22 mM ethylenediaminetetraacetic acid final; EDTA column, rows with +) were tested; without free metal ion, the HAS enzymes do not catalyze polymerization. After 1 hour incubation, the reactions were terminated and subjected to descending paper chromatography. Only pmHAS$^{1-703}$ could elongate HA tetramer even though all three membrane preparations were very active in the conventional HAS assay (incorporation of [$^{14}$C]GlcUA from UDP-GlcUA into polymer when supplied UDP-GlcNAc).

Figure 4:
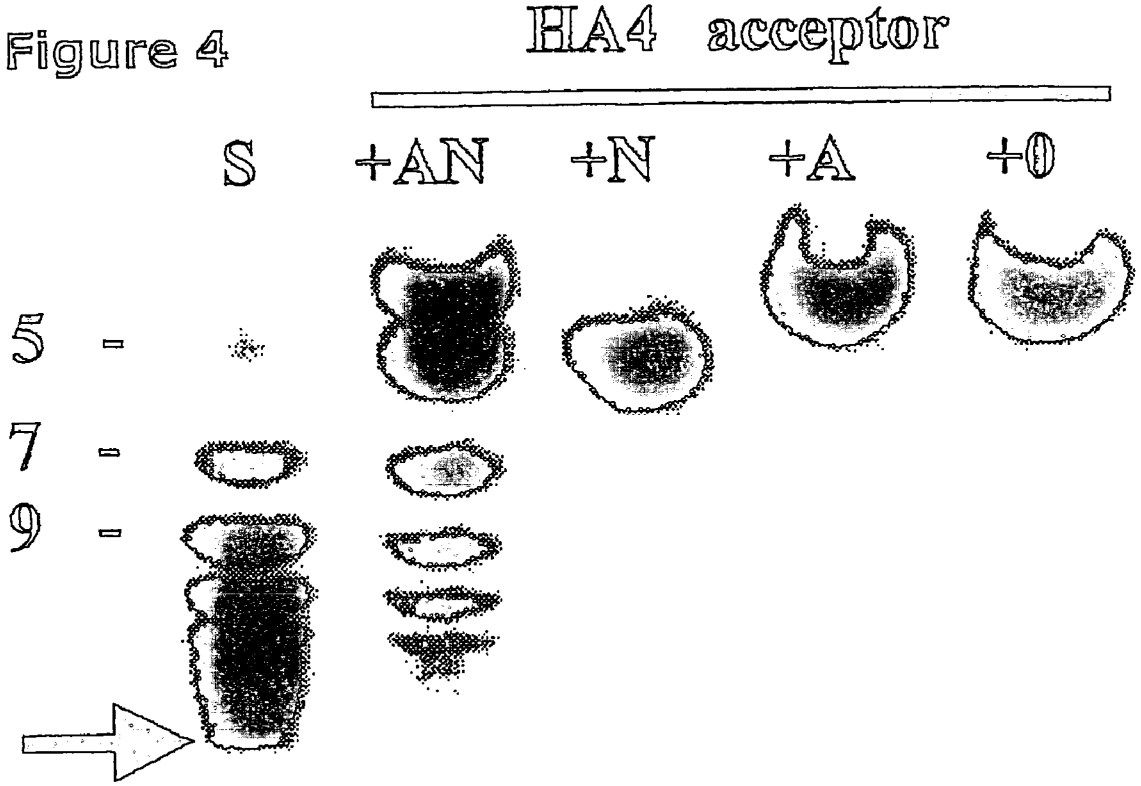
FIG. 4 is a graphical representation of a thin layer chromatography analysis of pmHAS extension of HA tetramer.

Thin layer chromatography was utilized to monitor the pmHAS-catalyzed elongation reactions containing $^3$H-labeled oligosaccharides and various combinations of UDP-sugar nucleotides. FIG. 4 demonstrates that pmHAS$^{1-703}$ elongated the HA-derived tetramer by a single sugar unit if the next appropriate UDP-sugar precursor was available in the reaction mixture. GlcNAc derived from UDP-GlcNAc was added onto the GlcUA residue at the nonreducing terminus of the tetramer acceptor to form a pentamer. On the other hand, inclusion of only UDP-GlcUA did not alter the mobility of the oligosaccharide. If both HA precursors are supplied, various longer products are made. In parallel reactions, control membranes prepared from host cells with a vector plasmid did not alter the mobility of the radiolabeled HA tetramer under any circumstances. In similar analyses monitored by TLC, pmHAS$^{1-703}$ did not utilize labeled chitopentaose as an acceptor.

As shown in FIG. 4, pmHAS extended an HA tetramer. In FIG. 4, radiolabeled HA tetramer (HA4 8×10$^3$ dpm $^3$H) with a GlcUA at the nonreducing terminus was incubated with various combinations of UDP-sugars (A, 360 M UDP-GlcUA; N, 750 M UDP-GlcNAc; 0, no UDP-sugar), and pmHAS (55 g membrane protein) in assay buffer for 60 minutes. The reactions (7 I total) were terminated by heating at 95 C for 1 minute and clarified by centrifugation. Portions (2.5 I) of the supernatant were spotted onto the application zone of a silica TLC plate and developed with solvent (1.25:1:1 butanol/acetic acid/water). The beginning of the analytical layer is marked by an arrow. The positions of odd-numbered HA oligosaccharides (S lane) are marked as number of monosaccharide units. The autoradiogram of FIG. 4 (4 day exposure) shows the single addition of a GlcNAc sugar onto the HA tetramer acceptor to form a pentamer when only the subsequent precursor is supplied (N). The mobility of the labeled tetramer is unchanged if only the inappropriate precursor, UDP-GlcUA (A), or no UDP-sugar (0) is present. If both UDP-sugars are supplied, then a ladder of products with sizes of 5, 7, 9, 11, and 13 sugars is formed (+AN). In a parallel experiment, chitopentaose (8×10$^4$ dpm $^3$H) was tested as an acceptor substrate. Under no condition was this structurally related molecule extended by pmHAS.

Figure 5:
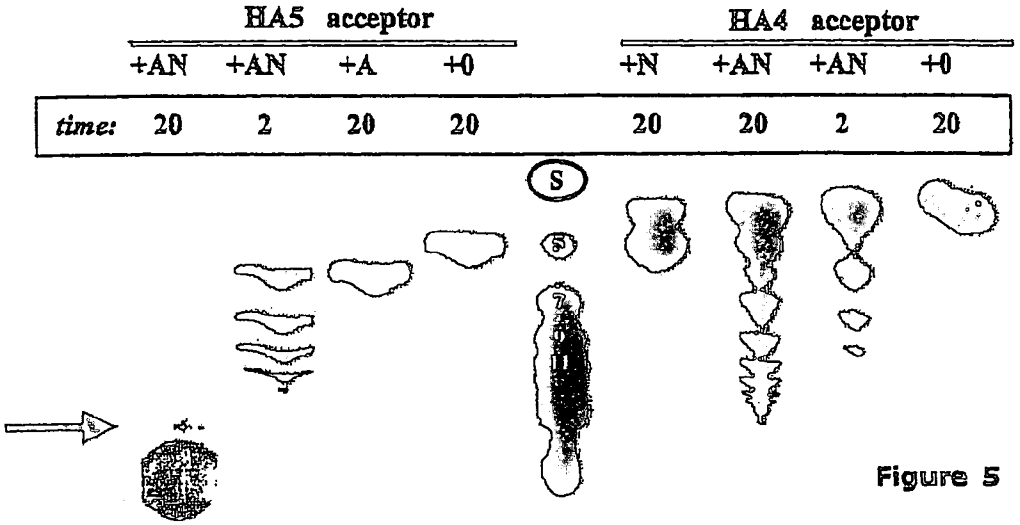
FIG. 5 is a graphical representation of thin layer chromatography analysis of the early stages of HA elongation.

HA-derived oligosaccharides with either GlcUA or GlcNAc at the nonreducing terminus served as acceptors for pmHAS$^{1-703}$ (FIG. 5). In FIG. 5, radiolabeled HA pentamer (HA5, 5×10$^3$ dpm $^3$H) or HA tetramer (HA4, 25×10$^3$ dpm $^3$H) was incubated with pmHAS$^{1-703}$ and various combinations of UDP-sugars (as in FIG. 4) for 2 or 20 minutes. Portions (1.5 I) of the supernatant were spotted onto the TLC plate and developed in 1.5:1:1 solvent. This autoradiogram (1 mo. exposure) shows the single addition of a sugar onto an acceptor when only the appropriate precursor is supplied (HA4, N lane and HA5, A lane). If both UDP-sugars are supplied (+AN lanes), then a ladder of products with final sizes of 6, 8, and 10 sugars is formed from either HA4 or HA5 in 2 minutes. After 20 minutes, a range of odd- and even-numbered product sugars are observed in reactions with HA4 and both UDP-sugars. In the 20 minute reaction with HA5 and both UDP-sugars, the HA products are so large that they do not migrate from the application zone.

Within two minutes, 2 to 6 sugar units were added, and after 20 minutes, at least of from about 9 to about 15 sugar units were added. In the experiments with the HA tetramer and both sugars, a ladder of even- and odd-numbered products is produced at the 20 minute time point. Therefore, in combination with the results of the single UDP-sugar experiments, the pmHAS$^{1-703}$ enzyme transfers individual monosaccharides sequentially during a polymerization reaction.

A series of truncated versions of pmHAS (normally a 972-residue membrane protein) were created and are tabulated (with functionality) in Table V that produce proteins with altered physical properties (i.e., proteins that are more conducive to high-level expression and purification) and altered function (i.e., single transferase activity). Polymerase chain reaction [PCR] was used to amplify a portion of the pmHAS gene using a primer corresponding to the authentic N-terminus sequence and a primer corresponding to an internal coding region which ended in a stop codon. The coding regions for the truncated proteins were cloned into an *Escherichia coli* expression plasmid (pKK223-3; Pharmacia) under control of the tac promoter. The DNA sequence was verified by automated sequencing.

The truncation series was generated and tested for activity. All proteins were made at the expected molecular weight, but not all proteins were active.

TABLE V

| Name | Residues of pmHAS-D | Activity | SEQ ID NO: |
|---|---|---|---|
| pmHAS$^{437-972}$ | 437-972 | N.D. | 13 |
| pmHAS$^{437-756}$ | 437-756 | N.D. | 14 |
| pmHAS$^{1-756}$ | 1-756 | HA Synthase | 20 |
| pmHAS$^{1-703}$ | 1-703 | HA Synthase | 9, 71 |
| pmHAS$^{1-650}$ | 1-650 | GlcNAc Transferase | 10 |
| pmHAS$^{152-756}$ | 152-756 | N.D. | 15 |

N.D.—no activity detected.

Figure 6:
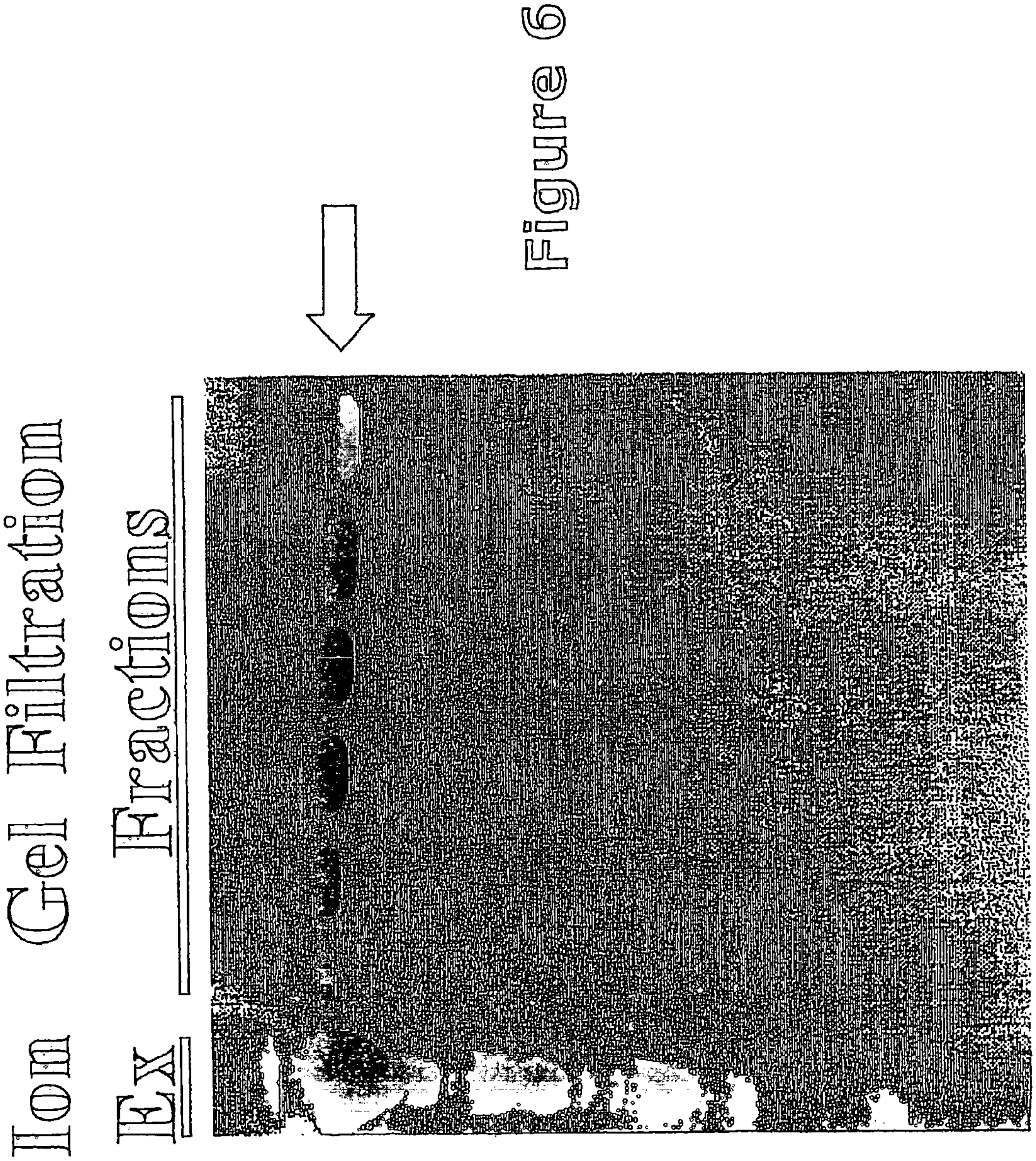
FIG. 6 is an electrophoresis gel showing the purification of $pmHAS^{1-703}$.

Analysis of induced cell cultures containing the plasmid with a 703-residue open reading frame revealed that a new 80-kDa protein, named pmHAS$^{1-703}$, was produced in large quantities. Furthermore, functional pmHAS$^{1-703}$ was present in the soluble fraction of the cell lysate; thus allowing for rapid extraction and assay of the enzyme. pmHAS$^{1-703}$ was purified by sequential chromatography steps shown in FIG. 6. In FIG. 6, a soluble, active form of the HA synthase was constructed with molecular biological techniques. The recombinant enzyme from *E. coli* was purified by conventional chromatography with yields of up to 20 mg/liter of cell culture. FIG. 6 is a stained electrophoretic gel loaded with samples of pmHAS$^{1-703}$ (marked with an arrow) during different stages of chromatography. This catalyst (and improved mutant versions) can be used to prepare HA coatings on artificial surfaces or HA extensions on suitable acceptor molecules.

The pmHAS$^{1-703}$ is highly active and at least 95% pure as assessed by denaturing polyacrylamide gel electrophoresis. Mass spectrometric analysis indicates that the pmHAS$^{1-703}$ is the desired protein due to the close agreement of the calculated and the observed mass values. A buffer system has also been developed to stabilize the enzymatic activity in the range of 0 to 37°.

Site-directed mutagenesis was then used to prepare versions of pmHAS$^{1-703}$ with altered enzymatic activity. Synthetic DNA oligonucleotides and multiple rounds of extension with Pfu DNA polymerase were used to add mutations to the coding region using the Quick-Change system from Stratagene. Through use of primers with mixed bases at certain positions, a wide variety of amino acid changes were generated. DNA sequencing was then employed to identify the changed residue. Several pmHAS$^{1-703}$ mutants have also been obtained having altered sugar transferase activity. Similar methodology has also been used to alter the HA-acceptor binding site of pmHAS$^{1-703}$.

Two positions of the pmHAS$^{1-703}$ sequence were mutated in the initial trials. Conserved aspartates at residue 196 or 477 were critical for HAS activity. Results are shown in Table VI.

TABLE VI

| Mutation (*) | HAS Activity | GlcNActase | GlcUAtase | SEQ ID NO: |
|---|---|---|---|---|
| D196E | W/O | W/O | YES | 16 |
| D196N | W/O | W/O | YES | 12 |
| D196K | W/O | W/O | YES | 17 |
| D477E | W/O | YES | W/O | 18 |
| D477N | W/O | YES | W/O | 11 |
| D477K | W/O | YES | W/O | 19 |
| WILD TYPE CONTROL | YES | YES | YES | 2 |

(*) Single letter code for amino acid changes at position 196 or 477 (as noted) in which wild type aspartate (D) is exchanged with an asparagine (N), glutamate (E), or lysine (K).
"W/O weak (<8% of wild-type) or no activity.

Figure 7:
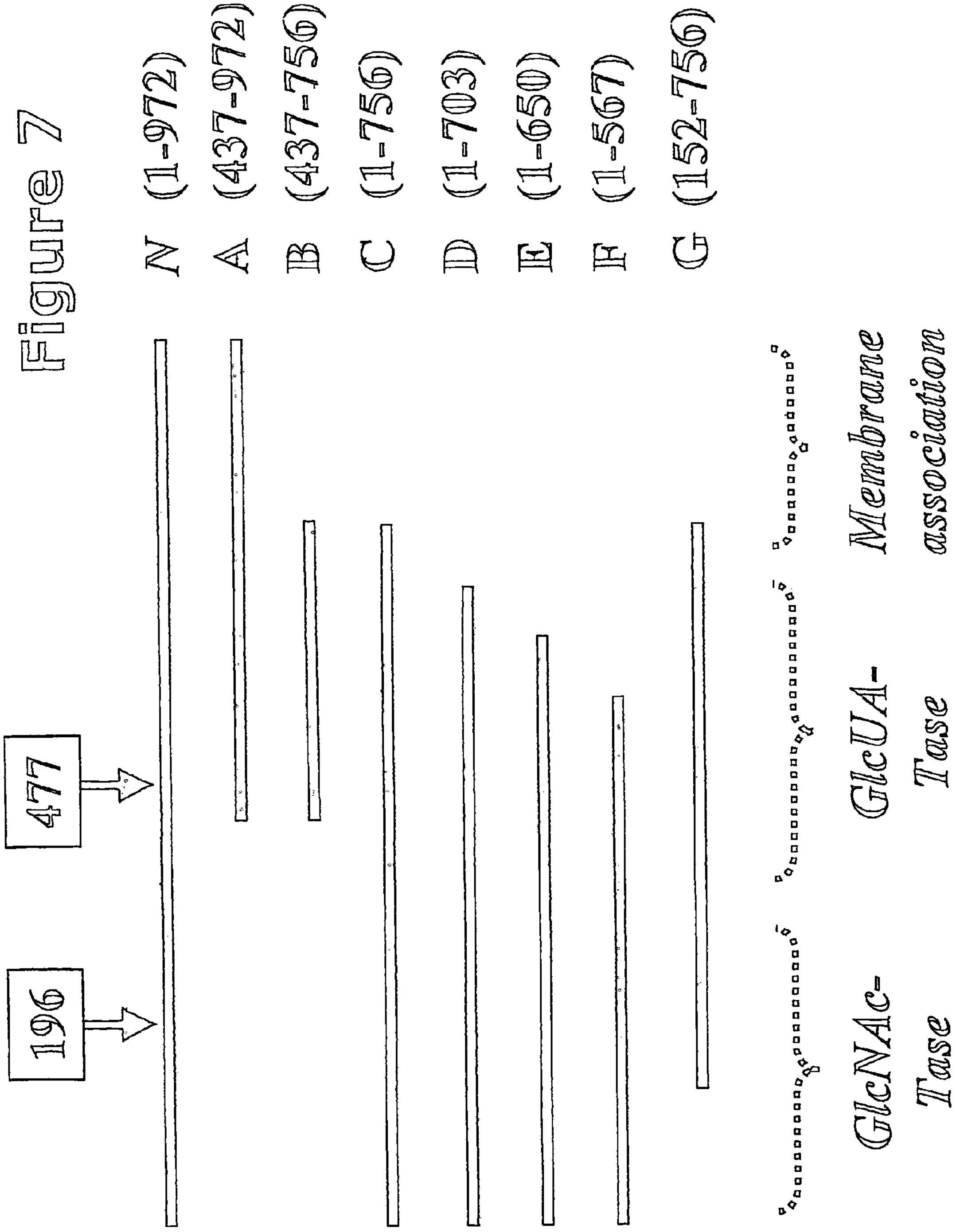
FIG. 7 is a pictorial representation of the pmHAS truncation mutants.

The mutant enzymes are useful for adding on a single GlcNAc or a single GlcUA onto the appropriate acceptor oligosaccharide. It appears that pmHAS$^{1-703}$ has two domains or two modules for transferring each sugar. One of ordinary skill in the art, given this specification, would be able to shift or to combine various domains to create new polysaccharide synthases capable of producing new polysaccharides with altered structures. Within such use, a variety of grafting techniques arise which utilize pmHAS$^{1-703}$ as the prototype. A graphical representation of each mutant as it relates to the pmHAS$^{1-703}$ sequence is shown in FIG. 7.

The critical structural elements of the HA oligosaccharide acceptor or primer molecule are currently being tested and identified. The smallest acceptor molecule with activity tested thus far is an HA disaccharide, although it is anticipated that molecules as short as a monosaccharides will be suitable for use with the present invention.

Chemically synthesized oligosaccharides (ref. Halkes, K. M. et al., 1998, Carbohydrate Research, 309, p. 161-174) were tested to see if they could be elongated by pmHAS$^{1-703}$. Each sugar was added individually to a final concentration of 0.05 mM to a series of 50 μL reaction mixtures containing 50 mM Tris, pH 7.2, 1 M ethylene glycol, 0.1 M ammonium sulfate, 10 mM $MnCl_2$, 800 μM UDP-GlcNAc, 600 μM UDP-[$^{14}$C]GlcUA ($6\times10^4$ dpm), and 2.5 μg pf pmHAS$^{1-703}$. After 20 minutes at 30 C, the HA polymer produced was quantitated by paper chromatography (polymer at the origin of the paper strip) and liquid scintillation counting (Jing and DeAngelis, 2000, Glycobiology, 10, p. 883-889).

TABLE VII

| Sugar* | [$^{14}$C]GlcUA incorporation (dpm) |
|---|---|
| 0 | 18 |
| N-MP | 16 |
| AN-MP | 24 |
| NA-MP | 140 |
| ANA-MP | 3540 |
| NAN-MP | 250 |
| ANAN-MP | 4000 |
| NANA-MP | 1710 |
| NANAN-MP | 2620 |
| ANANAN-MP | 3720 |

*Note: The sugar composition symbols: MP, methoxyphenyl group at the reducing end; N, GlcNAc; A, GlcUA.

It is obvious that the trisaccharide ANA (GlcUA-GlcNAc-GlcUA) is sufficient for high efficiency elongation by pmHAS, but certain disaccharides such as NA (GlcNAc-GlcUA), are also functional acceptors albeit at a lower efficiency than the longer sugars. Of course, one skilled in that art would expect that other sugar acceptors would be possible in light of the fact that pmHAS will elongate hyaluronic acid or chondroitin or chondroitin sulfate or heparin polysaccharides. The identity of the hexosamine and the availability of the hydroxyls (e.g., sulfated) may also be altered.

Recent data suggests that the pmHAS$^{1-703}$ enzyme has some flexibility with respect to the identity of the hexosamine group; i.e., other isomers will substitute for the GlcNAc sugar. For example, chondroitin pentamer [GalNAc-GlcUA-GalNAc-GlcUA-GalNAc], serves as an effective acceptor for pmHAS$^{1-703}$. Therefore, a synthetic molecule consisting of several hydroxyl groups, a pair of negatively charged groups (corresponding to the carboxyl groups of GlcUA sugar), and hydrophobic patches (analog of the carbon-rich side of the sugar ring) will work as a functional primer for pmHAS. Such an approach is not unprecedented as the polymerization of heparin, a glycosaminoglycan, can be primed with a rather simple aromatic xyloside instead of a complex proteoglycan core in vertebrate cells.

Computer modeling of HA oligosaccharides can visualize potential molecular shape. However, some proteins distort the sugar chains upon binding, thus making computer modeling somewhat more complicated. The most efficacious method of finding an artificial primer is a combinatorial chemistry approach. Closely related series of molecules are screened by high-throughput assay methodologies in order to detect HA elongation. pmHAS$^{1-703}$ is then tested for the ability to add an HA polymer onto synthetic primer candidates in a typical 96-well plate format. For example, a series of synthetic peptides (1 to 8 residues) terminating with a GlcNAc group using conventional $F_{moc}$ chemistry can be generated. Such peptides are particularly promising because they can adopt a variety of conformations and fit within the pmHAS$^{1-703}$ HA-binding pocket via an induced fit mechanism. Synthetic peptide chemistry is also much less cumbersome than carbohydrate chemistry. One of ordinary skill in the art, given the present specification, would be capable of using the known synthetic peptide chemistry techniques.

The amino acids are chosen with the goal of mimicking the properties of the GlcNAcGlcUA sugar repeats of HA. For example, glutamate or asparatate may be used as a substitute for the acid group of GlcUA, or glutamine or asparagine may be used as a substitute for the amide group of GlcNAc. Serine, threonine, or tyrosine can be used as substitutes for the hydroxyl groups and sugar rings in general. The peptide library terminates with a GlcNAc or GlcUA sugar group so that the demands on the pmHAS$^{1-703}$ enzyme s binding site and catalytic center are not overly burdensome. A vast variety of distinct peptides are made in parallel with a combinatorial approach; for example, with a hypothetical 6-7 residue peptide containing 1 to 3 different amino acids at each position, there are hundreds of possible peptides. The peptide combinatorial libraries will either be immobilized on plastic pins or plates.

The present invention also encompasses the development of a mutant version of pmHAS that utilizes a simpler molecule than an HA oligosaccharide as a primer. Chitopentaose (β1,4-GlcNAc homopolymer) is one such variant primer. Native pmHAS does not utilize chitopentaose as a primer, but a mutant pmHAS may elongate chitopentaose, a more readily available substance. The chitopentaose primer is attached to the solid phase by reductive amination to an amino-containing plate or to a carrier protein (albumin) for immobilization on a normal plastic plate. Various mutants could then be screened for function. Other potential non-sugar mimics contemplated for use are short poly(ethleneglycol)-based copolymers containing styrene, sulfonate, acrylate, and/or benzoate groups.

Certain experiments are useful for detecting a protein s binding sites. Photoaffinity labeling is used to cross-link a radioactive HA oligosaccharide analog containing an aryl azide to the pmHAS$^{1-703}$ protein. The binding site of the pmHAS$^{1-703}$ protein is obtained through peptide mapping and Edman sequencing. With this information, mutants are prepared with alterations at the binding site. In the chitopentaose example, removal of some of the basic residues of the HA-binding site (which normally contact the carboxylate of GlcUA) and substitution of neutral polar residues would be chosen. As described above, a variety of site-directed mutants using a mutagenic oligonucleotide with mixed bases at certain positions have been generated. Such a mixed-base approach economizes on the number of custom oligonucleotides and transformations required. A high-throughput screen is then used to assess the ability of the mutant pmHAS to elongate the synthetic primer with a HA chain. An empirical approach can also be used to randomly mutate pmHAS$^{1-703}$ (either chemical mutagens or with a passage through a mutator strain) and then screen.

Figure 8:
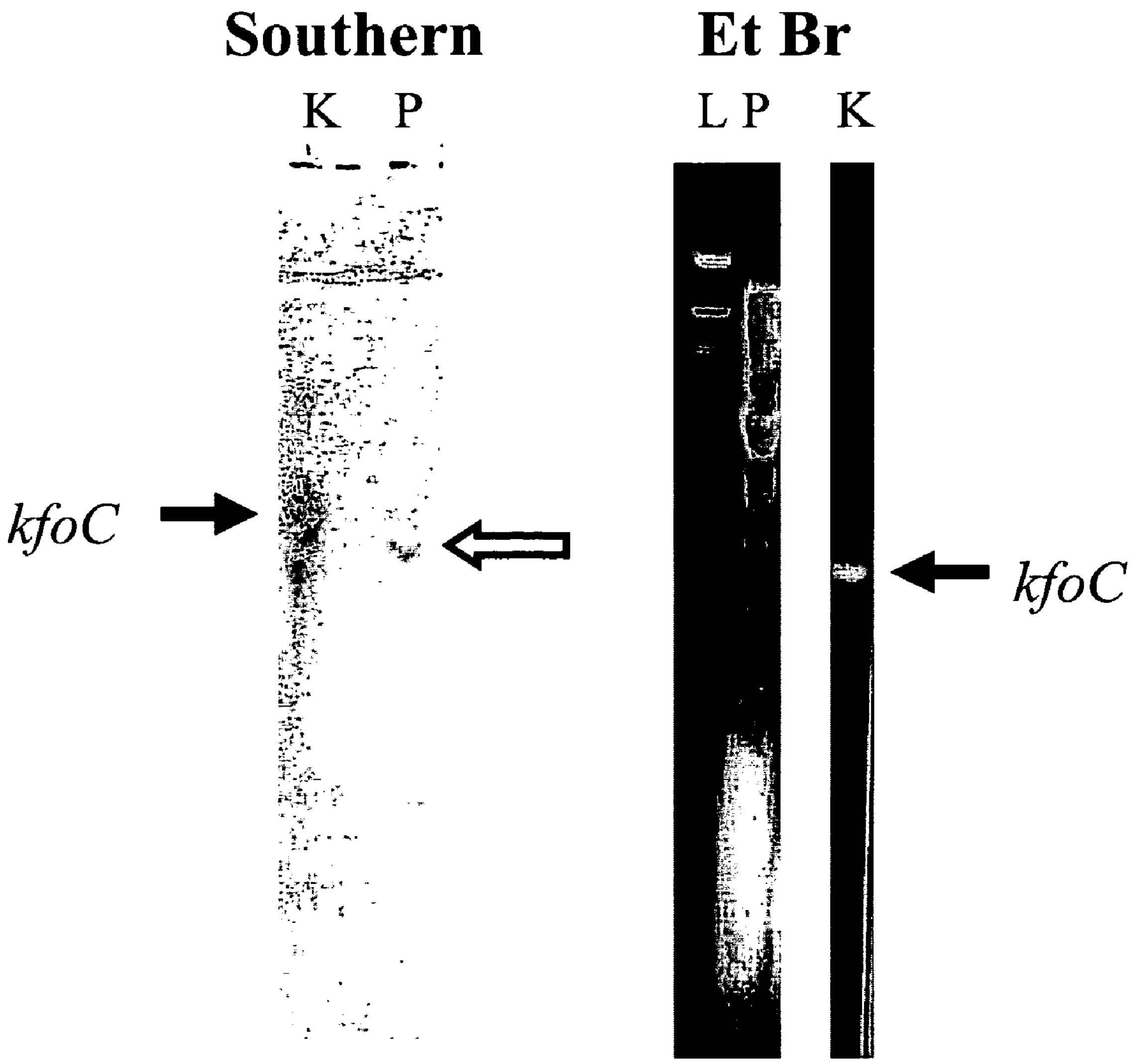
FIG. 8 is a Southern Blot showing the hybridization of the pmCS gene with the KfoC gene.

Recent work with the *E. coli* K5 KfiA and KfiC enzyme complex, which together with polymerizes heparosan, differ from the hereinafter described pmHS1 and PmHS2, which are both single proteins that can transfer both sugars to the nonreducing end of acceptor molecules in vitro. In 2002, an *E. coli* K4 enzyme, called KfoC which is 60% identical to pmCS and that hybridizes to pmCS, SEQ ID NO:3, under standard stringency hybridizations conditions, was described as being a chondroitin polymerase that adds on chains to chondroitin acceptors. In particular, the present applicants used the pmCS gene DNA as a hybridization probe for detecting other chondroitin synthase genes and in particular, the *E. coli* K4 kfoC gene DNA. In general, a commercial Southern blot kit (Dig Hi-Prime, Roche) was used to label restriction fragments containing pmCS with digoxigenin probe. This probe was used to analyze a Southern blot (FIG. 8) containing a PstI/EcoRI digest of Type F *Pasteurella multocida* genomic DNA (a positive control; P lane), a PCR product of the kfoC gene (corresponding to product of Ninomiya et al, 2002; lane K), or Lambda HindIII standard (lane L). The hybridization was carried out at 37 □C overnight in the manufacturer's buffer (Dig Easy Hyb) at 37 □C overnight. The blot was washed with 2×SSC, 0.1% SDS at 30 □C for 15 min twice, then for 30 min in 0.5×SSC, 0.1% SDS at 30 □C before using the manufacturer's Dig-antibody protocol for colorimetric detection. The kfoC band is apparent (KfoC black arrow) as well as the native *Pasteurella* gene (white arrow). No spurious hybridization signals were seen from other irrelevant DNA species. Therefore, the knowledge of the pmCS sequence can be used to identify other chondroitin synthase candidates by known standard methodology.

In order, to identify the important domains of the 972-residue pmHAS polypeptide, the protein was truncated at the amino- and/or the carboxyl-termini. Polymerase chain reaction with primers corresponding to various internal sequences was used to generate a series of recombinant proteins for expression (Table VIII).

TABLE VIII

| | | Enzyme Activity | | | |
|---|---|---|---|---|---|
| Protein* | Localization | HAS | GlcNAc-Tase | GLCUA-Tase | SEQ ID NO: |
| 1-972 | Membrane | + | + | + | 2 |
| 437-972 | Inclusion body | – | – | – | 13 |
| 437-756 | Inclusion body | – | – | – | 14 |
| 1-756 | Membrane | + | + | + | 20 |
| 1-703 | Soluble | + | + | + | 9 |
| 1-650 | Soluble | – | + | – | 10 |
| 1-567 | Inclusion body | – | – | – | 21 |
| 152-756 | Inclusion body | – | – | – | 15 |

+, active;
–, inactive

The different truncated proteins are described by their constituent amino acid residues.

Figure 9:
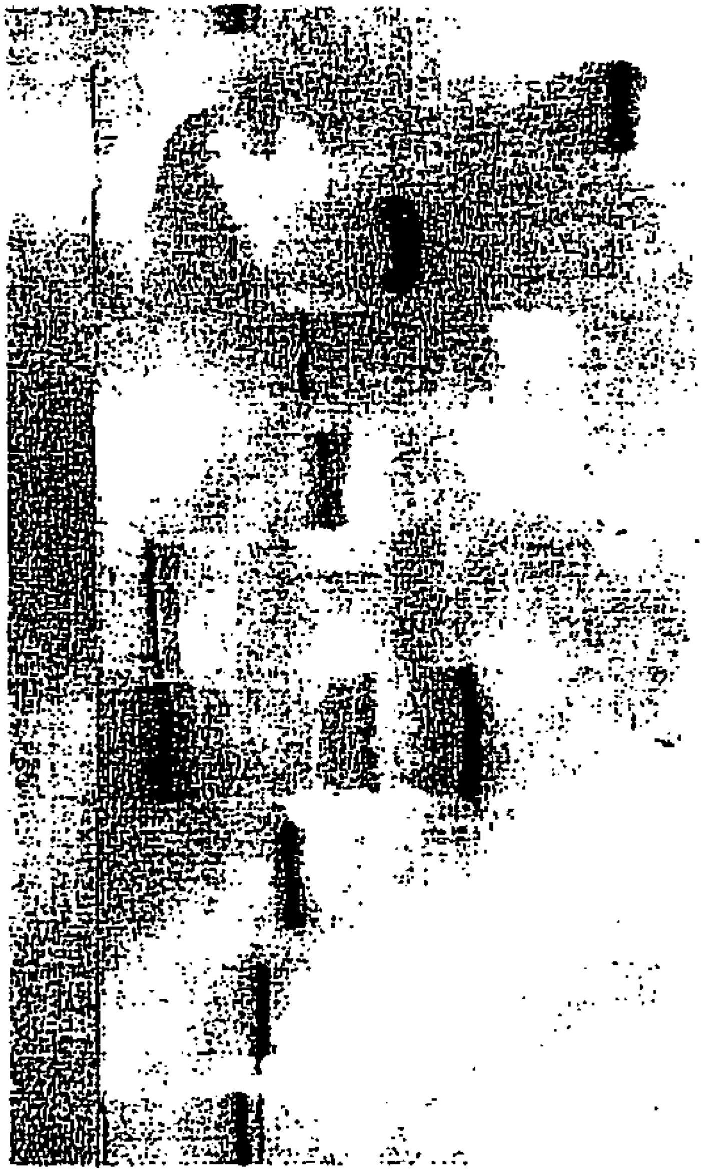
FIG. 9 is a Western Blot analysis showing the expression of pmHAS and its truncated forms. Either whole cell lysates ($pmHAS^{437-972}$, $pmHAS^{1-567}$, and $pmHAS^{152-756}$) or membrane preparations ($pmHAS^{437-756}$, $pmHAS^{1-567}$, r1-972, n1-972) or B-Per extract ($pmHAS^{1-703}$) were analyzed by Western blot (r,recombinant from *E. coli*; n, native from P-1059). The bars on the left denote the position of molecular weight standards (from top to bottom: 112, 95, 55, and 29 kDa).

The truncated polypeptides were expressed well in *E. coli* and the experimentally determined molecular weight corresponded to the predicted size (FIG. 9). In vitro assays were utilized to assess the HA synthase activity, or the two half-reactions, either GlcNAc-Tase or GlcUA-Tase, that comprise HA polymerization (Table VIII). Some of the truncations were inactive. pmHAS$^{1-756}$ (SEQ ID NO: 20), which lacks the carboxyl-terminal 216 amino acid residues, was an active HA synthase and, for the most part, membrane-associated. An interesting observation was that pmHAS$^{1-703}$ (SEQ ID NO: 9), which lacks a larger portion of the carboxyl terminus, retained HAS activity but was transformed into a cytoplasmic protein accounting for up to ~10% of the total cellular protein. Thus the carboxyl-terminus, especially residues 703-756, is responsible for the association of native pmHAS with the membrane. With the further deletion from carboxyl-terminus, pmHAS$^{1-650}$ (SEQ ID NO:10) was still expressed at a high level as a soluble protein, yet was inactive as a HA synthase. However, pmHAS$^{1-650}$ was capable of transferring GlcNAc to the nonreducing terminal GlcUA of HA-derived oligosaccharides. As expected from the lack of HAS activity, pmHAS$^{1-650}$ did not transfer GlcUA to HA oligosaccharides, which terminated with a GlcNAc residue. Thus residues 650-703 are required, either directly or indirectly, for transferring GlcUA to the HA chain. pmHAS$^{1-567}$ (SEQ ID NO:21), with a further truncation at the carboxyl terminus, and pmHAS$^{152-756}$ (SEQ ID NO:15) were insoluble, inactive proteins. These latter mutant proteins are likely to be misfolded inclusion bodies as they were not dissolved by a buffer containing the detergents NP40, sodium deoxycholate and SDS unless boiled; in contrast, full-length pmHAS was readily solubilized by this buffer at room temperature.

Figure 10:
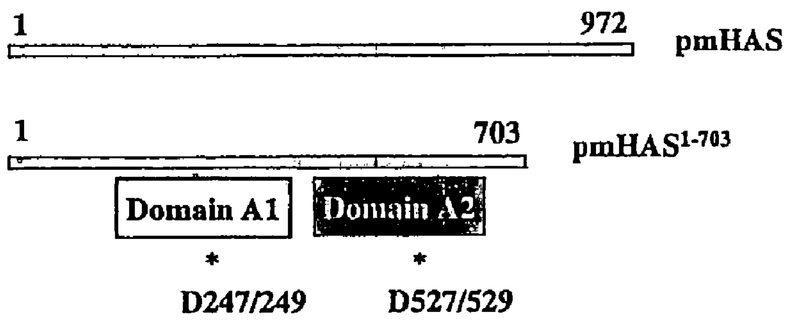
FIG. 10 is a pictorial representation of domains A1 and A2 of pmHAS. (A) The approximate relative positions of domain A1 and A2 in pmHAS and $pmHAS^{1-703}$. (B) Partial alignment of the amino acid sequences of the two domains (residue 161-267 and 443-547). The aspartate residues mutated in our studies were marked with *. Identical residues are in bold.

Site-directed mutagenesis of pmHAS$^{1-703}$. Based on similarities in the amino acid sequence and predicted topology, two families of HASs have been proposed. The only member of Class II, pmHAS, possesses motifs similar to two out of the seven putative conserved motifs of Class I HASs; these motifs contain DGS and DXD sequences. The pmHAS sequence has a duplication of a ~100-residue long element in the regions from residue 161-267 and from residue 443-547 with these conserved motifs. These two elements of pmHAS that contain the conserved motif are named domain A1 and domain A2, respectively. This nomenclature is based on the similarity of these pmHAS domains to the A domain proposed for other glycosyltransferases that make β-linked carbohydrates. FIG. 10 shows the amino acid alignment of the two putative domains and their relative position in pmHAS$^{1-703}$. The above truncation results show that the GlcNAc-transferase activity can be separated from the HA synthase activity of pmHAS. Therefore, the domain A1 is responsible for the GlcNAc-transferase function of HA synthase while domain A2 is responsible for GlcUA-transferase activity. $pmHAS^{1-703}$, a short polypeptide with complete HAS activity, was subjected to site-directed mutagenesis in order to further refine the results. We mutated the conserved aspartate residues (residue 196 and 477; underlined, FIG. 10) of the two DGS motifs in the two domains were mutated.

Six different mutants were produced containing the following changes: domain A1-D196E, D196N, D196K, and domain A2-D477N, D477E, D477K. Upon sequence verification of the complete open reading frame, it was found that mutants with D196K, D196N, or D477N also had spontaneous mutation of D702I. As it was the penultimate residue of $pmHAS^{1-703}$, and as $pmHAS^{1-650}$ was a functional GlcNAc-Tase, this undesired mutation does not greatly affect the interpretation of the results of the desired point mutations (as the results below demonstrate, the mutants with substitutions at D196 or D477 sharing the same D702I mutation had different transferase activities supporting this conclusion). All of the mutant proteins were produced at similar levels. All of the mutants were either inactive or made long HA polymer with low efficiency as measured by the full HAS assay (Table IX).

TABLE IX

| Mutants | Enzyme Specific Activity | | |
|---|---|---|---|
| | HAS | GlcNAc-Tase | GlcUA-Tase |
| D477N | 2 | 200% | 2% |
| D477K | 0.3 | 70% | 2% |
| D477E | 4 | 50% | 4% |
| D196N | 0.1 | 0% | 74% |
| D196K | 0.01 | 3% | 100% |
| D196E | 0.3 | 7% | 60% |

Specific activities of various $pmHAS^{1-703}$ mutants. Equivalent amounts of $pmHAS^{1-703}$ proteins (based on Western blot) were assayed. The specific activities (average of duplicate determinations) are indicated as the percentage of the wild-type sequence $pmHAS^{1-703}$ (set as 100%). The specific activities (picomoles of monosaccharide transfer/mg of protein/min) for wild-type enzyme in the three different assays were: HAS, 37; GlcNAc-Tase, 63; GlcUA-Tase, 76.

However, $pmHAS^{1-703}$ domain A1 mutants containing D196E, D196K or D196N maintained high levels of GlcUA-transferase activity. On the other hand, $pmHAS^{1-703}$ domain A2 mutants containing D477E, D477K or D477N had high levels of GlcNAc-transferase activity implying that the two aspartate residues were critical for HA synthase function. Thus, two distinct transferase domains exist in the pmHAS enzyme; domain A1 is the GlcNAc-transferase and domain A2 is the GlcUA-transferase.

$K_M$ analysis of mutants. In order to detect potential interaction or cross-talk between the two putative domains of pmHAS, the apparent affinity of the wild-type and the $pmHAS^{1-703}$ mutants were compared for the UDP-GlcNAc or for the UDP-GlcUA substrates by measuring their Michaelis constants ($K_M$) for the functional transferase activity. Titration of the UDP-sugars in the half assays for the GlcUA and GlcNAc transferases were performed (Table X).

TABLE X

| Enzyme | $K_M$ for UDP-GlcNAc (mM) | $K_M$ for UDP-GLcUA (mM) |
|---|---|---|
| wild type | 160 +/− 60 | 140 +/− 40 |
| D477N | +/−45 | ND* |
| D477K | +/−40 | ND |
| D477E | 150 +/− 30 | ND |
| D196N | ND | 240 +/− 140 |
| D196K | ND | 115 +/− 45 |
| D196E | ND | 140 +/− 35 |

$K_M$ values for UDP-sugar precursors of $pmHAS^{1-703}$ and mutant proteins. The results standard deviation are shown. The apparent affinities of the functional glycosyltransferase activities of the various enzymes are similar. The typical level of radiolabel incorporation at the saturating UDP-sugar concentration using 1 mg of total protein/assay point was 500-1000 dpm $[^{14}C]$GlcA or 200-800 dpm $[^{3}H]$GlcNAc for the UDP-GlcNAc or UDP-GlcUA $K_M$ values, respectively.
ND, not done.

The results indicate that the KM values of the domain A1 or A2 mutants were not very different from the wild-type sequence $pmHAS^{1-703}$. Thus, the functional disruption of one glycosyltransferase domain of pmHAS does not affect greatly the other domain.

Figure 11:
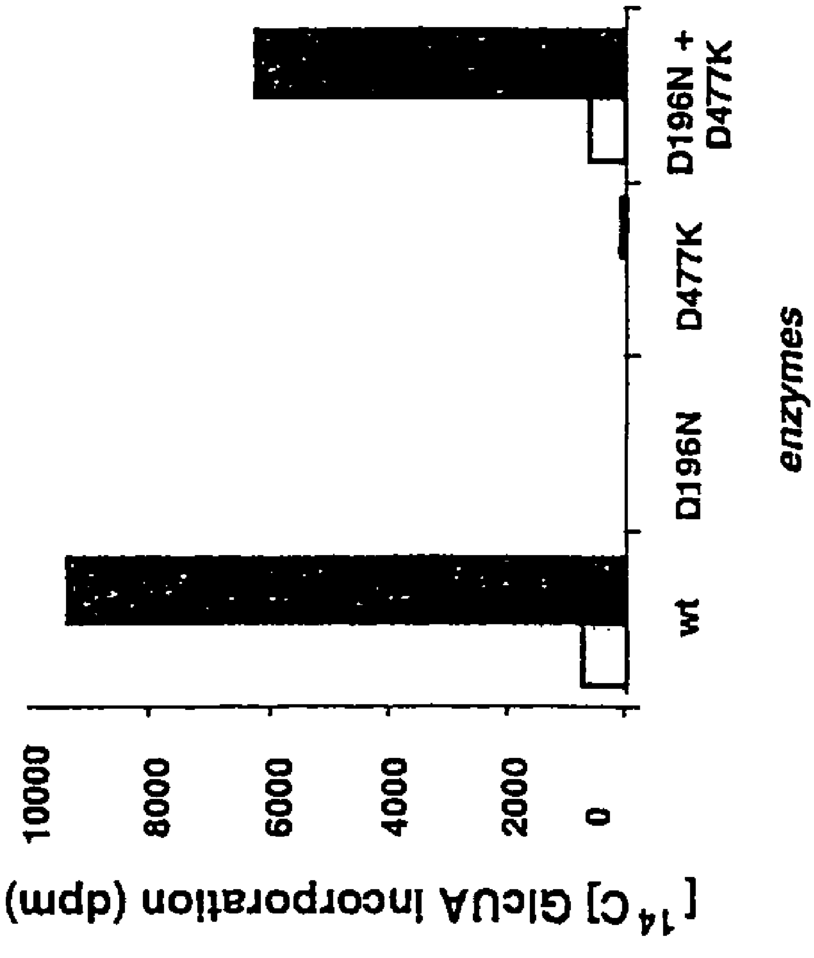
FIG. 11 is a graphical representation of the complementation of the HAS activity of mutant enzymes in vitro. HAS enzyme assays with HA-derived acceptor were performed in the presence of either wild type $pmHAS^{1-703}$ alone, or D196 mutant alone, or D477 mutant alone or in the presence of both D196 and D477 mutants, for either 25 minutes (open bars) or 1.5 hours (solid bars).

Complementation of HAS activity with two mutant proteins in vitro. The domain A1 and the domain A2 mutants fulfill the complete function of a HAS even if present on separate polypeptide molecules if the mutants are mixed together in the same reaction. The standard HA synthesis assay was performed with extracts containing either the truncated wild-type sequence $pmHAS^{1-703}$ enzyme, or a GlcNAc-Tase mutant enzyme (D196N) alone, or a GlcUA-Tase mutant enzyme (D477K) alone, or a mixture of the two mutant enzymes. These two mutants were selected as they were the least active in the HA synthase assay (Table IX). Equivalent amounts of wild-type $pmHAS^{1-703}$ polypeptide (2 μg of total protein) or mutant $pmHAS^{1-703}$ polypeptide (based on Western blot analysis) were used for these assays. In the mixture, the same amount of each mutant polypeptide was added (equivalent to 4 μg of total protein of wild-type extract). The D196N mutant alone or the D477K mutant alone did not produce detectable amounts of HA chains (FIG. 11), but when the mutant polypeptides were incubated together, along with a HA oligosaccharide acceptor (4-10 sugars long), longer HA polymers were made. The amount and the rate of HAS activity of the combination of the two mutants was similar to the parallel reaction containing the wild-type $pmHAS^{1-703}$. Without HA oligosaccharide acceptor, the wild-type $pmHAS^{1-703}$ enzyme could still make HA, albeit with lower efficiency (2 μg total protein in 3 hr assay incorporated 220 dpm). The combination of the two mutant extracts, however, did not make detectable amounts of HA polymer in absence of the HA acceptor (incorporation 4 dpm). These results suggest that in the presence of HA oligosaccharide acceptor, the two kinds of transferases could work together and sequentially transfer GlcNAc and GlcUA monosaccharides to an existing HA chain in an alternating fashion. Apparently chain initiation requires two active transferases to be present on the same polypeptide.

*P. multocida* Chondroitin Synthase pmCS

As mentioned previously, chondroitin $[\beta(1,4)GlcUA-\beta(1,3)GalNAc]_n$, heparin/heparan $[\alpha(1,4)GlcUA-\beta(1,4)GlcNAc]_n$, and hyaluronan $[\beta(1,4)GlcUA-\beta(1,3)GlcNAc]_n$ are the three most prevalent GAGs found in humans. In the former two polymers, usually n=20 to 100 while in the case of HA, $n=10^{3-4}$. Chondroitin and heparin/heparan, but not HA, are synthesized as glycoproteins and are sulfated at various positions in vertebrates. A substantial fraction of the GlcUA residues of heparin are epimerized to form iduronic acid. Many lower animals possess these same GAGs or very similar molecules. A chondroitin synthase from *P. multocida* (pmCS) is described and enabled in copending U.S. Ser. No. 09/842,484 which is expressly incorporated herein in its entirety by reference.

Briefly, the glycosyltransferase responsible for polymerizing the chondroitin backbone component of the capsular polysaccharide has also been molecularly cloned and was named pmCS (SEQ ID NO:4). The pmCS enzyme appears to be a close homolog of the pmHAS enzyme (FIG. 12). In pmHAS one domain, called A1, is responsible for GlcNAc transfer and the other domain, called A2, is responsible for GlcUA transfer. Comparison of the pmHAS and the pmCS sequences reveals that the majority of the sequence differences exist in the A1 domain. The pmCS enzyme transfers a different hexosamine, GalNAc, thus this observation is consistent with the two-domain structure for pmHAS.

Mutant enzymes derived from the soluble $pmCS^{1-704}$ parental dual-action chondroitin synthase were also created with the ability to elongate HA or chondroitin-based oligosaccharides by adding a single β3-GalNAc monosaccharide to the non-reducing terminus. The mutants were formed by targeting the DXD motif in Domain A2 (also found in pmHAS) by site-directed mutagenesis (same general procedure as with pmHAS); the two aspartate (D) groups were converted into asparagine (N) residues forming the NXN mutants. Several independent clones producing mutant $pmCS^{1-704}$ NXN enzyme were assayed individually for the ability to transfer $[^3H]$GalNAc to HA oligosaccharides using UDP-GalNAc in analogy to pmHAS transferring $[^3H]$GalNAc to HA oligosaccharides using UDP-GlcNAc as described hereinabove. The NXN mutants could transfer a single GalNAc sugar like the wild-type sequence $pmCS^{1-704}$ enzyme.

The NXN mutants could not, however, make long chondroitin chains when assayed in a different system that only detected the addition of both GlcUA and GalNAc. This system utilizes leech hayluronidase-generated HA8-12mer oligosaccharide (this acceptor has a non-reducing end GlcNAc; 1.5 ug), 15 mM UDP-GlcUA, 0.1 mM UDP-$[^3H]$GalNAc ($4.4\times10^5$ dpm) in 20 μL reaction mixtures containing 50 mM Tris, pH 7.2, 1 M ethylene glycol, 0.1 M ammonium sulfate, 10 mM $MnCl_2$. Extracts containing either the wild-type $pmCS^{1-704}$ (CS-WT) or the NXN mutant extracts were assayed for 120 minutes at 30°. After the reaction, the labeled polymer produced was quantitated by paper chromatography (polymer at the origin of the paper strip) and liquid scintillation counting. The NXN mutants (3 different clones: 2, 3, or 7) do not display high incorporation in this assay because these single-action enzymes cannot add the required GlcUA to the acceptor terminus: without prior GlcUA transfer, the radioactive GalNAc is never added (See Table XI). In contrast, the parental dual-action pmCS enzyme can perform GlcUA addition thus allowing the radioactive GalNAc to be added; furthermore, multiple rounds of GlcUA and GalNAc addition are possible with wild-type enzyme yielding a very high signal. Overall, such controllable single-action enzymes are useful for bioreactor systems for oligosaccharide syntheses or for construction of sugar libraries.

TABLE XI

| Enzyme | $[^3H]$GalNAc (dpm) |
|---|---|
| None | 2 |
| CS-NXN-2 | 141 |
| CS-NXN-3 | 152 |
| CS-NXN-7 | 242 |
| CS-WT | 173,000 |

Additional pmHAS Mutants pmHAS and pmCS both utilize two relatively independent glycosyltransferase sites. Other sequence motifs are also discussed with respect to their roles in polysaccharide biosynthesis. Hereinafter is the analysis of truncated pmHAS proteins used to delineate essential regions.

In order to analyze the contribution of the amino terminal region of pmHAS, various recombinant truncated polypeptides ($pmHAS^{46-703}$ SEQ ID NO:27, $pmHAS^{72-703}$ SEQ ID NO:28, $pmHAS^{96-703}$ SEQ ID NO:29 and $pmHAS^{118-703}$ SEQ ID NO:30) were produced in *E. coli*. The experimentally determined molecular weights corresponded to the predicted sizes. The truncated versions $pmHAS^{46-703}$ and $pmHAS^{72-703}$ were as active as $pmHAS^{1-703}$, a soluble polypeptide with complete HAS activity. $pmHAS^{96-703}$ expressed at a very low level compared with other constructs but was active. $pmHAS^{118-703}$ expressed better than $pmHAS^{96-703}$ and still elongated HA chains. Therefore, further deletion beyond residue 72 appears to affect the overall folding efficiency of the entire polypeptide. Observation of lower molecular weight degradation bands derived from $pmHAS^{118-703}$ on Western blots also suggests that improper folding occurs to some extent. Overall, these findings suggest that the amino-terminal 117 residues are not required for HA synthase activity.

It was discussed hereinabove that $pmHAS^{1-650}$ (SEQ ID NO:10) lost its GlcUA-transferase activity. To further delineate the GlcUA-transferase domain within the carboxyl terminal region, two slightly longer mutants, $pmHAS^{1-668}$ SEQ ID NO:31 and $pmHAS^{1-686}$ SEQ ID NO:32 were created. Both mutants also could not polymerize HA due to the loss of GlcUA-transferase activity, indicating that the carboxyl-terminal boundary of the GlcUA-transferase resides between residues 686 and 703.

Others of ordinary skill in the art have used hydrophobic cluster analysis to identify two types of domains conserved in a variety of β-linked glycosyltransferases that use nucleotide diphospho sugar as donors, termed Domain A and Domain B. Characterization of two conserved DGS motifs in the two A domains of pmHAS indicate that the two aspartate residues are essential for HAS activity. The existence of a third potential DGS sequence motif in pmHAS is also located at position 563-565. In order to determine if this motif is critical for synthase activity in the same manner as the other two DGS motifs, D563 of $pmHAS^{1-703}$ was mutated into a glutamate, asparagine or lysine residue. All of the mutants behaved like wild-type $pmHAS^{1-703}$ indicating that the third motif DGS is not essential for the catalytic activity of pmHAS. This also demonstrates that certain residues may be changed, but the enzyme remains a functional synthase—i.e. with respet to the "functionality" language of the hereafter appended claims.

Figure 13:
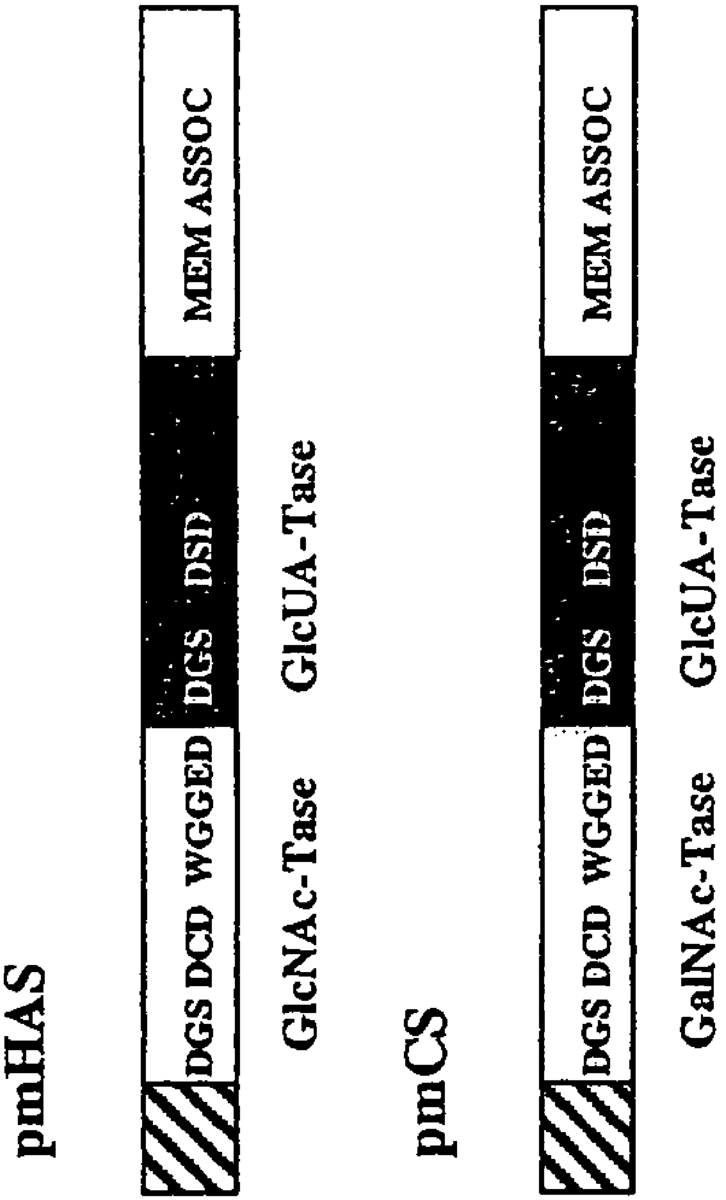
FIG. 13 is a pictorial representation of a model of the two putative glycosyltransferase sites of pmHAS and pmCS. PmHAS and pmCS contain two distinct and relatively independent glycosyltransferase sites. Each site possesses a DGS and a DXD amino acid motif. A WGGED motif is found near the junction of the two domains, and is involved in hexosamine-transferase activity. The carboxyl-terminus is involved in membrane association (MEM ASSOC), but is not required for catalytic activity. Residues 1-117 (cross-hatched) appear dispensable for catalysis of sugar transfer but may contain structure scaffolding or play other roles.

The DXD motif is found in many glycosyltransferases. pmHAS has two DXD motifs, one in domain A1 and another in domain A2 (FIG. 13). X-ray crystallography of the *Bacillus* SpsA protein/UDP-complex suggests that the DXD motif is involved in binding metal ion coordinated with the beta phosphate and the ribose moiety of the UDP-sugar. The involvement of the individual aspartate residues of DXD in pmHAS, therefore, was characterized. The aspartate residues (residue 247, 249, 527 or 529) of the two DXD motifs of $pmHAS^{1-703}$ were mutated in the two domains. Mutants were produced containing the following changes in domain A1-D247E (SEQ ID NO:33), D247N (SEQ ID NO:34), D247K (SEQ ID NO:35), D249E (SEQ ID NO:36), D249N (SEQ ID NO:37), or D249K (SEQ ID NO:38) and in domain A2-D527N (SEQ ID NO:39), D527E (SEQ ID NO:40), D527K (SEQ ID NO:41), D529E (SEQ ID NO:42), D529N (SEQ ID NO:43), or D529K (SEQ ID NO:44). Upon sequence verification of the complete open reading frame, mutants with D247N, D249K, D529E and D527K were found to also have a mutation of D702I that did not affect HAS activity. All of the mutant proteins were produced at similar levels in soluble form. In vitro assays were utilized to assess the HA synthase activity (e.g., polymerization of long HA chains), or the two half-reactions, either GlcNAc-transferase or GlcUA-transferase activity. All of the mutants were inactive as HA synthases except D529E which had only 10% of the wild type activity (Table XII).

As predicted, the enzymes containing mutations at position 247 or 249 (domain A1 mutants) maintained high levels of GlcUA-transferase activity. On the other hand, the enzymes containing mutations at position 527 or 529 (domain A2 mutants) had high levels of GlcNAc-transferase activity. Therefore, all of the four aspartate residues were critical for HA synthase function. These results confirm the model of two distinct transferase sites in a single pmHAS polypeptide; domain A1 is essential for GlcNAc-transferase activity and domain A2 is essential for GlcUA-transferase activity.

TABLE XII

| | Specific Activity | | |
|---|---|---|---|
| Enzyme | HAS | GlcNAc-Transferase | GlcUA-Transferase |
| D247N | <0.1 | <0.1% | 110% |
| D247K | <0.1 | <0.1% | 130% |
| D247E | <0.1 | <0.1% | 90% |
| D249K | <0.1 | <0.1% | 100% |
| D249E | <0.1 | <0.1% | 105% |
| D527K | <0.1 | 115% | <0.1% |
| D527E | <0.1 | 120% | 0.1% |
| D529N | <0.1 | 230% | <0.1% |
| D529K | 5% | 360% | <0.1% |
| D529E | 10% | 110% | 15% |

Specific activities of the various $pmHAS^{1-703}$ DXD mutants. Equivalent amounts of $pmHAS^{1-703}$ proteins (based on Western blot) were assayed. The specific activities are indicated as the percentage of the wild-type sequence $pmHAS^{1-703}$ (set as 100%). The specific activities for wild-type enzyme in the three assays were 6-34 picomole of monosaccharide transfer/mg/min. The DXD motif of each domain is involved in HA polymerization.

The two DXD motifs of pmHAS are predicted to be involved in metal ion binding based on the SpsA structure. Experiments were designed to examine (a) if other metal ions could rescue mutant activity, and (b) if the two separate active sites have similar metal ion preference. The presence of $Co^{2+}$, $Mg^{2+}$ or $Ca^{2+}$ did not convert the DXD mutants into functional HASs. GlcNAc-transferase or GlcUA-transferase assays were performed with wild-type $pmHAS^{1-703}$ in the presence of 20 mM $Mn^{2+}$, $Co^{2+}$ or $Mg^{2+}$. Although the highest activities were obtained in the presence of 20 mM of $Mn^{2+}$, the GlcNAc-transferase activity preferred $Co^{2+}$ over $Mg^{2+}$ while the GlcUA-transferase activity preferred $Mg^{2+}$ over $Co^{2+}$ (Table XIII).

TABLE XIII

| | Specific Activity | | | |
|---|---|---|---|---|
| | GlcNAc-Transferase | | GlcUA-Transferase | |
| Enzyme | $Co^{2+}$ | $Mg^{2+}$ | $Co^{2+}$ | $Mg^{2+}$ |
| D247N | | | 15% | 52% |
| D247K | | | 1% | 37% |
| D247E | | | 9% | 55% |
| D249N | | | 14% | 58% |
| D249K | | | 10% | 46% |
| D527E | 87% | 27% | | |
| D529N | 75% | 59% | | |
| Wt | 77% | 39% | 18% | 66% |

Metal ion preference of the GlcNAc-transferases and the GlcA-transferase activities. Equivalent amounts of wild type $pmHAS^{1-703}$ protein (wt) or DXD mutants were assayed in the presence of 20 mM of $Mn^{2+}$, $Co^{2+}$ or $Mg^{2+}$. The activities are indicated as the percentage of their activities in the presence of $Mn^{2+}$ (set as 100%). Overall, $Mn^{2+}$ is the best cofactor, but in its absence, the GlcNAc-transferase preferred $Co^{2+}$ while the GlcUA-transferase preferred $Mg^{2+}$. The active sites of domain A1 and A2 are similar yet distinct.

Similar results were obtained when assays were performed with the $pmHAS^{1-703}$ mutants that have only a single transferase activity. In a preferred embodiment, both Ds (aspartates) are mutated to Ns (asparagines): one D can be changed to N but the resulting mutant enzyme may retain some sloppiness—i.e., the enzyme may incorporate both natural sugars. As such, it may be preferred to mutate both Ds of the DXD motif to Ns in order to truly kill or knock-out the enzymatic activity of the domain.

In the pmHAS polypeptide sequence, there is a segment similar to portions of mammalian UDP-GalNAc:polypeptide N-acetylgalactosaminyltransferases (ppGaNTransferases) that catalyzes the initial step for making the oligosaccharide moiety on O-linked glycoproteins. The W366GGED370 motif, which resides between the putative domain A1 and domain A2, does not exist in the sequences of other HA synthases from *Streptococcus*, vertebrates, or *Chlorella* virus. To study the function of the WGGED motif in pmHAS, E369 or D370 were mutated. Six different mutants were produced each containing one of the following changes, E369D (SEQ ID NO:45), E369Q (SEQ ID NO:46), E369H (SEQ ID NO:47), D370E (SEQ ID NO:48), D370N (SEQ ID NO:49), or D370K (SEQ ID NO:50). All the mutants were expressed at comparable levels with the wild type enzyme. Based on the results of the HAS assays and the two half assays, mutation at either of these two sites resulted in the loss of only GlcNAc-transferase activity, but not the GlcUA-transferase activity (Table XIV), suggesting that the WGGED motif in pmHAS-D is essential for GlcNAc-transferase activity.

TABLE XIV

| | Specific Activity | | |
|---|---|---|---|
| Enzyme | HAS | GlcNAc-Transferase | GlcUA-Transferase |
| D370N | <0.1 | 1% | 80% |
| D370K | <0.1 | 2% | 80% |
| D370E | 1% | <0.1% | 105% |

TABLE XIV-continued

| | Specific Activity | | |
|---|---|---|---|
| Enzyme | HAS | GlcNAc-Transferase | GlcUA-Transferase |
| E369H | <0.1 | 5% | 130% |
| E369D | <0.1 | 1% | 55% |
| E369Q | 1% | 1% | 60% |

Specific activities of the pmHAS$^{1-703}$ WGGED mutants. Equivalent amounts of pmHAS$^{1-703}$ proteins (based on Western blot) were assayed. The activities are indicated as the percentage of the wild type pmHAS$^{1-703}$ (100%). The WGGED motif is involved in the transfer of GlcNAc.

As described hereinabove, a combination of two DGS motif mutants, D196N, a GlcUA-transferase and D477K, a GlcNAc-transferase, fulfill the complete function of a HAS when mixed together in the same reaction along with a HA oligosaccharide acceptor. Hereinafter the standard HA synthesis activity assay was performed with several different combinations of DXD or WGGED mutants. One GlcNAc-transferase mutant enzyme (a D527 or D529 mutant) and one GlcUA-transferase mutant enzyme (a D247, D249, E370, or D369 mutant) were combined in these tests. When the mutant polypeptides were incubated together, along with a HA oligosaccharide acceptor (4-10 sugars long), HA polymers were made. This demonstration further enables the proposition that two independent transferase sites sequentially transfer GlcNAc and GlcUA monosaccharides to an existing HA chain in an alternating fashion.

The chondroitin synthase, pCS, from Type F *P. multocida* is about 90% identical to pmHAS at the protein level. The majority of sequence differences exist in the vicinity of the domain A1 of pmHAS while their carboxyl-terminal halves are almost identical (described hereinabove). This is to be expected because the carboxyl-terminal half of pmHAS contains domain A2 which has the GlcUA-transferase active site. The pmCS also possesses two separate transferase sites with respect to pmCS, but the amino-terminal half is a GalNAc-transferase while the carboxyl-terminal half is a GlcUA-transferase. Thus, swapping the carboxyl-terminal GlcUA-transferase site between pmHAS and pmCS does not affect the sugar polymerizing activity. On the other hand, swapping of the amino-half of either pmHAS or pmCS changes the hexosamine transfer specificity. In order to test such swapping abilities, domain swapping between pmHAS and pmCS was performed by the PCR-overlapping-extension method (as described in Horton et al., 1989, which is expressly incorporated herein by reference in its entirety).The active truncated versions of the synthases, pmCS$^{1-704}$ and pmHAS$^{1-703}$, were used as the starting materials for the construction. Residues 427/428 of pmHAS and the equivalent site of pmCS, residues 420/421, were chosen as the initial splicing site based on comparisons of the amino acid sequences of pmHAS, pmCS and other GlcNAc-transferases.

The combination of residues 1-427 from pmHAS and residues 421-704 from pmCS (pmAC construct: SEQ ID NO:51) resulted in an active HAS. The opposite combination, consisting of residues 1-420 from pmCS and residues 428-703 from pmHAS (pmBD construct: SEQ ID NO:52), resulted in an active chondroitin synthase (Table XV).

TABLE XV

| Enzyme | Chondroitin Synthase | HA synthase |
|---|---|---|
| pmHAS$^{1-703}$ | − | + |
| pmCS$^{1-704}$ | + | − |
| pm-AC | − | + |
| pm-BD | + | − |

Activity of chimeric or hybrid *Pasteurella* synthases. The wild type enzymes and the chimeric or hybrid constructs (pm-AC, pmHAS$^{1-427}$-pmCS$^{421-704}$; pm-BD, pmCS$^{1-420}$-pmHAS$^{428-703}$) were tested in the HA or the chondroitin synthase assays. Domain A1 is responsible for hexosamine transfer and domain A2 is responsible for GlcUA transfer.

This finding indicates that the domain A1 dictates hexosamine transfer specificity. Also, the source of the GlcUA-transferase domain A2 does not affect the specificity of either the GalNAc-transferase or the GlcNAc-transferase activity. The two single-action transferase sites of pmHAS and pmCS are relatively independent.

The DXD motif is conserved in many glycosyltransferases from different families and the aspartates have been shown to be crucial for activity in enzymes whose function and sequences are highly divergent. pmHAS possesses a DXD motif in both domain A1 and domain A2. Mutagenesis of any of these four aspartates indicates that they are involved in HA polymerization in agreement with the presumed critical role of the motif. Mutation of the domain A1 DXD results in the loss of only GlcNAc-transferase activity while mutation of the domain A2 DXD results in the loss of only GlcUA-transferase activity.

Although the importance of the DXD motif was previously hypothesized, its function was not clear until very recently. Based on an X-ray crystal structure of SpsA, a family 2 glycosyltransferase, the DXD motif is now known as a nucleotide-binding element. The first aspartate forms a hydrogen bond with the ribose ring and the second aspartate coordinates with the metal cation bound to the phosphate to assist leaving group departure. The involvement of the DXD motif in nucleotide binding and in metal ion interaction is supported by several other available glycosyltransferase structures which were solved later, including bovine β4-galactosytransferase, rabbit N-acetylglucosaminyltransferase I (in which the motif is in the form of EDD and the last aspartate, D213, makes the only direct interaction with the bound $Mn^{2+}$), and human β1,3-glucuronyltansferase I. A retaining enzyme, bovine β1,3-galactosyltransferase, contains a DXD motif with a similar structure for UDP-binding.

In the case of pmHAS, which possesses two separate transferase sites each with a DXD motif, each transferase site contains a set of UDP-precursor-binding sites and catalytic residues. The two DXD motifs of each site are similar but not identical. The two half-activities of pmHAS prefer $Mn^{2+}$, but the two sites differ in their relative preference for $Co^{2+}$ and $Mg^{2+}$. The underlying reason for this selectivity is not known, but it can be speculated that various metal ions confer different coordination angles and geometry to the sugar nucleotide/enzyme binding site complex. Indeed, the X-ray crystal structure of SpsA showed that the two phosphate groups of UDP are ordered differently in the presence of $Mn^{2+}$ or $Mg^{2+}$.

The WGGED motif was first noted among β4-galactosyltransferases and a similar motif, WGXEXXE, was found among UDP-GalNAc:polypeptide N-acetylgalactosaminyltransferases. Residues in this Gal/GalNAcT motif have been shown to be essential for enzyme activity. The X-ray crystal structure of bovine β4-galactosyltransferase showed that E317D residues in WGGE317D segment are located at the bottom of the proposed UDP-Gal binding pocket. It was speculated that the E or the D residue was a good candidate for making the nucleophilic attack on the 4-hydroxyl group of the acceptor substrate GlcNAc ring. The assignment of the role of catalytic base to an E or D residue is supported by structural studies on several other glycosyltransferases. There is only one WGGED motif in pmHAS. The GlcNAc-transferase, but not the GlcUA-transferase, activity of pmHAS depends on the WGGED motif. The homologous pmCS enzyme also possesses this motif. The WGGED motif plays the same role in the hexosamine transfer reaction of the *Pasteurella* synthases as it does in the Gal-/GalNAc-transferases.

Saxena proposed two types of putative domains, Domain A and Domain B, among many beta-glycosyltransferases that use nucleotide diphospho sugars as donors. Saxena noticed that processive enzymes, which add a number of sugar residues without releasing the nascent chain, possess both Domains A and B, while those enzymes that add a single sugar residue have only Domain A. In general, Domain A resides in the N-terminal half of the polypeptide and possesses two invariant Asp residues, while Domain B resides in the C-terminal half and with an invariant Asp residue along with a characteristic QXXRW motif. Saxena, et al. hypothesized that the production of heteropolysaccharides with alternating sugar residues, such as HA, is fulfilled by specializing Domain A for one sugar and Domain B for a different sugar.

The only known member of Class II HA synthases, pmHAS, possesses two tandem copies of Domain A and does not contain Domain B. Data from the activity analysis of the truncated versions and the point mutants of pmHAS indicate that two active sites coexist in one polypeptide. Overall, pmHAS appears to be a polypeptide with two coordinated but intrinsically nonprocessive activities. Support for this characterization is found in the pmHAS mutant in vitro complementation study; two distinct polypeptide molecules can act together to polymerize HA chains in a rapid fashion. The HA chain must be released by one mutant to be acted on by the other mutant. The distinct Class I HA synthases, however, do not appear to release the nascent chain during synthesis.

PmCS is 90% identical to pmHAS and possesses two similar sets of putative nucleotide-binding elements. Therefore, pmCS utilizes the same structural organization and general catalytic mechanism as pmHAS. Dissection of the two transferase activities in pmHAS provides direct evidence for a two-active center model (FIG. 13). The *E. coli* K4 chondroitin polymerase (named a polymerase rather than synthase due to its apparent absolute requirement for an acceptor chain), KfoC, was recently reported (Ninomiya, et al., 2002). This protein is about 60% identical to pmHAS and pmCS, and thus probably utilizes similar motifs and domains. Another case of the "one polypeptide, two active center" model is the eukaryotic glycosyltransferase FT85, an enzyme involved in the glycosylation of Skp1 protein in Dictyostelium. This bifunctional glycosyltransferase mediates the ordered addition of β1,3-linked Gal and α1,2-linked Fuc to the Skp1 glycomoiety. The overall architecture of FT85 resembles pmHAS in that it contains two glycosyltransferase domains.

In the live bacterium, the pmHAS or the pmCS polypeptide engages with the polysaccharide export apparatus. In order to retain the nascent chain during polymerization in vivo, other proteins may help maintain the interaction of the transferase with the elongating GAG chain. The catalytic reaction mechanism and/or the intrinsic nature of pmHAS or pmCS are probably not the major chain retaining mechanisms.

pmHS1 and PmHS2 Identification and Molecular Cloning

As stated hereinabove, Pasteurella multocida Type D, a causative agent of atrophic rhinitis in swine and pasteurellosis in other domestic animals, produces an extracellular polysaccharide capsule that is a putative virulence factor. It has been reported that the capsule of Type D was removed by treating microbes with heparin lyase III. A 617-residue enzyme, pmHS1 (SEQ ID NOS:5 and 70), and a 651-residue enzyme, PmHS2 (SEQ ID NO:8), which are both authentic heparosan (unsulfated, unepimerized heparin) synthase enzymes have been molecularly cloned and are presently claimed and disclosed in copending U.S. application Ser. No. 10/142,143, incorporated herein previously by reference. Recombinant *Escherichia coli*-derived pmHS1 or PmHS2 catalyzes the polymerization of the monosaccharides from UDP-GlcNAc and UDP-GlcUA. Other structurally related sugar nucleotides do not substitute. Synthase activity was stimulated about 7- to 25-fold by the addition of an exogenous polymer acceptor. Molecules composed of ~500 to 3,000 sugar residues were produced in vitro. The polysaccharide was sensitive to the action of heparin lyase III but resistant to hyaluronan lyase. The sequence of pmHS1 enzyme is not very similar to the vertebrate heparin/heparan sulfate glycosyltransferases, EXT1/2 (SEQ ID NOS:65/66), or to other *Pasteurella* glycosaminoglycan synthases that produce hyaluronan or chondroitin. Certain motifs do exist however, between the pmHS1, pmHS2, and KfiA (SEQ ID NO:65) and KfiC (SEQ ID NO:64) thereby leading to deduced amino acid motifs that are conserved throughout this class of GAG synthases for the production of heparin/heparosan. The pmHS1 and PmHS2 enzymes are the first microbial dual-action glycosyltransferase to be described that form a polysaccharide composed of β4GlcUA-α4GlcNAc disaccharide repeats. In contrast, heparosan biosynthesis in *E. coli* K5 requires at least two separate polypeptides, KfiA and KfiC, to catalyze the same polymerization reaction.

Molecular Cloning of the Type D *P. multocida* Heparosan Synthase—A PCR product which contained a portion of the Type D UDP-glucose dehydrogenase gene was used as a hybridization probe to obtain the rest of the Type D *P. multocida* capsular locus from a lambda library. We found a functional heparosan synthase, which we named pmHS1, in several distinct Type D strains from different host organisms isolated around the world (i.e., A2 clone SEQ ID NOS:5 and 6; bioclone SEQ ID NOS:69 and 70). In every case, an open reading frame of 617 residues with very similar amino acid sequence (98-99% identical) was obtained. In the lafter stages of our experiments, another group deposited a sequence from the capsular locus of a Type D organism in GenBank[15]. In their annotation, the carboxyl terminus of the pmHS1 homolog is truncated and mutated to form a 501-residue protein that was called DcbF (GenBank Accession Number AAK17905) (SEQ ID NOS:61 and 62). No functional role for the protein except glycosyltransferase was described and no activity experiments were performed. As described herein, membranes or cell lysates prepared from *E. coli* with the recombinant dcbF gene do not possess heparosan synthase activity. The gene annotated as DcbF (SEQ ID NO:62) is truncated at the carboxyl terminus in comparison to the presently claimed and described *P. multocida* HS clones. The truncated (T) or the full-length (FL) open reading frames of DcbF were cloned into the expression system pETBlue-1 vector, as described hereinabove. Membranes isolated from the same host strain, *E. coli* Tuner with the various recombinant plasmids were tested in HS assays with both radiolabeled UDP-sugars. The results of these experiments are summarized in Table XVI.

TABLE XVI

| Clone | [14C]GlcUA Incorp. (dpm) | [3H]GlcNAc Incorp. (dpm) |
|---|---|---|
| Negative Control | 160 | 40 |
| B1(FL) | 710(*) | 1040(*) |
| 012(T) | 40 | 265 |
| 013(T) | 70 | 1610 |
| 019(T) | 55 | 1105 |
| N2(T) | 70 | 1910 |
| N4(T) | 70 | 880 |
| N5(T) | 80 | 650 |

Five-fold less FL enzyme than T enzymes were tested in these parallel assays. At most, only a single GlcNAc sugar is added to the exogenously supplied acceptor in the truncated enzymes (T). Full-length HS from Type D *P. multocida*, however, adds both sugars (*) to the nascent chain. Thus, the previously annotated and deposited DcbF gene is not a functional heparosan synthase.

Another deduced gene was recently uncovered by the University of Minnesota in their Type A *P. multocida* genome project, called PmHS2 (GenBank Accession Number AAK02498), encoding 651 amino acids that are similar to pmHS1 (73% identical in the major overlapping region). However, the PmHS2 gene (SEQ ID NO:7) is not located in the putative capsule locus. This group made no annotation of the function of PmHS2. Our studies show that this PmHS2 protein (SEQ ID NO:8) also polymerizes GlcUA and GlcNAc residues to form heparosan. We also found that a Type D strain and a Type F strain also appear to contain a homologous PmHS2 gene as shown by PCR and activity analysis.

As mentioned before, during the pmHS1 cloning project in the present Applicant(s)' laboratory, investigators at the University of Minnesota published the complete genome of a *Pasteurella multocida* isolate. The fragments of the presently claimed and disclosed pmHS1 gene were utilized as the query in a BLAST search against this *P. multocida* genome. A gene annotated as pmHS2, but with no ascribed, predicted or demonstrated function was found to be very similar to the pmHS1 gene. The pmHS2 gene is not in the main capsule locus found by either the DeAngelis or the Adler groups. The pmHS2 open reading frame was obtained from two different encapsulated strains: Type A (P-1059 from a turkey—this strain is not the same as the Univ. of Minnesota strain—clones denoted as "A") and Type D (P-3881 from a cow—clones denoted as "D"). The pmHS2 gene was amplified from chromosomal templates prepared by method of Pitcher et al (*Letters in Applied Microbiology,* 1989 which is expressly incorporated herein by reference in its entirety). PCR with Taq polymerase (18 cycles) using custom flanking oligonucleotide primers that correspond to the region of the start codon and the stop codon of pmHS2. An appropriate size amplicon corresponding to the pmHS2 gene was found in both Type A and D strains; this result was rather unexpected if one considers that the capsular compositions are HA and N-acetylheparosan polysaccharides, for Type A and Type D strains, respectively. The resulting ~1.9 kilobase PCR amplicons were ligated into an expression vector, pETBlue-1 (Novagen), transformed into the cloning host, *E. coli* Novablue (Novagen), and selected on LB carbenicillin and tetracycline plates at 30°. The colonies were screened for the presence of insert in the proper orientation by PCR with a combination of vector and insert primers. Clones were streak isolated, small cultures were grown, and preparations of the plasmid DNA were made. The plasmids were transformed into the expression host, *E. coli* Tuner (Novagen), and selected on LB with carbenicillin and chloramphenicol.

After streak isolation, small cultures were grown at 30° as the starting inoculum (1:100) for larger cultures (50 ml) for protein expression and activity assay. These cultures were grown in the same LB supplemented with 1% casein amino acids and trace element solution with vigorous shaking (250 rpm) at 30°. The cells were grown to mid-logarithmic phase (2.5 hours), induced with 0.5 mm IPTG, and grown for 4.5 hours. Cells were collected by centrifugation and frozen at −80° overnight. The membrane preparations were isolated by cold lysozyme/ultrasonication method of DeAngelis et. al. (J. Biol. Chem.,1998; pmHAS isolation the contents of which are expressly incorporated herein in their entirety) except that 0.1 mM mercaptoethanol was used as the reducing agent. The membranes were assayed for radioactive sugar incorporation and descending paper chromatography (according to the methodology of DeAngelis and Padget-McCue, *J. Biol. Chem.,* 2000, the contents of which are expressly incorporated herein in their entirety).

In general, a mixture with membranes, 50 mM Tris, pH 7.2, 10 mM $MgCl_2$, 10 mM $MnCl_2$, 0.4 mM UDP-[$^3$H]GlcNAc, 0.2 mM UDP-[$^{14}$C]GlcUA, and heparin oligosaccharide acceptor (2 μg uronic acid) were incubated at 300 for 2.5 hours before analysis by paper chromatography. As expected for a polysaccharide synthase, both sugars were incorporated into polymer (Table XVII). Negative controls using membranes from a plasmid with an irrelevant control insert did not show incorporation. Therefore, PmHS2 is a dual-action synthase capable of sugar biosynthesis as shown by functional expression of activity of one recombinant gene in a foreign host that normally does not make GlcUA/GlcNAc polymers. The relaxed specificity of UDP-sugar incorporation of PmHS2 should be of use for the design and production of new polymers with altered characteristics.

TABLE XVII

In vitro incorporation of sugar by membranes containing recombinant pmHS2

| CLONE | [$^3$H]GlcNAc (dpm) | [$^{14}$C]GlcUA (dpm) |
|---|---|---|
| PmHS2-A2 | 50,400 | 54,900 |
| PmHS2-A4 | 39,100 | 41,000 |
| PmHS2-D4 | 32,500 | 34,200 |
| PmHS2-D7 | 44,800 | 46,600 |

The typical background for negative controls is less than 200 dpm incorporation. Type A and Type D isolates have the PmHS2, a synthase that incorporates both GlcUA and GlcNAc sugars. (A=Type A; D=Type D; #=independent clone number). Table XVIII shows PmHS2 Sugar Specificity test results. The experiments summarized in Table XVIII are similar to the experiments summarized in Table XVII (with less enzyme) except that other UDP-sugars that are not normally found in heparin or heparosan were also tested (note—60 minute incubation times, 50 μl reactions). The Type A and the Type D enzymes behave in a similar fashion with relaxed sugar specificity in this test. The PmHS2 system can add a glucose instead of a GlcNAc sugar. The ability to co-polymerize the sugars that compose the authentic heparin backbone were tested by performing two parallel reactions:

UDP-[$^{14}$C]GlcUA+various combinations of $2^{nd}$ UDP-sugars.

UDP-[$^3$H]GlcNAc+various combinations of $2^{nd}$ UDP-sugars.

*P. multocida* Type F-derived recombinant pmHS2 is thus also a heparosan synthase. As shown in the following Table XX, the Type F PmHS2 can incorporate the authentic heparin sugars.

TABLE XVIII

| Panel I. Type A PmHS2-A2 | |
|---|---|
| $2^{nd}$ Sugar | [$^3$H]GlcNAc Incorporated into Polymer (dpm) |
| none | 450 |
| UDP-GlcUA | 12,900 |
| UDP-GalUA | 400 |
| UDP-Glc | 430 |
| $2^{nd}$ Sugar | [$^{14}$C]GlcUA Incorporated into Polymer (dpm) |
| none | 60 |
| UDP-GlcNAc | 7,700 |
| UDP-GalNAc | 60 |
| UDP-Glc | 985 |
| Panel II. Type D PmHS2-D7 | |
| $2^{nd}$ Sugar | [$^3$H]GlcNAc Incorporated into Polymer (dpm) |
| None | 570 |
| UDP-GlcUA | 13,500 |
| UDP-GalUA | 530 |
| UDP-Glc | 500 |
| $2^{nd}$ Sugar | [$^{14}$C]GlcUA Incorporated into Polymer (dpm) |
| None | 60 |
| UDP-GlcNAc | 6,500 |
| UDP-GalNAc | 40 |
| UDP-Glc | 660 |

TABLE XIX

Acceptor Usage of PmHS2 from Types A and D
The Type A and the Type D clones were tested for stimulation by addition of the Type D polysaccharide acceptor (described hereinbefore with respect to pmHS1). Weaker stimulation of activity by acceptor on pmHS2 was observed in comparison to pmHS1 (comparison is not shown here).

| | [$^{14}$C-GlcUA] incorporation | |
|---|---|---|
| Clone | Acceptor | NO Acceptor |
| A2 | 1560 | 1210 |
| D7 | 1240 | 1080 |

TABLE XX

| Activity of pmHS2 from Type F | | | |
|---|---|---|---|
| Membranes | Acceptor | $^3$H-GlcNAc (dpm) | $^{14}$C-GlcUA (dpm) |
| Blank | 0 | 8 | 8 |
| PmHS2 F 3 | + | 7100 | 3100 |
| PmHS2 F 4 | 0 | 6100 | 3800 |
| PmHS2 F 4 | + | 11000 | 6400 |
| PmHS2 F 18 | 0 | 20000 | 10000 |
| PmHS2 F 18 | + | 23000 | 12000 |
| PmHS2 D 7 | 0 | 36000 | 17000 |

The pmHS2 homolog of *P. multocida* Type F strain P-4218 was amplified with flanking primers as described for the Type A and D strains. The ORF was subcloned into the pETBlue-1 system in *E. coli* Tuner cells for use as a source of membrane preparations as described. Three independent clones (F 3, 4, 18) were assayed under standard HS assay measuring radiolabeled sugar incorporation with paper chromatography. A negative control, membranes from "Blank" vector and a positive control, the Type D pmHS2 clone D7, were tested in parallel. Reactions plus/minus the Type D polymer acceptor were assayed.

Figure 14:
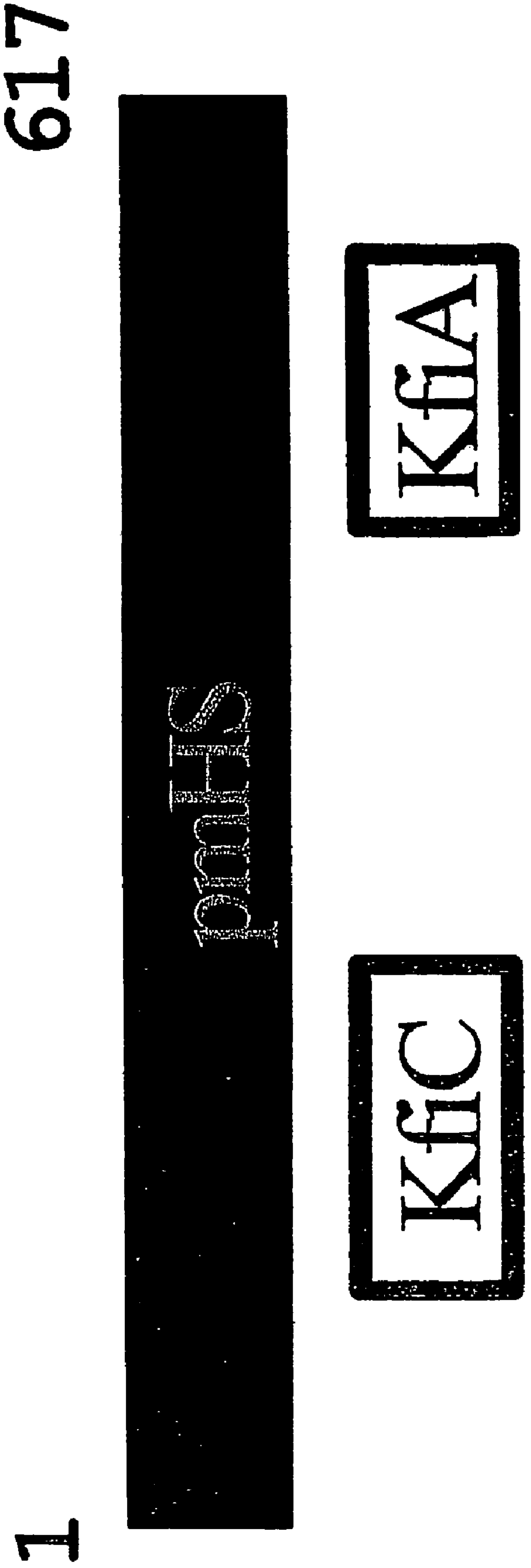
FIG. 14 graphically depicts Sequence Similarity of pmHS1 with KfiA and KfiC. Elements of the *Pasteurella heparosan* synthase, HS1 (containing residues 91-240) and HS2 (containing residues 441-540) are very similar to portions of two proteins from the *E. coli* K5 capsular locus (A, residues 75-172 of KfiA; C, residues 262- 410 of KfiC) as shown by this modified Multalin alignment (ref. 21; numbering scheme corresponds to the pmHS1 sequence). The HS1 and HS2 elements may be important for hexosamine transferase or for glucuronic acid transferase activities, respectively. (con, consensus symbols: asterisks, [K or R] and [S or T]; %, any one of F,Y,W; $, any one of L,M; !, any one of I,V; #, any one of E,D,Q,N).

The next best heterologous matches for the pmHS1 enzyme in the Genbank database are KfiA and KfiC proteins from *E. coli* K5; these two proteins work together to make the heparosan polymer. There is a good overall alignment of the enzyme sequences if smaller portions of pmHS1 ORF are aligned separately with KfiA (pmHS12, SEQ ID NO:63)and KfiC (pmHS11, SEQ ID NO:64) (FIG. 14). The MULTALIN alignment program (Corpet, 1988) identified regions that were very similar. Some of the most notable sequence similarities occur in the regions containing variants of the DXD amino acid sequence motif. Indeed, the first 1-360 residues of pmHS1 align with an approximate 38% identity to the *E. coli* KfiC, a single action GlcUA-transferase, while the 361-617 residues of pmHS12 align with an approximate 31% identity to the *E. coli* KfiA, a GlcNAc-transferase (FIG. 15). Thus, the pmHS1 is a naturally occurring fusion of two different glycosyltransferase domains. The pmHS1 is a dual action enzyme that alone makes heparin/heparosan polymers because both sugar transferase sites exist in one polypeptide enzyme.

The amino acid sequence of the heparosan synthase, pmHS1, however, is very different from other *Pasteurella* GAG synthases, pmHAS and pmCS. The pmHAS and pmHS1 enzymes both perform the task of polymerizing the identical monosaccharides; HA and heparin only differ with respect to their linkages. The creation of different anomeric linkages probably requires very distinct active sites due to the disparity between a retaining (to form α-linkages) and an inverting (to form β-linkages) transfer mechanism. The putative dual-action vertebrate heparin synthases, EXT1 (SEQ ID NO:65) and EXT2 (SEQ ID NO:66), also appear to have two transferase domains, but the amino acid sequences are not similar to pmHS1. Thus, by aligning pmHS2, pmHS1 (B10 and A2 clones), KfiA, or KfiC, deduced amino acid sequence motifs have been identified. Such motifs are listed below and the alignment is shown in FIG. 15A-D.

Comparisons of the two known sets of heparin/heparosan biosynthesis enzymes from the *E. coli* K5 Kfi locus, the PmHS2 enzyme, and the pmHS1 from Type D capsular locus, allows for the initial assessment and bioinformatic prediction of new enzymes based on the amino acid sequence data. The closer the match (% identity) in a single polypeptide for the two sequence motifs described hereinafter (corresponding to the critical elements of the GlcUA-transferase and the GlcNAc-transferase), the higher the probability that the query enzyme is a new heparin/heparosan synthase (a single dual-action enzyme). The closer the match (% identity) in two polypeptides (especially if encoded in the same operon or transcriptional unit) for the two sequence motifs, the higher the probability that the query enzymes are a pair of single-action glycosyltransferases. Thus, one of ordinary skill in the art would appreciate that given the following motifs, one would be able to ascertain and ascribe a probable heparin synthase function to a newly discovered enzyme and then test this ascribed function in a manner to confirm the enzymatic activity. Thus, single dual-action enzymes possessing enzymatic activity to produce heparin/heparosan and having at least one of the two disclosed motifs are contemplated as being encompassed by the presently claimed and disclosed invention.

```
Motif I:
                                              (SEQ ID NO:67)
QTYXN(L/I)EX4DDX(S/T)(S/T)D(K/N)(T/S)X6IAX(S/T)

(S/T)(S/T)(K/R)V(K/R)X6NXGXYX16FQDXDDX(C/S)H

(H/P)ERIXR

Motif II:
                                              (SEQ ID NO:68)
(K/R)DXGKFIX12-17DDDI(R/I)YPXDYX3MX40-50 VNXLGTGTV
```

Motif I corresponds to the GlcUA transferase portion of the enzyme, while Motif II corresponds to the GlcNAc transferase portion of the enzyme. With respect to the motifs:

X=any residue parentheses enclose a subset of potential residues [separated by a slash] that may be at a particular position (e.g.,—(K/R) indicates that either K or R may be found at the position—i.e., there are semiconserved residues at that position.

The consensus X spacing is shown with the number of residues in subscript (e.g., X12-17), but there are weaker constraints on these particular residues, thus spacing may be longer or shorter. Conserved residues may be slightly different in a few places especially if a chemically similar amino acid is substituted (e.g., K for a R, or E for a D). Overall, at the 90% match level, the confidence in this predictive method is very high, but even a 70-50% match level without excessive gap introduction (e.g., altered spacing between conserved residues) or rearrangements (miss-positioning with respect to order of appearance in the amino to carboxyl direction) would also be considered to be within the scope of these motifs. One of ordinary skill in the art, given the present specification, general knowledge of the art, as well as the extensive literature of sequence similarity and sequence statistics (e.g., the BLAST information website at www.ncbi.nlm.mih.gov), would appreciate the ability of a practitioner to identify potential new heparin/heparosan synthases based upon sequence similarity or adherence to the motifs presented herein and thereafter test for functionality by means of heterozologous expression, to name but one example.

pmHS1 and PmHS2 Polymer Grafting and Use of Chimeric or Hybrid or Mutant Transferases As mentioned hereinabove, it was first discovered and disclosed that pmHAS-catalyzed synthesis in vitro was unique in comparison to all other existing HA synthases of *Streptococcus*, bacteria, humans or an algal virus. Specifically, recombinant pmHAS can elongate exogenously supplied functional acceptors (described herein) into longer glycosaminoglycans. The pmHAS synthase adds monosaccharides one at a time in a step-wise fashion to the growing chain. The pmHAS exquisite sugar transfer specificity results in the repeating sugar backbone of the GAG chain. The pmCS enzyme, which is 90% identical at the amino acid level to pmHAS, performs the same synthesis reactions but incorporates GalNAc instead of GlcNAc. The pmHS1 and PmHS2 enzymes can also add heparosan chains onto exogenous supplied functional acceptors such as long or short heparosan polymers.

The *Pasteurella* GAG synthases (pmHAS, pmCS, pmHS1 and PmHS2) are very specific glycosyltransferases with respect to the sugar transfer reaction: usually only the authentic sugar is added onto acceptors. The epimers or closely structurally related molecules (e.g., UDP-glucose) are not utilized. However, these GAG synthases from *Pasteurella* do utilize heterologous acceptor sugars. For example, pmHAS elongates short chondroitin acceptors with HA chains. Additionally, pmHS1 adds heparosan chains onto HA acceptor oligosaccharides. Thus, a diverse range of hybrid of chimeric or hybrid GAG oligosaccharides can be made with the disclosed GAG synthases (i.e., pmHAS, pmCS, pmHS1, and PmHS2). The chemoenzymatic methodology can be used in either a liquid-phase synthesis of soluble, free sugars or in a solid-phase synthesis to build sugars on surfaces (as disclosed hereinafter).

Synthase activity assays (2.5 hours, 30°) with subsequent paper chromatography separations and liquid scintillation counting of the origin zone. Typical reaction buffer (Tris & Mn ion; DeAngelis & White 2001) contained both radioactive UDP-GlcNAc and UDP-GlcUA and various acceptor sugars (as noted in table). Unless noted, the HA was from testicular Haase digestions (Leech means leech HAase). Hep2 or Hep2 are synthetic heparosan disaccharide or trisaccharide analogs, respectively (Haller & Boons, 2001). Recombinant *E. coli* derived membranes from cell with plasmids containing pmHS1 gene or no insert (vector). With no membranes and no acceptor sugar, the background was 70 and 35 dpm, respectively.

TABLE XXI

Acceptor Sugar Usage of pmHS1 Test

| Acceptor Sugar | PmHS1 3H-GlcNAc (dpm) | PmHS1 14C-GlcUA (dpm) | Vector 3H-GlcNAc (dpm) | Vector 14C-GlcUA (dpm) |
|---|---|---|---|---|
| None | 690 | 580 | 55 | 60 |
| Type D (0.38 μg) sonicated | 4400 | 4500 | 80 | 60 |
| Heparin (10 μg) porcine | 570 | 560 | 50 | 65 |
| HA4 (12.5 μg) | 5900 | 6500 | 85 | 65 |
| HA4 (0.5 μg) | 2200 | 2600 | 60 | 75 |
| HA4-10 (25 μg) | 7400 | 6900 | 75 | 70 |
| HA4-10 (1 μg) | 2300 | 2200 | 120 | 70 |
| HA4 leech (12.5 μg) | 880 | 670 | 45 | 85 |
| HA8-14 leech (25 μg) | 1100 | 1000 | 70 | 90 |
| Hep2 (1 μg) | 1800 | 1700 | 70 | 95 |
| Hep3 (25 μg) | 5800 | 5600 | 55 | 75 |
| Hep3 (1 μg) | 9700 | 10000 | 45 | 90 |

Thus, chimeric or hybrid GAGS can be made using the *Pasteurella* GAG synthases of the presently claimed and disclosed invention. As shown in Table XXI, synthetic di- and tri-saccharides of heparosan, and HA can be elongated. Naturally derived HA tetramers can also be elongated. The reducing end is not required to be in a free state (aglycons are not a problem), therefore, the reducing end can serve as the tether site onto a surface, drug, or other synthetic or natural molecule. Exemplary compounds that can be made using the *Pasteurella* GAGs of the presently claimed and disclosed invention include, but are not limited to:

HA-C CS-HAC-HA HA-HP C-HP HA-C-HA

CS-HA-C C-HA-C HA-C-HP CS-HA-HP C-HA-HP and so forth, and one of ordinary skill in the art given this specification would appreciate and be able to construct any number of chimeric or hybrid GAG molecules using the *Pasteurella* GAG synthases disclosed and claimed herein. With respect to the above-referenced chimeric or hybrid GAGs, HA=hyaluronan; C=chondroitin; CS=chondroitin sulfate; and HP=heparosan or heparin like molecules.

Figure 16:
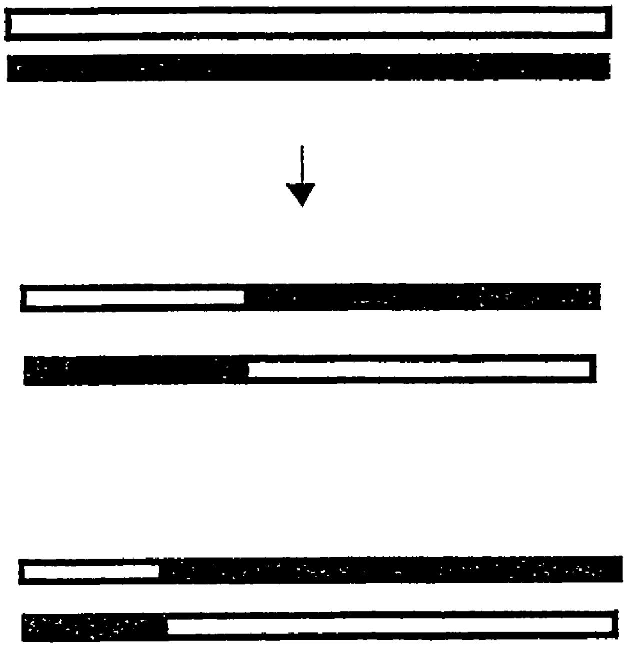
FIG. 16 depicts chimeric constructs of pm-EG, pm-FH, pm-IK, and pm-JL. PCR-overlap-extension was performed. Pm-EG contains residues 1-265 from pmHAS and residues 259-704 from pmCS and is a GlcUA-Tase. Pm-FH contains residues 1-258 from pmCS and residues 266-703 from pmHAS and is an active chondrotin synthase. Pm-IK contains residues 1-221 from pmHAS and residues 215-704 from pmCS and is a Glc-UA-Tase. Pm-JL contains residues 1-214 from pmCS and residues 222-703 from pmHAS and is an active HA synthase. The switch of Gal-NAc-transferring activity into GlcNAc-transferring activity indicated that 222-265 of pmHAS and possibly the corresponding residues 215-258 of pmCS play critical role in the selectivity between binding and/or transferring of GalNAc and GlcNAc substrate.

The C-terminal halves of pmHAS and pmCS (the putative GlcUA-transferase) can be switched and the sugar-transfer specificity for GlcNAc and GalNAc is not disturbed. This finding suggested that the hexosamine specificity determinants of the enzymes between GlcNAc- and GlcUA-transfer are located in their amino-terminal halves. To define the critical residues or regions that specify sugar transfer, further domain swapping were performed by PCR-overlap-extension (FIG. 16).

Certain chimeric or hybrid constructs, such as pm-EG and pm-IK (FIG. 16), are not dual-action enzymes and do not have either pmHAS or pmCS activities. But pm-FH, which possesses pmCS residues 1-258, is an active pmCS, although its remaining part is from pmHAS residues 266-703. When more of the pmCS sequence is replaced by pmHAS sequence as in pm-JL enzyme construct (which possesses pmCS residues 1-214 at the amino-terminal and pmHAS residues 222-703 at the carboxyl-terminal), the enzyme is converted into a catalyst with HAS activity. The conversion of GalNAc-transferring activity into GlcNAc-transferring activity indicated that residues 222-265 of pmHAS and probably the corresponding residues 215-258 of pmCS play critical role in the selectivity between binding and/or transferring of GalNAc and GlcNAc substrate.

Figure 17:
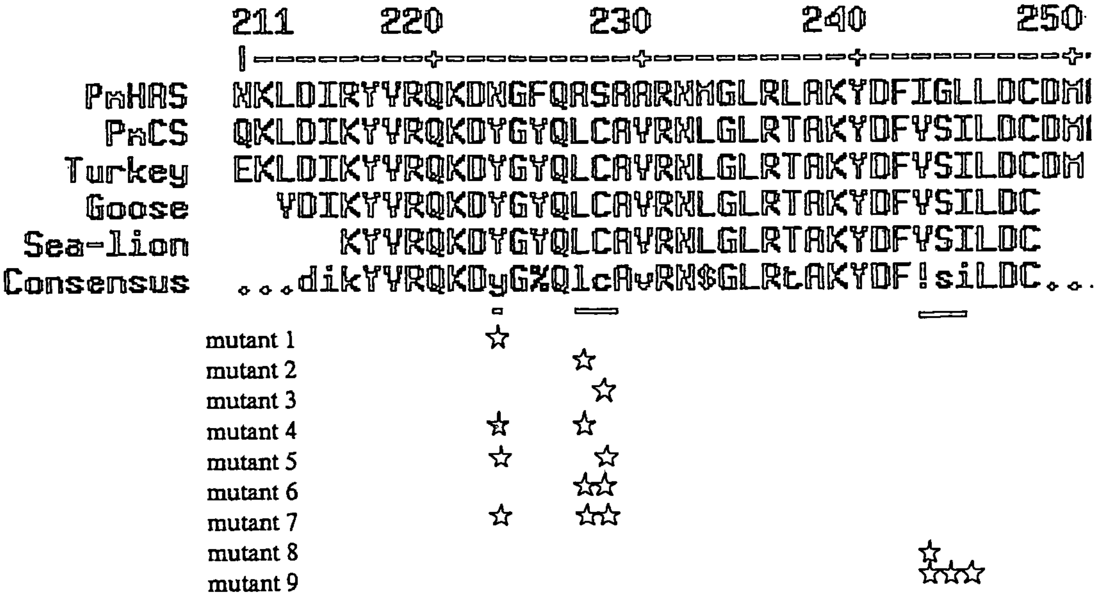
FIG. 17 depicts a comparison of partial primary sequences of pmHAS and different pmCSs. Primary sequences of presumably chondroitin synthases from different Type F *Pasteurella multocida* were obtained by directly sequencing the products of colony-lysis PCR. The MULTALIN alignment indicates that most of the differences between pmHAS and pmCS are conserved among these independent strains. Residues that were substituted in site-mutagenesis studies were underlined. The mutant polypeptides contain a single or combination of different mutations, indicated by star(s). None of these mutations changes the specificity of the original enzymes.

Site-directed mutagenesis of region HAS222-265/CS215-258: none of the residues tested in this region are sufficient alone to switch the sugar transfer specificity between pmHAS and pmCS. In the above identified regions, there are 14 residues that are different between pmHAS and pmCS. We checked the primary sequences of the predicted chondroitin synthases from several independent type F Pasteurella multocida in the region of 215to 258. Based on the comparison of these amino acid sequences, most of the differences between pmHAS and pmCS are conserved among those independent strains (FIG. 17). To identify possible critical individual residues that might be important for the selectivity between GalNAc and GlcNAc substrate, we utilized site-directed mutagenesis to change a single or multiple residues in this region. We used either pmHAS1-703 DNA (for I243-, I243/G244/L245-containing mutants) or pmCS$^{1-704}$ DNA (for Y216-, L220-, or C221-containing mutants) as templates and replaced the target residue(s) with the corresponding one(s) in the other enzyme (FIG. 17). Results from enzymatic assays showed that all pmCS$^{1-704}$ mutants transfer GalNAc instead of GlcNAc and all pmHAS$^{1-703}$ mutants transfer GlcNAc instead of GalNAc. This finding indicates that none of the residues that we tested here are sufficient alone to switch the sugar transfer specificity between pmHAS and pmCS.

Figure 18:
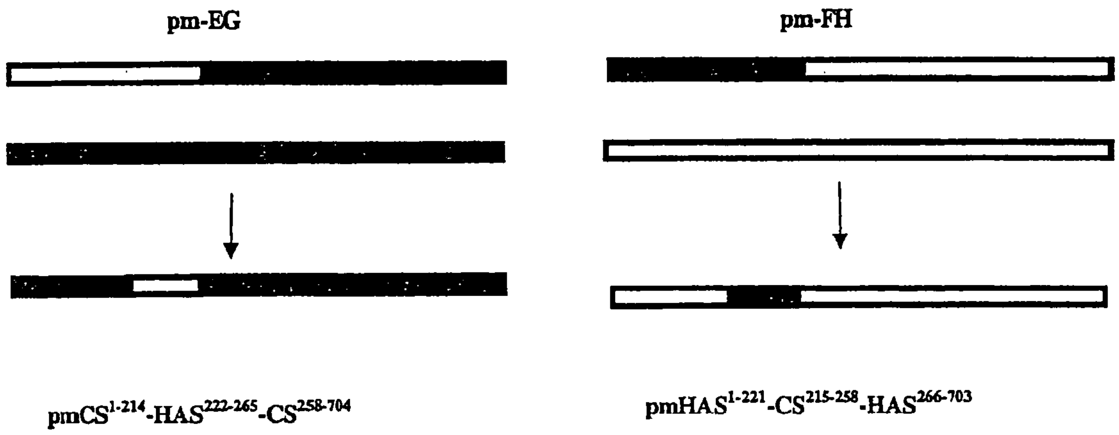
FIG. 18 depicts chimeric constructs of $pmHAS^{1-221}$-$CS^{215-258}$-$HAS^{266-703}$ and $pmCS^{1-214}$-$HAS^{222-265}$-$CS^{258-704}$. Pm-FH and pPm7A DNA were used to create $pmHAS^{1-221}$-$CS^{215-258}$-$HAS^{266-703}$. A very interesting result was that $pmCS^{1-214}$-$HAS^{222-265}$-$CS^{258-704}$ can transfer both GalNAc and GlcNAc to HA oligomer acceptor; this enzyme displays relaxed sugar specificity.

Domain Swapping Between pmHAS and pmCS: pmCS$^{1-214}$-HAS$^{222-265}$-CS$^{258-704}$ Transfers Both GlcNAc and GalNAc and GlcN Based on the above studies, we hypothesized that additional residues in the 44-residues region were important for the selectivity between GalNAc and GlcNAc transferase. To prove our hypothesis, this region was swapped between pmHAS$^{1-703}$ and pmCS$^{1-704}$ by PCR-overlap-extension. Pm-EG and pPmF4A (a library clone containing pmCS gene locus) DNAs were used to create pMCS$^{1-214}$-HAS$^{222-265}$-CS$^{258-704}$. Pm-FH and pPm7A (a library clone containing pmHAS gene locus) DNAs were used to create pmHAS$^{222-265}$-CS$^{258-258}$-HAS$^{266-703}$ (FIG. 18). PmHAS$^{1-221}$-CS$^{215-258}$-HAS$^{266-703}$ did not express. Interestingly, pmCS$^{1-214}$-HAS$^{222-265}$-CS$^{258-704}$ could transfer both GlcNAc and GalNAc with preference for UDP-GalNAc as judged by HAS assay and CS assay, supporting our conclusion that this region in pmHAS and pmCS plays a critical role in determination of sugar substrate specificity. We also obtained a pmCS$^{1-214}$-HAS$^{222-265}$-CS$^{258-704}$ clone that possesses an additional mutation of I243V; this clone lost GlcNAc-transferring activity and was switched back into a chondroitin synthase. This finding suggests that I243 in pmHAS, and probably V236 in pmCS, plays important yet unknown roles in the determination of sugar substrate specificity.

In order to examine whether pMCS$^{1-214}$ HAS$^{222-265}$-CS$^{258-704}$ could transfer sugars other than GlcNAc and GalNAc, different sugar substrates, including UDP-glucose, UDP-galactose, UDP-mannose, UDP-xylose and UDP-glucosamine (GlcN), along with isotope-labeled GlcUA and HA oligosaccharide acceptor, were included when performing the polymerization assay. The results demonstrated that pmCS$^{1-214}$-HAS$^{222-265}$-CS$^{258-704}$ will use UDP-GlcNAc, UDP-GalNAc, or UDP-glucosamine Table XXII. This observation indicated that although swapping of the small region between pmCS and pmHAS resulted in relaxation of substrate selectivity, the enzyme is not so promiscuous that all UDP-sugars will substitute.

Figure 19:
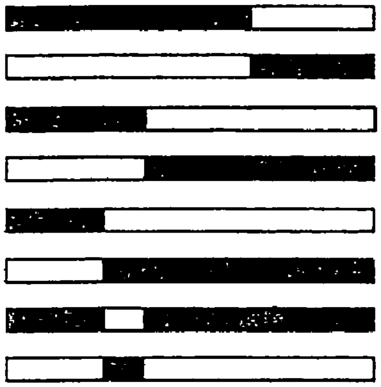
FIG. 19 depicts a summary of enzyme activities of chimeric proteins. The enzymes are drawn as bars. Black bars represent pmCS. White bars represent pmHAS. +, active; –, inactive. PmCHC represents $pmCS^{1-214}$-$HAS^{222-265}$-$CS^{258-704}$. The roles of the two domains are confirmed and we have localized a 44-residue region critical for distinguishing C4 epimers of the hexosamine precursor.

We exploited the possibility that the chimeric or hybrid enzyme could synthesize hybrid polymers with a blend of HA- and chondroitin-like sugars. We performed reactions containing $^{3}$H-UDP-GalNAc, $^{14}$C-UDP-GlcNAc, UDP-GlcUA and HA acceptor. The ratio of the incorporation of $^{3}$H-GalNAc and $^{14}$C-GlcNAc changed according to the UDP-sugar ratio in the reaction mixture included in the reaction. Gel filtration analysis of the polymerization products demonstrated that the molecules contain both $^{3}$H and $^{14}$C. The characterization of all the chimeric or hybrid proteins is summarized in FIG. 19.

TABLE XXII

Sugar substrate specificity of pmCS$^{1-214}$-HAS$^{222-265}$-CS$^{258-704}$
Standard polymerization assay were performed in the presence of isotope-labeled GlcUA, HA oligosaccharide acceptor, and one of the following sugar substrates. The sugar incorporation was indicated as the percentage of the incorporation of UDP-GalNAc. PmCS$^{1-214}$-HAS$^{222-265}$-CS$^{258-704}$ can transfer GalNAc, GlcNAc, and Glucosamine.

| substrate sugar | incorporation |
|---|---|
| UDP-GalNAc | 100% |
| UDP-GlcNAc | 28% |
| UDP-Glucosamine | 2% |
| UDP-Galactose | not detectable |
| UDP-Glucose | not detectable |
| UDP-Mannose | not detectable |
| UDP-Xylose | not detectable |

Truncation analysis of pmHAS has identified a carboxyl-terminal region that appears to be responsible for the membrane association of pmHAS. Site-directed mutagenesis studies focused on several conserved motifs indicated that these conserved residues are critical for function. Evidence is provided that pmHAS and pmCS each contain two separate glycosyltransferase sites (FIG. 13). Thus the novel "one polypeptide, two active sites" theory has been confirmed. A 44-residue region of the enzymes has been demonstrated to be critical for sugar-transfer specificity. Based on this discovery, an enzyme that can transfer GalNAc, GlcN, and GlcNAc has been engineered.

Type A *Pasteurella multocida* produces a hyaluronan [HA] capsule to enhance infection. The 972-residue hyaluronan synthase, pmHAS, polymerizes the linear HA polysaccharide chain composed of GlcNAc and GlcUA. PmHAS possesses two separate glycosyltransferase sites. Protein truncation studies demonstrated that residues 1-117 can be deleted without affecting catalytic activity. The carboxyl-terminal boundary of the GlcUA-transferase resides within residues 686-

703. Both sites contain a DXD motif. All four aspartate residues are essential for HA synthase activity. D247 and D249 mutants possessed only GlcUA-transferase activity while D527 and D529 mutants possessed only GlcNAc-transferase activity. These results further confirm our previous assignment of the active sites within the synthase polypeptide. The WGGED sequence motif appears to be involved in GlcNAc-transferase activity because E396 mutants and D370 mutants possessed only GlcUA-transferase activity.

Type F *P. multocida* synthesizes an unsulfated chondroitin GalNAc and GlcUA capsule. Domain swapping between pmHAS and the homologous chondroitin synthase, pmCS, was performed. A chimeric or hybrid enzyme consisting of residues 1-427 of pmHAS and residues 421-704 of pmCS was an active HA synthase. On the other hand, the converse chimeric or hybrid enzyme consisting of residues 1420 of pmCS and residues 428-703 of pmHAS was an active chondroitin synthase. Overall, these findings support the model of two independent transferase sites within a single polypeptide as well as further delineate the site boundaries.

pmHAS utilizes two separate glycosyltransferase sites to catalyze the transfer of GlcNAc and GlcUA to form the HA polymer. Within the pmHAS sequence, there is a pair of duplicated domains which are similar to the "Domain A" proposed by Saxena. Both domains of pmHAS possess a short sequence motif containing DGS that is conserved among many β-glycosyltransferases. Changing the aspartate in either motif to asparagines, glutamate, or lysine significantly reduced or eliminated the HAS activity. However, the D196 mutants and the D477 mutants maintain high level of GlcUA-transferase and GlcNAc-transferase activity, respectively.

pmCS contains 965 amino acid residues and is about 90% identical to pmHAS. A soluble recombinant *Escherichia coli*-derived pmCS$^{1-704}$ catalyzes the repetitive addition of sugars from UDP-GalNAc and UDP-GlcUA to chondroitin oligosaccharide acceptors in vitro.

In order to analyze the contribution of the amino terminal region of pmHAS, various recombinant truncated polypeptides were produced (pmHAS$^{46-703}$, pmHAS$^{72-703}$, pmHAS$^{96-703}$ and pmHAS$^{118-703}$) in *E. coli*. The truncated versions pmHAS$^{46-703}$ and pmHAS$^{72-703}$ were as active as pmHAS$^{1-703}$, a soluble polypeptide with complete HAS activity. PmHAS$^{96-703}$ expressed at a very low level compared with other constructs but was active. PmHAS$^{118-703}$ expressed better than pmHAS$^{96-703}$ and still elongated HA chains. Therefore, it is probable that further deletion beyond residue 72 affected the overall folding efficiency of the entire polypeptide. Observation of lower molecular weight degradation bands derived from pmHAS$^{118-703}$ on Western blots also suggests that improper folding occurs to some extent. Overall, these findings suggest that the amino-terminal 117 residues are not required for HA synthase activity.

pmHAS$^{1-650}$ loses its GlcUA-transferase activity. To further delineate the GlcUA-transferase domain within the carboxyl terminal region, two slightly longer mutants, pmHAS$^{1-868}$ and pmHAS$^{1-686}$ were created. Both mutants also could not polymerize HA due to the loss of GlcUA-transferase activity, indicating that the carboxyl-terminal boundary of the GlcUA-transferase resides between residues 686 and 703.

Monodisperse Glycosaminoglycan Polymer Synthesis

The size of the hyaluronan [HA] polysaccharide dictates its biological effect in many cellular and tissue systems based on many reports in the literature. However, no source of very defined, uniform HA polymers with sizes greater than 5 kDa is currently available. This situation is complicated by the observation that long and short HA polymers appear to have antagonistic or inverse effects on some biological systems. Therefore, HA preparations containing a mixture of both size populations may yield contradictory or paradoxical results. One embodiment of the novel method of the present invention produces HA with very narrow, monodisperse size distributions that are referred to herein as "selectHA."

The *Pasteurella* bacterial HA synthase enzyme, pmHAS, catalyzes the synthesis of HA polymers utilizing monosaccharides from UDP-sugar precursors in vivo and in vitro. pmHAS will also elongate exogenously supplied HA oligosaccharide acceptors in vitro; in fact, HA oligosaccharides substantially boost the overall incorporation rate. A purified recombinant, pmHAS derivative was employed herein to produce either native composition HA or derivatized HA.

HA polymers of a desired size were constructed by controlling stoichiometry (i.e., ratio of precursors and acceptor molecules). The polymerization process is synchronized in the presence of acceptor, thus all polymer products are very similar. In contrast, without the use of an acceptor, the polymer products are polydisperse in size. In the present examples, stoichiometrically controlled synchronized synthesis reactions yielded a variety of HA preparations in the range of ~15 kDa to about 1.5 MDa. Each specific size class had a polydispersity value in the range of 1.01 for polymers up to 0.5 MDa or ~1.2 for polymers of ~1.5 MDa (1 is the ideal monodisperse size distribution) as assessed by size exclusion chromatography/multi-angle laser light scattering analysis. The selectHA preparations migrate on electrophoretic gels (agarose or polyacrylamide) as very tight bands.

The use of a modified acceptor allows the synthesis of selectHA polymers containing radioactive (e.g., 3H, 125I), fluorescent (e.g., fluorescein, rhodamine), detection (i.e., NMR or X-ray), affinity (e.g., biotin) or medicant tags. In this scheme, each molecule has a single detection agent located at the reducing terminus. Alternatively, the use of radioactive UDP-sugar precursors allows the synthesis of uniformly labeled selectHA polymers with very high specific activities.

Overall, the selectHA reagents should assist in the elucidation of the numerous roles of HA in health and disease due to their monodisperse size distributions and defined compositions. It must be emphasized that unpredicted kinetic properties of the *Pasteurella* GAG synthases in a recombinant virgin state in the presence of defined, unnatural reaction conditions facilitates targeted size range production of monodisperse polymers that are not synthesizable by previously reported methods.

Figure 20:
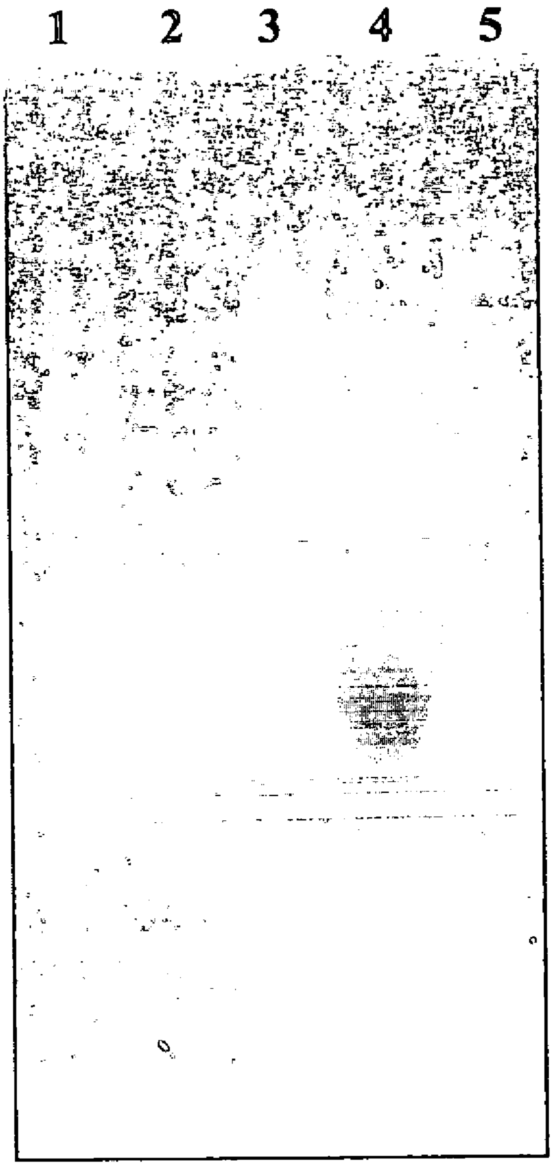
FIG. 20 is a graphical representation illustrating in vitro HA synthesis in the presence or absence of HA4 acceptor. Reactions were carried out at 30° C. for 48 hours. The 100 il reaction contains 1 ig/il of pmHAS, 30 mM UDP-GlcNAc, 30 mM UDP-GlcUA and with (lane 3) or without (lane 4) 0.03 ig/il of HA4. 0.2 il of reactions were loaded on 0.7% agarose gel and stained with STAINS-ALL. Lane 1, 3 ig of HA from Genzyme. Lane 2, DNA of BIOLINE HyperLadder (from top to bottom is 10 kb, 8 kb, 6 kb, 5 kb, 4 kb, 3 kb, 2.5 kb, 2 kb, 1.5 kb, 1 kb, 800 bp, 600 bp, 400 bp, 200 bp). Lane 5, Invitrogen high-Mw DNA ladder (top band is 48.5 kb).

Affect of HA acceptor on pmHAS-catalyzed polymerization. HA polymerization reactions were performed with purified pmHAS and UDP-sugar precursors under various conditions, and the reaction products were analyzed by agarose gel or acrylamide gel electrophoresis. The size distribution of HA products obtained were observed to be quite different based on the presence or absence of the HA4 acceptor in the reaction (FIG. 20A). When 30 mM of UDP-sugars were present as well as 0.03 ug/ul of HA4, pmHAS synthesized smaller chains with a narrow size distribution. The Mn determined by MALLS is 551.5 kDa and its polydispersity (Mw/Mn) is 1.006 (FIG. 20B). However, without HA4, pmHAS synthesized a more polydisperse product with the same amount of precursor sugars. The Mn determined by MALLS is 1.53 MDa and its polydispersity (Mw/Mn) is 1.169.

Figure 21:
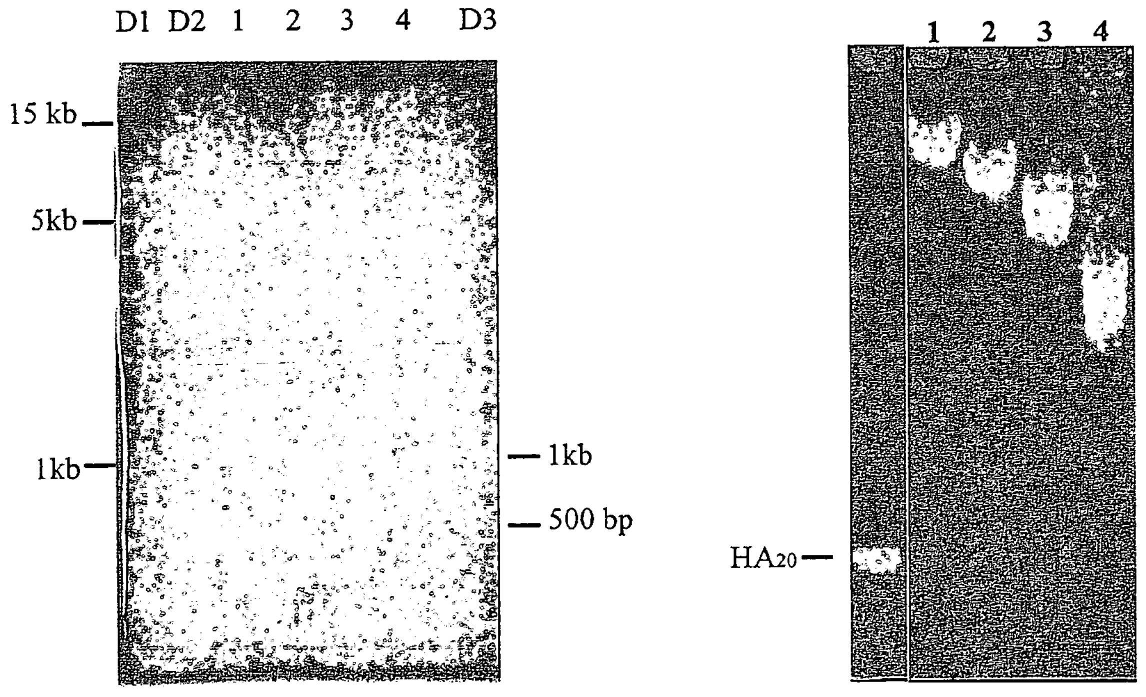
FIG. 21 are electrophoresis gels illustrating intermediate size HA polysaccharides as acceptors. The starting 20 il reaction contain 15 ig of pmHAS, 10 mM UDP-sugars and 5 ig HA4. 5 il of 40 mM UDP-sugars and 15 ig of pmHAS were supplied additionally every 48 hours ("feeding"). A. 0.1% agarose gel electrophoresis. Lane 1, 3 feedings. Lane 2, 2 feedings. Lane3, one feedings. Lane 4, no feeding. D1, Bio-Rad 1 kb DNA ruler. D2 Lambda HindIII DNA. D3, Bio-Rad 100 bp DNA ruler. B. 15% acrylamide gel electrophoresis. Lanel-4, same as in panel A.

To verify whether pmHAS can utilize HA acceptors of various sizes, parallel assays were set up using the same starting conditions, and at various times additional UDP-sugars were added to the reaction. The result indicated that intermediate products were utilized as starting material for later chain elongation by pmHAS. (FIG. 21).

Figure 22:
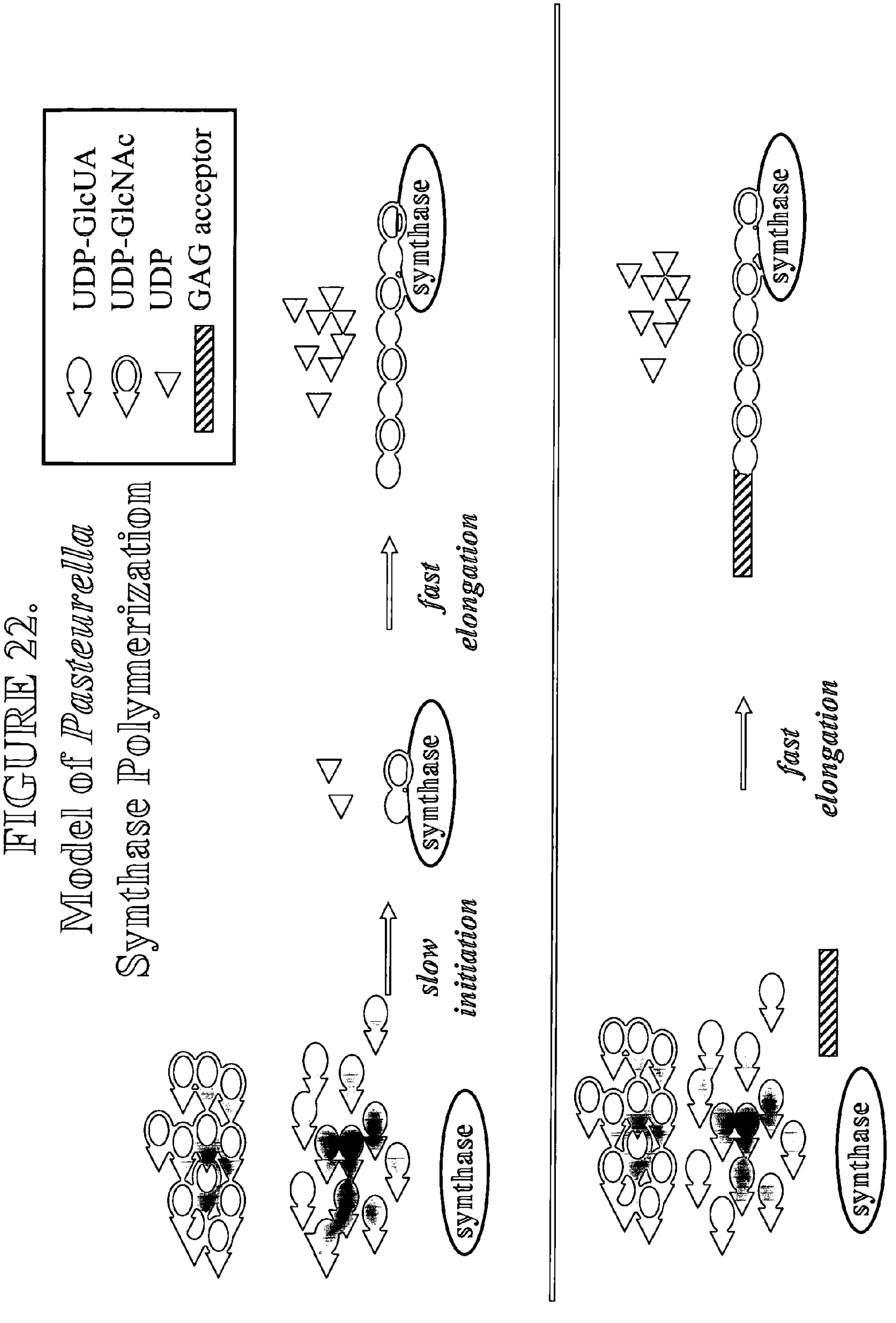
FIG. 22 is a graphical representation of a model of *Pasteurella* synthase polymerization.
Figure 23:
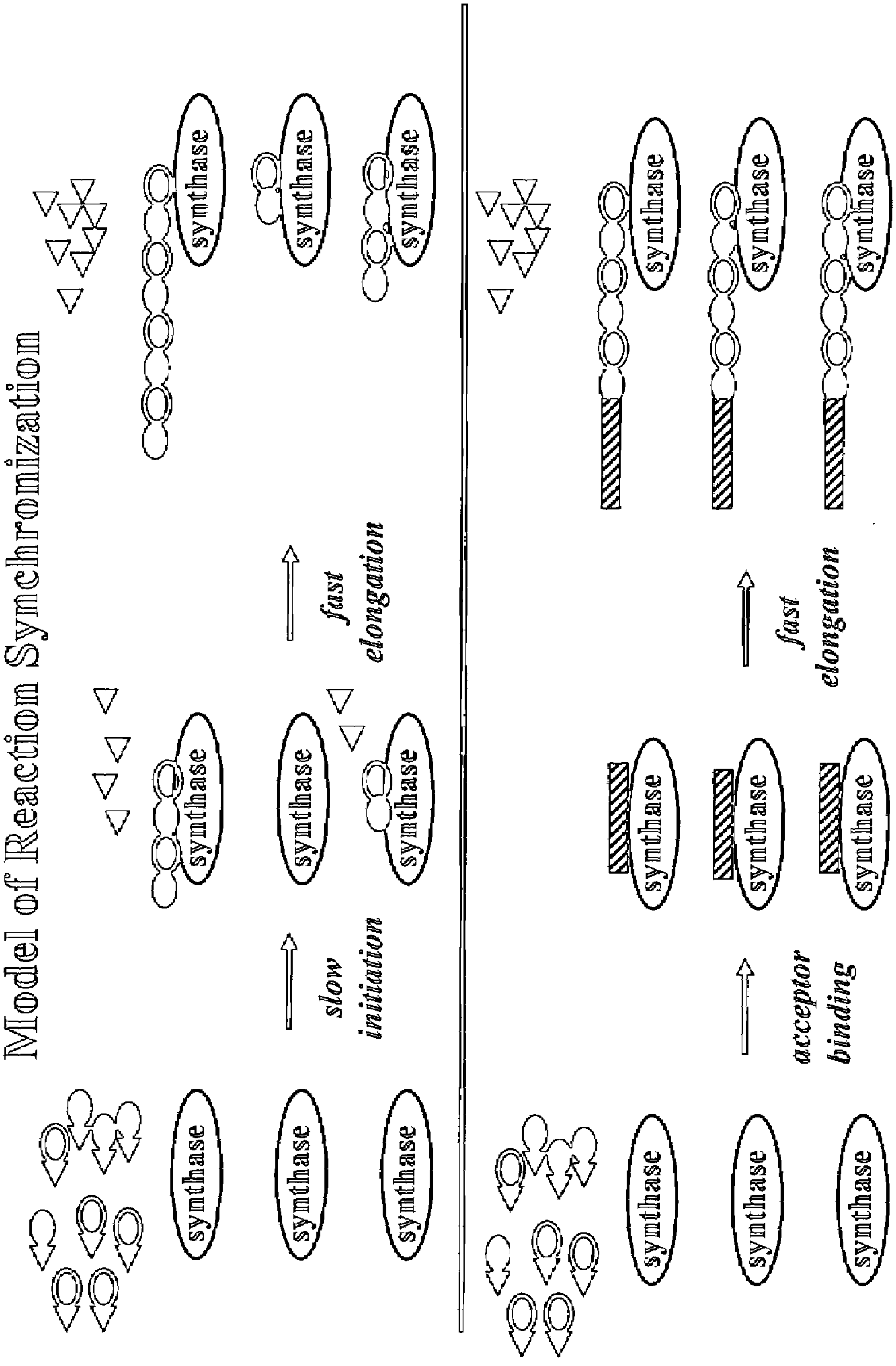
FIG. 23 is a graphical representation of a model of reaction synchronization.

Size control of HA. The polymerization by pmHAS in the presence of HA acceptor is a synchronized process, and thus a more defined HA preparation can be obtained with pmHAS. This synchronization is probably due to the difference in rate or efficiency of new chain initiation versus chain elongation as speculated earlier in DeAngelis, 199 and depicted in FIG. 22 model. The addition of acceptor appears to bypass the slower initiation step; thus all chains are elongated in parallel resulting in a more homogenous final population. A model demonstrating *Pasteurella* synthase reaction synchronization mediated by acceptor usage is shown in FIG. 23.

Figure 24:
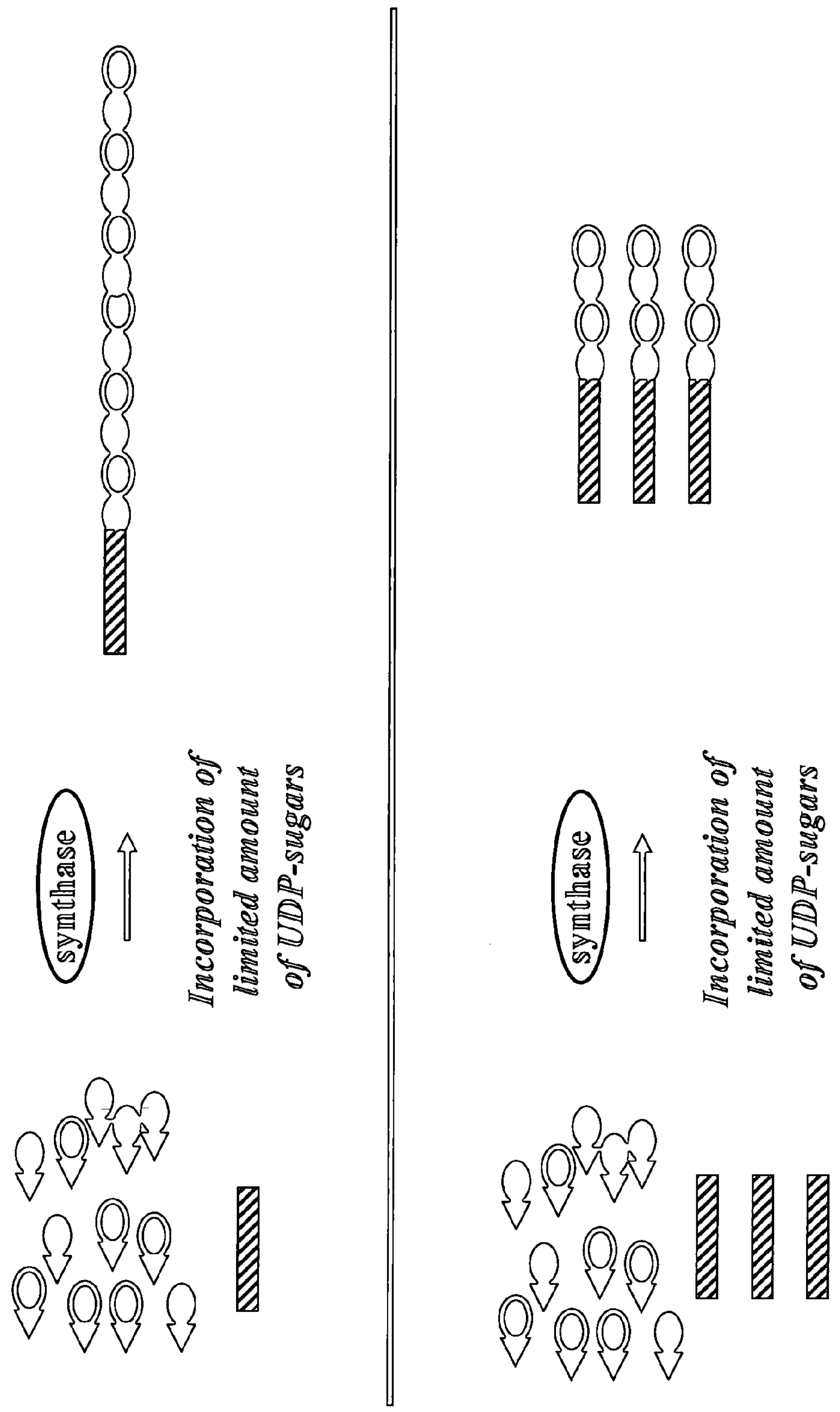
FIG. 24 is a graphical representation of a model of stoichiometric control of polymer size.
Figure 25:
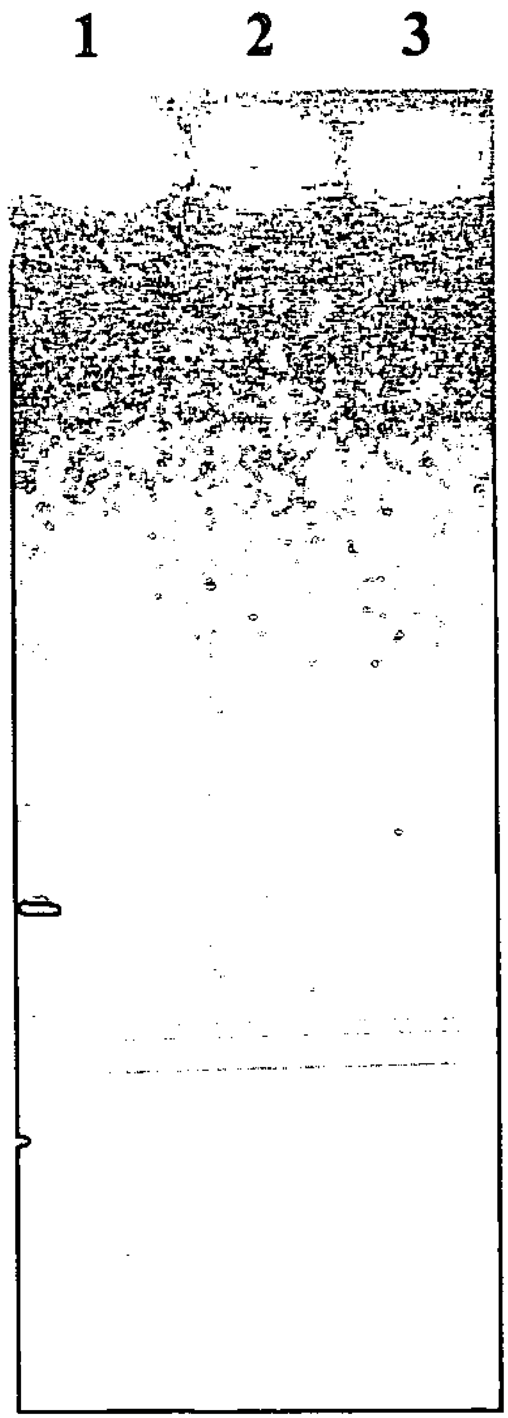
FIG. 25 is an electrophoresis gel illustrating that in vitro generated HA can reach the molecular mass of 1.3 MDa. The reaction condition is the same as in FIG. 31 except with 0.2 ig of HA4. 1.2 ig of purified HA was loaded on 1.0% agarose gel. Lane 2, Bio-Rad 1 kilobase DNA ruler with the top band of 15 kb. Lane 3, Bioline DNA hyperLadder with the top band of 10 kb.
Figure 26:
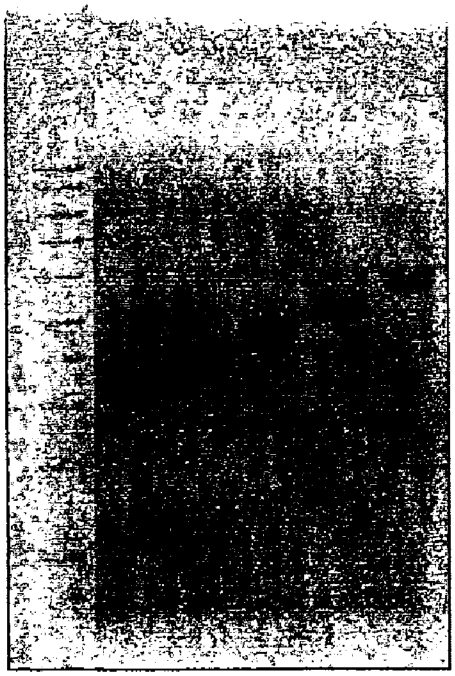
FIG. 26 is a graphical representation illustrating control of HA product size by acceptor concentration. 100 il of reactions were setup with 0.7 ig/il of pmHAS, 32 mM of UDP-GlcNAc, 32 mM of UDP-GlcUA and decreasing amount of HA4. HA were purified as described and 1 ig of each sample were loaded on a 1.2% agarose gel (A). The molecular mass of HA were determined by MALLS and the results were listed in the table (B). The item numbers in the table correspond to lane number in Panel A. M, Bioline DNA HyperLadder.
Figure 27:
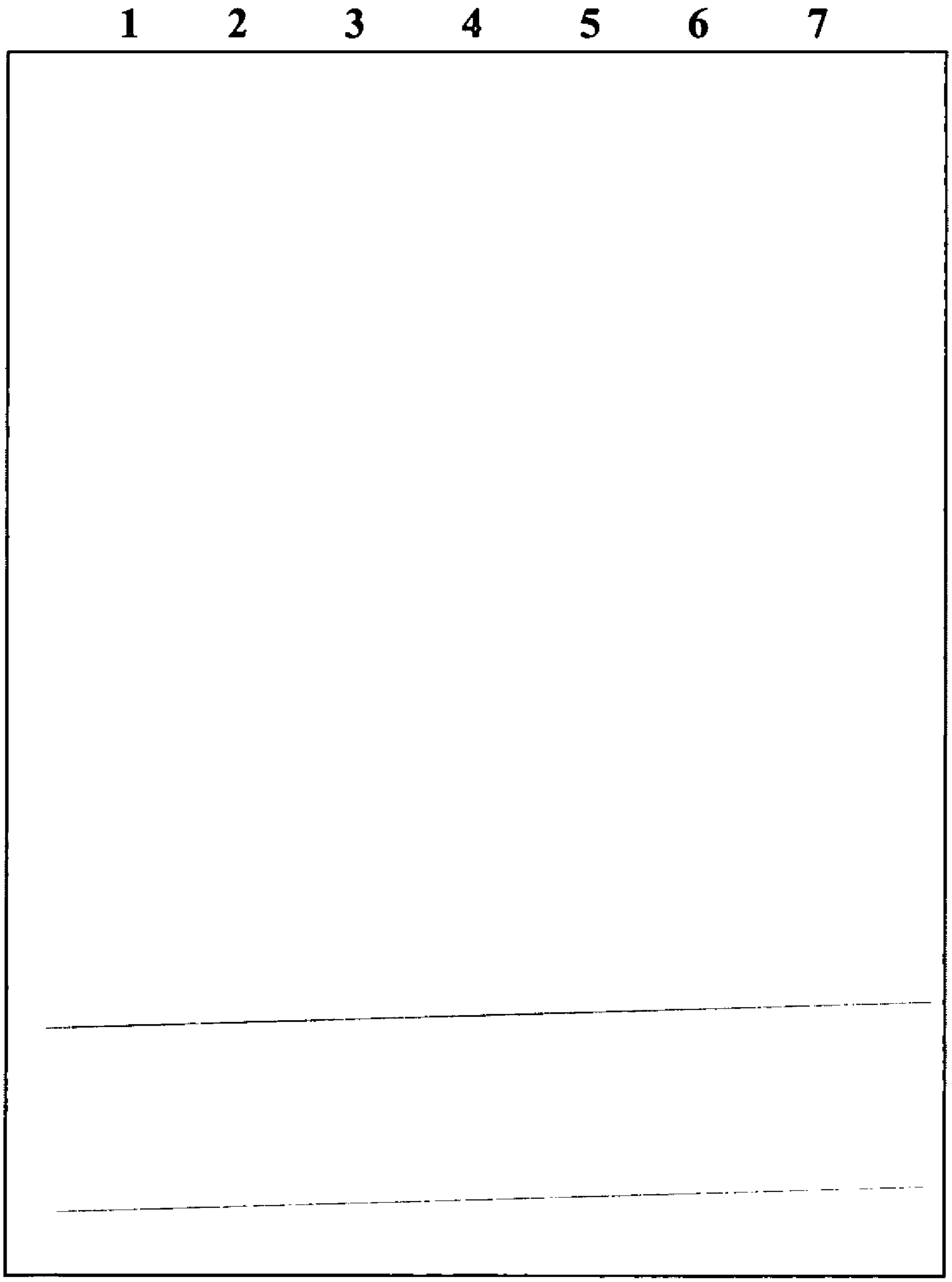
FIG. 27 is an electrophoresis gel illustrating in vitro synthesis of fluorescent HA. 20 il of reactions were setup with 2 ig/il of pmHAS various amounts of fluorescent HA4 and UDP-sugars. Reaction products were analyzed with 0.8% agarose gel electrophoresis and viewed under UV light.

The synthase enzyme will preferentially add available UDP-sugar precursors to the acceptor termini. If there are many acceptors, thus many termini, then a limited amount of UDP-sugars will be distributed among many molecules and thus result in many short polymer chain extensions. Conversely, if there are few acceptors, thus few termini, then the limited amount of UDP-sugars will be distributed among few molecules and thus result in a few long polymer chain extensions (modeled in FIG. 24). It has previously been observed that chain initiation is the rate-limiting step for pmHAS, and the enzyme prefers to transfer sugars onto existing HA chains when acceptor is included in the reaction. If the polymerization is indeed a synchronized process, then the amount of HA4 should affect the final size of the HA product when the same amount of UDP-sugar is present. To test this speculation, assays were performed with various levels of HA4 with fixed amount of UDP-sugar and pmHAS (FIG. 25A). To determine the size and polydispersity of these HA products, HA polymer sizes were determined by size exclusion chromatography—Multi Angle Laser Light Scattering (SEC-MALLS, FIG. 25B). Using the same strategy HA was generated from 27 kDa to 1.3 MDa with polydispersity ranging from 1.001 to 1.2. FIG. 26 demonstrates the monodispersity of the various HA polymers resulting from reaction synchronization In vitro synthesis of fluorescent HA. The in vitro technology for the production of monodisperse glycosaminoglycans also allows the use of modified acceptor to synthesize HA polymers containing various types of foreign moieties. An example is shown using fluorescent HA4 to produce fluorescent monodisperse HA of various sizes (FIG. 27). Similarly, radioactive (e.g., $^{3}H$, $^{125}I$), affinity (e.g., biotin), detection (e.g., probe for NMR or X-ray uses or a reporter enzyme), or medicant tagged glycosaminoglycan polymers are possible with the appropriate modified acceptor. However, the invention is not limited to the tags described herein, and other tags known to a person having ordinary skill in the art may be utilized in accordance with the present invention.

Figure 28:
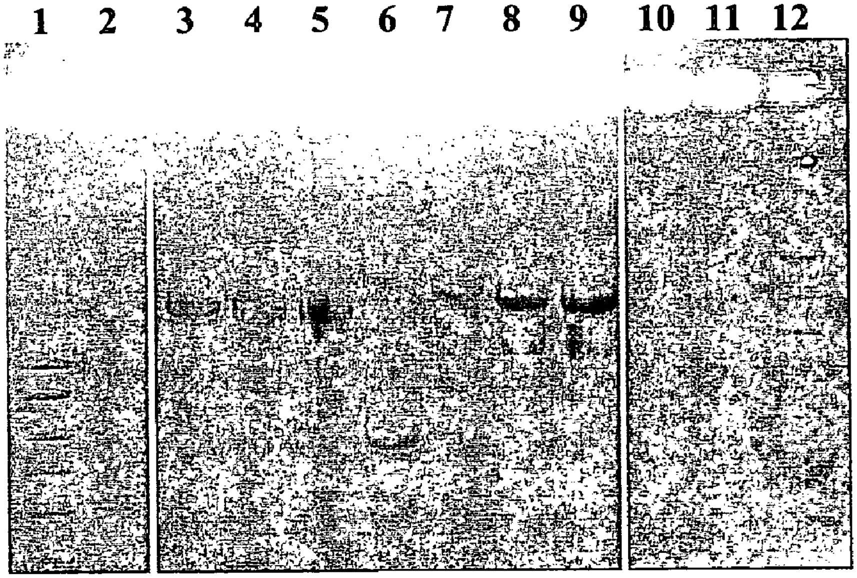
FIG. 28 is an electrophoresis gel illustrating utilization of large HA acceptors. Reactions were carried out at 30° for 48 hours. The 60 il reaction contained 0.28 ig/il of pmHAS, 3.3 mM UDP-GlcNAc, 3.3 mM UDP-GlcUA and without (lane 2) or with various amounts of acceptors (lanes 3-5, 7-9 and 10). 1.0 il of each reaction was loaded on 0.7% agarose gel and stained with STAINS-ALL. Lane 1, BIORAD kb ladder (top band is 15 kb). Lane 6, 0.5 ig of 970 kDa HA starting acceptor. Lane 11, 3 ig of Genzyme HA starting acceptor. Lane 12, Invitrogen DNA HyperLadder (top band is 48.5 kB).

In addition to the small sugar chains (e.g., tetrasaccharide HA4), larger HA polymers can be used as starting acceptor for pmHAS; the enzyme will elongate existing chains with more sugars. Experiments were performed using 575 kDa HA and 970 kDa HA (synthesized in vitro with pmHAS and HA4 as acceptor, using the previously described methods) and a commercially available HA sample (~2 MDa; Genzyme) as acceptors. The results indicate that the existing HA chains were further elongated (FIG. 28). For example, the ~2 MDa starting material in lane 11 was elongated to produce the larger (i.e., slower migrating) material in lane 10. Therefore, a method for creating higher value longer polymers is also described by the present invention. The length of the final product can be controlled stoichiometrically as shown in lanes 7-9; a lower starting acceptor concentration (lane 7) results in longer chains because the same limited amount of UDP-sugars is consumed, making a few long chains instead of many shorter chains (lane 9).

The molecular weights of naturally existing HA polymers usually range from hundreds of thousands up to several millions of Daltons. For research requiring smaller HA polymers, enzymatic degradation is usually the first choice. However, this process is not satisfactory because it is time-consuming and the final yield of the targeted HA size fraction is low, and demanding chromatography is required. With the in vitro synthesis techniques of the present invention, HA as small as 10 kDa can be generated with polydispersity around 1.001.

High molecular HAs are commercially available from animal or bacterial sources. Problems with those include possible contaminants leading to immunological responses as well as broad size distribution (Soltes etc., 2002). Polydispersities (Mw/Mn) are commonly higher than 1.5. Conclusions drawing from experimental data during biological research with these HA could be misleading. Thus there exists a need for uniform HA to perform biological study, as agreed by Uebelhart and Williams (1999).

To determine the exact average molecular mass of HA, MALLS is usually the choice. Yet many people have the need to quickly estimate the mass. For this purpose, some groups investigated the correlation of HA migration on agarose gel with DNA (Lee and Cowman, 1994). The drawback of this method is that, first, the HA samples used were not uniform, and second, the migration of HA and DNA on agarose gel changes differently with the change of the concentration of agarose gel. The in vitro generated HA of defined size distribution provide excellent series of standards for this purpose (FIG. 29).

In general, the unique technologies of the present invention allow the generation of a variety of defined, monodisperse HA tools for elucidating the numerous roles of HA in health and disease due to their monodisperse size distributions and defined compositions.

In addition to making HA polymers, the relaxed acceptor specificity of pmHAS allows the use of various chondroitin acceptors. This allows the production of monodisperse hybrid GAGs that have utility in medicine including tissue engineering and surgical aids. In particular, new protein-free proteoglycans are now possible that do not have antigenicity or allergenicity concerns compared to animal-derived products.

Figure 30:
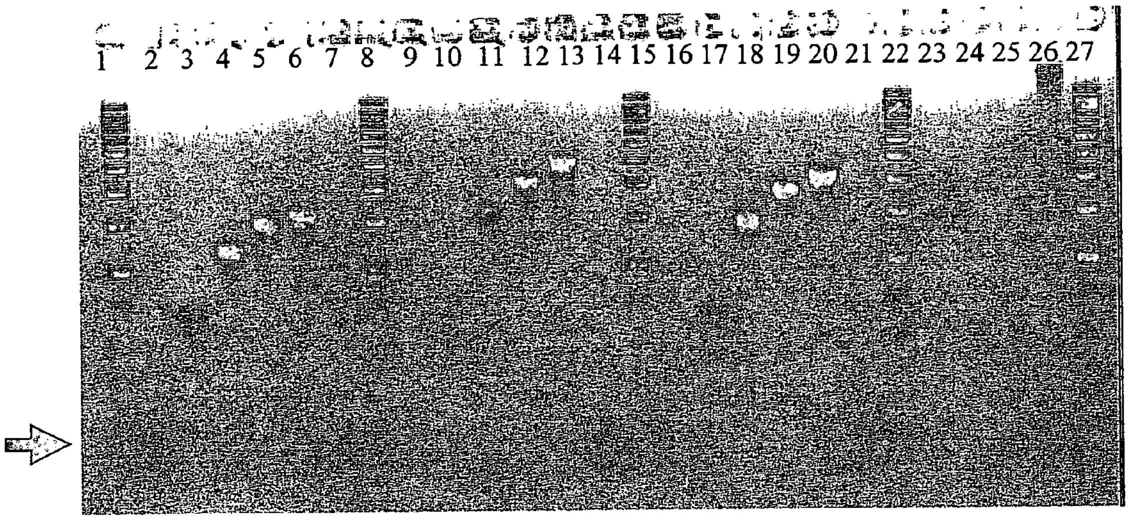
FIG. 30 is an electrophoresis gel illustrating various mondisperse chondroitin sulfate HA hybrid GAGs. The 1% agarose gel stained with STAINS-ALL shows a variety of chondroitin sulfates (either A, B or C) that were elongated with pmHAS, thus adding HA chains. Lanes 1, 8, 15, 22 and 27 contain the Kilobase DNA ladder; lanes 2 and 7 contain starting CSA, while lanes 3-6 contain CSA-HA at 2 hrs, 4 hrs, 6 hrs and O/N, respectively; lanes 9 and 14 contain starting CSB, while lanes 10-13 contain CSB-HA at 2 hrs, 4 hrs, 6 hrs and O/N, respectively; lanes 16 and 21 contain starting CSC, while lanes 17-20 contain CSC-HA at 2 hrs, 4 hrs, 6 hrs and O/N, respectively; lanes 23-26 contain no acceptor at 2 hrs, 4 hrs, 6 hrs and O/N, respectively.

In FIG. 30, various monodisperse chondroitin sulfate HA hybrid GAGs are created by elongating a variety of chondroitin sulfates (A, B, and C) with pmHAS, thus adding HA chains. Various amounts of HA were added to the preparations (at various times during reaction as noted) by adding more UDP-sugars. For example, lanes 3-6 show hybrids with a constant amount of chondroitin sulfate and increasing HA chain lengths. The starting chondroitin sulfates stain weakly here, and the band position is marked with an arrow. Without the acceptor (lanes 23-26), no such defined bands are seen; after a long period, some HA polymer shows up (lane 26) which results from de novo initiation without acceptor.

Figure 31:
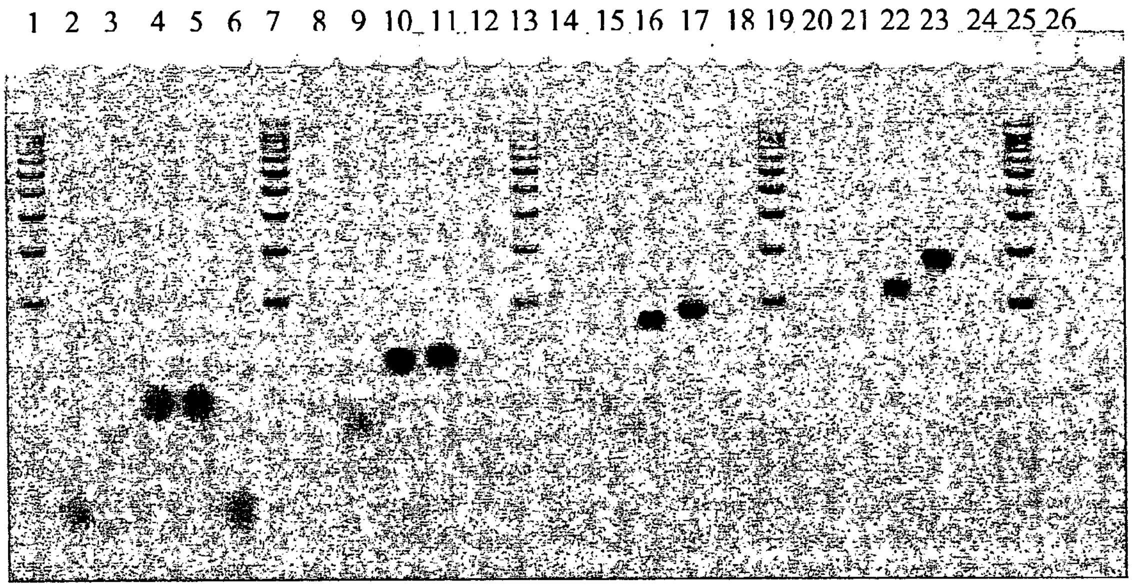
FIG. 31 is an electrophoresis gel illustrating control of hybrid GAG size by stoichiometric control. The 1% agarose gel stained with STAINS-ALL shows chondroitin sulfate A that was elongated with pmHAS, thus adding HA chains. Lanes 1, 7, 13, 19 and 25 contain the Kilobase ladder; lanes 2 and 6 contain 225 ig starting CSA, while lanes 3-5 contain 225 ig CSA-HA at 2 hrs, 6 hrs and O/N, respectively; lanes 8 and 12 contain 75 ig starting CSA, while lanes 9-11 contain 75 ig CSA-HA at 2 hrs, 6 hrs and O/N, respectively; lanes 14 and 18 contain 25 ig starting CSA, while lanes 15-17 contain 25 ig CSA-HA at 2 hrs, 6 hrs and O/N, respectively; lanes 20 and 24 contain 8.3 ig starting CSA, while lanes 21-23 contain 8.3 ig CSA-HA at 2 hrs, 6 hrs and O/N, respectively.

In FIG. 31, chondroitin sulfate A was elongated with pmHAS, thus adding HA chains. Various amounts of HA were added to the preparations by controlling the level of chondroitin acceptor (thus changing the UDP-sugar/acceptor ratio) as well as adding more UDP-sugars during the reaction. By changing the UDP-sugar/acceptor ratio, stoichiometric control of the hybrid GAG size was demonstrated.

In addition to extension with a HA synthase, other GAG synthases may be used in the methods of the present invention. For example, a chondroitin synthase such as but not limited to pmCS can be used to elongate an existing chondroitin sulfate polymer or HA polymer to produce defined hybrid GAG molecules of various structures. Again, these molecules may have use as surgical aids or tissue engineering scaffolds.

Figure 32:
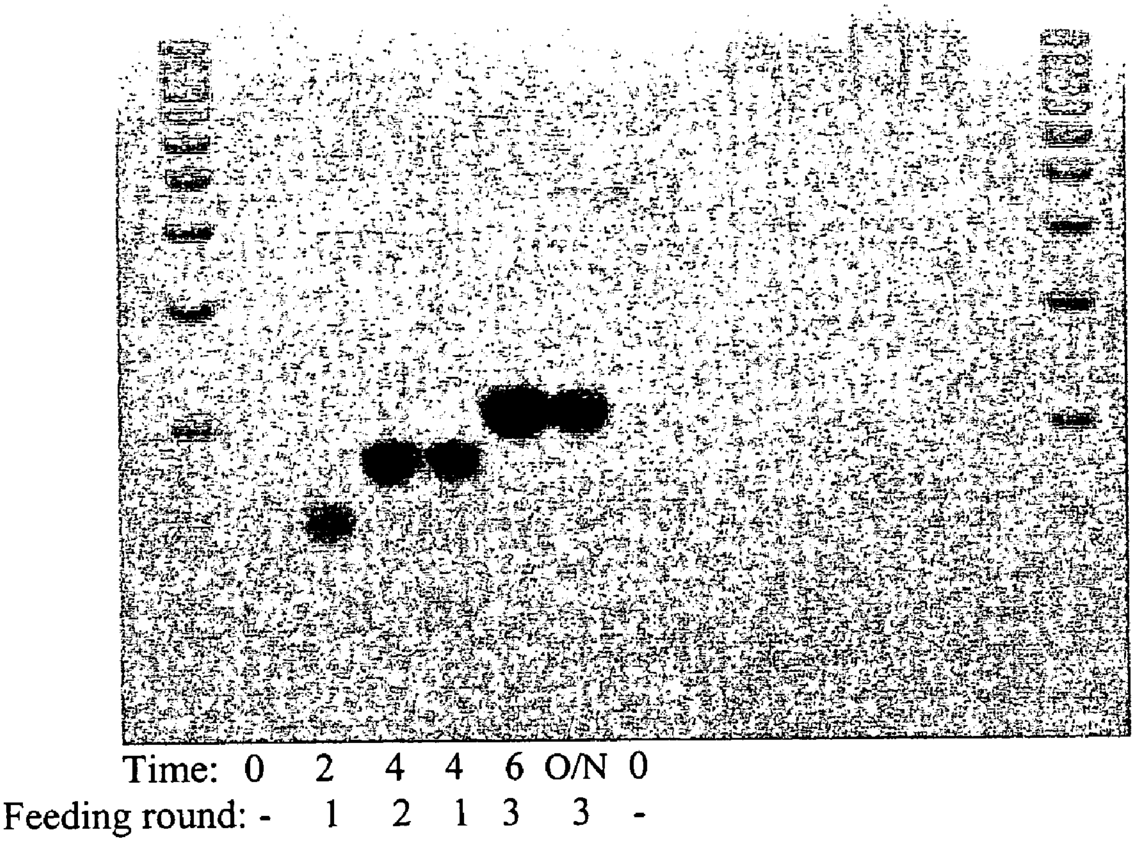
FIG. 32 is an electrophoresis gel illustrating extension of HA with chondroitin chains using pmCS. The 1.2% agarose gel stained with STAINS-ALL shows a reaction with pmCS and UDP-GlcUA, UDP-GalNAC with eithera 81 kDa HA acceptor (lanes 3-7) or no acceptor (lanes 9-13). Lanes 1 and 15 contain the Kilobase DNA standard. Lanes 2, 8 and 14 contain starting 81 kDa HA. Lanes 3-7: contain HA acceptor +HA-C at 2 hr, 4 hr, 4 hr (set O/N in incubator without 4 hr feeding), 6 hr and O/N, respectively. Lanes 9-13: contain no acceptor (minus) –HA-C at 2 hr, 4 hr, 4 hr (set O/N in incubator without 4 hr feeding), 6 hr and O/N, respectively.

In FIG. 32, pmCS and UDP-GlcUA, UDP-GalNAc were reacted with either a 81 kDa HA acceptor (lanes 3-7) or no acceptor (lanes 9-13). Various lengths of chondroitin were added to the HA chains (at longer times with more UDP-sugars producing longer hybrid chains). Without the acceptor, no such defined bands were seen; after a long period, some long pure chondroitin polymer shows up which results from de novo initiation without acceptor.

In FIG. 33, Size exclusion (or gel filtration) chromatography analysis coupled with multi-angle laser light scattering detection confirms the monodisperse nature of polymers created by the present invention. In the FIG. 33A, HA (starting MW 81 kDa) extended with chondroitin chains using pmCS (same sample used in FIG. 32, lane #7, overnight [O/N] extension) was analyzed; the material was 280,000 Mw and polydispersity (Mw/Mn) was 1.003±0.024. Chondroitin sulfate HA extended with HA chains using pmHAS (same sample used in FIG. 30, lane #23) was analyzed and shown in FIG. 33B; the material was 427,000 Mw and polydispersity (Mw/Mn) was 1.006±0.024.

Figure 34:
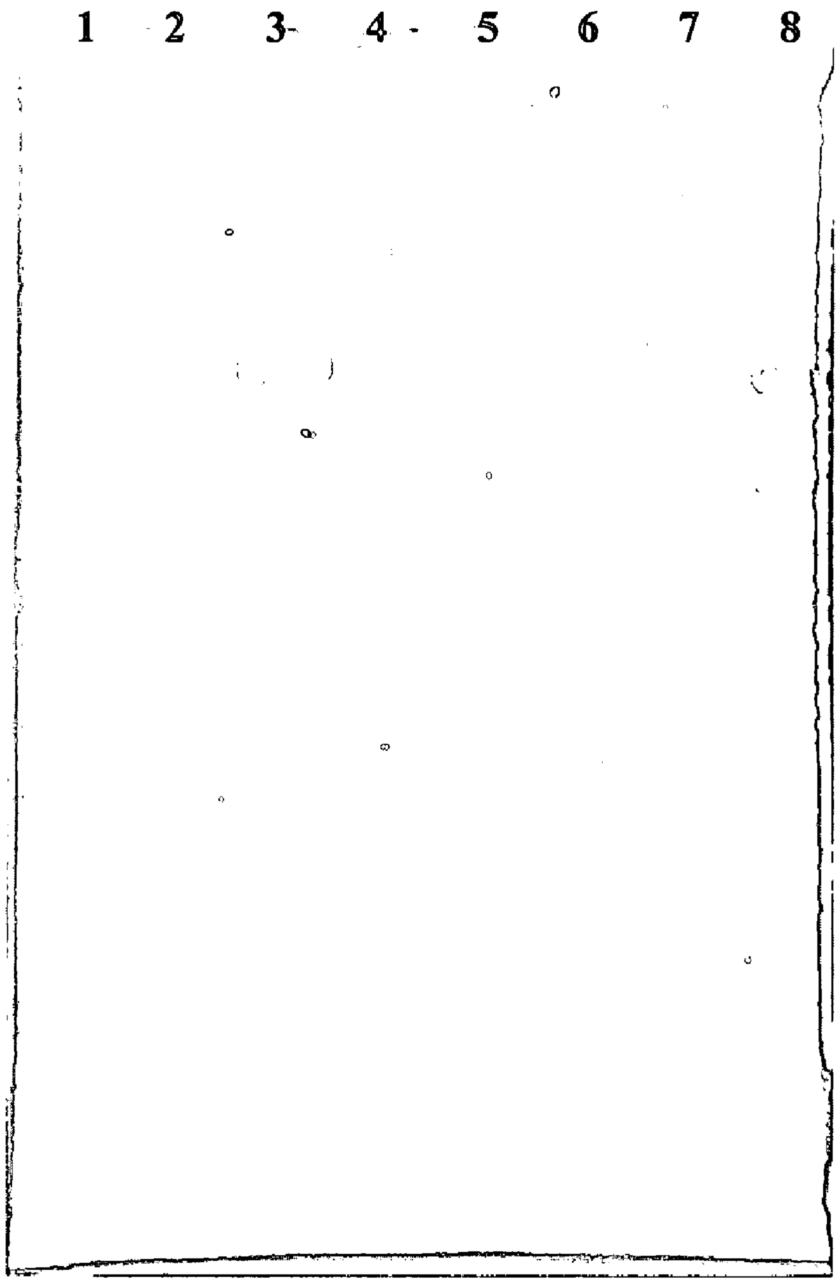
FIG. 34 is an 0.7% agarose gel detected with Stains-all compares the monodisperse, 'select HA' to commercially produced HA samples.

In FIG. 34 a 0.7% agarose gel detected with Stains-all compares the monodisperse, 'select HA' to commercially produce HA samples is shown. In lanes 1-3, the mixture of various monodisperse HAs made by the present invention (separate reaction products that were recombined to run all in one lane; sizes from top to bottom of lane: 1.27 MDa, 946 kDa, 575 kDa, 284 kDa, 27 kDa) run as discrete, tight bands. In contrast, in lanes 4-7, the commercially produced HA samples run as polydisperse smears (lane 4, 1.1 MDa; 5, 810 kDa; 6, 587 kDa; 7, 350 kDa). Remarkably, the monodisperse HA bands look almost as narrow as the single-molecule species of DNA present in lane 8 (BIOLINE standard).

Biomaterials and Methods of Making Same

Biomaterials also play a pivotal role in the field of tissue engineering. Biomimetic synthetic polymers have been created to elicit specific cellular functions and to direct cell-cell interactions both in implants that are initially cell-free, which may serve as matrices to conduct tissue regeneration, and in implants to support cell transplantation. Biomimetic approaches have been based on polymers endowed with bioadhesive receptor-binding peptides and mono- and oligosaccharides. These materials have been patterned in two- and three-dimensions to generate model multicellular tissue architectures, and this approach may be useful in future efforts to generate complex organizations of multiple cell types. Natural polymers have also played an important role in these efforts, and recombinant polymers that combine the beneficial aspects of natural polymers with many of the desirable features of synthetic polymers have been designed and produced. Biomaterials have been employed to conduct and accelerate otherwise naturally occurring phenomena, such as tissue regeneration in wound healing in the otherwise healthy subject; to induce cellular responses that might not be normally present, such as healing in a diseased subject or the generation of a new vascular bed to receive a subsequent cell transplant; and to block natural phenomena, such as the immune rejection of cell transplants from other species or the transmission of growth factor signals that stimulate scar formation.

Approximately 10 years ago, the concept of bioadhesion was introduced into the pharmaceutical literature and has since stimulated much research and development both in academia and in industry. The first generation of bioadhesive drug delivery systems (BBDS) were based on so-called mucoadhesive polymers, i.e., natural or synthetic macromolecules, often already well accepted and used as pharmaceutical excipients for other purposes, which show the remarkable ability to 'stick' to humid or wet mucosal tissue surfaces. While these novel dosage forms were mainly expected to allow for a possible prolongation, better localization or intensified contact to mucosal tissue surfaces, it had to be realized that these goals were often not so easily accomplished, at least not by means of such relatively straightforward technology. However, although not always convincing as a glue, some of the mucoadhesive polymers were found to display other, possibly even more important biological activities, namely to inhibit proteolytic enzymes and/or to modulate the permeability of usually tight epithelial tissue barriers. Such features were found to be particularly useful in the context of peptide and protein drug delivery.

The primary goal of bioadhesive controlled drug delivery is to localize a delivery device within the body to enhance the drug absorption process in a site-specific manner. Bioadhesion is affected by the synergistic action of the biological environment, the properties of the polymeric controlled release device, and the presence of the drug itself. The delivery site and the device design are dictated by the drug's molecular structure and its pharmacological behavior.

One such bioadhesive known in the art is fibrin glue and compositions which include one or more types of fibrin glue in combination with a medicament have been studied. For example, in order to test the effect on the handling properties of two component fibrin glue, the viscosity of the fibrin glue was increased with sodium hyaluronate and the glue was applied to a microvascular anastomosis in rats. The femoral artery of each rat was anastomosed with three conventional sutures and then sealed with the fibrin glue. Three glues with different viscosities were tested: original Tisseel fibrin glue (Immuno AG, Vienna); Tisseel with 0.9% sodium chloride added to the fibrinogen component; and Tisseel with a high molecular weight sodium hyaluronate (10 mg/ml, Healon, Pharmacia, Sweden) added to the fibrinogen component. The increased viscosity of the fibrin glue to which hyaluronate had been added resulted in a significantly higher patency rate 20 minutes after completion of the anastomosis ($p<0.01$), and reduced the amount of fibrin that entered the vessels. Wadstrom et al. Fibrin glue (Tisseel) added with sodium hyaluronate in microvascular anastomosing. Scand J Plast Reconstr Surg Hand Surg December 27, 1993(4):257-61.

The typical properties of the bioadhesive fibrin system described above ensue from its physiological properties. Filling the wound enhances natural biological processes of healing. The tissue reaction to the applied tissue fibrin coagulum is favorable. The treated parenchymatous organs, liver and spleen, heal with a smooth scar. The number of adhesions in the peritoneal cavity in all known treated experimental animals after treatment of the spleen was similar. Fewer adhesions are also observed when using a bioadhesive for repairing liver injuries in rabbits. The macroscopic appearance of the scar was similar; the scar was less visible in the liver parenchyma. The histological appearance was similar. The bioadhesive did not damage the tissue surrounding the parenchyma and did not act as a foreign body. These results confirm the biocompatibility of the fibrin glue as well as tissue tolerance and satisfactory healing without a reaction to the bioadhesive. After healing the bioadhesive is typically replaced by natural fibrous tissue.

Despite the effectiveness and successful use of the fibrin glue by medical practitioners in Europe, neither fibrin glue nor its essential component fibrinogen is widely used in the United States at the present time because of the general risks and problems of infection from pooled blood products contaminated with lipid-enveloped viruses such as HIV, associated with AIDS, and the hepatitis causing viruses such as HBV and HCV, as well as cytomegalovirus (CMV), Epstein-Barr virus, and the herpes simplex viruses in fibrinogen preparations. Thus, a naturally occurring or recombinantly produced bioadhesive which is not derived from pooled blood sources is actively being sought. The bioadhesive of the present invention fulfills such a need.

For example, one embodiment of the present invention is the use of sutures or bandages with HA-chains grafted on the surface or throughout the material in combination with the fibrinogen glue. The immobilized HA does not diffuse away as in current formulations, but rather remains at the wound site to enhance and stimulate healing.

Organic materials have also been postulated for use as bioadhesives. Bioadhesive lattices of water-swollen poly (acrylic acid) nano-and microparticles have been synthesized using an inverse (W/O) emulsion polymerization method. They are stabilized by a co-emulsifier system consisting of Span™ 80 and Tween™ 80 dispersed in aliphatic hydrocarbons. The initial polymerization medium contains emulsion droplets and inverse micelles which solubilize a part of the monomer solution. The polymerization is then initiated by free radicals, and particle dispersions with a narrow size distribution are obtained. The particle size is dependent on the type of radical initiator used. With water-soluble initiators, for example ammonium persulfate, microparticles are obtained in the size range of 1 to 10 micrometer, indicating that these microparticles originate from the emulsion droplets since the droplet sizes of the W/O emulsion show similar distribution. When lipophilic radical initiators, such as azo-bis-isobutyronitrile, are used, almost exclusively nanoparticles are generated with diameters in the range of 80 to 150 nm, due to the limited solubility of oligomeric poly(acrylic acid) chains in the lipophilic continuous phase. These poly (acrylic acid) micro- and nanoparticles yielded excellent bioadhesive properties in an in-vitro assay and may, therefore, be suitable for the encapsulation of peptides and other hydrophilic drugs.

In the present invention, HA or chondroitin chains would be the natural substitute for poly(acrylic-acid) based materials. HA is a negatively-charged polymer as is poly(acrylic-acid), but HA is a naturally occurring molecule in the vertebrate body and would not invoke an immune response like a poly(acrylic-acid) material.

The interest in realizing ‘true’ bioadhesion continues: instead of mucoadhesive polymers, plant or bacterial lectins, i.e., adhesion molecules which specifically bind to sugar moieties of the epithelial cell membrane are now widely being investigated as drug delivery adjuvants. These second-generation bioadhesives not only provide for cellular binding, but also for subsequent endo- and transcytosis. This makes the novel, specifically bioadhesive molecules particularly interesting for the controlled delivery of DNA/RNA molecules in the context of antisense or gene therapy.

For the efficient delivery of peptides, proteins, and other biopharmaceuticals by nonparenteral routes, in particular via the gastrointestinal, or GI, tract, novel concepts are needed to overcome significant enzymatic and diffusional barriers. In this context, bioadhesion technologies offer some new perspectives. The original idea of oral bioadhesive drug delivery systems was to prolong and/or to intensify the contact between controlled-release dosage forms and the stomach or gut mucosa. However, the results obtained during the past decade using existing pharmaceutical polymers for such purposes were rather disappointing. The encountered difficulties were mainly related to the physiological peculiarities of GI mucus. Nevertheless, research in this area has also shed new light on the potential of mucoadhesive polymers. First, one important class of mucoadhesive polymers, poly(acrylic acid), could be identified as a potent inhibitor of proteolytic enzymes. Second, there is increasing evidence that the interaction between various types of bio(muco)adhesive polymers and epithelial cells has direct influence on the permeability of mucosal epithelia. Rather than being just adhesives, mucoadhesive polymers may therefore be considered as a novel class of multifunctional macromolecules with a number of desirable properties for their use as biologically active drug delivery adjuvants.

In the present invention, HA or other glycosaminoglycan polysaccharides are used. As HA is known to interact with numerous proteins (i.e., RHAMM, CD44) found throughout the healthy and diseased body, then naturally occurring adhesive interactions can be utilized to effect targeting, stabilization, or other pharmacological parameters. Similarly, chondroitin interacts with a different subset of proteins (i.e. platelet factor 4, thrombin); it is likely that this polymer will yield properties distinct from HA and widen the horizon of this technology.

In order to overcome the problems related to GI mucus and to allow longer lasting fixation within the GI lumen, bioadhesion probably may be better achieved using specific bioadhesive molecules. Ideally, these bind to surface structures of the epithelial cells themselves rather than to mucus by receptor-ligand-like interactions. Such compounds possibly can be found in the future among plant lectins, novel synthetic polymers, and bacterial or viral adhesion/invasion factors. Apart from the plain fixation of drug carriers within the GI lumen, direct bioadhesive contact to the apical cell membrane possibly can be used to induce active transport processes by membrane-derived vesicles (endo- and transcytosis). The nonspecific interaction between epithelia and some mucoadhesive polymers induces a temporary loosening of the tight intercellular junctions, which is suitable for the rapid absorption of smaller peptide drugs along the paracellular pathway. In contrast, specific endo- and transcytosis may ultimately allow the selectively enhanced transport of very large bioactive molecules (polypeptides, polysaccharides, or polynucleotides) or drug carriers across tight clusters of polarized epi- or endothelial cells, whereas the formidable barrier function of such tissues against all other solutes remains intact.

Bioadhesive systems are presently playing a major role in the medical and biological fields because of their ability to maintain a dosage form at a precise body-site for a prolonged period of time over which the active principle is progressively released. Additional uses for bioadhesives include: bioadhesives/mucoadhesives in drug delivery to the gastrointestinal tract; nanoparticles as a gastroadhesive drug delivery system; mucoadhesive buccal patches for peptide delivery; bioadhesive dosage forms for buccal/gingival administration; semisolid dosage forms as buccal bioadhesives; bioadhesive dosage forms for nasal administration; ocular bioadhesive delivery systems; nanoparticles as bioadhesive ocular drug delivery systems; and bioadhesive dosage forms for vaginal and intrauterine applications.

The bioadhesive may also contain liposomes. Liposomes are unilamellar or multilamellar lipid vesicles which entrap a significant fraction of aqueous solution. The vesicular microreservoirs of liposomes can contain a variety of water-soluble materials, which are thus suspended within the emulsion. The preparation of liposomes and the variety of uses of liposomes in biological systems has been disclosed in U.S. Pat. Nos. 4,708,861, 4,224,179, and 4,235,871. Liposomes are generally formed by mixing long chain carboxylic acids, amines, and cholesterol, as well as phospholipids, in aqueous buffers. The organic components spontaneously form multilamellar bilayer structures called liposomes. Depending on their composition and storage conditions, liposomes exhibit varying stabilities. Liposomes serve as models of cell membranes and also are used as drug delivery systems.

Most attempts to use liposomes as drug delivery vehicles have envisioned liposomes as entities which circulate in blood, to be taken up by certain cells or tissues in which their degradation would slowly release their internal aqueous drug-containing contents. In an effort to aid in their up-take by a given target tissue, some liposomes have been Atailored@ by binding specific antibodies or antigens to the outer surface. Liposomes have also been devised as controlled release systems for the delivery of their contents in vivo. Compositions in which liposomes containing biologically active agents are maintained and immobilized in polymer matrices, such as methylcellulose, collagen and agarose, for sustained release of the liposome contents, are described in U.S. Pat. No. 4,708,861 to Popescu et al.

In this manner, the present invention contemplates a bioadhesive comprising HA or chondroitin or heparin produced from pmHAS, pmCS, pmHS1, or PmHS2. The present invention also contemplates a composition containing a bioadhesive comprising HA or chondroitin or heparin produced from pmHAS, pmCS, pmHS1, or PmHS2 and an effective amount of a medicament, wherein the medicament can be entrapped or grafted directly within the HA or chondroitin or heparin bioadhesive or be suspended within a liposome which is entrapped or grafted within the HA or chondroitin or heparin bioadhesive. These compositions are especially suited to the controlled release of medicaments.

Such compositions are useful on the tissues, skin, and mucus membranes (mucosa) of an animal body, such as that of a human, to which the compositions adhere. The compositions so adhered to the mucosa, skin, or other tissue slowly release the treating agent to the contacted body area for relatively long periods of time, and cause the treating agent to be sorbed (absorbed or adsorbed) at least at the vicinity of the contacted body area. Such time periods are longer than the time of release for a similar composition that does not include the HA bioadhesive.

The treating agents useful herein are selected generally from the classes of medicinal agents and cosmetic agents. Substantially any agent of these two classes of materials that is a solid at ambient temperatures may be used in a composition or method of the present invention. Treating agents that are liquid at ambient temperatures, e.g., nitroglycerine, can be used in a composition of this invention, but are not preferred because of the difficulties presented in their formulation. The treating agent may be used singly or as a mixture of two or more such agents.

One or more adjuvants may also be included with a treating agent, and when so used, an adjuvant is included in the meaning of the phrase treating agent or medicament. Exemplary of useful adjuvants are chelating agents such as EDTA that bind calcium ions and assist in passage of medicinal agents through the mucosa and into the blood stream. Another illustrative group of adjuvants are the quaternary nitrogen-containing compounds such as benzalkonium chloride that also assist medicinal agents in passing through the mucosa and into the blood stream.

The treating agent is present in the compositions of this invention in an amount that is sufficient to prevent, cure and/or treat a condition for a desired period of time for which the composition of this invention is to be administered, and such an amount is referred herein as an effective amount. As is well known, particularly in the medicinal arts, effective amounts of medicinal agents vary with the particular agent involved, the condition being treated and the rate at which the composition containing the medicinal agent is eliminated from the body, as well as varying with the animal in which it is being used, and the body weight of that animal. Consequently, effective amounts of treating agents may not be defined for each agent. Thus, an effective amount is that amount which in a composition of this invention provides a sufficient amount of the treating agent to provide the requisite activity of treating agent in or on the body of the treated animal for the desired period of time, and is typically less than that amount usually used.

Inasmuch as amounts of particular treating agents in the blood stream that are suitable for treating particular conditions are generally known, as are suitable amounts of treating agents used in cosmetics, it is a relatively easy laboratory task to formulate a series of controlled release compositions of this invention containing a range of such treating agent for a particular composition of this invention.

The second principle ingredient of this embodiment of the present invention is a bioadhesive comprising an amount of hyaluronic acid (HA) from pmHAS or chondroitin from PmCS or heparin from pmHS1 or PmHS2. Such a glycosaminoglycan bioadhesive made from a HA or chondroitin or heparin chain directly polymerized onto a molecule with the desired pharmacological property or a HA or chondroitin or heparin chain polymerized onto a matrix or liposome which in turn contains or binds the medicament.

Woodfield et al. (2002) describe that articular cartilage lesions resulting from trauma or degenerative diseases are commonly encountered clinical problems. It is well-established that adult articular cartilage has limited regenerative capacity, and, although numerous treatment protocols are currently employed clinically, few approaches exist that are capable of consistently restoring long-term function to damaged articular cartilage. Tissue engineering strategies that focus on the use of three-dimensional scaffolds for repairing articular cartilage lesions offer many advantages over current treatment strategies. Appropriate design of biodegradable scaffold conduits (either preformed or injectable) allow for the delivery of reparative cells bioactive factors, or gene factors to the defect site in an organized manner. This review seeks to highlight pertinent design considerations and limitations related to the development, material selection, and processing of scaffolds for articular cartilage tissue engineering, evidenced over the last decade. In particular, considerations for novel repair strategies that use scaffolds in combination with controlled release of bioactive factors or gene therapy.

The various glycosaminoglycans produced by the methods of the present invention, especially the hybrid or chimeric polymers, are promising materials for incorporation, either directly or indirectly, into a scaffold for cell growth and implantation. In addition, the polymers may be attached to surfaces or devices via acceptor moiety or a direct chain interaction.

Bello et al. (2001) describe that tissue-engineered skin is a significant advance in the field of wound healing and was developed due to limitations associated with the use of autografts. These limitations include the creation of a donor site which is at risk of developing pain, scarring, infection and/or slow healing. A number of products are commercially available and many others are in development. Cultured epidermal autografts can provide permanent coverage of large area from a skin biopsy. However, 3 weeks are needed for graft cultivation. Cultured epidermal allografts are available immediately and no biopsy is necessary. They can be cryopreserved and banked, but are not currently commercially available. A nonliving allogeneic acellular dermal matrix with intact basement membrane complex (Alloderm) is immunologically inert. It prepares the wound bed for grafting allowing improved cultured allograft 'take' and provides an intact basement membrane. A nonliving extracellular matrix of collagen and chondroitin-6-sulfate with silicone backing (Integra) serves to generate neodermis. A collagen and glycosaminoglycan dermal matrix inoculated with autologous fibroblasts and keratinocytes has been investigated but is not commercially available. It requires 3 to 4 weeks for cultivation. Dermagraft consists of living allogeneic dermal fibroblasts grown on degradable scaffold. It has good resistance to tearing. An extracellular matrix generated by allogeneic human dermal fibroblasts (TransCyte) serves as a matrix for neodermis generation. Apligraf is a living allogeneic bilayered construct containing keratinocytes, fibroblasts and bovine type I collagen. It can be used on an outpatient basis and avoids the need for a donor site wound. Another living skin equivalent, composite cultured skin (OrCel), consists of allogeneic fibroblasts and keratinocytes seeded on opposite sides of bilayered matrix of bovine collagen. There are limited clinical data available for this product, but large clinical trials are ongoing. Limited data are also available for 2 types of dressing material derived from pigs: porcine small intestinal submucosa acellular collagen matrix (Oasis) and an acellular xenogeneic collagen matrix (E-Z-Derm). Both products have a long shelf life. Other novel skin substitutes are being investigated. The potential risks and benefits of using tissue-engineered skin need to be further evaluated in clinical trials but it is obvious that they offer a new option for the treatment of wounds.

The various glycosaminoglycans produced by the methods of the present invention, especially the hybrid or chimeric polymers, are promising components for tissue engineered organs including skin.

Vlodavsky et al. (1996) disclose that heparan sulfate proteoglycans (HSPGs) are ubiquitous macromolecules associated with the cell surface and extracellular matrix (ECM) of a wide range of cells of vertebrate and invertebrate tissues. The basic HSPG structure consists of a protein core to which several linear heparan sulfate (HS) chains are covalently attached. The polysaccharide chains are typically composed of repeating hexuronic and D-glucosamine disaccharide units that are substituted to a varying extent with N— and O-linked sulfate moieties and N-linked acetyl groups. Beside serving as a scaffold for the attachment of various ECM components (e.g., collagen, laminin, fibronectin), the binding of HS to certain proteins has been suggested to induce a conformational change which may lead to the exposure of novel reactive determinants or conversely stabilize an inert protein configuration. Of particular significance is the interaction of HS with fibroblast growth factors (FGFs), mediating their sequestration, stabilization and high affinity receptor binding and signaling. Cellular responses to FGFs may hence be modulated by metabolic inhibitors of HS synthesis and sulfation, HS-degrading enzymes, and synthetic mimetics of heparin/HS. HS is involved in basic FGF (bFGF) receptor binding and mitogenic activity and its modulation by species of heparin, HS, and synthetic polyanionic 'heparin-mimicking' compounds. The results are discussed in relation to the current thoughts on the dual involvement of low and high affinity receptor sites in the growth promoting and angiogenic activities of bFGF and other heparin-binding growth factors.

The mimetics based on the various glycosaminoglycans produced by the methods of the present invention, including the hybrid or chimeric polymers, are promising due to their inherent abilities to interact, trigger, or bind a variety of molecules including cytokines, receptors, and growth factors. These GAG molecules should thus serve as modulators of cell behavior and/or growth via numerous natural pathways in mammals and humans.

Iivanainen et al. (2003) disclose that dynamic interactions between endothelial cells and components of their surrounding extracellular matrix are necessary for the invasion, migration, and survival of endothelial cells during angiogenesis. These interactions are mediated by matrix receptors that initiate intracellular signaling cascades in response to binding to specific extracellular matrix molecules. The interactions between endothelial cells and their environment are also modulated by enzymes that degrade different matrix components and thus enable endothelial invasion. Recent reports on gene targeting in mice have confirmed the role of two classes of matrix receptors, integrins and cell surface heparan sulfate proteoglycans, and a group of matrix degrading proteolytic enzymes, matrix metalloproteinases, in angiogenesis. The significance of endothelial cell-matrix interactions is further supported by several ongoing clinical trials that analyze the effects of drugs blocking this interaction on angiogenesis-dependent growth of human tumors.

The mimetics based on various glycosaminoglycans produced by the methods of the present invention, including the hybrid or chimeric polymers, are promising due to their inherent abilities to intearct, trigger, or bind a variety of molecules including cytokines, receptors, and growth factors. These molecules should thus serve as modulators of cell behavior and/or growth.

Song et al. (2002) teach that glypicans are a family of heparan sulfate proteoglycans that are bound to the cell surface by a glycosyl-phosphatidylinositol anchor. Six members of this family have been identified in mammals. In general, glypicans are highly expressed during development, and their expression pattern suggests that they are involved in morphogenesis. One member of this family, glypican-3, is mutated in the Simpson-Golabi-Behmel syndrome. This syndrome is characterized by overgrowth and various developmental abnormalities that indicate that glypican-3 inhibits proliferation and cell survival in the embryo. It has consequently been proposed that glypicans can regulate the activity of several growth factors that play a critical role in morphogenesis.

The various glycosaminoglycans produced by the methods of the present invention, especially the hybrid or chimeric polymers, are promising materials for incorporation, either directly or indirectly, onto cell surfaces. The polymers may be attached to cell surfaces or devices via acceptor moiety (for example, but not by way of limitation, a lipid conjugate).

Materials and Methods

Membrane preparations containing recombinant pmHAS (GenBank AF036004) (SEQ. ID NOS:1 and 2) were isolated from *E. coli* SURE(pPmHAS). Membrane preparations containing native pmHAS were obtained from the *P. multocida* strain P-1059 (ATCC #15742). pmHAS was assayed in 50 mM Tris, pH 7.2, 20 mM $MnC1_2$, and UDP-sugars (UDP-[$^{14}$C]GlcUA, 0.3 μCi/mmol, NEN and UDP-GlcNAc) at 30 C. The reaction products were analyzed by various chromatographic methods as described below. Membrane preparations containing other recombinant HAS enzymes, Group A streptococcal HasA or *Xenopus* DG42 produced in the yeast *Saccharomyces cerevisiae*, were prepared.

Uronic acid was quantitated by the carbazole method. Even-numbered HA oligosaccharides [(GlcNAc-GlcUA)$_n$] were generated by degradation of HA (from Group A *Streptococcus*) with either bovine testicular hyaluronidase Type V (n=2-5) or *Streptomyces hyaluroniticus* HA lyase (n=2 or 3) in 30 mM sodium acetate, pH 5.2, at 30° overnight. The latter enzyme employs an elimination mechanism to cleave the chain resulting in an unsaturated GlcUA residue at the non-reducing terminus of each fragment. For further purification and desalting, some preparations were subjected to gel filtration with P-2 resin (BioRad) in 0.2 M ammonium formate and lyophilization. Odd-numbered HA oligosaccharides [GlcNAc(GlcUA-GlcNAc)$_n$] ending in a GlcNAc residue were prepared by mercuric acetate-treatment of partial HA digests generated by HA lyase (n=2-7). The masses of the HA oligosaccharides were verified by matrix-assisted laser desorption ionization time-of-flight mass spectrometry. Sugars in water were mixed with an equal volume of 5 mg/ml 6-azo-2-thiothymine in 50% acetonitrile/0.1% trifluoroacetic acid, and rapidly air-dried on the target plate. The negative ions produced by pulsed nitrogen laser irradiation were analyzed in linear mode (20 kV acceleration; Perceptive Voyager).

Other oligosaccharides that are structurally similar to HA were also tested in HAS assays. The structure of heparosan pentamer derived from the *E. coli* K5 capsular polysaccharide is β4GlcUA-α4GlcNAc; this carbohydrate has the same composition as HA but the glycosidic linkages between the monosaccharides are different. The chitin-derived oligosaccharides, chitotetraose and chitopentaose, are β4GlcNAc polymers made of 4 or 5 monosaccharides, respectively.

Various oligosaccharides were radiolabeled by reduction with 4 to 6 equivalents of sodium borotritide (20 mM, NEN; 0.2 μCi/mmol) in 15 mM NaOH at 30 C for 2 hrs. $^3$H-oligosaccharides were desalted on a P-2 column in 0.2 M ammonium formate to remove unincorporated tritium and lyophilized. Some labeled oligosaccharides were further purified preparatively by paper chromatography with Whatman 1 developed in pyridine/ethyl acetate/acetic acid/$H_2O$ (5:5:1:3) before use as an acceptor.

Paper chromatography with Whatman 3M developed in ethanol/1M ammonium acetate, pH 5.5 (65:35) was used to separate high molecular weight HA product (which remains at the origin) from UDP-sugars and small acceptor oligosaccharides. In the conventional HAS assay, radioactive UDP-sugars are polymerized into HA. To obtain the size distribution of the HA polymerization products, some samples were also separated by gel filtration chromatography with Sephacryl S-200 (Pharmacia) columns in 0.2 M NaCl, 5 mM Tris, pH 8. Columns were calibrated with dextran standards. The identity of the polymer products was assessed by sensitivity to specific HA lyase and the requirement for the simultaneous presence of both UDP-sugar precursors during the reaction. Thin layer chromatography [TLC] on high performance silica plates with application zones (Whatman) utilizing butanol/acetic acid/water (1.5:1:1 or 1.25:1:1) development solvent separated $^3$H-labeled oligosaccharides in reaction mixes. Radioactive molecules were visualized after impregnation with EnHance spray (NEN) and fluorography at ~80°.

Membrane preparations containing recombinant full length pmHAS, pmHAS$^{437-972}$, pmHAS$^{437-756}$, pmHAS$^{1-756}$, pmHAS$^{1-567}$ and pmHAS$^{152-756}$ were isolated from *E. coli* as described. For soluble truncated pmHAS proteins, pmHAS$^{1-703}$, pmHAS$^{1-650}$, and pmHAS$^{1-703}$-derived mutants, cells were extracted with B-Per™ II Bacterial Protein Extraction Reagent (Pierce) according to the manufacturer s instruction except that the procedure was performed at 7° in the presence of protease inhibitors. Membrane preparations of *P. multocida* P-1059 (ATCC 15742) were made as described. In order to test whether the truncated recombinant polypeptides were formed as insoluble inclusion bodies, membrane preparations were suspended in RIPA buffer (1% NP40, 1% sodium deoxycholate and 0.1% SDS in 50 mM Tris, pH 7.2) for 20 minutes at room temperature. After centrifugation at 20,000×g for 10 minutes, the supernatants were saved and the pellets were resuspended in RIPA buffer. The supernatants and the pellets were analyzed by SDS-polyacrylamide gel electrophoresis and Western blot analysis as described later.

Membranes and extracts were analyzed using standard 8% polyacrylamide SDS gels. Following electrophoresis, proteins were transferred with a semi-dry apparatus to nitrocellulose membranes (S&S) and detected with a monospecific antibody directed against a synthetic peptide corresponding to residues 526 to 543 of pmHAS. The peptide, acetyl-LDSDDYLEPDAVELCLKE-amide (SEQ ID NO:22) (Quantum), was coupled to ovalbumin to form the initial immunogen for injection into female New Zealand white rabbits (HTI Bioscience protocols). In the subsequent boosts, free peptide was utilized. The specific antipeptide IgG was purified from ammonium sulfate fractionated sera (after third boost) using an immobilized peptide column (internal cysteine coupled to lodoacetyl beads; Pierce). The desired IgG was eluted with 0.1 M glycine, pH 2.5, neutralized, and exchanged into phosphate-buffered saline. Immunoreactive bands on Western blots were detected with a protein A-alkaline phosphatase conjugate and were visualized with 5-bromo-4-chloro-3-indolyl phosphate and nitroblue tetrazolium reagent.

The size of HA polymers was analyzed by chromatography on a Phenomenex PolySep-GFC-P 3000, P 4000 or P5000 column (300×7.8 mm) eluted with 0.2 M sodium nitrate at 0.6 ml/min on a Waters 600E system. The column was standardized with various size fluorescent dextrans (580, 50, and 12 kDa). Radioactive components were detected with a LB508 Radioflow Detector (EG & G Berthold) and Zinsser cocktail (1.8 ml/min). In comparison to the full HAS assay using paper chromatography described above, these 3 minute reactions contained twice the UDP-sugar concentrations, 0.06 μCi UDP-[$^{14}$C]GlcUA, and 0.25 μg even-numbered HA oligosaccharide. Also, addition of ethylenediamine tetracetic acid (final conc. 22 mM) and boiling (2 min) was employed to terminate the reactions instead of addition of SDS.

A lambda library of Sau3A partially digested Type F *P. multocida* P-4679 DNA (~4-9 kb average length insert) was made using the BamHI-cleaved Zap Express vector system (Stratagene). The plaque lifts were screened by hybridization (5×SSC, 50°; 16 hrs) with the digoxigenin-labeled probe using the manufacturer guidelines for colorimetric development. *E. coli* XLI-Blue MRF was co-infected with the purified, individual positive lambda clones and ExAssist helper phage to yield phagemids. The resulting phagemids were transfected into *E. coli* XLOLR cells to recover the plasmids. Sequence analysis of the plasmids revealed a novel open reading frame, which we called pmCS, with high homology to pmHAS.

In previous studies with pmHAS, it was found that a functional, soluble enzyme would be created if a portion of the carboxyl terminus was truncated by molecular genetic means. Therefore, a portion of the pmCS ORF (residues 1-704) in the insert of one of the excised lambda clones, pPmF4A, was amplified by 20 cycles of PCR with Taq polymerase. The sense primer corresponded to the sequence at the deduced amino terminus of the ORF and the antisense primer encoded the new carboxyl terminus followed by an artificial stop codon. The resulting PCR product was purified and concentrated using GeneClean. This insert was cloned using the pETBlue-1 Acceptor system (Novagen) according to the manufacturer s instructions. The Taq-generated single A overhang is used to facilitate the cloning of the open reading frame downstream of the T7 promoter and the ribosome binding site of the vector. The ligated products were transformed into *E. coli* NovaBlue and plated on LB carbenicillin (50 μg/ml) under conditions for blue/white screening. White or light blue colonies were analyzed by restriction digestion. A clone containing a plasmid with the desired truncated ORF, pPm-$CS^{1-}$$_{704}$, was transformed into *E. coli* Tuner, the T7 RNA polymerase-containing expression host, and maintained on LB media with carbenicillin and chloramphenicol (34 μg/ml) at 30 C. Log phase cultures were induced with β-isopropylthiogalactoside (0.2 mM final) for 5 hrs. The cells were harvested by centrifugation, frozen, and extracted for 20 min with a mild detergent (bper II reagent, Pierce) at 7° in the presence of a broad-range protease inhibitor cocktail. The cells were removed by centrifugation and the soluble extract was used as the source of CS enzyme for in vitro assays.

Truncated polypeptides were generated by amplifying the pPm7A insert by 13 cycles of PCR with Taq polymerase (Fisher) and synthetic oligonucleotide primers corresponding to various portions of the pmHAS open reading frame. Except for the construction of $pmHAS^{1-686}$ and $pmHAS^{1-668}$, the primers contained EcoRI and PstI restriction sites to facilitate cloning into the expression plasmid pKK223-3 (tac promoter; Pharmacia). The resulting recombinant constructs were transformed into *E. coli* TOP 10F cells (Invitrogen) and maintained on Luria-Bertani media with ampicillin selection. The DNA encoding $pmHAS^{1-686}$ and $pmHAS^{1-668}$ were cloned into pETBlue-1 plasmid and expressed in Tuner (DE3)pLacI cells (Novagen) according to manufacturing instructions; these cells were maintained on Luria-Bertani media with carbenicillin and chloramphenicol selection.

Point mutations were made using the QuickChange site-directed mutagenesis method (Stratagene) with the plasmid pKK223/$pmHAS^{1-703}$ DNA as template. The sequences of the mutant open reading frames were verified by automated DNA sequencing (Oklahoma State University Recombinant DNA/Protein Resource Facility).

Recombinant *E. coli* were grown in Luria-Bertani media with drug selection until $OD_{600}$ was 0.3-0.6 when cells were induced with 0.5 mM isopropyl-1-thio-β-D-galactoside. Cells were harvested 5 hours after induction. For soluble truncated proteins and $pmHAS^{1-703}$-derived mutants expressed in *E. coli* TOP10F' cell, cells were extracted with B-Per™ II Bacterial Protein Extraction Reagent (an octylthioglucoside-based solution; Pierce) according to the manufacturer s instruction except that the procedure was performed at 7° in the presence of protease inhibitors. For proteins expressed in Tuner(DE3)pLacI, lysis by ultrasonication followed by subcellular fractionation was performed and the supernatant after centrifugation at 100,000×g was used.

Five assays were designed to detect either (a) the polymerization of long HA chains, (b) the addition of a single GlcNAc to a GlcUA-terminated HA oligosaccharide acceptor, (c) the addition of a single GlcUA to a GlcNAc-terminated HA oligosaccharide acceptor, (d) the polymerization of long chondroitin chains, or (e) the addition of a single GalNAc to a GlcUA-terminated HA oligosaccharide acceptor. The first three assays were described hereinabove. For the chondroitin synthase assay, the same conditions as the HA synthase assay were used except that the other hexosamine precursor, UDP-GalNAc, was employed and there is no ammonium sulfate or ethylene glycol in the assay system. GalNAc-transferase activity was assayed under the same conditions as the GlcNAc-transferase assay except that 0.3 mM UDP-[$^3$H]GalNAc (0.2 μCi; NEN) was used instead of UDP-[$^3$H]GlcNAc. Reactions were terminated by the addition of SDS to 2% (w/v). The reaction products were separated from substrates by descending paper (Whatman 3M) chromatography with ethanol/1 M ammonium acetate, pH 5.5, development solvent (65:35 for the HAS, chondroitin synthase, and GlcUA-transferase assays; 75:25 for GlcNAc-transferase and GalNAc-transferase assay). All assays were adjusted to be linear with regard to incubation time and to protein concentration. Radiolabeled products were quantitated by liquid scintillation counting (Biosafe II, Research Products International).

The pmHAS polypeptides in membranes and extracts were analyzed using standard 8% polyacrylamide SDS gels and Western blotting utilizing a monospecific antibody directed against a synthetic peptide corresponding to residues 526 to 543 of pmHAS (acetyl-LDSDDYLEPDAVELCLKE-amide) as described hereinabove.

The DNA encoding different segments of pmHAS-D or pmCS were generated by amplifying the pPm7A insert or pPmF4A insert, respectively, by 15 cycles of PCR with Taq polymerase (Fisher) and synthetic oligonucleotide primers corresponding to various portions of the pmHAS-D or pmCS open reading frame. Each internal primer contained overlaps with the other segment to allow joining of the two desired segments. The forward and reverse primers for pmHAS residue 1-427 (A segment) were P1=5'-ATGAACACATTATCACAAGCAATAAAAGC-3' (SEQ ID NO:53) and P2=5'-GCGAATCTTCTATTGGTAAAAGYTTTC-3' (SEQ ID NO:54) (Y=C/T), respectively. The forward and reverse primers for pmCS residue 421-704 (C segment) were P3=5'-CTTTTACCAATAGAAGATTCGCATAT-3' (SEQ ID NO:55) and P4=5'-GAAGACGTCTTAGGCATCTTTATTCTGMTGAG-3' (SEQ ID NO:56), respectively. The forward and reverse primers for pmCS-residue 1-420 (D segment) were P1 and P2. The forward and reverse primers for pmHAS residue 428-703 (B segment) were P3 and P5=5'-GGGAATTCTGCAGTTAAATATCTTTTAAGATATCAATCTCTTC-3' (SEQ ID NO:57), respectively. The chimeric or hybrid synthases were created by 15 cycles of PCR with the gel-purified (GeneClean; Bio101) segments and outer primers (pm-AC used A and C segments with primer P1 and P4; pm-BD used B and D segments with primer P1 and P5). The purified PCR products were cloned into pETBlue-1 vector and the chimeric or hybrid proteins were expressed in Tuner(DE3)pLacI cells (Novagen). The complete open reading frames of multiple clones of both constructs were sequenced. A pmAC construct that was perfect, was found but both of the two pmBD constructs that we had sequenced completely had secondary undesired mutations (#1, E695 and I697F; #2, I302V). However, these mutations were in different locations and the enzyme transferase activities were identical. Several other pmBD clones have the identical phenotype but their complete sequences were not determined.

Analysis of Genomic DNA and Isolation of Capsule Biosynthesis Locus DNA—Preliminary data from Southern blot analysis using pmHAS-based hybridization probes[(12)] suggested that the Type A synthase and the putative Type D synthase were not very similar at the DNA level. However, PCR suggested that the UDP-glucose dehydrogenase genes, which encode an enzyme that produces the UDP-GlcUA precursor required for both HA and heparin biosynthesis, were very homologous. In most encapsulated bacteria, the precursor-forming enzymes and the transferases are located in the same operon. To make a hybridization probe predicted to detect the capsule locus, Type D chromosomal DNA served as a template in PCR reactions utilizing degenerate oligonucleotide primers (sense: GARTTYBTIMRIGARGGIAARGCIYTITAYGAY (SEQ ID NO:58); antisense: RCARTAICCICCRTAICCRAAISWXGGRTTRTTRTARTG (SEQ ID NO:59), where I=inosine; R=A or G; S=C or G; W=A or T; Y=C or T) corresponding to a conserved central region in many known UDP-glucose dehydrogenase genes. The ~0.3-kb amplicon was generated using Taq DNA polymerase (Fisher), gel-purified, and labeled with digoxigenin (High Prime system, Boehringer Mannheim).

A lambda library of Sau3A partially digested Type D *P. multocida* P-3881 DNA (~4-9 kb average length insert) was made using the BamHI-cleaved λZap Express™ vector system (Stratagene). The plaque lifts were screened by hybridization (5×SSC, 50 C; 16 hrs) with the digoxigenin-labeled probe using the manufacturer guidelines for colorimetric development. *E. coli* XLI-Blue MRF was co-infected with the purified, individual positive lambda clones and ExAssist helper phage to yield phagemids. The resulting phagemids were transfected into *E. coli* XLOLR cells to recover the plasmids. Sequence analysis of the plasmids using a variety of custom primers as well as the GPS-1 Genome Priming System (New England Biolabs) revealed a novel open reading frame, which we called pmHS1 (DNA sequence facilities at Oklahoma State University and University of Oklahoma HSC). We amplified and sequenced the ORF from several highly encapsulated isolates (see hereinbelow); very similar sequences were obtained.

Expression of Recombinant *P. multocida* Heparosan Synthase. The pmHS1 ORF (617 amino acids) was amplified from the various Type D genomic DNA template by 18 cycles of PCR with Taq polymerase. For constructing the full-length enzyme, the sense primer (ATGAGCTTATTTAAACGTGCTACTGAGC—SEQ ID NO:58) corresponded to the sequence at the deduced amino terminus of the ORF and the antisense primer (TTTACTCGTTATAAAAAGATAAACACGGMTAAG—SEQ ID NO:59) encoded the carboxyl terminus including the stop codon. In addition, a truncated version of pmHS1 was produced by PCR with the same sense primer but a different antisense primer (TATATTTACAGCAGTATCATTTTCTAAAGG—SEQ ID NO:60) to yield a predicted 501-residue protein, DcbF (SEQ ID NO:61) (GenBank Accession Number AAK17905); this variant corresponds to residues 1-497 of pmHS1 followed by the residues TFRK.

The HA4 molecule was converted into a fluorescent derivative in two steps. First, reductive amination of HA4 with cyanoborohydride and excess diaminobutane in 0.1 M borate buffer, pH 8.5, was used to make an amino-HA4 derivative that was purified by gel filtration on P2 resin. Second, the amino-HA4 was derivatized with the N-hydroxysuccinimide ester of Oregon green 488 (Molecular Probes) and the Fluor-HA4 was purified by preparative normal-phase thin layer chromatography (silica developed with 2:1:1 n-butanol/acetic acid/water).

Catalyst preparation and in vitro synthesis. The catalyst, pmHAS1-703 or pmCS1-704, are soluble purified *E. coli*-derived recombinant protein. The enzyme in the octyl-thioglucoside extracts of the cell paste was purified by chromatography on Toyopearl Red AF resin (Tosoh) using salt elution (50 mM HEPES, pH 7.2, 1 M ethylene glycol with 0 to 1.5 M NaCl gradient in 1 hour). The fractions containing the synthase protein (~90% pure by SDS-PAGE/Coomassie-staining) were concentrated by ultrafiltration and exchanged into reaction buffer (1 M ethylene glycol, 50 mM Tris, pH 7.2). The syntheses in general contained synthase, UDP-GlcNAc, UDP-GlcUA, and 5 mM MnCl2 in reaction buffer. Reactions are incubated at 30° for 6 to 48 hrs.

Analysis of in vitro synthesized HA. HA are analyzed on agarose gels as described in Lee and Cowman. In brief, agarose gels (0.7-1.2%) in 1× TAE buffer were run at 40V. Gels are stained with Stains-All dye (0.005% w/v in ethanol) overnight and destained with water. HA was analyzed on acrylamide gels (15-20%) as described in Ikegami-Kawai and Takahashi. To purify HA, pmHAS was removed by choloroform extraction and HA are precipitated with three volumes of ethanol and the pellets were redisolved in water. Alternatively, the unincorporated precursor sugars were removed by ultrafiltration with Microcon units (Millipore). The concentration was determined by carbazole assay (ref) and a glucuronic acid standard.

Gel filtration/multi-angle laser light scattering analysis was used to determine the absolute molecular weights. Polymers were separated on tandem Toso Biosep TSK-GEL columns (6000PWXL followed by 4000PWXL; each 7.8 mm 30 cm; Japan or equivalent) eluted in 50 mM sodium phosphate, 150 mM NaCl, pH 7 at 0.5 mL/min. The eluant flowed through an Optilab DSP interferometric refractometer and then a Dawn DSF laser photometer (632.8 nm; Wyatt Technology, Santa Barbara, Calif.) in the multi-angle mode. The manufacturer's software package was used to determine the absolute average molecular weight using a dn/dC coefficient of 0.153.

Although the foregoing invention has been described in detail by way of illustration and example for purposes of clarity of understanding, it will be obvious to those skilled in the art that certain changes and modifications may be practiced without departing from the spirit and scope thereof, as described in this specification and as defined in the appended claims below.

REFERENCES

The following references, to the extent that they provide exemplary procedural or other details supplementary to those set forth herein, are specifically incorporated herein by reference in their entirety as though set forth herein particular.

Asplund, T., J. Brinck, M. Suzuki, M. J. Briskin, and P. Heldin. (1998) *Biochim. Biophys. Acta.* 1380, 377-388.

Ausubel, F. M., R. Brent, R. E. Kingston, D. D. Moore, J. G. Seidman, J. A. Smith, and K. Struhl. (1995) *Short Protocols in Molecular Biology,* 3rd Ed., John Wiley & Sons Inc., New York.

Bello, Y M, Falabella, A F, and Eaglstein, W H. (2001) *Am J Clin Dermatol,* 2:305-313.

Bertram, J., M. Stratz, and P. Durre. Natural transfer of conjugative transposon Tn916 between Gram-positive and Gram-negative bacteria. *J. Bact.* 1991; 173: 443-8.

Bitter, T. and H. M. Muir. (1962) *Anal. Biochem.* 4, 330-334.

Bradford, M. M., (1976) *Anal. Biochem.* 72, 248-254.

Breton, C. and A. Imberty. (1999) *Curr. Opin. Struc. Biol.* 9, 563-571.

Busch, C., F. Hofmann, J. Seizer, S. Munro, S. Jeckel, and K. Aktories. (1998) A common motif of eukaryotic glycosyltransferases is essential for the enzyme activities of large clostridial cytotoxins. *J. Biol. Chem.,* 273, 19566-19572.

Campbell, R. E., S. C. Mosimann, I. van de Rijn, M. E. Tanner, and N. C. J. Strynadke. (2000) *Biochemistry* 39, 7012-7023.

Carter, G. R. and E. Annau. (1953) *Am. J. Vet Res.* 14, 475-478.

Charnock, S. J. and G. J. Davies. (1999) Structure of the nucleotide-diphospho-sugar transferases, spsA from *Bacillus subtilis*, in native and nucleotide-complexed forms. *Biochemistry*, 38, 6380-6385.

Chen, W Y. and Abstangelo G. (1999) Functions of hyaluronan in wound repair. *Wound Repair Regen*, 7,79-89.

Chung, J. Y., I. Wilkie, J. D. Boyce, K. M. Townsend, A. J. Frost, M. Ghoddusi, and B. Adler. (2001) Role of capsule in the pathogenesis of fowl cholera caused by *Pasteurella multocida* Serogroup A. *Infect. Immun.*, 69, 2487-2492.

Corpet, F. (1998) *Nucleic Acids Res.* 16, 10881-10890.

Crater, D. L., and I. van de Rijn. (1995) *J. Biol. Chem.* 270, 18452-18458.

DeAngelis, P. L., M. H. Graves, and J. L. Van Etten, unpublished results.

DeAngelis, P. L., J. Papaconstantinou, and P. H. Weigel. Isolation of a *Streptococcus* pyogenes gene locus that directs hylauronan biosynthesis in acapsular mutants and in heterologous bacteria. *J. Biol. Chem.*, 268, 14568-14571, 1993.

DeAngelis, P. L., J. Papaconstantinou, and P. H. Weigel. Molecular cloning, identification and sequence of the hyaluronan synthase gene from Group A *Streptococcus* pyogenes. *J. Biol. Chem.*, 268, 19181-19184, 1993.

DeAngelis, P. L. and P. H. Weigel. Immunochemical confirmation of the primary structure of streptococcal hyaluronan synthase and synthesis of high molecular weight product by the recombinant enzyme. *Biochemistry*, 33, 9033-9039, 1994.

DeAngelis, P. L., W. Jing, M. V. Graves, D. E. Burbank, and J. L. Van Etten. Hyaluronan synthase of *chlorella* virus PBCV-1. *Science*, 278, 1800-1803, 1997.

DeAngelis, P. L. Hyaluronan synthases: fascinating glycosyltransferases from vertebrates, bacterial pathogens and algal viruses. *Cell. Mol. Life Sci.*, 56, 670-682, 1999.

DeAngelis, P. L. Microbial glycosoaminoglycan glycosyltransferases. *Glycobiology*. 12(1):9R-16R. Review. 2002.

DeAngelis, P. L., and C. L. White. Identification and molecular cloning of a heparosan synthase from *Pasteurella multocida* type D. *J. Biol. Chem.* 277(9):7209-13, 2002.

DeAngelis, P. L. Polysachharide labeling with N-methylisatioic anyhydride: generation of ultraviolet chromophores and blue fluorophores. *Anal. Biochem.* 284(1):167-9, 2000.

DeAngelis, P. L. and A. J. Padgett-McCue. Identification and molecular cloning of a chondroitin synthase from Pasteurella multocida type F. *J. Biol. Chem.* 275(31):24124-9, 2000.

DeAngelis, P. L. Molecular directionality of polysaccharide polymerization by the *Pasteurella multocida* hyaluronan synthase. *J. Biol. Chem.* 274(37);26557-62, 1999.

DeAngelis P. L. Transposon Tn916 insetional mutagenesis of *Pasteurella multocida* and direct sequencing of disruption site. *Microb. Pathog.* 24(4):203-9, 1998.

DeAngelis, P. L., W. Jing, R. R. Drake, and A. M. Achyuthan. Identification and molecular cloning of a unique hyaluronan synthase from *Pasturella multocida*. *J. Biol. Chem.* 273(14):8454-8, 1998.

DeAngelis, P. L., W. Jing, M. V. Graves, D. E. Burbank, and J. L. Van Etten. Hyaluronan synthase of chlorella virus PBCV-1. *Science*. 278(5344):1800-3, 1997.

DeAngelis, P. L., and A. M. Achyuthan. Yeast-derived recombinant DG42 protein of *Xenopus* can synthesize hyaluronan in vitro. *J. Biol. Chem.* 271(39):23657-60, 1996.

DeAngelis, P. L. Enzymological characterization of the *Pasteurella multocida* hyaluronic acid synthase. *Biochemistry*. 35(30):9768-71, 1996.

DeAngelis, P. L., Oatman, L. C. and Gay, D. F. (2003) Rapid chemoenzymatic synthesis of monodisperse hyaluronan oligosaccharides with immobilized enzyme reactor. *J. Biol. Chem.*, 278, in press.

DeLuca, S. and J. E. Silbert. (1968) *J. Biol. Chem.* 243, 2725-2729.

Doughtery, B. A., and I. van de Rijn. (1994) Molecular characterization of hasA from an operon required for hyaluronic acid synthesis in Group A *Streptococci*. *J. Biol. Chem.*, 269, 169-175.

Drake, C. R., I. S. Roberts, B. Jann, K. Jann, and G. J. Boulnois (1990) Molecular cloning and expression of the genes encoding the *Escherichia coli* K4 capsular polysaccharide, a fructose-substituted chondroitin. *FEMS Microbiol. Lett.*, 54, 227-230.

Duncan, G., C. McCormick, and F. Tufaro. (2001) The link between heparan sulfate and hereditary bone disease: finding a function for the EXT family of the putative tumor suppressor proteins. *J. Clin. Invest.*, 108, 511-516.

Esko, J. D. and U. Lindahl. (2001) Molecular diversity of heparan sulfate. *J. Clin. Invest.* 108, 169-173.

Finke, A., D. Bronne, A. V. Nikolaev, B. Jann, and K. Jann. (1991) Biosynthesis of the *Escherichia coli* K5 polysaccharide, a representative of group II capsular polysaccharides: polymerization in vitro and characterization of the product. *J. Bacteriol.*, 173, 4088-4094.

Gastinel, L. N., C. Cambillau, and Y. Bourne. (1999) *EMBO J.* 18, 3546-3557.

Gastinel, L. N., C. Bignon, A. K. Misra, O. Hindsgaul, J. H. Shaper, and D. H. Joziasse. (2001) *EMBO J.* 20, 638-649.

Gherezghiher, T., M. C. Koss, R. E. Nordquist, and C. P. Wilkinson. (1987) *J. Chromatogr.* 413, 9-15.

Gietz, R. D., R. H. Schiestl, A. R. Willems, and R. A. Woods. (1995) *Yeast* 11, 355-360.

Griffiths, G., N. J. Cook, E. Gottfridson, T. Lind, K. Lidholt, and I. S. Roberts. Characterization of the glycosyltransferase enzyme from the *Escherichia coli* K5 capsule gene cluster and identification and characterization of the flucuronyl active site. *J. Biol. Chem.*, 273, 11752-11757, 1998.

Hagopian, A. and E. H. Eylar. Glycoprotein biosynthesis: studies on the receptor specificity of the polypeptidyl: N-acetylgalactosaminyl transferase from bovine submaxillary glands. *Arch. Biochim. Biophys.*, 128, 422-433.

Hall, N. A. and A. D. Patrick. (1989) *Anal. Biochem.* 178, 378-384.

Hansen, L. M. and D. C. Hirch. (1989) *Vet Microbiol.* 21, 177-184.

Hardingham, T. E. and A. J. Fosang. (1992) *FASEB J.* 6, 861-870.

Harmon, B. G., J. Glisson, K. S. Latimer, W. L. Stephens, and J. C. Nunnally. (1991) *Am. J. Vet. Res.* 52, 1507-1511.

Hascall, V. C. and G. K. Hascall. (1981) in *Cell Biology of Extracellular Matrix* (Hay, E. D., ed) pp. 39-78, Plenum Publishing Corp. New York.

Heldermon, C., P. L. DeAngelis, and P. H. Weigel. (2001) Topological organization of the hyaluronan synthase from *Streptococcus pyogenes*. *J. Biol. Chem.*, 276, 2037-2046.

Hempel, J., J. Perozich, H. Romavacek, A. Hinich, I. Kuo, and D. S. Feingold. (1994) *Protein Sci.* 3, 1074-1080.

Hodson, N., G. Griffiths, N. Cook, M. Pourhossein, E. Gottfridson, T. Lind, K. Lindholt, and I. S. Roberts. (2000) Identification that KfiA, a protein essential for the biosynthesis of the *Escherichia coli* K5 capsular polysaccharide, is an alpha-UDP-GlcNAc glycosyltransferase. The formation of a membrane-associated K5 biosynthetic complex requires KfiA, KfiB, and KfiC. J. Biol. Chem., 275, 27311-27315.

Hofmann, K. and W. Stoffel. (1993) *Biol. Chem.* Hoppe-Seyler 347, 166 (abstr.)

Iivanainen, E., Kahari, V M., Heino, J., and Elenius, K. (2003) *Microsc Res Tech,* 60:13-22.

Ikegami-Kawai, M. and Takahashi, T. (2002) Microanalysis of hyaluronan oligosaccharides by polyacrylamide gel electrophoresis and its application to assay of hyaluronidase activity. *Analytical Biochem,* 311, 157-165.

Itano, N., T. Sawai, M. Yoshida, P. Lenas, Y. Yamada, M. Imagawa, T. Shinomura, M. Hamaguchi, Y. Yoshida, Y. Ohnuki, S. Miyauchi, A. P. Spicer, J. A. McDonald, and K. Kimata. (1999) *J. Biol. Chem.* 274, 25085-25092.

Jing, W. and P. L. DeAngelis. Dissection of the two transferase activities of the *Pasturella multocida* hyaluronan synthase: two acitve sites exist in one polypeptide. *Glycobiology.* 10(9):883-9, 2000.

Kitagawa, H., T. Uyama, and K. Sugahara. (2001) Molecular cloning and expression of a human chondroitin synthase. *J. Biol. Chem.,* 276, 38721-38726.

Knudson, C. B. and W. Knudson (1993) *FASEB. J.* 7, 1233-1241.

Koyama, M., W. Helbert, T. Imai, J. Sugiyama, and B. Henrissat. (1997) *Proc. Natl. Acad. Sci. U.S.A.* 94, 9091-9095.

Kroll, J. S., B. Loynds, L. N. Brophy, and E. R. Moxon. (1990) *Mol. Microbiol.* 4, 1853-1862.

Kumari, K. and P. H. Weigel. (1997) Molecular cloning, expression, and characterization of the authentic hyaluronan synthase from Group C *Streptococcus equisimilis. J. Biol. Chem.,* 272, 32539-32546.

Laurent, T. C., and J. R. E. Fraser. (1992) *FASEB J.* 6, 2397-2404.

Lee, C. J. (1987) Bacterial capsular polysaccharides-biochemistry, immunity and vaccine. *Mol. Immunol.,* 24, 1005-1019.

Lee, H G and Cowman, M K (1994) An agarose gel electrophoretic method for analysis of hyaluronan molecular weight size distribution. *Analytical Biochem.* 219, 278-287.

Li, J., D. M. Rancour, M. L. Allende, C. A. Worth, D. S. Darling, J. B. Gilbert, A. K. Menon and W. W. Young Jr. (2001) The DXD motif is required for GM2 synthase activity but is not critical for nucleotide binding. *Glycobiology,* 11, 217-229.

Lidholt, K. (1997) *Biochem. Soc. Trans.* 25, 866-870.

Lidholt, K. and M. Fjelstad. (1997) Biosynthesis of the *Escherichia coli* K4 capsule polysaccharide. A parallel system for sutdies of gylcosyl-transferases in chondroitin formation. *J. Biol. Chem.* 272, 2682-2687.

Lidholt, K. and U. Lindahl. (1992) *Biochem J.* 287, 21-29.

Lindahl, U. and M. Hook. (1978) *Annu. Rev. Biochem.* 47, 385-417.

Lind, T., U. Lindahl, and K. Lidholt. (1993) *J. Biol. Chem.* 268, 20705-20708.

Lind, T., Tufaro, F., McCormick, C., Lindahl, U., and K. Lidholt. (1998) *J. Biol. Chem.* 273, 11752-11757.

Ludwigs, U., A. Elgavish, J. D. Esko, E. Meexan, and L. Roden. Reaction of unsaturated uronic acid residues with mercuric salts. Cleavage of the hyaluronic acid disaccharide 2-acetamido-2-deoxy-3-O-(β-D-gluco-4-enepyranosyluronic acid)-D-glucose. *Biochem. J.,* 245, 795-804, 1987.

Marks, D. L., M. Dominguez, K. Wu, and R. E. Pagano. (2001) *J. Biol. Chem.* 276, 26492-26498.

Markovitz, A., J. A. Cifonelli, and A. Dorfman. (1959) *J. Biol. Chem.* 234, 2343-2350.

May, B. J., Q. Zhang, L. Li, M. L. Paustian, T. S. Whittam, and V. Kapur. (2001) *Proc. Natl. Acad. Sci. U.S.A.* 98, 3460-3465.

Meyer, M. F., and G. Kreil (1996) *Proc. Natl. Acad. Sci. U.S.A.* 93, 4543-4547.

Morera, S., A. Imberty, U. Aschke-Sannenborn, P. S. Freemont, J. Janin, and W. Ruger. (1999) *J. Mol. Biol.* 311, 569-577.

Morera, S. L. Lariviere, J. Kurzeck, U. Aschke-Sannenborn, P. S. Freemont, J. Janin, and W. Ruger. (2001) *J. Mol. Biol.,* 311, 569-577.

Ohya, T. and Y. Kaneko. (1970) *Biochim. Biophys. Acta* 198, 607-609.

Pedersen, L. C., K. Tsuchida, H. Kitagawa, K. Sugahara, T. A. Darden, and M. Negishi. (2000) Heparan/chondroitin sulfate biosynthesis. Structure and mechanism of human glucuronyltransferase I. *J. Biol. Chem.,* 275, 34580-34585.

Persson, K., H. D. Ly, M. Dieckelmann, W. W. Wakarchuk, S. G. Withers, and N. C. J. Strynadka. (2001) *Nat. Struct. Biol.* 8, 166-175.

Petit, C., G. P. Rigg, C. Pazzani, A. Smith, V. Sieberth, M. Stevens, G. Boulnois, K. Jann, and I. S. Roberts. Region 2 of the *Escherichia coli* K5 capsule gene cluster encoding proteins for the biosynthesis of the K5 polysaccharide. *Mol. Microbiol.,* 17, 611-620.

Prehm, P. (1983) *Biochem. J.* 211, 181-189.

Prehm, P. (1983) *Biochem. J.* 211, 191-198.

Pummill, P. E., and P. L. DeAngelis. Evaluation of Critical Structural Elements of UDP-Sugar Substrates and Certain Cysteine Residues of a Vertebrate Hyaluronan Synthase. *J. Biol. Chem.* 277(24):21610-6, 2002.

Pummill P. E., A. M. Achyuthan, and P. L. DeAngelis. Enzymological characterization of recombinant *xenopus* DG42, a vertebrate hyaluronan synthase. *J. Biol. Chem.* 273 (9):4976-81, 1998.

Quinn, A. W., and K. P. Sing. (1957) *Proc. Soc. Exp. Biol. Med.* 95, 290-294.

Radominska, A. and R. R. Drake. (1994) *Methods Enzymol.* 230, 330-339.

Rahemtulla, F. and S. Lovtrup. (1975) *Comp. Biochem. Physiol.* 50B, 631-635.

Ramakrishnan, B. and P. Qasba. (2001) *J. Mol. Biol.* 310, 205-218.

Rimler, R. B. (1994) Presumptive identification of Pasteurella multocida Serogroups A, D and F by capsule depolymerisation with mucopolysaccharidases. *Vet. Rec.* 134, 191-192.

Rimler, R. B. and K. R. Rhodes. (1987) *J. Clin. Microbiol.* 25, 615-618.

Rimler, R. B. (1994) *Vet. Rec.* 134, 191-192.

Rimler, R. B., K. B. Register, T. Magyar, and M. R. Ackermann. (1995) *Vet. Microbiol.* 47, 287-294.

Roberts, I. S. (1996) The biochemistry and genetics of capsular polysaccharide production in bacteria. *Annu. Rev. Microbiol.* 50, 285-315.

Roberts, I. S., R. Mountford, R. Hodge, K. B. Jann, and G. Boulnois. (1988) *J. Bacteriol.* 170, 1305-1310.

Roden, L. (1980) in *The Biochemistry of Glycoproteins and Proteoglycans* (Lennarz, W. J., ed) pp. 267-371, Plenum Publishing Corp. New York.

Rodriguez, M. L, B. Jann, and K. Jann. (1988) Structure and serological characteristics of the capsular K4 antigen of *Escherichia coli* O5:K4:H4, a fructose-containing polysaccharide with a chondroitin backbone. *Eur. J. Biochem.* 177, 117-124.

Rohozinski, J., L. E. Girton, and J. L. Van Elten. *Virology* 168, 363 (1989).

Rosa, F., T. D. Sargent, M. L. Rebbert, G. S. Michaels, M. Jamrich, H. Grunz, E. Jonas, J. A. Winkles, and I. B. Dawid. (1988) *Dev. Biol.* 129, 114-123.

Rosner, H., H. D. Grimmecke, Y. A. Knirel, and A. S. Shashkov. (1992) *Carbohydr. Res.* 223, 329-333.

Sambrook, J., E. F. Fritshc, and T. Maniatis. *Molecular Cloning: A Laboratory Manual,* $2^{nd}$ edn. Cold Spring Harbor, NY: Cold Spring Laboratory Press. 1989.

Saxena, I. M., R. M. Brown, M. Fevre, R. A. Geremia, and B. Henrissat. Multidomain architecture of β-glycosyl transferases: implications for mechanism of action. *J. Bacteriol.,* 177, 1419-1424, 1995.

Semino, C. E. and P. W. Robbins. (1995) *Proc. Natl. Acad. Sci. U.S.A.* 92, 3498-3501.

Semino, C. E., C. A. Specht, A. Raimondi, and P. W. Robbins. (1996) *Proc. Natl. Acad. Sci. U.S.A.* 93, 4548-4553.

Soltes, L., Mendichi, R., Lath, D., Mach, M. and Bakos, D. (2002) Molecular characteristics of some commercial high-molecular-weight hyaluronans. *Biomed. Chromatogr.* 16, 459-462.

Song, H H. and Filmus, J. (2002) *Biochim Biophys Acta,* 1573:241-246.

Spicer, A. P. and J. A. McDonald. (1998) *J. Biol. Chem.* 273,1923-1932.

Stoolmiller, A. C. and A. Dorfman. (1969) The biosynthesis of hyaluronic acid by Streptococcus. *J. Biol. Chem.* 244, 236-346.

Sugahara, K., N. B. Schwartz and A. Dorfman. (1979) Biosynthesis of hyaluronic acid by Streptococcus. *J. Biol. Chem.* 254, 6252-6261.

Sunthankar, P. I. Pastuszak, A. Rooke, A. D. Elbein, I. van de Rijn, W. M. Canfield, and R. R. Drake. (1998) Synthesis of 5-azido-UDP-N-acetylhexosamine photoaffinity analogs and radiolabeled UDP-N-acetylhexosamines. *Anal. Biochem.,* 258(2): 195-201.

Svanborg-Eden, C., L. Hagberg, R. Hull, S. Hull, K. E. Magnusson, and L. Tarbouriech, N., S. J. Charnock, and G. J. Davies. (2001) *J. Mol. Biol.* 314, 655-661.

Taylor, K. A., and J. G. Buchanan-Smith. (1992) *Anal. Biochem.* 201, 190-196.

Telser, A., H. C. Robinson, and A. Dorfman. (1965) *Proc. Natl. Acad. Sci. U.S.A.* 54, 912-919.

Tengblad, A. (1980) *Biochem. J.* 185, 101-105.

Tiapak-Simmons, V. L., E. S. Kempner, B. A. Baggenstoss, and P. H. Weigel. (1998) The active streptococcal hyaluronan synthases (HASs) contain a single HAS monomer and multiple cardiolipin molecules. *J. Biol. Chem.,* 273, 26100-26109.

Tlapak-Simmons, V. L., B. A. Baggenstoss, K. Kumari, C. Heldermon, and P. H. Weigel. (1999) *J. Biol. Chem.* 274, 4246-4253.

Townsend, K. M., J. D. Boyce, J. Y. Chung, A. J. Frost, and B. Adler. (2001) Genetic organization of *Pasteurella multocida* cap loci and develpment of a multiplex capsular PCR typing system. *J. Clin. Microbiol.,* 39, 924-929.

Tsuchida, K., T. Lind, H. Kitagawa, U. Lindahl, K. Sugahara, and K. Lindholt. (1999) *Eur. J. Biochem.* 264, 461-467.

Uebelhart, D. and Williams, J M. (1999) Effects of hyaluronic acid on cartilage degradation. *Curr. Opin in Rhematology,* 11, 427.

Unligil, U. M. and J. M. Rini. (2000) *Curr. Opin. Struct. Biol.* 10, 510-517.

Unligil, U. M., S. Zhou, S. Yuwaraj, M. Sarkar, H. Schachter, and J. M. Rini. (2000) *EMBO J.* 19, 5269-5280.

van de Rijn, I. and R. R. Drake (1992) *J. Biol. Chem.* 267, 24302-24306.

van de Rijn, l. and R. E. Kessler. (1980) *Infect Immun.* 27, 444-448.

Van Etten, J. L., D. E. Burbank, A. M. Schuster, and R. H. Meints, *Virology,* 140, 135 (1985).

Vann, W. F., M. A. Schmidt, B. Jann, and K. Jann. (1981) The structure of the capsular polysaccharide (K5 antigen) of urinary-tract-inefective *Escherichia coli* 010:K5:H4. A polymer similar to desulfo-heparin. *Eur. J. Biochem.* 116, 359-364.

Varki, A. (1996) *Proc. Natl. Acad. Sci. U.S.A.* 93, 4523-4525.

Vimr, E. R., W. Aaronson, and R. P. Silver. (1989) *J. Bacteriol.* 171, 1106-1117.

Vlodavsky, I Miao, H Q, Medalion, B., Danager, P., and Ron, D. (1996) *Cancer Metastasis,* 15:177-186.

Vrielink, A., W. Ruger, H. P. C. Driessen, and P. S. Freemont. (1994) *EMBO J.* 15, 3413-3422.

Weigel, P. H., V. C. Hascall, and M. Tammi. Hyalruonan synthases. *J. Biol. Chem.,* 272, 13997-14000, 1997.

Wessels, M. R., A. E. Moses, J. B. Goldberg, and T. J. DiCesare. (1991) *Proc. Natl. Acad. Sci. U.S.A.* 88,8317-8321.

Wiggins, C. A. R., and S. Munro. (1998) *Proc. Natl. Acad. Sci. U.S.A.* 95, 7945-7950.

Wilson, K. Preparation of genomic DNA from bacteria. In: Ausbel F M, Brent R, Kingston R E, et al., Eds. *Current Protocols in Molecular Biology.* New York: Wiley Interscience Publishing, 1987: 2.4.1-2.4.5.

Woodfield, T B, Bezemer, J M, Pieper, J S, van Blitterswijk, C A, and Riesle, J. (2002) *Crit Rev Eukaryot Gene Expr,* 12:209-236.

Yamada, T., T. Higashiyama, and T. Fukuda, *Appl. Environ. Microbiol.* 57, 3433 (1991).

Yoshida, M., N. Itano, Y. Yamada, and K. Kimata. In vitro synthesis of hyaluronan by a single protein derived from mouse HAS1 gene and characterization of amino acid residues essential for the activity. *J. Biol. Chem.,* 275, 497-506, 2000.

SEQUENCE LISTING

```
<160> NUMBER OF SEQ ID NOS: 71

<210> SEQ ID NO 1
<211> LENGTH: 2920
<212> TYPE: DNA
<213> ORGANISM: Pasteurella multocida

<400> SEQUENCE: 1

atgaatacat tatcacaagc aataaaagca tataacagca atgactatca attagcactc      60

aaattatttg aaaagtcggc ggaaatctat ggacggaaaa ttgttgaatt tcaaattacc     120
```

-continued

```
aaatgcaaag aaaaactctc agcacatcct tctgttaatt cagcacatct ttctgtaaat    180
aaagaagaaa aagtcaatgt ttgcgatagt ccgttagata ttgcaacaca actgttactt    240
tccaacgtaa aaaaattagt actttctgac tcggaaaaaa acacgttaaa aaataaatgg    300
aaattgctca ctgagaagaa atctgaaaat gcggaggtaa gagcggtcgc ccttgtacca    360
aaagattttc ccaaagatct ggttttagcg cctttacctg atcatgttaa tgattttaca    420
tggtacaaaa agcgaaagaa aagacttggc ataaaacctg aacatcaaca tgttggtctt    480
tctattatcg ttacaacatt caatcgacca gcaattttat cgattacatt agcctgttta    540
gtaaaccaaa aaacacatta cccgtttgaa gttatcgtga cagatgatgg tagtcaggaa    600
gatctatcac cgatcattcg ccaatatgaa aataaattgg atattcgcta cgtcagacaa    660
aaagataacg gttttcaagc cagtgccgct cggaatatgg gattacgctt agcaaaatat    720
gactttattg gcttactcga ctgtgatatg gcgccaaatc cattatgggt tcattcttat    780
gttgcagagc tattagaaga tgatgattta acaatcattg gtccaagaaa atacatcgat    840
acacaacata ttgacccaaa agacttctta aataacgcga gtttgcttga atcattacca    900
gaagtgaaaa ccaataatag tgttgccgca aaaggggaag gaacagtttc tctggattgg    960
cgcttagaac aattcgaaaa aacagaaaat ctccgcttat ccgattcgcc tttccgtttt   1020
tttgcggcgg gtaatgttgc tttcgctaaa aaatggctaa ataaatccgg tttctttgat   1080
gaggaattta atcactgggg tggagaagat gtggaatttg gatatcgctt attccgttac   1140
ggtagtttct ttaaaactat tgatggcatt atggcctacc atcaagagcc accaggtaaa   1200
gaaaatgaaa ccgatcgtga agcgggaaaa aatattacgc tcgatattat gagagaaaag   1260
gtcccttata tctatagaaa acttttacca atagaagatt cgcatatcaa tagagtacct   1320
ttagtttcaa tttatatccc agcttataac tgtgcaaact atattcaacg ttgcgtagat   1380
agtgcactga atcagactgt tgttgatctc gaggtttgta tttgtaacga tggttcaaca   1440
gataatacct tagaagtgat caataagctt tatggtaata atcctagggt acgcatcatg   1500
tctaaaccaa atggcggaat agcctcagca tcaaatgcag ccgtttcttt tgctaaaggt   1560
tattacattg ggcagttaga ttcagatgat tatcttgagc ctgatgcagt tgaactgtgt   1620
ttaaaagaat ttttaaaaga taaaacgcta gcttgtgttt ataccactaa tagaaacgtc   1680
aatccggatg gtagcttaat cgctaatggt tacaattggc cagaattttc acgagaaaaa   1740
ctcacaacgg ctatgattgc tcaccacttt agaatgttca cgattagagc ttggcattta   1800
actgatggat tcaatgaaaa aattgaaaat gccgtagact atgacatgtt cctcaaactc   1860
agtgaagttg gaaaatttaa acatcttaat aaaatctgct ataaccgtgt attacatggt   1920
gataacacat caattaagaa acttggcatt caaaagaaaa accattttgt tgtagtcaat   1980
cagtcattaa atagacaagg cataacttat tataattatg acgaatttga tgatttagat   2040
gaaagtagaa agtatatttt caataaaacc gctgaatatc aagaagagat tgatatctta   2100
aaagatatta aaatcatcca gaataaagat gccaaaatcg cagtcagtat tttttatccc   2160
aatacattaa acggcttagt gaaaaaacta aacaatatta ttgaatataa taaaaatata   2220
ttcgttattg ttctacatgt tgataagaat catcttacac cagatatcaa aaaagaaata   2280
ctagccttct atcataaaca tcaagtgaat attttactaa ataatgatat ctcatattac   2340
acgagtaata gattaataaa aactgaggcg catttaagta atattaataa attaagtcag   2400
ttaaatctaa attgtgaata catcattttt gataatcatg acagcctatt cgttaaaaat   2460
```

-continued

```
gacagctatg cttatatgaa aaaatatgat gtcggcatga atttctcagc attaacacat   2520

gattggatcg agaaaatcaa tgcgcatcca ccatttaaaa agctcattaa aacttatttt   2580

aatgacaatg acttaaaaag tatgaatgtg aaaggggcat cacaaggtat gtttatgacg   2640

tatgcgctag cgcatgagct tctgacgatt attaaagaag tcatcacatc ttgccagtca   2700

attgatagtg tgccagaata taacactgag gatatttggt tccaatttgc acttttaatc   2760

ttagaaaaga aaaccggcca tgtatttaat aaaacatcga ccctgactta tatgccttgg   2820

gaacgaaaat tacaatggac aaatgaacaa attgaaagtg caaaaagagg agaaaatata   2880

cctgttaaca agttcattat taatagtata actctataaa                         2920


<210> SEQ ID NO 2
<211> LENGTH: 972
<212> TYPE: PRT
<213> ORGANISM: Pasteurella multocida

<400> SEQUENCE: 2

Met Asn Thr Leu Ser Gln Ala Ile Lys Ala Tyr Asn Ser Asn Asp Tyr
1               5                   10                  15

Gln Leu Ala Leu Lys Leu Phe Glu Lys Ser Ala Glu Ile Tyr Gly Arg
            20                  25                  30

Lys Ile Val Glu Phe Gln Ile Thr Lys Cys Lys Glu Lys Leu Ser Ala
        35                  40                  45

His Pro Ser Val Asn Ser Ala His Leu Ser Val Asn Lys Glu Glu Lys
    50                  55                  60

Val Asn Val Cys Asp Ser Pro Leu Asp Ile Ala Thr Gln Leu Leu Leu
65                  70                  75                  80

Ser Asn Val Lys Lys Leu Val Leu Ser Asp Ser Glu Lys Asn Thr Leu
                85                  90                  95

Lys Asn Lys Trp Lys Leu Leu Thr Glu Lys Lys Ser Glu Asn Ala Glu
            100                 105                 110

Val Arg Ala Val Ala Leu Val Pro Lys Asp Phe Pro Lys Asp Leu Val
        115                 120                 125

Leu Ala Pro Leu Pro Asp His Val Asn Asp Phe Thr Trp Tyr Lys Lys
    130                 135                 140

Arg Lys Lys Arg Leu Gly Ile Lys Pro Glu His Gln His Val Gly Leu
145                 150                 155                 160

Ser Ile Ile Val Thr Thr Phe Asn Arg Pro Ala Ile Leu Ser Ile Thr
                165                 170                 175

Leu Ala Cys Leu Val Asn Gln Lys Thr His Tyr Pro Phe Glu Val Ile
            180                 185                 190

Val Thr Asp Asp Gly Ser Gln Glu Asp Leu Ser Pro Ile Ile Arg Gln
        195                 200                 205

Tyr Glu Asn Lys Leu Asp Ile Arg Tyr Val Arg Gln Lys Asp Asn Gly
    210                 215                 220

Phe Gln Ala Ser Ala Ala Arg Asn Met Gly Leu Arg Leu Ala Lys Tyr
225                 230                 235                 240

Asp Phe Ile Gly Leu Leu Asp Cys Asp Met Ala Pro Asn Pro Leu Trp
                245                 250                 255

Val His Ser Tyr Val Ala Glu Leu Leu Glu Asp Asp Asp Leu Thr Ile
            260                 265                 270

Ile Gly Pro Arg Lys Tyr Ile Asp Thr Gln His Ile Asp Pro Lys Asp
        275                 280                 285

Phe Leu Asn Asn Ala Ser Leu Leu Glu Ser Leu Pro Glu Val Lys Thr
```

-continued

```
    290                 295                 300

Asn Asn Ser Val Ala Ala Lys Gly Glu Gly Thr Val Ser Leu Asp Trp
305                 310                 315                 320

Arg Leu Glu Gln Phe Glu Lys Thr Glu Asn Leu Arg Leu Ser Asp Ser
                325                 330                 335

Pro Phe Arg Phe Phe Ala Ala Gly Asn Val Ala Phe Ala Lys Lys Trp
            340                 345                 350

Leu Asn Lys Ser Gly Phe Phe Asp Glu Glu Phe Asn His Trp Gly Gly
        355                 360                 365

Glu Asp Val Glu Phe Gly Tyr Arg Leu Phe Arg Tyr Gly Ser Phe Phe
    370                 375                 380

Lys Thr Ile Asp Gly Ile Met Ala Tyr His Gln Glu Pro Pro Gly Lys
385                 390                 395                 400

Glu Asn Glu Thr Asp Arg Glu Ala Gly Lys Asn Ile Thr Leu Asp Ile
                405                 410                 415

Met Arg Glu Lys Val Pro Tyr Ile Tyr Arg Lys Leu Leu Pro Ile Glu
            420                 425                 430

Asp Ser His Ile Asn Arg Val Pro Leu Val Ser Ile Tyr Ile Pro Ala
        435                 440                 445

Tyr Asn Cys Ala Asn Tyr Ile Gln Arg Cys Val Asp Ser Ala Leu Asn
    450                 455                 460

Gln Thr Val Val Asp Leu Glu Val Cys Ile Cys Asn Asp Gly Ser Thr
465                 470                 475                 480

Asp Asn Thr Leu Glu Val Ile Asn Lys Leu Tyr Gly Asn Asn Pro Arg
                485                 490                 495

Val Arg Ile Met Ser Lys Pro Asn Gly Gly Ile Ala Ser Ala Ser Asn
            500                 505                 510

Ala Ala Val Ser Phe Ala Lys Gly Tyr Tyr Ile Gly Gln Leu Asp Ser
        515                 520                 525

Asp Asp Tyr Leu Glu Pro Asp Ala Val Glu Leu Cys Leu Lys Glu Phe
    530                 535                 540

Leu Lys Asp Lys Thr Leu Ala Cys Val Tyr Thr Thr Asn Arg Asn Val
545                 550                 555                 560

Asn Pro Asp Gly Ser Leu Ile Ala Asn Gly Tyr Asn Trp Pro Glu Phe
                565                 570                 575

Ser Arg Glu Lys Leu Thr Thr Ala Met Ile Ala His His Phe Arg Met
            580                 585                 590

Phe Thr Ile Arg Ala Trp His Leu Thr Asp Gly Phe Asn Glu Lys Ile
        595                 600                 605

Glu Asn Ala Val Asp Tyr Asp Met Phe Leu Lys Leu Ser Glu Val Gly
    610                 615                 620

Lys Phe Lys His Leu Asn Lys Ile Cys Tyr Asn Arg Val Leu His Gly
625                 630                 635                 640

Asp Asn Thr Ser Ile Lys Lys Leu Gly Ile Gln Lys Lys Asn His Phe
                645                 650                 655

Val Val Val Asn Gln Ser Leu Asn Arg Gln Gly Ile Thr Tyr Tyr Asn
            660                 665                 670

Tyr Asp Glu Phe Asp Asp Leu Asp Glu Ser Arg Lys Tyr Ile Phe Asn
        675                 680                 685

Lys Thr Ala Glu Tyr Gln Glu Glu Ile Asp Ile Leu Lys Asp Ile Lys
    690                 695                 700

Ile Ile Gln Asn Lys Asp Ala Lys Ile Ala Val Ser Ile Phe Tyr Pro
705                 710                 715                 720
```

-continued

```
Asn Thr Leu Asn Gly Leu Val Lys Lys Leu Asn Asn Ile Ile Glu Tyr
                725                 730                 735

Asn Lys Asn Ile Phe Val Ile Val Leu His Val Asp Lys Asn His Leu
            740                 745                 750

Thr Pro Asp Ile Lys Lys Glu Ile Leu Ala Phe Tyr His Lys His Gln
        755                 760                 765

Val Asn Ile Leu Leu Asn Asn Asp Ile Ser Tyr Tyr Thr Ser Asn Arg
    770                 775                 780

Leu Ile Lys Thr Glu Ala His Leu Ser Asn Ile Asn Lys Leu Ser Gln
785                 790                 795                 800

Leu Asn Leu Asn Cys Glu Tyr Ile Ile Phe Asp Asn His Asp Ser Leu
                805                 810                 815

Phe Val Lys Asn Asp Ser Tyr Ala Tyr Met Lys Lys Tyr Asp Val Gly
            820                 825                 830

Met Asn Phe Ser Ala Leu Thr His Asp Trp Ile Glu Lys Ile Asn Ala
        835                 840                 845

His Pro Pro Phe Lys Lys Leu Ile Lys Thr Tyr Phe Asn Asp Asn Asp
    850                 855                 860

Leu Lys Ser Met Asn Val Lys Gly Ala Ser Gln Gly Met Phe Met Thr
865                 870                 875                 880

Tyr Ala Leu Ala His Glu Leu Leu Thr Ile Ile Lys Glu Val Ile Thr
                885                 890                 895

Ser Cys Gln Ser Ile Asp Ser Val Pro Glu Tyr Asn Thr Glu Asp Ile
            900                 905                 910

Trp Phe Gln Phe Ala Leu Leu Ile Leu Glu Lys Lys Thr Gly His Val
        915                 920                 925

Phe Asn Lys Thr Ser Thr Leu Thr Tyr Met Pro Trp Glu Arg Lys Leu
    930                 935                 940

Gln Trp Thr Asn Glu Gln Ile Glu Ser Ala Lys Arg Gly Glu Asn Ile
945                 950                 955                 960

Pro Val Asn Lys Phe Ile Ile Asn Ser Ile Thr Leu
                965                 970


<210> SEQ ID NO 3
<211> LENGTH: 2979
<212> TYPE: DNA
<213> ORGANISM: Pasteurella multocida

<400> SEQUENCE: 3

ttataaactg attaaagaag gtaaacgatt caagcaaggt taatttttaa aggaaagaaa      60

atgaatacat tatcacaagc aataaaagca tataacagca atgactatga attagcactc     120

aaattatttg agaagtctgc tgaaacctac gggcgaaaaa tcgttgaatt ccaaattatc     180

aaatgtaaag aaaaactctc gaccaattct tatgtaagtg aagataaaaa aaacagtgtt     240

tgcgatagct cattagatat cgcaacacag ctcttacttt ccaacgtaaa aaaattaact     300

ctatccgaat cagaaaaaaa cagtttaaaa aataaatgga aatctatcac tgggaaaaaa     360

tcggagaacg cagaaatcag aaaggtggaa ctagtaccca aagattttcc taaagatctt     420

gttcttgctc cattgccaga tcatgttaat gattttacat ggtacaaaaa tcgaaaaaaa     480

agcttaggta taaagcctgt aaataagaat atcggtcttt ctattattat tcctacattt     540

aatcgtagcc gtattttaga tataacgtta gcctgtttgg tcaatcagaa aacaaactac     600

ccatttgaag tcgttgttgc agatgatggt agtaaggaaa acttacttac cattgtgcaa     660
```

-continued

```
aaatacgaac aaaaacttga cataaagtat gtaagacaaa aagattatgg atatcaattg    720
tgtgcagtca gaaacttagg tttacgtaca gcaaagtatg attttgtctc gattctagac    780
tgcgatatgg caccacaaca attatgggtt cattcttatc ttacagaact attagaagac    840
aatgatattg ttttaattgg acctagaaaa tatgtggata ctcataatat taccgcagaa    900
caattcctta acgatccata tttaatagaa tcactacctg aaaccgctac aaataacaat    960
ccttcgatta catcaaaagg aaatatatcg ttggattgga gattagaaca tttcaaaaaa   1020
accgataatc tacgtctatg tgattctccg tttcgttatt ttagttgcgg taatgttgca   1080
ttttctaaag aatggctaaa taaagtaggt tggttcgatg aagaatttaa tcattggggg   1140
ggcgaagatg tagaatttgg ttacagatta tttgccaaag gctgtttttt cagagtaatt   1200
gacggcggaa tggcatacca tcaagaacca cctggtaaag aaaatgaaac agaccgcgaa   1260
gctggtaaaa gtattacgct taaaattgtg aaagaaaagg taccttacat ctatagaaag   1320
cttttaccaa tagaagattc acatattcat agaatacctt tagtttctat ttatatcccc   1380
gcttataact gtgcaaatta tattcaaaga tgtgtagata gtgctcttaa tcaaactgtt   1440
gtcgatctcg aggtttgtat ttgtaacgat ggttcaacag ataatacctt agaagtgatc   1500
aataagcttt atggtaataa tcctagggta cgcatcatgt ctaaaccaaa tggcggaata   1560
gcctcagcat caaatgcagc cgtttctttt gctaaaggtt attacattgg gcagttagat   1620
tcagatgatt atcttgagcc tgatgcagtt gaactgtgtt taaaagaatt tttaaaagat   1680
aaaacgctag cttgtgttta taccactaat agaaacgtca atccggatgg tagcttaatc   1740
gctaatggtt acaattggcc agaattttca cgagaaaaac tcacaacggc tatgattgct   1800
caccatttta gaatgtttac gattagagct tggcatttaa cggatggatt taacgaaaat   1860
attgaaaacg ccgtggatta tgacatgttc cttaaactca gtgaagttgg aaaatttaaa   1920
catcttaata aaatctgcta taaccgcgta ttacatggtg ataacacatc cattaagaaa   1980
ctcggcattc aaaagaaaaa ccattttgtt gtagtcaatc agtcattaaa tagacaaggc   2040
atcaattatt ataattatga caaatttgat gatttagatg aaagtagaaa gtatatcttc   2100
aataaaaccg ctgaatatca agaagaaatg gatattttaa aagatcttaa actcattcaa   2160
aataaagatg ccaaaatcgc agtcagtatt ttctatccca atacattaaa cggcttagtg   2220
aaaaaactaa acaatattat tgaatataat aaaaatatat tcgttattat tctacatgtt   2280
gataagaatc atcttacacc agacatcaaa aaagaaatat tggctttcta tcataagcac   2340
caagtgaata ttttactaaa taatgacatc tcatattaca cgagtaatag actaataaaa   2400
actgaggcac atttaagtaa tattaataaa ttaagtcagt taaatctaaa ttgtgaatac   2460
atcatttttg ataatcatga cagcctattc gttaaaaatg acagctatgc ttatatgaaa   2520
aaatatgatg tcggcatgaa tttctcagca ttaacacatg attggatcga gaaaatcaat   2580
gcgcatccac catttaaaaa gctgattaaa acctatttta atgacaatga cttaagaagt   2640
atgaatgtga aggggcatc acaaggtatg tttatgaagt atgcgctacc gcatgagctt   2700
ctgacgatta ttaaagaagt catcacatcc tgccaatcaa ttgatagtgt gccagaatat   2760
aacactgagg atatttggtt ccaatttgca cttttaatct tagaaaagaa aaccggccat   2820
gtatttaata aaacatcgac cctgacttat atgccttggg aacgaaaatt acaatggaca   2880
aatgaacaaa ttcaaagtgc aaaaaaaggc gaaaatatcc ccgttaacaa gttcattatt   2940
aatagtataa cgctataaaa catttgcatt ttattaaaa                          2979
```

-continued

<210> SEQ ID NO 4
<211> LENGTH: 965
<212> TYPE: PRT
<213> ORGANISM: Pasteurella multocida

<400> SEQUENCE: 4

```
Met Asn Thr Leu Ser Gln Ala Ile Lys Ala Tyr Asn Ser Asn Asp Tyr
1               5                   10                  15

Glu Leu Ala Leu Lys Leu Phe Glu Lys Ser Ala Glu Thr Tyr Gly Arg
            20                  25                  30

Lys Ile Val Glu Phe Gln Ile Ile Lys Cys Lys Glu Lys Leu Ser Thr
        35                  40                  45

Asn Ser Tyr Val Ser Glu Asp Lys Lys Asn Ser Val Cys Asp Ser Ser
    50                  55                  60

Leu Asp Ile Ala Thr Gln Leu Leu Leu Ser Asn Val Lys Lys Leu Thr
65                  70                  75                  80

Leu Ser Glu Ser Glu Lys Asn Ser Leu Lys Asn Lys Trp Lys Ser Ile
                85                  90                  95

Thr Gly Lys Lys Ser Glu Asn Ala Glu Ile Arg Lys Val Glu Leu Val
            100                 105                 110

Pro Lys Asp Phe Pro Lys Asp Leu Val Leu Ala Pro Leu Pro Asp His
        115                 120                 125

Val Asn Asp Phe Thr Trp Tyr Lys Asn Arg Lys Lys Ser Leu Gly Ile
    130                 135                 140

Lys Pro Val Asn Lys Asn Ile Gly Leu Ser Ile Ile Ile Pro Thr Phe
145                 150                 155                 160

Asn Arg Ser Arg Ile Leu Asp Ile Thr Leu Ala Cys Leu Val Asn Gln
                165                 170                 175

Lys Thr Asn Tyr Pro Phe Glu Val Val Val Ala Asp Asp Gly Ser Lys
            180                 185                 190

Glu Asn Leu Leu Thr Ile Val Gln Lys Tyr Glu Gln Lys Leu Asp Ile
        195                 200                 205

Lys Tyr Val Arg Gln Lys Asp Tyr Gly Tyr Gln Leu Cys Ala Val Arg
    210                 215                 220

Asn Leu Gly Leu Arg Thr Ala Lys Tyr Asp Phe Val Ser Ile Leu Asp
225                 230                 235                 240

Cys Asp Met Ala Pro Gln Gln Leu Trp Val His Ser Tyr Leu Thr Glu
                245                 250                 255

Leu Leu Glu Asp Asn Asp Ile Val Leu Ile Gly Pro Arg Lys Tyr Val
            260                 265                 270

Asp Thr His Asn Ile Thr Ala Glu Gln Phe Leu Asn Asp Pro Tyr Leu
        275                 280                 285

Ile Glu Ser Leu Pro Glu Thr Ala Thr Asn Asn Asn Pro Ser Ile Thr
    290                 295                 300

Ser Lys Gly Asn Ile Ser Leu Asp Trp Arg Leu Glu His Phe Lys Lys
305                 310                 315                 320

Thr Asp Asn Leu Arg Leu Cys Asp Ser Pro Phe Arg Tyr Phe Ser Cys
                325                 330                 335

Gly Asn Val Ala Phe Ser Lys Glu Trp Leu Asn Lys Val Gly Trp Phe
            340                 345                 350

Asp Glu Glu Phe Asn His Trp Gly Gly Glu Asp Val Glu Phe Gly Tyr
        355                 360                 365

Arg Leu Phe Ala Lys Gly Cys Phe Phe Arg Val Ile Asp Gly Gly Met
    370                 375                 380
```

-continued

```
Ala Tyr His Gln Glu Pro Pro Gly Lys Glu Asn Glu Thr Asp Arg Glu
385                 390                 395                 400

Ala Gly Lys Ser Ile Thr Leu Lys Ile Val Lys Glu Lys Val Pro Tyr
                405                 410                 415

Ile Tyr Arg Lys Leu Leu Pro Ile Glu Asp Ser His Ile His Arg Ile
            420                 425                 430

Pro Leu Val Ser Ile Tyr Ile Pro Ala Tyr Asn Cys Ala Asn Tyr Ile
        435                 440                 445

Gln Arg Cys Val Asp Ser Ala Leu Asn Gln Thr Val Val Asp Leu Glu
    450                 455                 460

Val Cys Ile Cys Asn Asp Gly Ser Thr Asp Asn Thr Leu Glu Val Ile
465                 470                 475                 480

Asn Lys Leu Tyr Gly Asn Asn Pro Arg Val Arg Ile Met Ser Lys Pro
                485                 490                 495

Asn Gly Gly Ile Ala Ser Ala Ser Asn Ala Ala Val Ser Phe Ala Lys
            500                 505                 510

Gly Tyr Tyr Ile Gly Gln Leu Asp Ser Asp Asp Tyr Leu Glu Pro Asp
        515                 520                 525

Ala Val Glu Leu Cys Leu Lys Glu Phe Leu Lys Asp Lys Thr Leu Ala
    530                 535                 540

Cys Val Tyr Thr Thr Asn Arg Asn Val Asn Pro Asp Gly Ser Leu Ile
545                 550                 555                 560

Ala Asn Gly Tyr Asn Trp Pro Glu Phe Ser Arg Glu Lys Leu Thr Thr
                565                 570                 575

Ala Met Ile Ala His His Phe Arg Met Phe Thr Ile Arg Ala Trp His
            580                 585                 590

Leu Thr Asp Gly Phe Asn Glu Asn Ile Glu Asn Ala Val Asp Tyr Asp
        595                 600                 605

Met Phe Leu Lys Leu Ser Glu Val Gly Lys Phe Lys His Leu Asn Lys
    610                 615                 620

Ile Cys Tyr Asn Arg Val Leu His Gly Asp Asn Thr Ser Ile Lys Lys
625                 630                 635                 640

Leu Gly Ile Gln Lys Lys Asn His Phe Val Val Val Asn Gln Ser Leu
                645                 650                 655

Asn Arg Gln Gly Ile Asn Tyr Tyr Asn Tyr Asp Lys Phe Asp Asp Leu
            660                 665                 670

Asp Glu Ser Arg Lys Tyr Ile Phe Asn Lys Thr Ala Glu Tyr Gln Glu
        675                 680                 685

Glu Met Asp Ile Leu Lys Asp Leu Lys Leu Ile Gln Asn Lys Asp Ala
    690                 695                 700

Lys Ile Ala Val Ser Ile Phe Tyr Pro Asn Thr Leu Asn Gly Leu Val
705                 710                 715                 720

Lys Lys Leu Asn Asn Ile Ile Glu Tyr Asn Lys Asn Ile Phe Val Ile
                725                 730                 735

Ile Leu His Val Asp Lys Asn His Leu Thr Pro Asp Ile Lys Lys Glu
            740                 745                 750

Ile Leu Ala Phe Tyr His Lys His Gln Val Asn Ile Leu Leu Asn Asn
        755                 760                 765

Asp Ile Ser Tyr Tyr Thr Ser Asn Arg Leu Ile Lys Thr Glu Ala His
    770                 775                 780

Leu Ser Asn Ile Asn Lys Leu Ser Gln Leu Asn Leu Asn Cys Glu Tyr
785                 790                 795                 800

Ile Ile Phe Asp Asn His Asp Ser Leu Phe Val Lys Asn Asp Ser Tyr
```

-continued

```
                805                 810                 815
Ala Tyr Met Lys Lys Tyr Asp Val Gly Met Asn Phe Ser Ala Leu Thr
            820                 825                 830
His Asp Trp Ile Glu Lys Ile Asn Ala His Pro Pro Phe Lys Lys Leu
        835                 840                 845
Ile Lys Thr Tyr Phe Asn Asp Asn Asp Leu Arg Ser Met Asn Val Lys
    850                 855                 860
Gly Ala Ser Gln Gly Met Phe Met Lys Tyr Ala Leu Pro His Glu Leu
865                 870                 875                 880
Leu Thr Ile Ile Lys Glu Val Ile Thr Ser Cys Gln Ser Ile Asp Ser
                885                 890                 895
Val Pro Glu Tyr Asn Thr Glu Asp Ile Trp Phe Gln Phe Ala Leu Leu
            900                 905                 910
Ile Leu Glu Lys Lys Thr Gly His Val Phe Asn Lys Thr Ser Thr Leu
        915                 920                 925
Thr Tyr Met Pro Trp Glu Arg Lys Leu Gln Trp Thr Asn Glu Gln Ile
    930                 935                 940
Gln Ser Ala Lys Lys Gly Glu Asn Ile Pro Val Asn Lys Phe Ile Ile
945                 950                 955                 960
Asn Ser Ile Thr Leu
                965
```

<210> SEQ ID NO 5
<211> LENGTH: 1851
<212> TYPE: DNA
<213> ORGANISM: Pasteurella multocida

<400> SEQUENCE: 5

```
atgagcttat ttaaacgtgc tactgagcta tttaagtcag gaaactataa agatgcacta     60
actctatatg aaaatatagc taaaatttat ggttcagaaa gccttgttaa atataatatt    120
gatatatgta aaaaaaatat aacacaatca aaaagtaata aaatagaaga agataatatt    180
tctggagaaa acaaattttc agtatcaata aaagatctat ataacgaaat aagcaatagt    240
gaattaggga ttacaaaaga aagactagga gcccccccctc tagtcagtat tataatgact    300
tctcataata cagaaaaatt cattgaagcc tcaattaatt cactattatt gcaaacatac    360
aataacttag aagttatcgt tgtagatgat tatagcacag ataaaacatt tcagatcgca    420
tccagaatag caaactctac aagtaaagta aaaacattcc gattaaactc aaatctaggg    480
acatactttg cgaaaaatac aggaatttta aagtctaaag gagatattat tttctttcag    540
gatagcgatg atgtatgtca ccatgaaaga atcgaaagat gtgttaatgc attattatcg    600
aataaagata atatagctgt tagatgtgca tattctagaa taaatctaga aacacaaaat    660
ataataaaag ttaatgataa taaatacaaa ttaggattaa taactttagg cgtttataga    720
aaagtattta atgaaattgg tttttttaac tgcacaacca aagcatcgga tgatgaattt    780
tatcatagaa taattaaata ctatggtaaa aataggataa ataacttatt tctaccactg    840
tattataaca caatgcgtga agattcatta ttttctgata tggttgagtg ggtagatgaa    900
aataatataa agcaaaaaac ctctgatgct agacaaaatt atctccatga attccaaaaa    960
atacacaatg aaaggaaatt aaatgaatta aaagagattt ttagctttcc tagaattcat   1020
gacgccttac ctatatcaaa agaaatgagt aagctcagca accctaaaat tcctgtttat   1080
ataaatatat gctcaatacc ttcaagaata aaacaacttc aatacactat tggagtacta   1140
aaaaaccaat gcgatcattt tcatatttat cttgatggat atccagaagt acctgatttt   1200
```

-continued

```
ataaaaaaac tagggaataa agcgaccgtt attaattgtc aaaacaaaaa tgagtctatt   1260

agagataatg gaaagtttat tctattagaa aaacttataa aggaaaataa agatggatat   1320

tatataactt gtgatgatga tatccggtat cctgctgact acacaaacac tatgataaaa   1380

aaaattaata aatacaatga taaagcagca attggattac atggtgttat attcccaagt   1440

agagtcaaca agtatttttc atcagacaga attgtctata attttcaaaa acctttagaa   1500

aatgatactg ctgtaaatat attaggaact ggaactgttg cctttagagt atctattttt   1560

aataaatttt ctctatctga ttttgagcat cctggcatgg tagatatcta tttttctata   1620

ctatgtaaga aaaacaatat actccaagtt tgtatatcac gaccatcgaa ttggctaaca   1680

gaagataaca aaaacactga gaccttattt catgaattcc aaaatagaga tgaaatacaa   1740

agtaaactca ttatttcaaa caacccttgg ggatactcaa gtatatatcc actattaaat   1800

aataatgcta attattctga acttattccg tgtttatctt tttataacga g            1851
```

<210> SEQ ID NO 6
<211> LENGTH: 615
<212> TYPE: PRT
<213> ORGANISM: Pasteurella multocida

<400> SEQUENCE: 6

```
Met Ser Leu Phe Lys Arg Ala Thr Glu Leu Phe Lys Ser Gly Asn Tyr
1               5                   10                  15

Lys Asp Ala Leu Thr Leu Tyr Glu Asn Ile Ala Lys Ile Tyr Gly Ser
            20                  25                  30

Glu Ser Leu Val Lys Tyr Asn Ile Asp Ile Cys Lys Lys Asn Ile Thr
        35                  40                  45

Gln Ser Lys Ser Asn Lys Ile Glu Glu Asp Asn Ile Ser Gly Glu Asn
    50                  55                  60

Lys Phe Ser Val Ser Ile Lys Asp Leu Tyr Asn Glu Ile Ser Asn Ser
65                  70                  75                  80

Glu Leu Gly Ile Thr Lys Glu Arg Leu Gly Ala Pro Pro Leu Val Ser
                85                  90                  95

Ile Ile Met Thr Ser His Asn Thr Glu Lys Phe Ile Glu Ala Ser Ile
            100                 105                 110

Asn Ser Leu Leu Leu Gln Thr Tyr Asn Leu Glu Val Ile Val Val Asp
        115                 120                 125

Asp Tyr Ser Thr Asp Lys Thr Phe Gln Ile Ala Ser Arg Ile Ala Asn
    130                 135                 140

Ser Thr Ser Lys Val Lys Thr Phe Arg Leu Asn Ser Asn Leu Gly Thr
145                 150                 155                 160

Tyr Phe Ala Lys Asn Thr Gly Ile Leu Lys Ser Lys Gly Asp Ile Ile
                165                 170                 175

Phe Phe Gln Ser Asp Asp Val Cys His His Glu Arg Ile Glu Arg Cys
            180                 185                 190

Val Asn Ala Leu Leu Ser Asn Lys Asp Asn Ile Ala Val Arg Cys Ala
        195                 200                 205

Tyr Ser Arg Ile Asn Leu Glu Thr Gln Asn Ile Ile Lys Val Asn Asp
    210                 215                 220

Asn Lys Tyr Lys Leu Gly Leu Ile Thr Leu Gly Val Tyr Arg Lys Val
225                 230                 235                 240

Phe Asn Glu Ile Gly Phe Phe Asn Cys Thr Thr Lys Ala Ser Asp Asp
                245                 250                 255
```

-continued

```
Glu Phe Tyr His Arg Ile Ile Lys Tyr Tyr Gly Lys Asn Arg Ile Asn
            260                 265                 270

Asn Leu Phe Leu Pro Leu Tyr Tyr Asn Thr Met Arg Glu Asp Ser Leu
        275                 280                 285

Phe Ser Asp Met Val Glu Trp Val Asp Glu Asn Asn Ile Lys Gln Lys
    290                 295                 300

Thr Ser Asp Ala Arg Gln Asn Tyr Leu His Glu Phe Gln Lys Ile His
305                 310                 315                 320

Asn Glu Arg Lys Leu Asn Glu Leu Lys Glu Ile Phe Ser Phe Pro Arg
                325                 330                 335

Ile His Asp Ala Leu Pro Ile Ser Lys Glu Met Ser Lys Leu Ser Asn
            340                 345                 350

Pro Lys Ile Pro Val Tyr Ile Asn Ile Cys Ser Ile Pro Ser Arg Ile
        355                 360                 365

Lys Gln Leu Gln Tyr Thr Ile Gly Val Leu Lys Asn Gln Cys Asp His
    370                 375                 380

Phe His Ile Tyr Leu Asp Gly Tyr Pro Glu Val Pro Asp Phe Ile Lys
385                 390                 395                 400

Lys Leu Gly Asn Lys Ala Thr Val Ile Asn Cys Gln Asn Lys Asn Glu
                405                 410                 415

Ser Ile Arg Asp Asn Gly Lys Phe Ile Leu Leu Glu Lys Leu Ile Lys
            420                 425                 430

Glu Asn Lys Asp Gly Tyr Tyr Ile Thr Cys Asp Asp Asp Ile Arg Tyr
        435                 440                 445

Pro Ala Asp Tyr Thr Asn Thr Met Ile Lys Lys Ile Asn Lys Tyr Asn
    450                 455                 460

Asp Lys Ala Ala Ile Gly Leu His Gly Val Ile Phe Pro Ser Arg Val
465                 470                 475                 480

Asn Lys Tyr Phe Ser Ser Asp Arg Ile Val Tyr Asn Phe Gln Lys Pro
                485                 490                 495

Leu Glu Asn Asp Thr Ala Val Asn Ile Leu Gly Thr Gly Thr Val Ala
            500                 505                 510

Phe Arg Val Ser Ile Phe Asn Lys Phe Ser Leu Ser Asp Phe Glu His
        515                 520                 525

Pro Gly Met Val Asp Ile Tyr Phe Ser Ile Leu Cys Lys Lys Asn Asn
    530                 535                 540

Ile Leu Gln Val Cys Ile Ser Arg Pro Ser Asn Trp Leu Thr Glu Asp
545                 550                 555                 560

Asn Lys Asn Thr Glu Thr Leu Phe His Glu Phe Gln Asn Arg Asp Glu
                565                 570                 575

Ile Gln Ser Lys Leu Ile Ile Ser Asn Asn Pro Trp Gly Tyr Ser Ser
            580                 585                 590

Ile Tyr Pro Leu Leu Asn Asn Asn Ala Asn Tyr Ser Glu Leu Ile Pro
        595                 600                 605

Cys Leu Ser Phe Tyr Asn Glu
    610                 615
```

<210> SEQ ID NO 7
<211> LENGTH: 1940
<212> TYPE: DNA
<213> ORGANISM: Pasteurella multocida

<400> SEQUENCE: 7

```
aacaggggat aaggtcagta aatttaggat gatttttgac taatggataa atacttgaat      60
```

-continued

```
atccccatgg accgttttcc atgatcagct gagtttgttg ctcatcattg tctcgatatt    120
gatgatagag tgtttcgctg tctctattat cttccgttag ccagtttgct ggtcttgaaa    180
tacaaatctg aagaatatta tttttcttac acaagagaga gaaatagata tcagccatgc    240
ctgaatgggt aaagtcagaa agagaaaatt gattaaagag actgactcta aagctaacag    300
ttcctgtacc taatacattg accgctttgt ctttttccag aggtttatag aagctatata    360
ccagtctatc cgccgaaaaa tatttggtca ttctacttgg aaagagaatg ccgtgtaaac    420
caataaccgc tttatcatcg tattcattca gcttcttgat catcgtattg atgtaatcgc    480
ttggatagat aatgtcatca tcacaggtta tataatatcc atcttgattt ttttcaatca    540
actcttccag taaaatgaat ttgccattat ctctaatgga gttatcttta tctttgcaat    600
gaacaacggt tgctttatta cctaaatttt ttatgaagtc agggatttct acatagccat    660
caagataaat atgaaaatga tcacattgat tttttagtat gccgataata cgtcgtaatt    720
gcgctattct tgagggaata gaacaaatat tgatataaac aggaatctta ggattggaca    780
acttactcat ttcttgtggt actggtaagg catcgtaaat acgagggaat tgaaaaagat    840
ttttgaaatc atgtgaggca gtttcgttat gcatcgcttg aaacagggtt gcataatgtt    900
gtctggtatc agacattttc tgtattatgt tatgattgtc tatccattca accatatcag    960
taaataaaga gttttctctc attgtgttgt agtataacgg caagagtaaa tttttttattt  1020
tttcttttcc ataatatttc gcaattctat gaaaaaactc atcatctgag cctttagtcg   1080
tacaattgaa gaaaccaatt tcttgaaata cttttctgtg catacccaag gttataaaac   1140
ctaatctata atccatatta ttgactttaa tgatatgttg tgtttctggt gctagtcttg   1200
agtatgcaca acgaacagca atagtttctt tattagctaa taatatattt acacatcttt   1260
ctattctttc atgatgacat acatcatcac tatcttgaaa gaaaataatg tcacctttag   1320
attttaatat gcctgtattt ttcgcaaagt aagttcctag gtttgaattt aatctaaata   1380
ctctgacttt gcttgttgta ttcgctattc tcgaggcaat ttcaaatgta ttatccgagc   1440
tatcatcatc tacaataata atttctatgt ttttatatgt ttgtaacaat aatgaattaa   1500
tagaagcttc gataaattgc gctgtattgt gagatgtcat gataatactg actaatggat   1560
ttacgctgtt ggtttctttg actaacccta aatcactttt agcgacttca ttatataaat   1620
ctgttattga tgttgtttgc ttatcttttt ctagctttgc ttctaatgct tgattatagg   1680
tatatatttt ttcaaattct tgcagaacca attggagttg ttttaataaa agtttatttt   1740
cgttttcaag ggatgcggat agcggatgtt tactgtcctg ttttgccaat aaagtttgtt   1800
gagaaataat gtctttgttt aaagttgttt ttagactatc aattttattt tgaaaggtgt   1860
tgagttcatt ttctttttca tgttgggggg gatttttagt catttgtttt tgagtcatct   1920
cttttttttct cttcatttca                                               1940
```

<210> SEQ ID NO 8
<211> LENGTH: 651
<212> TYPE: PRT
<213> ORGANISM: Pasteurella multocida

<400> SEQUENCE: 8

```
Met Lys Arg Lys Lys Glu Met Thr Gln Lys Gln Met Thr Lys Asn Pro
1               5                   10                  15

Pro Gln His Glu Lys Glu Asn Glu Leu Asn Thr Phe Gln Asn Lys Ile
            20                  25                  30

Asp Ser Leu Lys Thr Thr Leu Asn Lys Asp Ile Ile Ser Gln Gln Thr
```

-continued

```
        35                  40                  45

Leu Leu Ala Lys Gln Asp Ser Lys His Pro Leu Ser Ala Ser Leu Glu
    50                  55                  60

Asn Glu Asn Lys Leu Leu Leu Lys Gln Leu Gln Leu Val Leu Gln Glu
65                  70                  75                  80

Phe Glu Lys Ile Tyr Thr Tyr Asn Gln Ala Leu Glu Ala Lys Leu Glu
                85                  90                  95

Lys Asp Lys Gln Thr Thr Ser Ile Thr Asp Leu Tyr Asn Glu Val Ala
            100                 105                 110

Lys Ser Asp Leu Gly Leu Val Lys Glu Thr Asn Ser Val Asn Pro Leu
        115                 120                 125

Val Ser Ile Ile Met Thr Ser His Asn Thr Ala Gln Phe Ile Glu Ala
    130                 135                 140

Ser Ile Asn Ser Leu Leu Leu Gln Thr Tyr Lys Asn Ile Glu Ile Ile
145                 150                 155                 160

Ile Val Asp Asp Asp Ser Ser Asp Asn Thr Phe Glu Ile Ala Ser Arg
                165                 170                 175

Ile Ala Asn Thr Thr Ser Lys Val Arg Val Phe Arg Leu Asn Ser Asn
            180                 185                 190

Leu Gly Thr Tyr Phe Ala Lys Asn Thr Gly Ile Leu Lys Ser Lys Gly
        195                 200                 205

Asp Ile Ile Phe Phe Gln Asp Ser Asp Asp Val Cys His His Glu Arg
    210                 215                 220

Ile Glu Arg Cys Val Asn Ile Leu Leu Ala Asn Lys Glu Thr Ile Ala
225                 230                 235                 240

Val Arg Cys Ala Tyr Ser Arg Leu Ala Pro Glu Thr Gln His Ile Ile
                245                 250                 255

Lys Val Asn Asn Met Asp Tyr Arg Leu Gly Phe Ile Thr Leu Gly Met
            260                 265                 270

His Arg Lys Val Phe Gln Glu Ile Gly Phe Phe Asn Cys Thr Thr Lys
        275                 280                 285

Gly Ser Asp Asp Glu Phe Phe His Arg Ile Ala Lys Tyr Tyr Gly Lys
    290                 295                 300

Glu Lys Ile Lys Asn Leu Leu Leu Pro Leu Tyr Tyr Asn Thr Met Arg
305                 310                 315                 320

Glu Asn Ser Leu Phe Thr Asp Met Val Glu Trp Ile Asp Asn His Asn
                325                 330                 335

Ile Ile Gln Lys Met Ser Asp Thr Arg Gln His Tyr Ala Thr Leu Phe
            340                 345                 350

Gln Ala Met His Asn Glu Thr Ala Ser His Asp Phe Lys Asn Leu Phe
        355                 360                 365

Gln Phe Pro Arg Ile Tyr Asp Ala Leu Pro Val Pro Gln Glu Met Ser
    370                 375                 380

Lys Leu Ser Asn Pro Lys Ile Pro Val Tyr Ile Asn Ile Cys Ser Ile
385                 390                 395                 400

Pro Ser Arg Ile Ala Gln Leu Arg Arg Ile Ile Gly Ile Leu Lys Asn
                405                 410                 415

Gln Cys Asp His Phe His Ile Tyr Leu Asp Gly Tyr Val Glu Ile Pro
            420                 425                 430

Asp Phe Ile Lys Asn Leu Gly Asn Lys Ala Thr Val Val His Cys Lys
        435                 440                 445

Asp Lys Asp Asn Ser Ile Arg Asp Asn Gly Lys Phe Ile Leu Leu Glu
    450                 455                 460
```

-continued

```
Glu Leu Ile Glu Lys Asn Gln Asp Gly Tyr Tyr Ile Thr Cys Asp Asp
465                 470                 475                 480

Asp Ile Ile Tyr Pro Ser Asp Tyr Ile Asn Thr Met Ile Lys Lys Leu
                485                 490                 495

Asn Glu Tyr Asp Asp Lys Ala Val Ile Gly Leu His Gly Ile Leu Phe
            500                 505                 510

Pro Ser Arg Met Thr Lys Tyr Phe Ser Ala Asp Arg Leu Val Tyr Ser
        515                 520                 525

Phe Tyr Lys Pro Leu Glu Lys Asp Lys Ala Val Asn Val Leu Gly Thr
    530                 535                 540

Gly Thr Val Ser Phe Arg Val Ser Leu Phe Asn Gln Phe Ser Leu Ser
545                 550                 555                 560

Asp Phe Thr His Ser Gly Met Ala Asp Ile Tyr Phe Ser Leu Leu Cys
                565                 570                 575

Lys Lys Asn Asn Ile Leu Gln Ile Cys Ile Ser Arg Pro Ala Asn Trp
            580                 585                 590

Leu Thr Glu Asp Asn Arg Asp Ser Glu Thr Leu Tyr His Gln Tyr Arg
        595                 600                 605

Asp Asn Asp Glu Gln Gln Thr Gln Leu Ile Met Glu Asn Gly Pro Trp
    610                 615                 620

Gly Tyr Ser Ser Ile Tyr Pro Leu Val Lys Asn His Pro Lys Phe Thr
625                 630                 635                 640

Asp Leu Ile Pro Cys Leu Pro Phe Tyr Phe Leu
                645                 650


<210> SEQ ID NO 9
<211> LENGTH: 703
<212> TYPE: PRT
<213> ORGANISM: Pasteurella multocida

<400> SEQUENCE: 9

Met Asn Thr Leu Ser Gln Ala Ile Lys Ala Tyr Asn Ser Asn Asp Tyr
1               5                   10                  15

Gln Leu Ala Leu Lys Leu Phe Glu Lys Ser Ala Glu Ile Tyr Gly Arg
            20                  25                  30

Lys Ile Val Glu Phe Gln Ile Thr Lys Cys Lys Glu Lys Leu Ser Ala
        35                  40                  45

His Pro Ser Val Asn Ser Ala His Leu Ser Val Asn Lys Glu Glu Lys
    50                  55                  60

Val Asn Val Cys Asp Ser Pro Leu Asp Ile Ala Thr Gln Leu Leu Leu
65                  70                  75                  80

Ser Asn Val Lys Lys Leu Val Leu Ser Asp Ser Glu Lys Asn Thr Leu
                85                  90                  95

Lys Asn Lys Trp Lys Leu Leu Thr Glu Lys Lys Ser Glu Asn Ala Glu
            100                 105                 110

Val Arg Ala Val Ala Leu Val Pro Lys Asp Phe Pro Lys Asp Leu Val
        115                 120                 125

Leu Ala Pro Leu Pro Asp His Val Asn Asp Phe Thr Trp Tyr Lys Lys
    130                 135                 140

Arg Lys Lys Arg Leu Gly Ile Lys Pro Glu His Gln His Val Gly Leu
145                 150                 155                 160

Ser Ile Ile Val Thr Thr Phe Asn Arg Pro Ala Ile Leu Ser Ile Thr
                165                 170                 175

Leu Ala Cys Leu Val Asn Gln Lys Thr His Tyr Pro Phe Glu Val Ile
```

-continued

```
            180                 185                 190

Val Thr Asp Asp Gly Ser Gln Glu Asp Leu Ser Pro Ile Ile Arg Gln
        195                 200                 205

Tyr Glu Asn Lys Leu Asp Ile Arg Tyr Val Arg Gln Lys Asp Asn Gly
    210                 215                 220

Phe Gln Ala Ser Ala Ala Arg Asn Met Gly Leu Arg Leu Ala Lys Tyr
225                 230                 235                 240

Asp Phe Ile Gly Leu Leu Asp Cys Asp Met Ala Pro Asn Pro Leu Trp
                245                 250                 255

Val His Ser Tyr Val Ala Glu Leu Leu Glu Asp Asp Asp Leu Thr Ile
            260                 265                 270

Ile Gly Pro Arg Lys Tyr Ile Asp Thr Gln His Ile Asp Pro Lys Asp
        275                 280                 285

Phe Leu Asn Asn Ala Ser Leu Leu Glu Ser Leu Pro Glu Val Lys Thr
    290                 295                 300

Asn Asn Ser Val Ala Ala Lys Gly Glu Gly Thr Val Ser Leu Asp Trp
305                 310                 315                 320

Arg Leu Glu Gln Phe Glu Lys Thr Glu Asn Leu Arg Leu Ser Asp Ser
                325                 330                 335

Pro Phe Arg Phe Phe Ala Ala Gly Asn Val Ala Phe Ala Lys Lys Trp
            340                 345                 350

Leu Asn Lys Ser Gly Phe Phe Asp Glu Glu Phe Asn His Trp Gly Gly
        355                 360                 365

Glu Asp Val Glu Phe Gly Tyr Arg Leu Phe Arg Tyr Gly Ser Phe Phe
    370                 375                 380

Lys Thr Ile Asp Gly Ile Met Ala Tyr His Gln Glu Pro Pro Gly Lys
385                 390                 395                 400

Glu Asn Glu Thr Asp Arg Glu Ala Gly Lys Asn Ile Thr Leu Asp Ile
                405                 410                 415

Met Arg Glu Lys Val Pro Tyr Ile Tyr Arg Lys Leu Leu Pro Ile Glu
            420                 425                 430

Asp Ser His Ile Asn Arg Val Pro Leu Val Ser Ile Tyr Ile Pro Ala
        435                 440                 445

Tyr Asn Cys Ala Asn Tyr Ile Gln Arg Cys Val Asp Ser Ala Leu Asn
    450                 455                 460

Gln Thr Val Val Asp Leu Glu Val Cys Ile Cys Asn Asp Gly Ser Thr
465                 470                 475                 480

Asp Asn Thr Leu Glu Val Ile Asn Lys Leu Tyr Gly Asn Asn Pro Arg
                485                 490                 495

Val Arg Ile Met Ser Lys Pro Asn Gly Gly Ile Ala Ser Ala Ser Asn
            500                 505                 510

Ala Ala Val Ser Phe Ala Lys Gly Tyr Tyr Ile Gly Gln Leu Asp Ser
        515                 520                 525

Asp Asp Tyr Leu Glu Pro Asp Ala Val Glu Leu Cys Leu Lys Glu Phe
    530                 535                 540

Leu Lys Asp Lys Thr Leu Ala Cys Val Tyr Thr Thr Asn Arg Asn Val
545                 550                 555                 560

Asn Pro Asp Gly Ser Leu Ile Ala Asn Gly Tyr Asn Trp Pro Glu Phe
                565                 570                 575

Ser Arg Glu Lys Leu Thr Thr Ala Met Ile Ala His His Phe Arg Met
            580                 585                 590

Phe Thr Ile Arg Ala Trp His Leu Thr Asp Gly Phe Asn Glu Lys Ile
        595                 600                 605
```

-continued

```
Glu Asn Ala Val Asp Tyr Asp Met Phe Leu Lys Leu Ser Glu Val Gly
    610                 615                 620

Lys Phe Lys His Leu Asn Lys Ile Cys Tyr Asn Arg Val Leu His Gly
625                 630                 635                 640

Asp Asn Thr Ser Ile Lys Lys Leu Gly Ile Gln Lys Lys Asn His Phe
                645                 650                 655

Val Val Val Asn Gln Ser Leu Asn Arg Gln Gly Ile Thr Tyr Tyr Asn
            660                 665                 670

Tyr Asp Glu Phe Asp Asp Leu Asp Glu Ser Arg Lys Tyr Ile Phe Asn
        675                 680                 685

Lys Thr Ala Glu Tyr Gln Glu Glu Ile Asp Ile Leu Lys Asp Ile
    690                 695                 700


<210> SEQ ID NO 10
<211> LENGTH: 1953
<212> TYPE: DNA
<213> ORGANISM: Pasteurella multocida

<400> SEQUENCE: 10

atgaatacat tatcacaagc aataaaagca tataacagca atgactatca attagcactc     60

aaattatttg aaaagtcggc ggaaatctat ggacggaaaa ttgttgaatt tcaaattacc    120

aaatgcaaag aaaaactctc agcacatcct tctgttaatt cagcacatct ttctgtaaat    180

aaagaagaaa aagtcaatgt ttgcgatagt ccgttagata ttgcaacaca actgttactt    240

tccaacgtaa aaaaattagt actttctgac tcggaaaaaa acacgttaaa aaataaatgg    300

aaattgctca ctgagaagaa atctgaaaat gcggaggtaa gagcggtcgc ccttgtacca    360

aaagattttc ccaaagatct ggttttagcg cctttacctg atcatgttaa tgattttaca    420

tggtacaaaa agcgaaagaa aagacttggc ataaaacctg aacatcaaca tgttggtctt    480

tctattatcg ttacaacatt caatcgacca gcaattttat cgattacatt agcctgttta    540

gtaaaccaaa aaacacatta cccgtttgaa gttatcgtga cagatgatgg tagtcaggaa    600

gatctatcac cgatcattcg ccaatatgaa aataaattgg atattcgcta cgtcagacaa    660

aaagataacg gttttcaagc cagtgccgct cggaatatgg gattacgctt agcaaaatat    720

gactttattg gcttactcga ctgtgatatg gcgccaaatc cattatgggt tcattcttat    780

gttgcagagc tattagaaga tgatgattta acaatcattg gtccaagaaa atacatcgat    840

acacaacata ttgacccaaa agacttctta aataacgcga gtttgcttga atcattacca    900

gaagtgaaaa ccaataatag tgttgccgca aaaggggaag gaacagtttc tctggattgg    960

cgcttagaac aattcgaaaa aacagaaaat ctccgcttat ccgattcgcc tttccgtttt   1020

tttgcggcgg gtaatgttgc tttcgctaaa aaatggctaa ataaatccgg tttctttgat   1080

gaggaattta atcactgggg tggagaagat gtggaatttg gatatcgctt attccgttac   1140

ggtagtttct ttaaaactat tgatggcatt atggcctacc atcaagagcc accaggtaaa   1200

gaaaatgaaa ccgatcgtga agcgggaaaa aatattacgc tcgatattat gagagaaaag   1260

gtcccttata tctatagaaa acttttacca atagaagatt cgcatatcaa tagagtacct   1320

ttagtttcaa tttatatccc agcttataac tgtgcaaact atattcaacg ttgcgtagat   1380

agtgcactga atcagactgt tgttgatctc gaggtttgta tttgtaacga tggttcaaca   1440

gataatacct tagaagtgat caataagctt tatggtaata atcctagggt acgcatcatg   1500

tctaaaccaa atggcggaat agcctcagca tcaaatgcag ccgtttcttt tgctaaaggt   1560
```

-continued tattacattg ggcagttaga ttcagatgat tatcttgagc ctgatgcagt tgaactgtgt 1620
ttaaaagaat ttttaaaaga taaaacgcta gcttgtgttt ataccactaa tagaaacgtc 1680
aatccggatg gtagcttaat cgctaatggt tacaattggc cagaattttc acgagaaaaa 1740
ctcacaacgg ctatgattgc tcaccacttt agaatgttca cgattagagc ttggcattta 1800
actgatggat tcaatgaaaa aattgaaaat gccgtagact atgacatgtt cctcaaactc 1860
agtgaagttg gaaaatttaa acatcttaat aaaatctgct ataaccgtgt attacatggt 1920
gataacacat caattaagaa acttggcatt caa 1953

<210> SEQ ID NO 11
<211> LENGTH: 2112
<212> TYPE: DNA
<213> ORGANISM: Pasteurella multocida

<400> SEQUENCE: 11
atgaatacat tatcacaagc aataaaagca tataacagca atgactatca attagcactc 60
aaattatttg aaaagtcggc ggaaatctat ggacggaaaa ttgttgaatt tcaaattacc 120
aaatgcaaag aaaaactctc agcacatcct tctgttaatt cagcacatct ttctgtaaat 180
aaagaagaaa aagtcaatgt ttgcgatagt ccgttagata ttgcaacaca actgttactt 240
tccaacgtaa aaaaattagt actttctgac tcggaaaaaa acacgttaaa aaataaatgg 300
aaattgctca ctgagaagaa atctgaaaat gcggaggtaa gagcggtcgc ccttgtacca 360
aaagattttc ccaaagatct ggttttagcg cctttacctg atcatgttaa tgattttaca 420
tggtacaaaa agcgaaagaa aagacttggc ataaaacctg aacatcaaca tgttggtctt 480
tctattatcg ttacaacatt caatcgacca gcaattttat cgattacatt agcctgttta 540
gtaaaccaaa aaacacatta cccgtttgaa gttatcgtga cagatgatgg tagtcaggaa 600
gatctatcac cgatcattcg ccaatatgaa aataaattgg atattcgcta cgtcagacaa 660
aaagataacg gttttcaagc cagtgccgct cggaatatgg gattacgctt agcaaaatat 720
gactttattg gcttactcga ctgtgatatg gcgccaaatc cattatgggt tcattcttat 780
gttgcagagc tattagaaga tgatgattta acaatcattg gtccaagaaa atacatcgat 840
acacaacata ttgacccaaa agacttctta aataacgcga gtttgcttga atcattacca 900
gaagtgaaaa ccaataatag tgttgccgca aaaggggaag gaacagtttc tctggattgg 960
cgcttagaac aattcgaaaa aacagaaaat ctccgcttat ccgattcgcc tttccgtttt 1020
tttgcggcgg gtaatgttgc tttcgctaaa aaatggctaa ataaatccgg tttctttgat 1080
gaggaattta atcactgggg tggagaagat gtggaatttg gatatcgctt attccgttac 1140
ggtagtttct ttaaaactat tgatggcatt atggcctacc atcaagagcc accaggtaaa 1200
gaaaatgaaa ccgatcgtga agcgggaaaa aatattacgc tcgatattat gagagaaaag 1260
gtcccttata tctatagaaa acttttacca atagaagatt cgcatatcaa tagagtacct 1320
ttagtttcaa tttatatccc agcttataac tgtgcaaact atattcaacg ttgcgtagat 1380
agtgcactga atcagactgt tgttgatctc gaggtttgta tttgtaacaa tggttcaaca 1440
gataatacct tagaagtgat caataagctt tatggtaata atcctagggt acgcatcatg 1500
tctaaaccaa atggcggaat agcctcagca tcaaatgcag ccgtttcttt tgctaaaggt 1560
tattacattg ggcagttaga ttcagatgat tatcttgagc ctgatgcagt tgaactgtgt 1620
ttaaaagaat ttttaaaaga taaaacgcta gcttgtgttt ataccactaa tagaaacgtc 1680
aatccggatg gtagcttaat cgctaatggt tacaattggc cagaattttc acgagaaaaa 1740

```
ctcacaacgg ctatgattgc tcaccacttt agaatgttca cgattagagc ttggcattta   1800

actgatggat tcaatgaaaa aattgaaaat gccgtagact atgacatgtt cctcaaactc   1860

agtgaagttg gaaaatttaa acatcttaat aaaatctgct ataaccgtgt attacatggt   1920

gataacacat caattaagaa acttggcatt caaaagaaaa accattttgt tgtagtcaat   1980

cagtcattaa atagacaagg cataacttat tataattatg acgaatttga tgatttagat   2040

gaaagtagaa agtatatttt caataaaacc gctgaatatc aagaagagat tgatatctta   2100

aaagatattt aa                                                      2112
```

<210> SEQ ID NO 12
<211> LENGTH: 2112
<212> TYPE: DNA
<213> ORGANISM: Pasteurella multocida

<400> SEQUENCE: 12

```
atgaatacat tatcacaagc aataaaagca tataacagca atgactatca attagcactc     60

aaattatttg aaaagtcggc ggaaatctat ggacggaaaa ttgttgaatt tcaaattacc    120

aaatgcaaag aaaaactctc agcacatcct tctgttaatt cagcacatct ttctgtaaat    180

aaagaagaaa aagtcaatgt ttgcgatagt ccgttagata ttgcaacaca actgttactt    240

tccaacgtaa aaaaattagt actttctgac tcggaaaaaa acacgttaaa aaataaatgg    300

aaattgctca ctgagaagaa atctgaaaat gcggaggtaa gagcggtcgc ccttgtacca    360

aaagattttc ccaaagatct ggttttagcg cctttacctg atcatgttaa tgattttaca    420

tggtacaaaa agcgaaagaa aagacttggc ataaaacctg aacatcaaca tgttggtctt    480

tctattatcg ttacaacatt caatcgacca gcaattttat cgattacatt agcctgttta    540

gtaaaccaaa aaacacatta cccgtttgaa gttatcgtga cagataatgg tagtcaggaa    600

gatctatcac cgatcattcg ccaatatgaa aataaattgg atattcgcta cgtcagacaa    660

aaagataacg gttttcaagc cagtgccgct cggaatatgg gattacgctt agcaaaatat    720

gactttattg gcttactcga ctgtgatatg gcgccaaatc cattatgggt tcattcttat    780

gttgcagagc tattagaaga tgatgattta acaatcattg gtccaagaaa atacatcgat    840

acacaacata ttgacccaaa agacttctta aataacgcga gtttgcttga atcattacca    900

gaagtgaaaa ccaataatag tgttgccgca aaaggggaag gaacagtttc tctggattgg    960

cgcttagaac aattcgaaaa aacagaaaat ctccgcttat ccgattcgcc tttccgtttt   1020

tttgcggcgg gtaatgttgc tttcgctaaa aaatggctaa ataaatccgg tttctttgat   1080

gaggaattta atcactgggg tggagaagat gtggaatttg gatatcgctt attccgttac   1140

ggtagtttct ttaaaactat tgatggcatt atggcctacc atcaagagcc accaggtaaa   1200

gaaaatgaaa ccgatcgtga agcgggaaaa aatattacgc tcgatattat gagagaaaag   1260

gtcccttata tctatagaaa acttttacca atagaagatt cgcatatcaa tagagtacct   1320

ttagtttcaa tttatatccc agcttataac tgtgcaaact atattcaacg ttgcgtagat   1380

agtgcactga atcagactgt tgttgatctc gaggtttgta tttgtaacga tggttcaaca   1440

gataatacct tagaagtgat caataagctt tatggtaata atcctagggt acgcatcatg   1500

tctaaaccaa atggcggaat agcctcagca tcaaatgcag ccgtttcttt tgctaaaggt   1560

tattacattg ggcagttaga ttcagatgat tatcttgagc ctgatgcagt tgaactgtgt   1620

ttaaaagaat ttttaaaaga taaaacgcta gcttgtgttt ataccactaa tagaaacgtc   1680
```

-continued

```
aatccggatg gtagcttaat cgctaatggt tacaattggc cagaattttc acgagaaaaa   1740

ctcacaacgg ctatgattgc tcaccacttt agaatgttca cgattagagc ttggcattta   1800

actgatggat tcaatgaaaa aattgaaaat gccgtagact atgacatgtt cctcaaactc   1860

agtgaagttg gaaaatttaa acatcttaat aaaatctgct ataaccgtgt attacatggt   1920

gataacacat caattaagaa acttggcatt caaaagaaaa accattttgt tgtagtcaat   1980

cagtcattaa atagacaagg cataacttat tataattatg acgaatttga tgatttagat   2040

gaaagtagaa agtatatttt caataaaacc gctgaatatc aagaagagat tgatatctta   2100

aaagatattt aa                                                       2112
```

<210> SEQ ID NO 13
<211> LENGTH: 1614
<212> TYPE: DNA
<213> ORGANISM: Pasteurella multocida

<400> SEQUENCE: 13

```
atcaatagag tacctttagt ttcaatttat atcccagctt ataactgtgc aaactatatt     60

caacgttgcg tagatagtgc actgaatcag actgttgttg atctcgaggt ttgtatttgt    120

aacgatggtt caacagataa taccttagaa gtgatcaata agctttatgg taataatcct    180

agggtacgca tcatgtctaa accaaatggc ggaatagcct cagcatcaaa tgcagccgtt    240

tcttttgcta aaggttatta cattgggcag ttagattcag atgattatct tgagcctgat    300

gcagttgaac tgtgtttaaa agaattttta aaagataaaa cgctagcttg tgtttatacc    360

actaatagaa acgtcaatcc ggatggtagc ttaatcgcta atggttacaa ttggccagaa    420

ttttcacgag aaaaactcac aacggctatg attgctcacc actttagaat gttcacgatt    480

agagcttggc atttaactga tggattcaat gaaaaaattg aaaatgccgt agactatgac    540

atgttcctca aactcagtga agttggaaaa tttaaacatc ttaataaaat ctgctataac    600

cgtgtattac atggtgataa cacatcaatt aagaaacttg gcattcaaaa gaaaaaccat    660

tttgttgtag tcaatcagtc attaaataga caaggcataa cttattataa ttatgacgaa    720

tttgatgatt tagatgaaag tagaaagtat attttcaata aaaccgctga atatcaagaa    780

gagattgata tcttaaaaga tattaaaatc atccagaata aagatgccaa aatcgcagtc    840

agtatttttt atcccaatac attaaacggc ttagtgaaaa aactaaacaa tattattgaa    900

tataataaaa atatattcgt tattgttcta catgttgata agaatcatct tacaccagat    960

atcaaaaaag aaatactagc cttctatcat aaacatcaag tgaatatttt actaaataat   1020

gatatctcat attacacgag taatagatta ataaaaactg aggcgcattt aagtaatatt   1080

aataaattaa gtcagttaaa tctaaattgt gaatacatca tttttgataa tcatgacagc   1140

ctattcgtta aaaatgacag ctatgcttat atgaaaaaat atgatgtcgg catgaatttc   1200

tcagcattaa cacatgattg gatcgagaaa atcaatgcgc atccaccatt taaaaagctc   1260

attaaaactt attttaatga caatgactta aaaagtatga atgtgaaagg ggcatcacaa   1320

ggtatgttta tgacgtatgc gctagcgcat gagcttctga cgattattaa agaagtcatc   1380

acatcttgcc agtcaattga tagtgtgcca gaatataaca ctgaggatat ttggttccaa   1440

tttgcacttt taatcttaga aaagaaaacc ggccatgtat ttaataaaac atcgaccctg   1500

acttatatgc cttgggaacg aaaattacaa tggacaaatg aacaaattga aagtgcaaaa   1560

agaggagaaa atatacctgt taacaagttc attattaata gtataactct ataa         1614
```

-continued

<210> SEQ ID NO 14
<211> LENGTH: 966
<212> TYPE: DNA
<213> ORGANISM: Pasteurella multocida

<400> SEQUENCE: 14
atcaatagag tacctttagt ttcaatttat atcccagctt ataactgtgc aaactatatt 60
caacgttgcg tagatagtgc actgaatcag actgttgttg atctcgaggt ttgtatttgt 120
aacgatggtt caacagataa taccttagaa gtgatcaata agctttatgg taataatcct 180
agggtacgca tcatgtctaa accaaatggc ggaatagcct cagcatcaaa tgcagccgtt 240
tcttttgcta aaggttatta cattgggcag ttagattcag atgattatct tgagcctgat 300
gcagttgaac tgtgtttaaa agaattttta aaagataaaa cgctagcttg tgtttatacc 360
actaatagaa acgtcaatcc ggatggtagc ttaatcgcta atggttacaa ttggccagaa 420
ttttcacgag aaaaactcac aacggctatg attgctcacc actttagaat gttcacgatt 480
agagcttggc atttaactga tggattcaat gaaaaaattg aaaatgccgt agactatgac 540
atgttcctca aactcagtga agttggaaaa tttaaacatc ttaataaaat ctgctataac 600
cgtgtattac atggtgataa cacatcaatt aagaaacttg gcattcaaaa gaaaaaccat 660
tttgttgtag tcaatcagtc attaaataga caaggcataa cttattataa ttatgacgaa 720
tttgatgatt tagatgaaag tagaaagtat attttcaata aaaccgctga atatcaagaa 780
gagattgata tcttaaaaga tattaaaatc atccagaata aagatgccaa aatcgcagtc 840
agtatttttt atcccaatac attaaacggc ttagtgaaaa aactaaacaa tattattgaa 900
tataataaaa atatattcgt tattgttcta catgttgata agaatcatct tacaccagat 960
atctaa 966

<210> SEQ ID NO 15
<211> LENGTH: 1821
<212> TYPE: DNA
<213> ORGANISM: Pasteurella multocida

<400> SEQUENCE: 15
atgaaacctg aacatcaaca tgttggtctt tctattatcg ttacaacatt caatcgacca 60
gcaattttat cgattacatt agcctgttta gtaaaccaaa aaacacatta cccgtttgaa 120
gttatcgtga cagatgatgg tagtcaggaa gatctatcac cgatcattcg ccaatatgaa 180
aataaattgg atattcgcta cgtcagacaa aaagataacg gttttcaagc cagtgccgct 240
cggaatatgg gattacgctt agcaaaatat gactttattg gcttactcga ctgtgatatg 300
gcgccaaatc cattatgggt tcattcttat gttgcagagc tattagaaga tgatgattta 360
acaatcattg gtccaagaaa atacatcgat acacaacata ttgacccaaa agacttctta 420
aataacgcga gtttgcttga atcattacca gaagtgaaaa ccaataatag tgttgccgca 480
aaaggggaag gaacagtttc tctggattgg cgcttagaac aattcgaaaa aacagaaaat 540
ctccgcttat ccgattcgcc tttccgtttt tttgcggcgg gtaatgttgc tttcgctaaa 600
aaatggctaa ataaatccgg tttctttgat gaggaattta atcactgggg tggagaagat 660
gtggaatttg gatatcgctt attccgttac ggtagtttct ttaaaactat tgatggcatt 720
atggcctacc atcaagagcc accaggtaaa gaaaatgaaa ccgatcgtga agcgggaaaa 780
aatattacgc tcgatattat gagagaaaag gtcccttata tctatagaaa acttttacca 840
atagaagatt cgcatatcaa tagagtacct ttagtttcaa tttatatccc agcttataac 900

-continued

```
tgtgcaaact atattcaacg ttgcgtagat agtgcactga atcagactgt tgttgatctc    960

gaggtttgta tttgtaacga tggttcaaca gataatacct tagaagtgat caataagctt   1020

tatggtaata atcctagggt acgcatcatg tctaaaccaa atggcggaat agcctcagca   1080

tcaaatgcag ccgtttcttt tgctaaaggt tattacattg ggcagttaga ttcagatgat   1140

tatcttgagc ctgatgcagt tgaactgtgt ttaaaagaat ttttaaaaga taaaacgcta   1200

gcttgtgttt ataccactaa tagaaacgtc aatccggatg gtagcttaat cgctaatggt   1260

tacaattggc cagaattttc acgagaaaaa ctcacaacgg ctatgattgc tcaccacttt   1320

agaatgttca cgattagagc ttggcattta actgatggat tcaatgaaaa aattgaaaat   1380

gccgtagact atgacatgtt cctcaaactc agtgaagttg gaaaatttaa acatcttaat   1440

aaaatctgct ataaccgtgt attacatggt gataacacat caattaagaa acttggcatt   1500

caaaagaaaa accattttgt tgtagtcaat cagtcattaa atagacaagg cataacttat   1560

tataattatg acgaatttga tgatttagat gaaagtagaa agtatatttt caataaaacc   1620

gctgaatatc aagaagagat tgatatctta aaagatatta aaatcatcca gaataaagat   1680

gccaaaatcg cagtcagtat tttttatccc aatacattaa acggcttagt gaaaaaacta   1740

aacaatatta ttgaatataa taaaaatata ttcgttattg ttctacatgt tgataagaat   1800

catcttacac cagatatcta a                                              1821
```

<210> SEQ ID NO 16
<211> LENGTH: 2112
<212> TYPE: DNA
<213> ORGANISM: Pasteurella multocida

<400> SEQUENCE: 16

```
atgaatacat tatcacaagc aataaaagca tataacagca atgactatca attagcactc     60

aaattatttg aaaagtcggc ggaaatctat ggacggaaaa ttgttgaatt tcaaattacc    120

aaatgcaaag aaaaactctc agcacatcct tctgttaatt cagcacatct ttctgtaaat    180

aaagaagaaa aagtcaatgt ttgcgatagt ccgttagata ttgcaacaca actgttactt    240

tccaacgtaa aaaaattagt actttctgac tcggaaaaaa acacgttaaa aaataaatgg    300

aaattgctca ctgagaagaa atctgaaaat gcggaggtaa gagcggtcgc ccttgtacca    360

aaagattttc ccaaagatct ggttttagcg cctttacctg atcatgttaa tgattttaca    420

tggtacaaaa agcgaaagaa aagacttggc ataaaacctg aacatcaaca tgttggtctt    480

tctattatcg ttacaacatt caatcgacca gcaattttat cgattacatt agcctgttta    540

gtaaaccaaa aaacacatta cccgtttgaa gttatcgtga cagatgaagg tagtcaggaa    600

gatctatcac cgatcattcg ccaatatgaa aataaattgg atattcgcta cgtcagacaa    660

aaagataacg gttttcaagc cagtgccgct cggaatatgg gattacgctt agcaaaatat    720

gactttattg gcttactcga ctgtgatatg gcgccaaatc cattatgggt tcattcttat    780

gttgcagagc tattagaaga tgatgattta acaatcattg gtccaagaaa atacatcgat    840

acacaacata ttgacccaaa agacttctta aataacgcga gtttgcttga atcattacca    900

gaagtgaaaa ccaataatag tgttgccgca aaaggggaag gaacagtttc tctggattgg    960

cgcttagaac aattcgaaaa aacagaaaat ctccgcttat ccgattcgcc tttccgtttt   1020

tttgcggcgg gtaatgttgc tttcgctaaa aaatggctaa ataaatccgg tttctttgat   1080

gaggaattta atcactgggg tggagaagat gtggaatttg gatatcgctt attccgttac   1140

ggtagtttct ttaaaactat tgatggcatt atggcctacc atcaagagcc accaggtaaa   1200
```

-continued

```
gaaaatgaaa ccgatcgtga agcgggaaaa aatattacgc tcgatattat gagagaaaag   1260
gtcccttata tctatagaaa acttttacca atagaagatt cgcatatcaa tagagtacct   1320
ttagtttcaa tttatatccc agcttataac tgtgcaaact atattcaacg ttgcgtagat   1380
agtgcactga atcagactgt tgttgatctc gaggtttgta tttgtaacga tggttcaaca   1440
gataatacct tagaagtgat caataagctt tatggtaata atcctagggt acgcatcatg   1500
tctaaaccaa atggcggaat agcctcagca tcaaatgcag ccgtttcttt tgctaaaggt   1560
tattacattg ggcagttaga ttcagatgat tatcttgagc ctgatgcagt tgaactgtgt   1620
ttaaaagaat tttaaaaaga taaaacgcta gcttgtgttt ataccactaa tagaaacgtc   1680
aatccggatg gtagcttaat cgctaatggt tacaattggc cagaattttc acgagaaaaa   1740
ctcacaacgg ctatgattgc tcaccacttt agaatgttca cgattagagc ttggcattta   1800
actgatggat tcaatgaaaa aattgaaaat gccgtagact atgacatgtt cctcaaactc   1860
agtgaagttg gaaaatttaa acatcttaat aaaatctgct ataaccgtgt attacatggt   1920
gataacacat caattaagaa acttggcatt caaaagaaaa accattttgt tgtagtcaat   1980
cagtcattaa atagacaagg cataacttat tataattatg acgaatttga tgatttagat   2040
gaaagtagaa agtatatttt caataaaacc gctgaatatc aagaagagat tgatatctta   2100
aaagatattt aa                                                       2112
```

<210> SEQ ID NO 17
<211> LENGTH: 2112
<212> TYPE: DNA
<213> ORGANISM: Pasteurella multocida

<400> SEQUENCE: 17

```
atgaatacat tatcacaagc aataaaagca tataacagca atgactatca attagcactc     60
aaattatttg aaaagtcggc ggaaatctat ggacggaaaa ttgttgaatt tcaaattacc    120
aaatgcaaag aaaaactctc agcacatcct tctgttaatt cagcacatct ttctgtaaat    180
aaagaagaaa aagtcaatgt ttgcgatagt ccgttagata ttgcaacaca actgttactt    240
tccaacgtaa aaaaattagt actttctgac tcggaaaaaa acacgttaaa aaataaatgg    300
aaattgctca ctgagaagaa atctgaaaat gcggaggtaa gagcggtcgc ccttgtacca    360
aaagattttc ccaaagatct ggttttagcg cctttacctg atcatgttaa tgattttaca    420
tggtacaaaa agcgaaagaa aagacttggc ataaaacctg aacatcaaca tgttggtctt    480
tctattatcg ttacaacatt caatcgacca gcaattttat cgattacatt agcctgttta    540
gtaaaccaaa aaacacatta cccgtttgaa gttatcgtga cagataaagg tagtcaggaa    600
gatctatcac cgatcattcg ccaatatgaa aataaattgg atattcgcta cgtcagacaa    660
aaagataacg gttttcaagc cagtgccgct cggaatatgg gattacgctt agcaaaatat    720
gactttattg gcttactcga ctgtgatatg gcgccaaatc cattatgggt tcattcttat    780
gttgcagagc tattagaaga tgatgattta acaatcattg gtccaagaaa atacatcgat    840
acacaacata ttgacccaaa agacttctta aataacgcga gtttgcttga atcattacca    900
gaagtgaaaa ccaataatag tgttgccgca aaaggggaag gaacagtttc tctggattgg    960
cgcttagaac aattcgaaaa aacagaaaat ctccgcttat ccgattcgcc tttccgtttt   1020
tttgcggcgg gtaatgttgc tttcgctaaa aaatggctaa ataaatccgg tttctttgat   1080
gaggaattta atcactgggg tggagaagat gtggaatttg gatatcgctt attccgttac   1140
```

-continued

```
ggtagtttct ttaaaactat tgatggcatt atggcctacc atcaagagcc accaggtaaa   1200
gaaaatgaaa ccgatcgtga agcgggaaaa aatattacgc tcgatattat gagagaaaag   1260
gtcccttata tctatagaaa acttttacca atagaagatt cgcatatcaa tagagtacct   1320
ttagtttcaa tttatatccc agcttataac tgtgcaaact atattcaacg ttgcgtagat   1380
agtgcactga atcagactgt tgttgatctc gaggtttgta tttgtaacga tggttcaaca   1440
gataatacct tagaagtgat caataagctt tatggtaata atcctagggt acgcatcatg   1500
tctaaaccaa atggcggaat agcctcagca tcaaatgcag ccgtttcttt tgctaaaggt   1560
tattacattg ggcagttaga ttcagatgat tatcttgagc ctgatgcagt tgaactgtgt   1620
ttaaaagaat ttttaaaaga taaaacgcta gcttgtgttt ataccactaa tagaaacgtc   1680
aatccggatg gtagcttaat cgctaatggt tacaattggc cagaattttc acgagaaaaa   1740
ctcacaacgg ctatgattgc tcaccacttt agaatgttca cgattagagc ttggcattta   1800
actgatggat tcaatgaaaa aattgaaaat gccgtagact atgacatgtt cctcaaactc   1860
agtgaagttg gaaaatttaa acatcttaat aaaatctgct ataaccgtgt attacatggt   1920
gataacacat caattaagaa acttggcatt caaaagaaaa accattttgt tgtagtcaat   1980
cagtcattaa atagacaagg cataacttat tataattatg acgaatttga tgatttagat   2040
gaaagtagaa agtatatttt caataaaacc gctgaatatc aagaagagat tgatatctta   2100
aaagatattt aa                                                       2112
```

<210> SEQ ID NO 18
<211> LENGTH: 2112
<212> TYPE: DNA
<213> ORGANISM: Pasteurella multocida

<400> SEQUENCE: 18

```
atgaatacat tatcacaagc aataaaagca tataacagca atgactatca attagcactc     60
aaattatttg aaaagtcggc ggaaatctat ggacggaaaa ttgttgaatt tcaaattacc    120
aaatgcaaag aaaaactctc agcacatcct tctgttaatt cagcacatct ttctgtaaat    180
aaagaagaaa aagtcaatgt ttgcgatagt ccgttagata ttgcaacaca actgttactt    240
tccaacgtaa aaaaattagt actttctgac tcggaaaaaa acacgttaaa aaataaatgg    300
aaattgctca ctgagaagaa atctgaaaat gcggaggtaa gagcggtcgc ccttgtacca    360
aaagatttc ccaaagatct ggttttagcg cctttacctg atcatgttaa tgattttaca    420
tggtacaaaa agcgaaagaa aagacttggc ataaaacctg aacatcaaca tgttggtctt    480
tctattatcg ttacaacatt caatcgacca gcaattttat cgattacatt agcctgttta    540
gtaaaccaaa aaacacatta cccgtttgaa gttatcgtga cagatgatgg tagtcaggaa    600
gatctatcac cgatcattcg ccaatatgaa aataaattgg atattcgcta cgtcagacaa    660
aaagataacg gttttcaagc cagtgccgct cggaatatgg gattacgctt agcaaaatat    720
gactttattg gcttactcga ctgtgatatg gcgccaaatc cattatgggt tcattcttat    780
gttgcagagc tattagaaga tgatgattta acaatcattg gtccaagaaa atacatcgat    840
acacaacata ttgacccaaa agacttctta aataacgcga gtttgcttga atcattacca    900
gaagtgaaaa ccaataatag tgttgccgca aaaggggaag gaacagtttc tctggattgg    960
cgcttagaac aattcgaaaa aacagaaaat ctccgcttat ccgattcgcc tttccgtttt   1020
tttgcggcgg gtaatgttgc tttcgctaaa aaatggctaa ataaatccgg tttctttgat   1080
gaggaattta atcactgggg tggagaagat gtggaatttg gatatcgctt attccgttac   1140
```

```
ggtagtttct ttaaaactat tgatggcatt atggcctacc atcaagagcc accaggtaaa   1200
gaaaatgaaa ccgatcgtga agcgggaaaa aatattacgc tcgatattat gagagaaaag   1260
gtcccttata tctatagaaa acttttacca atagaagatt cgcatatcaa tagagtacct   1320
ttagtttcaa tttatatccc agcttataac tgtgcaaact atattcaacg ttgcgtagat   1380
agtgcactga atcagactgt tgttgatctc gaggtttgta tttgtaacga aggttcaaca   1440
gataatacct tagaagtgat caataagctt tatggtaata atcctagggt acgcatcatg   1500
tctaaaccaa atggcggaat agcctcagca tcaaatgcag ccgtttcttt tgctaaaggt   1560
tattacattg ggcagttaga ttcagatgat tatcttgagc ctgatgcagt tgaactgtgt   1620
ttaaaagaat ttttaaaaga taaaacgcta gcttgtgttt ataccactaa tagaaacgtc   1680
aatccggatg gtagcttaat cgctaatggt tacaattggc cagaattttc acgagaaaaa   1740
ctcacaacgg ctatgattgc tcaccacttt agaatgttca cgattagagc ttggcattta   1800
actgatggat tcaatgaaaa aattgaaaat gccgtagact atgacatgtt cctcaaactc   1860
agtgaagttg gaaaatttaa acatcttaat aaaatctgct ataaccgtgt attacatggt   1920
gataacacat caattaagaa acttggcatt caaaagaaaa accattttgt tgtagtcaat   1980
cagtcattaa atagacaagg cataacttat tataattatg acgaatttga tgatttagat   2040
gaaagtagaa agtatatttt caataaaacc gctgaatatc aagaagagat tgatatctta   2100
aaagatattt aa                                                        2112
```

<210> SEQ ID NO 19
<211> LENGTH: 2112
<212> TYPE: DNA
<213> ORGANISM: Pasteurella multocida

<400> SEQUENCE: 19

```
atgaatacat tatcacaagc aataaaagca tataacagca atgactatca attagcactc     60
aaattatttg aaaagtcggc ggaaatctat ggacggaaaa ttgttgaatt tcaaattacc    120
aaatgcaaag aaaaactctc agcacatcct tctgttaatt cagcacatct ttctgtaaat    180
aaagaagaaa aagtcaatgt ttgcgatagt ccgttagata ttgcaacaca actgttactt    240
tccaacgtaa aaaaattagt actttctgac tcggaaaaaa acacgttaaa aaataaatgg    300
aaattgctca ctgagaagaa atctgaaaat gcggaggtaa gagcggtcgc ccttgtacca    360
aaagattttc ccaaagatct ggttttagcg cctttacctg atcatgttaa tgattttaca    420
tggtacaaaa agcgaaagaa aagacttggc ataaaacctg aacatcaaca tgttggtctt    480
tctattatcg ttacaacatt caatcgacca gcaattttat cgattacatt agcctgttta    540
gtaaaccaaa aaacacatta cccgtttgaa gttatcgtga cagatgatgg tagtcaggaa    600
gatctatcac cgatcattcg ccaatatgaa aataaattgg atattcgcta cgtcagacaa    660
aaagataacg gttttcaagc cagtgccgct cggaatatgg gattacgctt agcaaaatat    720
gactttattg gcttactcga ctgtgatatg gcgccaaatc cattatgggt tcattcttat    780
gttgcagagc tattagaaga tgatgattta acaatcattg gtccaagaaa atacatcgat    840
acacaacata ttgacccaaa agacttctta aataacgcga gtttgcttga atcattacca    900
gaagtgaaaa ccaataatag tgttgccgca aaaggggaag gaacagtttc tctggattgg    960
cgcttagaac aattcgaaaa aacagaaaat ctccgcttat ccgattcgcc tttccgtttt   1020
tttgcggcgg gtaatgttgc tttcgctaaa aaatggctaa ataaatccgg tttctttgat   1080
```

-continued

```
gaggaattta atcactgggg tggagaagat gtggaatttg gatatcgctt attccgttac   1140
ggtagtttct ttaaaactat tgatggcatt atggcctacc atcaagagcc accaggtaaa   1200
gaaaatgaaa ccgatcgtga agcgggaaaa aatattacgc tcgatattat gagagaaaag   1260
gtcccttata tctatagaaa acttttacca atagaagatt cgcatatcaa tagagtacct   1320
ttagtttcaa tttatatccc agcttataac tgtgcaaact atattcaacg ttgcgtagat   1380
agtgcactga atcagactgt tgttgatctc gaggtttgta tttgtaacaa aggttcaaca   1440
gataatacct tagaagtgat caataagctt tatggtaata atcctagggt acgcatcatg   1500
tctaaaccaa atggcggaat agcctcagca tcaaatgcag ccgtttcttt tgctaaaggt   1560
tattacattg ggcagttaga ttcagatgat tatcttgagc ctgatgcagt tgaactgtgt   1620
ttaaaagaat ttttaaaaga taaaacgcta gcttgtgttt ataccactaa tagaaacgtc   1680
aatccggatg gtagcttaat cgctaatggt tacaattggc cagaattttc acgagaaaaa   1740
ctcacaacgg ctatgattgc tcaccacttt agaatgttca cgattagagc ttggcattta   1800
actgatggat tcaatgaaaa aattgaaaat gccgtagact atgacatgtt cctcaaactc   1860
agtgaagttg gaaaatttaa acatcttaat aaaatctgct ataaccgtgt attacatggt   1920
gataacacat caattaagaa acttggcatt caaaagaaaa accattttgt tgtagtcaat   1980
cagtcattaa atagacaagg cataacttat tataattatg acgaatttga tgatttagat   2040
gaaagtagaa agtatatttt caataaaacc gctgaatatc aagaagagat tgatatctta   2100
aaagatattt aa                                                       2112
```

<210> SEQ ID NO 20
<211> LENGTH: 2271
<212> TYPE: DNA
<213> ORGANISM: Pasteurella multocida

<400> SEQUENCE: 20

```
atgaatacat tatcacaagc aataaaagca tataacagca atgactatca attagcactc     60
aaattatttg aaaagtcggc ggaaatctat ggacggaaaa ttgttgaatt tcaaattacc    120
aaatgcaaag aaaaactctc agcacatcct tctgttaatt cagcacatct ttctgtaaat    180
aaagaagaaa aagtcaatgt ttgcgatagt ccgttagata ttgcaacaca actgttactt    240
tccaacgtaa aaaaattagt actttctgac tcggaaaaaa acacgttaaa aaataaatgg    300
aaattgctca ctgagaagaa atctgaaaat gcggaggtaa gagcggtcgc ccttgtacca    360
aaagattttc ccaaagatct ggttttagcg cctttacctg atcatgttaa tgattttaca    420
tggtacaaaa agcgaaagaa aagacttggc ataaaacctg aacatcaaca tgttggtctt    480
tctattatcg ttacaacatt caatcgacca gcaattttat cgattacatt agcctgttta    540
gtaaaccaaa aaacacatta cccgtttgaa gttatcgtga cagatgatgg tagtcaggaa    600
gatctatcac cgatcattcg ccaatatgaa aataaattgg atattcgcta cgtcagacaa    660
aaagataacg gttttcaagc cagtgccgct cggaatatgg gattacgctt agcaaaatat    720
gactttattg gcttactcga ctgtgatatg gcgccaaatc cattatgggt tcattcttat    780
gttgcagagc tattagaaga tgatgattta acaatcattg gtccaagaaa atacatcgat    840
acacaacata ttgacccaaa agacttctta aataacgcga gtttgcttga atcattacca    900
gaagtgaaaa ccaataatag tgttgccgca aaaggggaag gaacagtttc tctggattgg    960
cgcttagaac aattcgaaaa aacagaaaat ctccgcttat ccgattcgcc tttccgtttt   1020
tttgcggcgg gtaatgttgc tttcgctaaa aaatggctaa ataaatccgg tttctttgat   1080
```

-continued gaggaattta atcactgggg tggagaagat gtggaatttg gatatcgctt attccgttac 1140
ggtagtttct ttaaaactat tgatggcatt atggcctacc atcaagagcc accaggtaaa 1200
gaaaatgaaa ccgatcgtga agcgggaaaa aatattacgc tcgatattat gagagaaaag 1260
gtcccttata tctatagaaa acttttacca atagaagatt cgcatatcaa tagagtacct 1320
ttagtttcaa tttatatccc agcttataac tgtgcaaact atattcaacg ttgcgtagat 1380
agtgcactga atcagactgt tgttgatctc gaggtttgta tttgtaacga tggttcaaca 1440
gataatacct tagaagtgat caataagctt tatggtaata atcctagggt acgcatcatg 1500
tctaaaccaa atggcggaat agcctcagca tcaaatgcag ccgtttcttt tgctaaaggt 1560
tattacattg ggcagttaga ttcagatgat tatcttgagc ctgatgcagt tgaactgtgt 1620
ttaaaagaat ttttaaaaga taaaacgcta gcttgtgttt ataccactaa tagaaacgtc 1680
aatccggatg gtagcttaat cgctaatggt tacaattggc cagaattttc acgagaaaaa 1740
ctcacaacgg ctatgattgc tcaccacttt agaatgttca cgattagagc ttggcattta 1800
actgatggat tcaatgaaaa aattgaaaat gccgtagact atgacatgtt cctcaaactc 1860
agtgaagttg gaaaatttaa acatcttaat aaaatctgct ataaccgtgt attacatggt 1920
gataacacat caattaagaa acttggcatt caaaagaaaa accattttgt tgtagtcaat 1980
cagtcattaa atagacaagg cataacttat tataattatg acgaatttga tgatttagat 2040
gaaagtagaa agtatatttt caataaaacc gctgaatatc aagaagagat tgatatctta 2100
aaagatatta aaatcatcca gaataaagat gccaaaatcg cagtcagtat tttttatccc 2160
aatacattaa acggcttagt gaaaaaacta aacaatatta ttgaatataa taaaaatata 2220
ttcgttattg ttctacatgt tgataagaat catcttacac cagatatcta a 2271

<210> SEQ ID NO 21
<211> LENGTH: 1704
<212> TYPE: DNA
<213> ORGANISM: Pasteurella multocida

<400> SEQUENCE: 21
atgaatacat tatcacaagc aataaaagca tataacagca atgactatca attagcactc 60
aaattatttg aaaagtcggc ggaaatctat ggacggaaaa ttgttgaatt tcaaattacc 120
aaatgcaaag aaaaactctc agcacatcct tctgttaatt cagcacatct ttctgtaaat 180
aaagaagaaa aagtcaatgt ttgcgatagt ccgttagata ttgcaacaca actgttactt 240
tccaacgtaa aaaaattagt actttctgac tcggaaaaaa acacgttaaa aaataaatgg 300
aaattgctca ctgagaagaa atctgaaaat gcggaggtaa gagcggtcgc ccttgtacca 360
aaagattttc ccaaagatct ggttttagcg cctttacctg atcatgttaa tgattttaca 420
tggtacaaaa agcgaaagaa aagacttggc ataaaacctg aacatcaaca tgttggtctt 480
tctattatcg ttacaacatt caatcgacca gcaattttat cgattacatt agcctgttta 540
gtaaaccaaa aaacacatta cccgtttgaa gttatcgtga cagatgatgg tagtcaggaa 600
gatctatcac cgatcattcg ccaatatgaa aataaattgg atattcgcta cgtcagacaa 660
aaagataacg gttttcaagc cagtgccgct cggaatatgg gattacgctt agcaaaatat 720
gactttattg gcttactcga ctgtgatatg gcgccaaatc cattatgggt tcattcttat 780
gttgcagagc tattagaaga tgatgattta acaatcattg gtccaagaaa atacatcgat 840
acacaacata ttgacccaaa agacttctta aataacgcga gtttgcttga atcattacca 900

-continued

```
gaagtgaaaa ccaataatag tgttgccgca aaaggggaag gaacagtttc tctggattgg    960

cgcttagaac aattcgaaaa aacagaaaat ctccgcttat ccgattcgcc tttccgtttt   1020

tttgcggcgg gtaatgttgc tttcgctaaa aaatggctaa ataaatccgg tttctttgat   1080

gaggaattta atcactgggg tggagaagat gtggaatttg gatatcgctt attccgttac   1140

ggtagtttct ttaaaactat tgatggcatt atggcctacc atcaagagcc accaggtaaa   1200

gaaaatgaaa ccgatcgtga agcgggaaaa aatattacgc tcgatattat gagagaaaag   1260

gtcccttata tctatagaaa acttttacca atagaagatt cgcatatcaa tagagtacct   1320

ttagtttcaa tttatatccc agcttataac tgtgcaaact atattcaacg ttgcgtagat   1380

agtgcactga atcagactgt tgttgatctc gaggtttgta tttgtaacga tggttcaaca   1440

gataatacct tagaagtgat caataagctt tatggtaata atcctagggt acgcatcatg   1500

tctaaaccaa atggcggaat agcctcagca tcaaatgcag ccgtttcttt tgctaaaggt   1560

tattacattg ggcagttaga ttcagatgat tatcttgagc ctgatgcagt tgaactgtgt   1620

ttaaaagaat ttttaaaaga taaaacgcta gcttgtgttt ataccactaa tagaaacgtc   1680

aatccggatg gtagcttaat ctaa                                          1704
```

<210> SEQ ID NO 22
<211> LENGTH: 18
<212> TYPE: PRT
<213> ORGANISM: artificial sequence
<220> FEATURE:
<223> OTHER INFORMATION: synthetic peptide based on residues 526-543 of pmHAS

<400> SEQUENCE: 22

```
Leu Asp Ser Asp Asp Tyr Leu Glu Pro Asp Ala Val Glu Leu Cys Leu
1               5                   10                  15

Lys Glu
```

<210> SEQ ID NO 23
<211> LENGTH: 24
<212> TYPE: DNA
<213> ORGANISM: Artificial sequence
<220> FEATURE:
<223> OTHER INFORMATION: primer Pm10

<400> SEQUENCE: 23

```
cactgtctaa ctttattgtt agcc                                            24
```

<210> SEQ ID NO 24
<211> LENGTH: 20
<212> TYPE: DNA
<213> ORGANISM: Artificial Sequence
<220> FEATURE:
<223> OTHER INFORMATION: primer Pm21

<400> SEQUENCE: 24

```
tttttaacga ataggctgtc                                                 20
```

<210> SEQ ID NO 25
<211> LENGTH: 19
<212> TYPE: PRT
<213> ORGANISM: artificial sequence
<220> FEATURE:
<223> OTHER INFORMATION: synthetic peptide based on residues 526 to 544 of pmHAS protein

<400> SEQUENCE: 25

-continued

Leu Asp Ser Asp Asp Tyr Leu Glu Pro Asp Ala Val Glu Leu Cys Leu
1 5 10 15

Lys Glu Phe

<210> SEQ ID NO 26
<211> LENGTH: 2115
<212> TYPE: DNA
<213> ORGANISM: Pasteurella multocida

<400> SEQUENCE: 26
atgaatacat tatcacaagc aataaaagca tataacagca atgactatga attagcactc 60
aaattatttg agaagtctgc tgaaacctac gggcgaaaaa tcgttgaatt ccaaattatc 120
aaatgtaaag aaaaactctc gaccaattct tatgtaagtg aagataaaaa aaacagtgtt 180
tgcgatagct cattagatat cgcaacacag ctcttacttt ccaacgtaaa aaaattaact 240
ctatccgaat cagaaaaaaa cagtttaaaa aataaatgga aatctatcac tgggaaaaaa 300
tcggagaacg cagaaatcag aaaggtggaa ctagtaccca aagattttcc taaagatctt 360
gttcttgctc cattgccaga tcatgttaat gattttacat ggtacaaaaa tcgaaaaaaa 420
agcttaggta taaagcctgt aaataagaat atcggtcttt ctattattat tcctacattt 480
aatcgtagcc gtattttaga tataacgtta gcctgtttgg tcaatcagaa aacaaactac 540
ccatttgaag tcgttgttgc agatgatggt agtaaggaaa acttacttac cattgtgcaa 600
aaatacgaac aaaaacttga cataaagtat gtaagacaaa aagattatgg atatcaattg 660
tgtgcagtca gaaacttagg tttacgtaca gcaaagtatg attttgtctc gattctagac 720
tgcgatatgg caccacaaca attatgggtt cattcttatc ttacagaact attagaagac 780
aatgatattg ttttaattgg acctagaaaa tatgtggata ctcataatat taccgcagaa 840
caattcctta acgatccata tttaatagaa tcactacctg aaaccgctac aaataacaat 900
ccttcgatta catcaaaagg aaatatatcg ttggattgga gattagaaca tttcaaaaaa 960
accgataatc tacgtctatg tgattctccg tttcgttatt ttagttgcgg taatgttgca 1020
ttttctaaag aatggctaaa taaagtaggt tggttcgatg aagaatttaa tcattggggg 1080
ggcgaagatg tagaatttgg ttacagatta tttgccaaag gctgtttttt cagagtaatt 1140
gacggcggaa tggcatacca tcaagaacca cctggtaaag aaaatgaaac agaccgcgaa 1200
gctggtaaaa gtattacgct taaaattgtg aaagaaaagg taccttacat ctatagaaag 1260
cttttaccaa tagaagattc acatattcat agaatacctt tagtttctat ttatatcccc 1320
gcttataact gtgcaaatta tattcaaaga tgtgtagata gtgctcttaa tcaaactgtt 1380
gtcgatctcg aggtttgtat ttgtaacgat ggttcaacag ataatacctt agaagtgatc 1440
aataagcttt atggtaataa tcctagggta cgcatcatgt ctaaaccaaa tggcggaata 1500
gcctcagcat caaatgcagc cgtttctttt gctaaaggtt attacattgg gcagttagat 1560
tcagatgatt atcttgagcc tgatgcagtt gaactgtgtt taaaagaatt tttaaaagat 1620
aaaacgctag cttgtgttta taccactaat agaaacgtca atccggatgg tagcttaatc 1680
gctaatggtt acaattggcc agaattttca cgagaaaaac tcacaacggc tatgattgct 1740
caccatttta gaatgtttac gattagagct tggcatttaa cggatggatt taacgaaaat 1800
attgaaaacg ccgtggatta tgacatgttc cttaaactca gtgaagttgg aaaatttaaa 1860
catcttaata aaatctgcta taaccgcgta ttacatggtg ataacacatc cattaagaaa 1920
ctcggcattc aaaagaaaaa ccattttgtt gtagtcaatc agtcattaaa tagacaaggc 1980

-continued atcaattatt ataattatga caaatttgat gatttagatg aaagtagaaa gtatatcttc 2040
aataaaaccg ctgaatatca agaagaaatg gatattttaa aagatcttaa actcattcaa 2100
aataaagatg cctaa 2115

<210> SEQ ID NO 27
<211> LENGTH: 1980
<212> TYPE: DNA
<213> ORGANISM: Pasteurella multocida

<400> SEQUENCE: 27
atgctctcag cacatccttc tgttaattca gcacatcttt ctgtaaataa agaagaaaaa 60
gtcaatgttt gcgatagtcc gttagatatt gcaacacaac tgttactttc caacgtaaaa 120
aaattagtac tttctgactc ggaaaaaaac acgttaaaaa ataaatggaa attgctcact 180
gagaagaaat ctgaaaatgc ggaggtaaga gcggtcgccc ttgtaccaaa agattttccc 240
aaagatctgg ttttagcgcc tttacctgat catgttaatg attttacatg gtacaaaaag 300
cgaaagaaaa gacttggcat aaaacctgaa catcaacatg ttggtctttc tattatcgtt 360
acaacattca atcgaccagc aattttatcg attacattag cctgtttagt aaaccaaaaa 420
acacattacc cgtttgaagt tatcgtgaca gatgatggta gtcaggaaga tctatcaccg 480
atcattcgcc aatatgaaaa taaattggat attcgctacg tcagacaaaa agataacggt 540
tttcaagcca gtgccgctcg gaatatggga ttacgcttag caaaatatga ctttattggc 600
ttactcgact gtgatatggc gccaaatcca ttatgggttc attcttatgt tgcagagcta 660
ttagaagatg atgatttaac aatcattggt ccaagaaaat acatcgatac acaacatatt 720
gacccaaaag acttcttaaa taacgcgagt ttgcttgaat cattaccaga agtgaaaacc 780
aataatagtg ttgccgcaaa aggggaagga acagtttctc tggattggcg cttagaacaa 840
ttcgaaaaaa cagaaaatct ccgcttatcc gattcgcctt tccgtttttt tgcggcgggt 900
aatgttgctt tcgctaaaaa atggctaaat aaatccggtt tctttgatga ggaatttaat 960
cactggggtg gagaagatgt ggaatttgga tatcgcttat tccgttacgg tagtttcttt 1020
aaaactattg atggcattat ggcctaccat caagagccac caggtaaaga aaatgaaacc 1080
gatcgtgaag cgggaaaaaa tattacgctc gatattatga gagaaaaggt cccttatatc 1140
tatagaaaac ttttaccaat agaagattcg catatcaata gagtaccttt agtttcaatt 1200
tatatcccag cttataactg tgcaaactat attcaacgtt gcgtagatag tgcactgaat 1260
cagactgttg ttgatctcga ggtttgtatt tgtaacgatg gttcaacaga taatacctta 1320
gaagtgatca ataagcttta tggtaataat cctagggtac gcatcatgtc taaaccaaat 1380
ggcggaatag cctcagcatc aaatgcagcc gtttcttttg ctaaaggtta ttacattggg 1440
cagttagatt cagatgatta tcttgagcct gatgcagttg aactgtgttt aaaagaattt 1500
ttaaaagata aaacgctagc ttgtgtttat accactaata gaaacgtcaa tccggatggt 1560
agcttaatcg ctaatggtta caattggcca gaattttcac gagaaaaact cacaacggct 1620
atgattgctc accactttag aatgttcacg attagagctt ggcatttaac tgatggattc 1680
aatgaaaaaa ttgaaaatgc cgtagactat gacatgttcc tcaaactcag tgaagttgga 1740
aaatttaaac atcttaataa aatctgctat aaccgtgtat tacatggtga taacacatca 1800
attaagaaac ttggcattca aaagaaaaac cattttgttg tagtcaatca gtcattaaat 1860
agacaaggca taacttatta taattatgac gaatttgatg atttagatga aagtagaaag 1920
tatattttca ataaaaccgc tgaatatcaa gaagagattg atatcttaaa agatatttaa 1980

-continued

<210> SEQ ID NO 28
<211> LENGTH: 1902
<212> TYPE: DNA
<213> ORGANISM: Pasteurella multocida

<400> SEQUENCE: 28
atgttagata ttgcaacaca actgttactt tccaacgtaa aaaaattagt actttctgac 60
tcggaaaaaa acacgttaaa aaataaatgg aaattgctca ctgagaagaa atctgaaaat 120
gcggaggtaa gagcggtcgc ccttgtacca aaagattttc ccaaagatct ggttttagcg 180
cctttacctg atcatgttaa tgattttaca tggtacaaaa agcgaaagaa aagacttggc 240
ataaaacctg aacatcaaca tgttggtctt tctattatcg ttacaacatt caatcgacca 300
gcaattttat cgattacatt agcctgttta gtaaaccaaa aaacacatta cccgtttgaa 360
gttatcgtga cagatgatgg tagtcaggaa gatctatcac cgatcattcg ccaatatgaa 420
aataaattgg atattcgcta cgtcagacaa aaagataacg gttttcaagc cagtgccgct 480
cggaatatgg gattacgctt agcaaaatat gactttattg gcttactcga ctgtgatatg 540
gcgccaaatc cattatgggt tcattcttat gttgcagagc tattagaaga tgatgattta 600
acaatcattg gtccaagaaa atacatcgat acacaacata ttgacccaaa agacttctta 660
aataacgcga gtttgcttga atcattacca gaagtgaaaa ccaataatag tgttgccgca 720
aaaggggaag gaacagtttc tctggattgg cgcttagaac aattcgaaaa aacagaaaat 780
ctccgcttat ccgattcgcc tttccgtttt tttgcggcgg gtaatgttgc tttcgctaaa 840
aaatggctaa ataaatccgg tttctttgat gaggaattta atcactgggg tggagaagat 900
gtggaatttg gatatcgctt attccgttac ggtagtttct ttaaaactat tgatggcatt 960
atggcctacc atcaagagcc accaggtaaa gaaaatgaaa ccgatcgtga agcgggaaaa 1020
aatattacgc tcgatattat gagagaaaag gtcccttata tctatagaaa acttttacca 1080
atagaagatt cgcatatcaa tagagtacct ttagtttcaa tttatatccc agcttataac 1140
tgtgcaaact atattcaacg ttgcgtagat agtgcactga atcagactgt tgttgatctc 1200
gaggtttgta tttgtaacga tggttcaaca gataatacct tagaagtgat caataagctt 1260
tatggtaata atcctagggt acgcatcatg tctaaaccaa atggcggaat agcctcagca 1320
tcaaatgcag ccgtttcttt tgctaaaggt tattacattg ggcagttaga ttcagatgat 1380
tatcttgagc ctgatgcagt tgaactgtgt ttaaaagaat ttttaaaaga taaaacgcta 1440
gcttgtgttt ataccactaa tagaaacgtc aatccggatg gtagcttaat cgctaatggt 1500
tacaattggc cagaattttc acgagaaaaa ctcacaacgg ctatgattgc tcaccacttt 1560
agaatgttca cgattagagc ttggcattta actgatggat tcaatgaaaa aattgaaaat 1620
gccgtagact atgacatgtt cctcaaactc agtgaagttg gaaaatttaa acatcttaat 1680
aaaatctgct ataaccgtgt attacatggt gataacacat caattaagaa acttggcatt 1740
caaaagaaaa accattttgt tgtagtcaat cagtcattaa atagacaagg cataacttat 1800
tataattatg acgaatttga tgatttagat gaaagtagaa agtatatttt caataaaacc 1860
gctgaatatc aagaagagat tgatatctta aaagatattt aa 1902

<210> SEQ ID NO 29
<211> LENGTH: 1830
<212> TYPE: DNA
<213> ORGANISM: Pasteurella multocida -continued
<400> SEQUENCE: 29
atgttaaaaa ataaatggaa attgctcact gagaagaaat ctgaaaatgc ggaggtaaga 60
gcggtcgccc ttgtaccaaa agattttccc aaagatctgg ttttagcgcc tttacctgat 120
catgttaatg attttacatg gtacaaaaag cgaaagaaaa gacttggcat aaaacctgaa 180
catcaacatg ttggtctttc tattatcgtt acaacattca atcgaccagc aattttatcg 240
attacattag cctgtttagt aaaccaaaaa acacattacc cgtttgaagt tatcgtgaca 300
gatgatggta gtcaggaaga tctatcaccg atcattcgcc aatatgaaaa taaattggat 360
attcgctacg tcagacaaaa agataacggt tttcaagcca gtgccgctcg gaatatggga 420
ttacgcttag caaaatatga ctttattggc ttactcgact gtgatatggc gccaaatcca 480
ttatgggttc attcttatgt tgcagagcta ttagaagatg atgatttaac aatcattggt 540
ccaagaaaat acatcgatac acaacatatt gacccaaaag acttcttaaa taacgcgagt 600
ttgcttgaat cattaccaga agtgaaaacc aataatagtg ttgccgcaaa aggggaagga 660
acagtttctc tggattggcg cttagaacaa ttcgaaaaaa cagaaaatct ccgcttatcc 720
gattcgcctt tccgtttttt tgcggcgggt aatgttgctt tcgctaaaaa atggctaaat 780
aaatccggtt tctttgatga ggaatttaat cactggggtg gagaagatgt ggaatttgga 840
tatcgcttat tccgttacgg tagtttcttt aaaactattg atggcattat ggcctaccat 900
caagagccac caggtaaaga aaatgaaacc gatcgtgaag cgggaaaaaa tattacgctc 960
gatattatga gagaaaaggt cccttatatc tatagaaaac ttttaccaat agaagattcg 1020
catatcaata gagtaccttt agtttcaatt tatatcccag cttataactg tgcaaactat 1080
attcaacgtt gcgtagatag tgcactgaat cagactgttg ttgatctcga ggtttgtatt 1140
tgtaacgatg gttcaacaga taatacctta gaagtgatca ataagcttta tggtaataat 1200
cctagggtac gcatcatgtc taaaccaaat ggcggaatag cctcagcatc aaatgcagcc 1260
gtttcttttg ctaaaggtta ttacattggg cagttagatt cagatgatta tcttgagcct 1320
gatgcagttg aactgtgttt aaaagaattt ttaaaagata aaacgctagc ttgtgtttat 1380
accactaata gaaacgtcaa tccggatggt agcttaatcg ctaatggtta caattggcca 1440
gaattttcac gagaaaaact cacaacggct atgattgctc accactttag aatgttcacg 1500
attagagctt ggcatttaac tgatggattc aatgaaaaaa ttgaaaatgc cgtagactat 1560
gacatgttcc tcaaactcag tgaagttgga aaatttaaac atcttaataa aatctgctat 1620
aaccgtgtat tacatggtga taacacatca attaagaaac ttggcattca aaagaaaaac 1680
cattttgttg tagtcaatca gtcattaaat agacaaggca taacttatta taattatgac 1740
gaatttgatg atttagatga aagtagaaag tatattttca ataaaaccgc tgaatatcaa 1800
gaagagattg atatcttaaa agatatttaa 1830

<210> SEQ ID NO 30
<211> LENGTH: 1764
<212> TYPE: DNA
<213> ORGANISM: Pasteurella multocida
<400> SEQUENCE: 30
atgcttgtac caaaagattt tcccaaagat ctggttttag cgcctttacc tgatcatgtt 60
aatgatttta catggtacaa aaagcgaaag aaaagacttg gcataaaacc tgaacatcaa 120
catgttggtc tttctattat cgttacaaca ttcaatcgac cagcaatttt atcgattaca 180
ttagcctgtt tagtaaacca aaaaacacat tacccgtttg aagttatcgt gacagatgat 240

-continued

```
ggtagtcagg aagatctatc accgatcatt cgccaatatg aaaataaatt ggatattcgc    300

tacgtcagac aaaaagataa cggttttcaa gccagtgccg ctcggaatat gggattacgc    360

ttagcaaaat atgactttat tggcttactc gactgtgata tggcgccaaa tccattatgg    420

gttcattctt atgttgcaga gctattagaa gatgatgatt taacaatcat tggtccaaga    480

aaatacatcg atacacaaca tattgaccca aaagacttct taaataacgc gagtttgctt    540

gaatcattac cagaagtgaa aaccaataat agtgttgccg caaaagggga aggaacagtt    600

tctctggatt ggcgcttaga acaattcgaa aaaacagaaa atctccgctt atccgattcg    660

cctttccgtt tttttgcggc gggtaatgtt gctttcgcta aaaaatggct aaataaatcc    720

ggtttctttg atgaggaatt taatcactgg ggtggagaag atgtggaatt tggatatcgc    780

ttattccgtt acggtagttt ctttaaaact attgatggca ttatggccta ccatcaagag    840

ccaccaggta aagaaaatga aaccgatcgt gaagcgggaa aaaatattac gctcgatatt    900

atgagagaaa aggtccctta tatctataga aaacttttac caatagaaga ttcgcatatc    960

aatagagtac ctttagtttc aatttatatc ccagcttata actgtgcaaa ctatattcaa   1020

cgttgcgtag atagtgcact gaatcagact gttgttgatc tcgaggtttg tatttgtaac   1080

gatggttcaa cagataatac cttagaagtg atcaataagc tttatggtaa taatcctagg   1140

gtacgcatca tgtctaaacc aaatggcgga atagcctcag catcaaatgc agccgtttct   1200

tttgctaaag gttattacat tgggcagtta gattcagatg attatcttga gcctgatgca   1260

gttgaactgt gtttaaaaga atttttaaaa gataaaacgc tagcttgtgt ttataccact   1320

aatagaaacg tcaatccgga tggtagctta atcgctaatg gttacaattg gccagaattt   1380

tcacgagaaa aactcacaac ggctatgatt gctcaccact ttagaatgtt cacgattaga   1440

gcttggcatt taactgatgg attcaatgaa aaaattgaaa atgccgtaga ctatgacatg   1500

ttcctcaaac tcagtgaagt tggaaaattt aaacatctta ataaaatctg ctataaccgt   1560

gtattacatg gtgataacac atcaattaag aaacttggca ttcaaaagaa aaaccatttt   1620

gttgtagtca atcagtcatt aaatagacaa ggcataactt attataatta tgacgaattt   1680

gatgatttag atgaaagtag aaagtatatt ttcaataaaa ccgctgaata tcaagaagag   1740

attgatatct taaaagatat ttaa                                          1764
```

<210> SEQ ID NO 31
<211> LENGTH: 2007
<212> TYPE: DNA
<213> ORGANISM: Pasteurella multocida

<400> SEQUENCE: 31

```
atgaatacat tatcacaagc aataaaagca tataacagca atgactatca attagcactc     60

aaattatttg aaaagtcggc ggaaatctat ggacggaaaa ttgttgaatt tcaaattacc    120

aaatgcaaag aaaaactctc agcacatcct tctgttaatt cagcacatct ttctgtaaat    180

aaagaagaaa aagtcaatgt ttgcgatagt ccgttagata ttgcaacaca actgttactt    240

tccaacgtaa aaaaattagt actttctgac tcggaaaaaa acacgttaaa aaataaatgg    300

aaattgctca ctgagaagaa atctgaaaat gcggaggtaa gagcggtcgc ccttgtacca    360

aaagattttc ccaaagatct ggttttagcg cctttacctg atcatgttaa tgattttaca    420

tggtacaaaa agcgaaagaa aagacttggc ataaaacctg aacatcaaca tgttggtctt    480

tctattatcg ttacaacatt caatcgacca gcaattttat cgattacatt agcctgttta    540
```

-continued

```
gtaaaccaaa aaacacatta cccgtttgaa gttatcgtga cagatgatgg tagtcaggaa    600
gatctatcac cgatcattcg ccaatatgaa aataaattgg atattcgcta cgtcagacaa    660
aaagataacg gttttcaagc cagtgccgct cggaatatgg gattacgctt agcaaaatat    720
gactttattg gcttactcga ctgtgatatg gcgccaaatc cattatgggt tcattcttat    780
gttgcagagc tattagaaga tgatgattta acaatcattg gtccaagaaa atacatcgat    840
acacaacata ttgacccaaa agacttctta aataacgcga gtttgcttga atcattacca    900
gaagtgaaaa ccaataatag tgttgccgca aaaggggaag gaacagtttc tctggattgg    960
cgcttagaac aattcgaaaa aacagaaaat ctccgcttat ccgattcgcc tttccgtttt   1020
tttgcggcgg gtaatgttgc tttcgctaaa aaatggctaa ataaatccgg tttctttgat   1080
gaggaattta atcactgggg tggagaagat gtggaatttg gatatcgctt attccgttac   1140
ggtagtttct ttaaaactat tgatggcatt atggcctacc atcaagagcc accaggtaaa   1200
gaaaatgaaa ccgatcgtga agcgggaaaa aatattacgc tcgatattat gagagaaaag   1260
gtcccttata tctatagaaa acttttacca atagaagatt cgcatatcaa tagagtacct   1320
ttagtttcaa tttatatccc agcttataac tgtgcaaact atattcaacg ttgcgtagat   1380
agtgcactga atcagactgt tgttgatctc gaggtttgta tttgtaacga tggttcaaca   1440
gataatacct tagaagtgat caataagctt tatggtaata atcctagggt acgcatcatg   1500
tctaaaccaa atggcggaat agcctcagca tcaaatgcag ccgtttcttt tgctaaaggt   1560
tattacattg ggcagttaga ttcagatgat tatcttgagc ctgatgcagt tgaactgtgt   1620
ttaaaagaat ttttaaaaga taaaacgcta gcttgtgttt ataccactaa tagaaacgtc   1680
aatccggatg gtagcttaat cgctaatggt tacaattggc cagaattttc acgagaaaaa   1740
ctcacaacgg ctatgattgc tcaccacttt agaatgttca cgattagagc ttggcattta   1800
actgatggat tcaatgaaaa aattgaaaat gccgtagact atgacatgtt cctcaaactc   1860
agtgaagttg gaaaatttaa acatcttaat aaaatctgct ataaccgtgt attacatggt   1920
gataacacat caattaagaa acttggcatt caaaagaaaa accattttgt tgtagtcaat   1980
cagtcattaa atagacaagg catataa                                       2007
```

<210> SEQ ID NO 32
<211> LENGTH: 2061
<212> TYPE: DNA
<213> ORGANISM: Pasteurella multocida

<400> SEQUENCE: 32

```
atgaatacat tatcacaagc aataaaagca tataacagca atgactatca attagcactc     60
aaattatttg aaaagtcggc ggaaatctat ggacggaaaa ttgttgaatt tcaaattacc    120
aaatgcaaag aaaaactctc agcacatcct tctgttaatt cagcacatct ttctgtaaat    180
aaagaagaaa aagtcaatgt ttgcgatagt ccgttagata ttgcaacaca actgttactt    240
tccaacgtaa aaaaattagt actttctgac tcggaaaaaa acacgttaaa aaataaatgg    300
aaattgctca ctgagaagaa atctgaaaat gcggaggtaa gagcggtcgc ccttgtacca    360
aaagattttc ccaaagatct ggttttagcg cctttacctg atcatgttaa tgattttaca    420
tggtacaaaa agcgaaagaa aagacttggc ataaaacctg aacatcaaca tgttggtctt    480
tctattatcg ttacaacatt caatcgacca gcaattttat cgattacatt agcctgttta    540
gtaaaccaaa aaacacatta cccgtttgaa gttatcgtga cagatgatgg tagtcaggaa    600
gatctatcac cgatcattcg ccaatatgaa aataaattgg atattcgcta cgtcagacaa    660
```

-continued

```
aaagataacg gttttcaagc cagtgccgct cggaatatgg gattacgctt agcaaaatat    720
gactttattg gcttactcga ctgtgatatg gcgccaaatc cattatgggt tcattcttat    780
gttgcagagc tattagaaga tgatgattta acaatcattg gtccaagaaa atacatcgat    840
acacaacata ttgacccaaa agacttctta aataacgcga gtttgcttga atcattacca    900
gaagtgaaaa ccaataatag tgttgccgca aaaggggaag gaacagtttc tctggattgg    960
cgcttagaac aattcgaaaa aacagaaaat ctccgcttat ccgattcgcc tttccgtttt   1020
tttgcggcgg gtaatgttgc tttcgctaaa aaatggctaa ataaatccgg tttctttgat   1080
gaggaattta atcactgggg tggagaagat gtggaatttg gatatcgctt attccgttac   1140
ggtagtttct ttaaaactat tgatggcatt atggcctacc atcaagagcc accaggtaaa   1200
gaaaatgaaa ccgatcgtga agcgggaaaa aatattacgc tcgatattat gagagaaaag   1260
gtcccttata tctatagaaa acttttacca atagaagatt cgcatatcaa tagagtacct   1320
ttagtttcaa tttatatccc agcttataac tgtgcaaact atattcaacg ttgcgtagat   1380
agtgcactga atcagactgt tgttgatctc gaggtttgta tttgtaacga tggttcaaca   1440
gataatacct tagaagtgat caataagctt tatggtaata atcctagggt acgcatcatg   1500
tctaaaccaa atggcggaat agcctcagca tcaaatgcag ccgtttcttt tgctaaaggt   1560
tattacattg ggcagttaga ttcagatgat tatcttgagc ctgatgcagt tgaactgtgt   1620
ttaaaagaat ttttaaaaga taaaacgcta gcttgtgttt ataccactaa tagaaacgtc   1680
aatccggatg gtagcttaat cgctaatggt tacaattggc cagaattttc acgagaaaaa   1740
ctcacaacgg ctatgattgc tcaccacttt agaatgttca cgattagagc ttggcattta   1800
actgatggat tcaatgaaaa aattgaaaat gccgtagact atgacatgtt cctcaaactc   1860
agtgaagttg gaaaatttaa acatcttaat aaaatctgct ataaccgtgt attacatggt   1920
gataacacat caattaagaa acttggcatt caaaagaaaa accattttgt tgtagtcaat   1980
cagtcattaa atagacaagg cataacttat tataattatg acgaatttga tgatttagat   2040
gaaagtagaa agtatattta a                                              2061
```

<210> SEQ ID NO 33
<211> LENGTH: 2112
<212> TYPE: DNA
<213> ORGANISM: Pasteurella multocida

<400> SEQUENCE: 33

```
atgaatacat tatcacaagc aataaaagca tataacagca atgactatca attagcactc     60
aaattatttg aaaagtcggc ggaaatctat ggacggaaaa ttgttgaatt tcaaattacc    120
aaatgcaaag aaaaactctc agcacatcct tctgttaatt cagcacatct ttctgtaaat    180
aaagaagaaa aagtcaatgt ttgcgatagt ccgttagata ttgcaacaca actgttactt    240
tccaacgtaa aaaaattagt actttctgac tcggaaaaaa acacgttaaa aaataaatgg    300
aaattgctca ctgagaagaa atctgaaaat gcggaggtaa gagcggtcgc ccttgtacca    360
aaagattttc ccaaagatct ggttttagcg cctttacctg atcatgttaa tgattttaca    420
tggtacaaaa agcgaaagaa aagacttggc ataaaacctg aacatcaaca tgttggtctt    480
tctattatcg ttacaacatt caatcgacca gcaattttat cgattacatt agcctgttta    540
gtaaaccaaa aaacacatta cccgtttgaa gttatcgtga cagatgatgg tagtcaggaa    600
gatctatcac cgatcattcg ccaatatgaa aataaattgg atattcgcta cgtcagacaa    660
```

-continued

```
aaagataacg gttttcaagc cagtgccgct cggaatatgg gattacgctt agcaaaatat    720

gactttattg gcttactcga atgtgatatg gcgccaaatc cattatgggt tcattcttat    780

gttgcagagc tattagaaga tgatgattta acaatcattg gtccaagaaa atacatcgat    840

acacaacata ttgacccaaa agacttctta aataacgcga gtttgcttga atcattacca    900

gaagtgaaaa ccaataatag tgttgccgca aaaggggaag gaacagtttc tctggattgg    960

cgcttagaac aattcgaaaa aacagaaaat ctccgcttat ccgattcgcc tttccgtttt   1020

tttgcggcgg gtaatgttgc tttcgctaaa aaatggctaa ataaatccgg tttctttgat   1080

gaggaattta atcactgggg tggagaagat gtggaatttg gatatcgctt attccgttac   1140

ggtagtttct ttaaaactat tgatggcatt atggcctacc atcaagagcc accaggtaaa   1200

gaaaatgaaa ccgatcgtga agcgggaaaa aatattacgc tcgatattat gagagaaaag   1260

gtcccttata tctatagaaa acttttacca atagaagatt cgcatatcaa tagagtacct   1320

ttagtttcaa tttatatccc agcttataac tgtgcaaact atattcaacg ttgcgtagat   1380

agtgcactga atcagactgt tgttgatctc gaggtttgta tttgtaacga tggttcaaca   1440

gataatacct tagaagtgat caataagctt tatggtaata atcctagggt acgcatcatg   1500

tctaaaccaa atggcggaat agcctcagca tcaaatgcag ccgtttcttt tgctaaaggt   1560

tattacattg ggcagttaga ttcagatgat tatcttgagc ctgatgcagt tgaactgtgt   1620

ttaaaagaat ttttaaaaga taaaacgcta gcttgtgttt ataccactaa tagaaacgtc   1680

aatccggatg gtagcttaat cgctaatggt tacaattggc cagaattttc acgagaaaaa   1740

ctcacaacgg ctatgattgc tcaccacttt agaatgttca cgattagagc ttggcattta   1800

actgatggat tcaatgaaaa aattgaaaat gccgtagact atgacatgtt cctcaaactc   1860

agtgaagttg gaaaatttaa acatcttaat aaaatctgct ataaccgtgt attacatggt   1920

gataacacat caattaagaa acttggcatt caaaagaaaa accattttgt tgtagtcaat   1980

cagtcattaa atagacaagg cataacttat tataattatg acgaatttga tgatttagat   2040

gaaagtagaa agtatatttt caataaaacc gctgaatatc aagaagagat tgatatctta   2100

aaagatattt aa                                                       2112
```

<210> SEQ ID NO 34
<211> LENGTH: 2112
<212> TYPE: DNA
<213> ORGANISM: Pasteurella multocida

<400> SEQUENCE: 34

```
atgaatacat tatcacaagc aataaaagca tataacagca atgactatca attagcactc     60

aaattatttg aaaagtcggc ggaaatctat ggacggaaaa ttgttgaatt tcaaattacc    120

aaatgcaaag aaaaactctc agcacatcct tctgttaatt cagcacatct ttctgtaaat    180

aaagaagaaa aagtcaatgt ttgcgatagt ccgttagata ttgcaacaca actgttactt    240

tccaacgtaa aaaaattagt actttctgac tcggaaaaaa acacgttaaa aaataaatgg    300

aaattgctca ctgagaagaa atctgaaaat gcggaggtaa gagcggtcgc ccttgtacca    360

aaagattttc ccaaagatct ggttttagcg cctttacctg atcatgttaa tgattttaca    420

tggtacaaaa agcgaaagaa aagacttggc ataaaacctg aacatcaaca tgttggtctt    480

tctattatcg ttacaacatt caatcgacca gcaattttat cgattacatt agcctgttta    540

gtaaaccaaa aaacacatta cccgtttgaa gttatcgtga cagatgatgg tagtcaggaa    600

gatctatcac cgatcattcg ccaatatgaa aataaattgg atattcgcta cgtcagacaa    660
```

```
aaagataacg gttttcaagc cagtgccgct cggaatatgg gattacgctt agcaaaatat    720
gactttattg gcttactcaa ctgtgatatg gcgccaaatc cattatgggt tcattcttat    780
gttgcagagc tattagaaga tgatgattta acaatcattg gtccaagaaa atacatcgat    840
acacaacata ttgacccaaa agacttctta aataacgcga gtttgcttga atcattacca    900
gaagtgaaaa ccaataatag tgttgccgca aaaggggaag gaacagtttc tctggattgg    960
cgcttagaac aattcgaaaa aacagaaaat ctccgcttat ccgattcgcc tttccgtttt   1020
tttgcggcgg gtaatgttgc tttcgctaaa aaatggctaa ataaatccgg tttctttgat   1080
gaggaattta atcactgggg tggagaagat gtggaatttg gatatcgctt attccgttac   1140
ggtagtttct ttaaaactat tgatggcatt atggcctacc atcaagagcc accaggtaaa   1200
gaaaatgaaa ccgatcgtga agcgggaaaa aatattacgc tcgatattat gagagaaaag   1260
gtcccttata tctatagaaa acttttacca atagaagatt cgcatatcaa tagagtacct   1320
ttagtttcaa tttatatccc agcttataac tgtgcaaact atattcaacg ttgcgtagat   1380
agtgcactga atcagactgt tgttgatctc gaggtttgta tttgtaacga tggttcaaca   1440
gataatacct tagaagtgat caataagctt tatggtaata atcctagggt acgcatcatg   1500
tctaaaccaa atggcggaat agcctcagca tcaaatgcag ccgtttcttt tgctaaaggt   1560
tattacattg ggcagttaga ttcagatgat tatcttgagc ctgatgcagt tgaactgtgt   1620
ttaaaagaat ttttaaaaga taaaacgcta gcttgtgttt ataccactaa tagaaacgtc   1680
aatccggatg gtagcttaat cgctaatggt tacaattggc cagaattttc acgagaaaaa   1740
ctcacaacgg ctatgattgc tcaccacttt agaatgttca cgattagagc ttggcattta   1800
actgatggat tcaatgaaaa aattgaaaat gccgtagact atgacatgtt cctcaaactc   1860
agtgaagttg gaaaatttaa acatcttaat aaaatctgct ataaccgtgt attacatggt   1920
gataacacat caattaagaa acttggcatt caaaagaaaa accattttgt tgtagtcaat   1980
cagtcattaa atagacaagg cataacttat tataattatg acgaatttga tgatttagat   2040
gaaagtagaa agtatatttt caataaaacc gctgaatatc aagaagagat tgatatctta   2100
aaagatattt aa                                                       2112
```

<210> SEQ ID NO 35
<211> LENGTH: 2112
<212> TYPE: DNA
<213> ORGANISM: Pasteurella multocida

<400> SEQUENCE: 35

```
atgaatacat tatcacaagc aataaaagca tataacagca atgactatca attagcactc     60
aaattatttg aaaagtcggc ggaaatctat ggacggaaaa ttgttgaatt tcaaattacc    120
aaatgcaaag aaaaactctc agcacatcct tctgttaatt cagcacatct ttctgtaaat    180
aaagaagaaa aagtcaatgt ttgcgatagt ccgttagata ttgcaacaca actgttactt    240
tccaacgtaa aaaaattagt actttctgac tcggaaaaaa acacgttaaa aaataaatgg    300
aaattgctca ctgagaagaa atctgaaaat gcggaggtaa gagcggtcgc ccttgtacca    360
aaagattttc ccaaagatct ggttttagcg cctttacctg atcatgttaa tgattttaca    420
tggtacaaaa agcgaaagaa aagacttggc ataaaacctg aacatcaaca tgttggtctt    480
tctattatcg ttacaacatt caatcgacca gcaattttat cgattacatt agcctgttta    540
gtaaaccaaa aaacacatta cccgtttgaa gttatcgtga cagatgatgg tagtcaggaa    600
```

-continued

```
gatctatcac cgatcattcg ccaatatgaa aataaattgg atattcgcta cgtcagacaa    660
aaagataacg gttttcaagc cagtgccgct cggaatatgg gattacgctt agcaaaatat    720
gactttattg gcttactcaa atgtgatatg gcgccaaatc cattatgggt tcattcttat    780
gttgcagagc tattagaaga tgatgattta acaatcattg gtccaagaaa atacatcgat    840
acacaacata ttgacccaaa agacttctta aataacgcga gtttgcttga atcattacca    900
gaagtgaaaa ccaataatag tgttgccgca aaaggggaag gaacagtttc tctggattgg    960
cgcttagaac aattcgaaaa aacagaaaat ctccgcttat ccgattcgcc tttccgtttt   1020
tttgcggcgg gtaatgttgc tttcgctaaa aaatggctaa ataaatccgg tttctttgat   1080
gaggaattta atcactgggg tggagaagat gtggaatttg gatatcgctt attccgttac   1140
ggtagtttct ttaaaactat tgatggcatt atggcctacc atcaagagcc accaggtaaa   1200
gaaaatgaaa ccgatcgtga agcgggaaaa aatattacgc tcgatattat gagagaaaag   1260
gtcccttata tctatagaaa acttttacca atagaagatt cgcatatcaa tagagtacct   1320
ttagtttcaa tttatatccc agcttataac tgtgcaaact atattcaacg ttgcgtagat   1380
agtgcactga atcagactgt tgttgatctc gaggtttgta tttgtaacga tggttcaaca   1440
gataatacct tagaagtgat caataagctt tatggtaata atcctagggt acgcatcatg   1500
tctaaaccaa atggcggaat agcctcagca tcaaatgcag ccgtttcttt tgctaaaggt   1560
tattacattg ggcagttaga ttcagatgat tatcttgagc ctgatgcagt tgaactgtgt   1620
ttaaaagaat tttaaaaga taaaacgcta gcttgtgttt ataccactaa tagaaacgtc   1680
aatccggatg gtagcttaat cgctaatggt tacaattggc cagaattttc acgagaaaaa   1740
ctcacaacgg ctatgattgc tcaccacttt agaatgttca cgattagagc ttggcattta   1800
actgatggat tcaatgaaaa aattgaaaat gccgtagact atgacatgtt cctcaaactc   1860
agtgaagttg gaaaatttaa acatcttaat aaaatctgct ataaccgtgt attacatggt   1920
gataacacat caattaagaa acttggcatt caaaagaaaa accattttgt tgtagtcaat   1980
cagtcattaa atagacaagg cataacttat tataattatg acgaatttga tgatttagat   2040
gaaagtagaa agtatatttt caataaaacc gctgaatatc aagaagagat tgatatctta   2100
aaagatattt aa                                                       2112
```

<210> SEQ ID NO 36
<211> LENGTH: 2112
<212> TYPE: DNA
<213> ORGANISM: Pasteurella multocida

<400> SEQUENCE: 36

```
atgaatacat tatcacaagc aataaaagca tataacagca atgactatca attagcactc     60
aaattatttg aaaagtcggc ggaaatctat ggacggaaaa ttgttgaatt tcaaattacc    120
aaatgcaaag aaaaactctc agcacatcct tctgttaatt cagcacatct ttctgtaaat    180
aaagaagaaa aagtcaatgt ttgcgatagt ccgttagata ttgcaacaca actgttactt    240
tccaacgtaa aaaaattagt actttctgac tcggaaaaaa acacgttaaa aaataaatgg    300
aaattgctca ctgagaagaa atctgaaaat gcggaggtaa gagcggtcgc ccttgtacca    360
aaagattttc ccaaagatct ggttttagcg cctttacctg atcatgttaa tgattttaca    420
tggtacaaaa agcgaaagaa aagacttggc ataaaacctg aacatcaaca tgttggtctt    480
tctattatcg ttacaacatt caatcgacca gcaattttat cgattacatt agcctgttta    540
gtaaaccaaa aaacacatta cccgtttgaa gttatcgtga cagatgatgg tagtcaggaa    600
```

-continued

```
gatctatcac cgatcattcg ccaatatgaa aataaattgg atattcgcta cgtcagacaa    660

aaagataacg gttttcaagc cagtgccgct cggaatatgg gattacgctt agcaaaatat    720

gactttattg gcttactcga ctgtgaaatg gcgccaaatc cattatgggt tcattcttat    780

gttgcagagc tattagaaga tgatgattta acaatcattg gtccaagaaa atacatcgat    840

acacaacata ttgacccaaa agacttctta aataacgcga gtttgcttga atcattacca    900

gaagtgaaaa ccaataatag tgttgccgca aaaggggaag gaacagtttc tctggattgg    960

cgcttagaac aattcgaaaa aacagaaaat ctccgcttat ccgattcgcc tttccgtttt   1020

tttgcggcgg gtaatgttgc tttcgctaaa aaatggctaa ataaatccgg tttctttgat   1080

gaggaattta atcactgggg tggagaagat gtggaatttg gatatcgctt attccgttac   1140

ggtagtttct ttaaaactat tgatggcatt atggcctacc atcaagagcc accaggtaaa   1200

gaaaatgaaa ccgatcgtga agcgggaaaa aatattacgc tcgatattat gagagaaaag   1260

gtcccttata tctatagaaa acttttacca atagaagatt cgcatatcaa tagagtacct   1320

ttagtttcaa tttatatccc agcttataac tgtgcaaact atattcaacg ttgcgtagat   1380

agtgcactga atcagactgt tgttgatctc gaggtttgta tttgtaacga tggttcaaca   1440

gataatacct tagaagtgat caataagctt tatggtaata atcctagggt acgcatcatg   1500

tctaaaccaa atggcggaat agcctcagca tcaaatgcag ccgtttcttt tgctaaaggt   1560

tattacattg ggcagttaga ttcagatgat tatcttgagc ctgatgcagt tgaactgtgt   1620

ttaaaagaat ttttaaaaga taaaacgcta gcttgtgttt ataccactaa tagaaacgtc   1680

aatccggatg gtagcttaat cgctaatggt tacaattggc cagaattttc acgagaaaaa   1740

ctcacaacgg ctatgattgc tcaccacttt agaatgttca cgattagagc ttggcattta   1800

actgatggat tcaatgaaaa aattgaaaat gccgtagact atgacatgtt cctcaaactc   1860

agtgaagttg gaaaatttaa acatcttaat aaaatctgct ataaccgtgt attacatggt   1920

gataacacat caattaagaa acttggcatt caaaagaaaa accattttgt tgtagtcaat   1980

cagtcattaa atagacaagg cataacttat tataattatg acgaatttga tgatttagat   2040

gaaagtagaa agtatatttt caataaaacc gctgaatatc aagaagagat tgatatctta   2100

aaagatattt aa                                                       2112
```

<210> SEQ ID NO 37
<211> LENGTH: 2112
<212> TYPE: DNA
<213> ORGANISM: Pasteurella multocida

<400> SEQUENCE: 37

```
atgaatacat tatcacaagc aataaaagca tataacagca atgactatca attagcactc     60

aaattatttg aaaagtcggc ggaaatctat ggacggaaaa ttgttgaatt tcaaattacc    120

aaatgcaaag aaaaactctc agcacatcct tctgttaatt cagcacatct ttctgtaaat    180

aaagaagaaa aagtcaatgt ttgcgatagt ccgttagata ttgcaacaca actgttactt    240

tccaacgtaa aaaaattagt actttctgac tcggaaaaaa acacgttaaa aaataaatgg    300

aaattgctca ctgagaagaa atctgaaaat gcggaggtaa gagcggtcgc ccttgtacca    360

aaagattttc ccaaagatct ggttttagcg cctttacctg atcatgttaa tgattttaca    420

tggtacaaaa agcgaaagaa aagacttggc ataaaacctg aacatcaaca tgttggtctt    480

tctattatcg ttacaacatt caatcgacca gcaattttat cgattacatt agcctgttta    540
```

-continued

```
gtaaaccaaa aaacacatta cccgtttgaa gttatcgtga cagatgatgg tagtcaggaa    600

gatctatcac cgatcattcg ccaatatgaa aataaattgg atattcgcta cgtcagacaa    660

aaagataacg gttttcaagc cagtgccgct cggaatatgg gattacgctt agcaaaatat    720

gactttattg gcttactcga ctgtaatatg gcgccaaatc cattatgggt tcattcttat    780

gttgcagagc tattagaaga tgatgattta acaatcattg gtccaagaaa atacatcgat    840

acacaacata ttgacccaaa agacttctta aataacgcga gtttgcttga atcattacca    900

gaagtgaaaa ccaataatag tgttgccgca aaaggggaag gaacagtttc tctggattgg    960

cgcttagaac aattcgaaaa aacagaaaat ctccgcttat ccgattcgcc tttccgtttt   1020

tttgcggcgg gtaatgttgc tttcgctaaa aaatggctaa ataaatccgg tttctttgat   1080

gaggaattta atcactgggg tggagaagat gtggaatttg gatatcgctt attccgttac   1140

ggtagtttct ttaaaactat tgatggcatt atggcctacc atcaagagcc accaggtaaa   1200

gaaaatgaaa ccgatcgtga agcgggaaaa aatattacgc tcgatattat gagagaaaag   1260

gtcccttata tctatagaaa acttttacca atagaagatt cgcatatcaa tagagtacct   1320

ttagtttcaa tttatatccc agcttataac tgtgcaaact atattcaacg ttgcgtagat   1380

agtgcactga atcagactgt tgttgatctc gaggtttgta tttgtaacga tggttcaaca   1440

gataatacct tagaagtgat caataagctt tatggtaata atcctagggt acgcatcatg   1500

tctaaaccaa atggcggaat agcctcagca tcaaatgcag ccgtttcttt tgctaaaggt   1560

tattacattg ggcagttaga ttcagatgat tatcttgagc ctgatgcagt tgaactgtgt   1620

ttaaaagaat ttttaaaaga taaaacgcta gcttgtgttt ataccactaa tagaaacgtc   1680

aatccggatg gtagcttaat cgctaatggt tacaattggc cagaattttc acgagaaaaa   1740

ctcacaacgg ctatgattgc tcaccacttt agaatgttca cgattagagc ttggcattta   1800

actgatggat tcaatgaaaa aattgaaaat gccgtagact atgacatgtt cctcaaactc   1860

agtgaagttg gaaaatttaa acatcttaat aaaatctgct ataaccgtgt attacatggt   1920

gataacacat caattaagaa acttggcatt caaaagaaaa accattttgt tgtagtcaat   1980

cagtcattaa atagacaagg cataacttat tataattatg acgaatttga tgatttagat   2040

gaaagtagaa agtatatttt caataaaacc gctgaatatc aagaagagat tgatatctta   2100

aaagatattt aa                                                       2112
```

<210> SEQ ID NO 38
<211> LENGTH: 2112
<212> TYPE: DNA
<213> ORGANISM: Pasteurella multocida

<400> SEQUENCE: 38

```
atgaatacat tatcacaagc aataaaagca tataacagca atgactatca attagcactc     60

aaattatttg aaaagtcggc ggaaatctat ggacggaaaa ttgttgaatt tcaaattacc    120

aaatgcaaag aaaaactctc agcacatcct tctgttaatt cagcacatct ttctgtaaat    180

aaagaagaaa aagtcaatgt ttgcgatagt ccgttagata ttgcaacaca actgttactt    240

tccaacgtaa aaaaattagt actttctgac tcggaaaaaa acacgttaaa aaataaatgg    300

aaattgctca ctgagaagaa atctgaaaat gcggaggtaa gagcggtcgc ccttgtacca    360

aaagattttc ccaaagatct ggttttagcg cctttacctg atcatgttaa tgattttaca    420

tggtacaaaa agcgaaagaa aagacttggc ataaaacctg aacatcaaca tgttggtctt    480

tctattatcg ttacaacatt caatcgacca gcaattttat cgattacatt agcctgttta    540
```

-continued

```
gtaaaccaaa aaacacatta cccgtttgaa gttatcgtga cagatgatgg tagtcaggaa    600
gatctatcac cgatcattcg ccaatatgaa aataaattgg atattcgcta cgtcagacaa    660
aaagataacg gttttcaagc cagtgccgct cggaatatgg gattacgctt agcaaaatat    720
gactttattg gcttactcga ctgtaaaatg gcgccaaatc cattatgggt tcattcttat    780
gttgcagagc tattagaaga tgatgattta acaatcattg gtccaagaaa atacatcgat    840
acacaacata ttgacccaaa agacttctta aataacgcga gtttgcttga atcattacca    900
gaagtgaaaa ccaataatag tgttgccgca aaaggggaag gaacagtttc tctggattgg    960
cgcttagaac aattcgaaaa aacagaaaat ctccgcttat ccgattcgcc tttccgtttt   1020
tttgcggcgg gtaatgttgc tttcgctaaa aaatggctaa ataaatccgg tttctttgat   1080
gaggaattta atcactgggg tggagaagat gtggaatttg gatatcgctt attccgttac   1140
ggtagtttct ttaaaactat tgatggcatt atggcctacc atcaagagcc accaggtaaa   1200
gaaaatgaaa ccgatcgtga agcgggaaaa aatattacgc tcgatattat gagagaaaag   1260
gtcccttata tctatagaaa acttttacca atagaagatt cgcatatcaa tagagtacct   1320
ttagtttcaa tttatatccc agcttataac tgtgcaaact atattcaacg ttgcgtagat   1380
agtgcactga atcagactgt tgttgatctc gaggtttgta tttgtaacga tggttcaaca   1440
gataatacct tagaagtgat caataagctt tatggtaata atcctagggt acgcatcatg   1500
tctaaaccaa atggcggaat agcctcagca tcaaatgcag ccgtttcttt tgctaaaggt   1560
tattacattg ggcagttaga ttcagatgat tatcttgagc ctgatgcagt tgaactgtgt   1620
ttaaaagaat ttttaaaaga taaaacgcta gcttgtgttt ataccactaa tagaaacgtc   1680
aatccggatg gtagcttaat cgctaatggt tacaattggc cagaattttc acgagaaaaa   1740
ctcacaacgg ctatgattgc tcaccacttt agaatgttca cgattagagc ttggcattta   1800
actgatggat tcaatgaaaa aattgaaaat gccgtagact atgacatgtt cctcaaactc   1860
agtgaagttg gaaaatttaa acatcttaat aaaatctgct ataaccgtgt attacatggt   1920
gataacacat caattaagaa acttggcatt caaaagaaaa accattttgt tgtagtcaat   1980
cagtcattaa atagacaagg cataacttat tataattatg acgaatttga tgatttagat   2040
gaaagtagaa agtatatttt caataaaacc gctgaatatc aagaagagat tgatatctta   2100
aaagatattt aa                                                       2112
```

<210> SEQ ID NO 39
<211> LENGTH: 2112
<212> TYPE: DNA
<213> ORGANISM: Pasteurella multocida

<400> SEQUENCE: 39

```
atgaatacat tatcacaagc aataaaagca tataacagca atgactatca attagcactc     60
aaattatttg aaaagtcggc ggaaatctat ggacggaaaa ttgttgaatt tcaaattacc    120
aaatgcaaag aaaaactctc agcacatcct tctgttaatt cagcacatct ttctgtaaat    180
aaagaagaaa aagtcaatgt ttgcgatagt ccgttagata ttgcaacaca actgttactt    240
tccaacgtaa aaaaattagt actttctgac tcggaaaaaa acacgttaaa aaataaatgg    300
aaattgctca ctgagaagaa atctgaaaat gcggaggtaa gagcggtcgc ccttgtacca    360
aaagattttc ccaaagatct ggttttagcg cctttacctg atcatgttaa tgattttaca    420
tggtacaaaa agcgaaagaa aagacttggc ataaaacctg aacatcaaca tgttggtctt    480
```

-continued

```
tctattatcg ttacaacatt caatcgacca gcaattttat cgattacatt agcctgttta    540

gtaaaccaaa aaacacatta cccgtttgaa gttatcgtga cagatgatgg tagtcaggaa    600

gatctatcac cgatcattcg ccaatatgaa aataaattgg atattcgcta cgtcagacaa    660

aaagataacg gttttcaagc cagtgccgct cggaatatgg gattacgctt agcaaaatat    720

gactttattg gcttactcga ctgtgatatg gcgccaaatc cattatgggt tcattcttat    780

gttgcagagc tattagaaga tgatgattta acaatcattg gtccaagaaa atacatcgat    840

acacaacata ttgacccaaa agacttctta aataacgcga gtttgcttga atcattacca    900

gaagtgaaaa ccaataatag tgttgccgca aaaggggaag gaacagtttc tctggattgg    960

cgcttagaac aattcgaaaa aacagaaaat ctccgcttat ccgattcgcc tttccgtttt   1020

tttgcggcgg gtaatgttgc tttcgctaaa aaatggctaa ataaatccgg tttctttgat   1080

gaggaattta atcactgggg tggagaagat gtggaatttg gatatcgctt attccgttac   1140

ggtagtttct ttaaaactat tgatggcatt atggcctacc atcaagagcc accaggtaaa   1200

gaaaatgaaa ccgatcgtga agcgggaaaa aatattacgc tcgatattat gagagaaaag   1260

gtcccttata tctatagaaa acttttacca atagaagatt cgcatatcaa tagagtacct   1320

ttagtttcaa tttatatccc agcttataac tgtgcaaact atattcaacg ttgcgtagat   1380

agtgcactga atcagactgt tgttgatctc gaggtttgta tttgtaacga tggttcaaca   1440

gataatacct tagaagtgat caataagctt tatggtaata atcctagggt acgcatcatg   1500

tctaaaccaa atggcggaat agcctcagca tcaaatgcag ccgtttcttt tgctaaaggt   1560

tattacattg ggcagttaaa ttcagatgat tatcttgagc ctgatgcagt tgaactgtgt   1620

ttaaaagaat ttttaaaaga taaaacgcta gcttgtgttt ataccactaa tagaaacgtc   1680

aatccggatg gtagcttaat cgctaatggt tacaattggc cagaattttc acgagaaaaa   1740

ctcacaacgg ctatgattgc tcaccacttt agaatgttca cgattagagc ttggcattta   1800

actgatggat tcaatgaaaa aattgaaaat gccgtagact atgacatgtt cctcaaactc   1860

agtgaagttg gaaaatttaa acatcttaat aaaatctgct ataaccgtgt attacatggt   1920

gataacacat caattaagaa acttggcatt caaaagaaaa accattttgt tgtagtcaat   1980

cagtcattaa atagacaagg cataacttat tataattatg acgaatttga tgatttagat   2040

gaaagtagaa agtatatttt caataaaacc gctgaatatc aagaagagat tgatatctta   2100

aaagatattt aa                                                       2112
```

```
<210> SEQ ID NO 40
<211> LENGTH: 2112
<212> TYPE: DNA
<213> ORGANISM: Pasteurella multocida

<400> SEQUENCE: 40
```

```
atgaatacat tatcacaagc aataaaagca tataacagca atgactatca attagcactc     60

aaattatttg aaaagtcggc ggaaatctat ggacggaaaa ttgttgaatt tcaaattacc    120

aaatgcaaag aaaaactctc agcacatcct tctgttaatt cagcacatct ttctgtaaat    180

aaagaagaaa aagtcaatgt ttgcgatagt ccgttagata ttgcaacaca actgttactt    240

tccaacgtaa aaaaattagt actttctgac tcggaaaaaa acacgttaaa aaataaatgg    300

aaattgctca ctgagaagaa atctgaaaat gcggaggtaa gagcggtcgc ccttgtacca    360

aaagattttc ccaaagatct ggttttagcg cctttacctg atcatgttaa tgattttaca    420

tggtacaaaa agcgaaagaa aagacttggc ataaaacctg aacatcaaca tgttggtctt    480
```

-continued tctattatcg ttacaacatt caatcgacca gcaattttat cgattacatt agcctgttta 540
gtaaaccaaa aaacacatta cccgtttgaa gttatcgtga cagatgatgg tagtcaggaa 600
gatctatcac cgatcattcg ccaatatgaa aataaattgg atattcgcta cgtcagacaa 660
aaagataacg gttttcaagc cagtgccgct cggaatatgg gattacgctt agcaaaatat 720
gactttattg gcttactcga ctgtgatatg gcgccaaatc cattatgggt tcattcttat 780
gttgcagagc tattagaaga tgatgattta acaatcattg gtccaagaaa atacatcgat 840
acacaacata ttgacccaaa agacttctta aataacgcga gtttgcttga atcattacca 900
gaagtgaaaa ccaataatag tgttgccgca aaaggggaag gaacagtttc tctggattgg 960
cgcttagaac aattcgaaaa aacagaaaat ctccgcttat ccgattcgcc tttccgtttt 1020
tttgcggcgg gtaatgttgc tttcgctaaa aaatggctaa ataaatccgg tttctttgat 1080
gaggaattta atcactgggg tggagaagat gtggaatttg gatatcgctt attccgttac 1140
ggtagtttct ttaaaactat tgatggcatt atggcctacc atcaagagcc accaggtaaa 1200
gaaaatgaaa ccgatcgtga agcgggaaaa aatattacgc tcgatattat gagagaaaag 1260
gtcccttata tctatagaaa acttttacca atagaagatt cgcatatcaa tagagtacct 1320
ttagtttcaa tttatatccc agcttataac tgtgcaaact atattcaacg ttgcgtagat 1380
agtgcactga atcagactgt tgttgatctc gaggtttgta tttgtaacga tggttcaaca 1440
gataatacct tagaagtgat caataagctt tatggtaata atcctagggt acgcatcatg 1500
tctaaaccaa atggcggaat agcctcagca tcaaatgcag ccgtttcttt tgctaaaggt 1560
tattacattg ggcagttaga atcagatgat tatcttgagc ctgatgcagt tgaactgtgt 1620
ttaaaagaat ttttaaaaga taaaacgcta gcttgtgttt ataccactaa tagaaacgtc 1680
aatccggatg gtagcttaat cgctaatggt tacaattggc cagaattttc acgagaaaaa 1740
ctcacaacgg ctatgattgc tcaccacttt agaatgttca cgattagagc ttggcattta 1800
actgatggat tcaatgaaaa aattgaaaat gccgtagact atgacatgtt cctcaaactc 1860
agtgaagttg gaaaatttaa acatcttaat aaaatctgct ataaccgtgt attacatggt 1920
gataacacat caattaagaa acttggcatt caaaagaaaa accattttgt tgtagtcaat 1980
cagtcattaa atagacaagg cataacttat tataattatg acgaatttga tgatttagat 2040
gaaagtagaa agtatatttt caataaaacc gctgaatatc aagaagagat tgatatctta 2100
aaagatattt aa 2112

<210> SEQ ID NO 41
<211> LENGTH: 2112
<212> TYPE: DNA
<213> ORGANISM: Pasteurella multocida

<400> SEQUENCE: 41
atgaatacat tatcacaagc aataaaagca tataacagca atgactatca attagcactc 60
aaattatttg aaaagtcggc ggaaatctat ggacggaaaa ttgttgaatt tcaaattacc 120
aaatgcaaag aaaaactctc agcacatcct tctgttaatt cagcacatct ttctgtaaat 180
aaagaagaaa aagtcaatgt ttgcgatagt ccgttagata ttgcaacaca actgttactt 240
tccaacgtaa aaaaattagt actttctgac tcggaaaaaa acacgttaaa aaataaatgg 300
aaattgctca ctgagaagaa atctgaaaat gcggaggtaa gagcggtcgc ccttgtacca 360
aaagattttc ccaaagatct ggttttagcg cctttacctg atcatgttaa tgattttaca 420

-continued

```
tggtacaaaa agcgaaagaa aagacttggc ataaaacctg aacatcaaca tgttggtctt    480

tctattatcg ttacaacatt caatcgacca gcaattttat cgattacatt agcctgttta    540

gtaaaccaaa aaacacatta cccgtttgaa gttatcgtga cagatgatgg tagtcaggaa    600

gatctatcac cgatcattcg ccaatatgaa aataaattgg atattcgcta cgtcagacaa    660

aaagataacg gttttcaagc cagtgccgct cggaatatgg gattacgctt agcaaaatat    720

gactttattg gcttactcga ctgtgatatg gcgccaaatc cattatgggt tcattcttat    780

gttgcagagc tattagaaga tgatgattta acaatcattg gtccaagaaa atacatcgat    840

acacaacata ttgacccaaa agacttctta aataacgcga gtttgcttga atcattacca    900

gaagtgaaaa ccaataatag tgttgccgca aaaggggaag gaacagtttc tctggattgg    960

cgcttagaac aattcgaaaa aacagaaaat ctccgcttat ccgattcgcc tttccgtttt   1020

tttgcggcgg gtaatgttgc tttcgctaaa aaatggctaa ataaatccgg tttctttgat   1080

gaggaattta atcactgggg tggagaagat gtggaatttg gatatcgctt attccgttac   1140

ggtagtttct ttaaaactat tgatggcatt atggcctacc atcaagagcc accaggtaaa   1200

gaaaatgaaa ccgatcgtga agcgggaaaa aatattacgc tcgatattat gagagaaaag   1260

gtcccttata tctatagaaa acttttacca atagaagatt cgcatatcaa tagagtacct   1320

ttagtttcaa tttatatccc agcttataac tgtgcaaact atattcaacg ttgcgtagat   1380

agtgcactga atcagactgt tgttgatctc gaggtttgta tttgtaacga tggttcaaca   1440

gataatacct tagaagtgat caataagctt tatggtaata atcctagggt acgcatcatg   1500

tctaaaccaa atggcggaat agcctcagca tcaaatgcag ccgtttcttt tgctaaaggt   1560

tattacattg ggcagttaaa atcagatgat tatcttgagc ctgatgcagt tgaactgtgt   1620

ttaaaagaat ttttaaaaga taaaacgcta gcttgtgttt ataccactaa tagaaacgtc   1680

aatccggatg gtagcttaat cgctaatggt tacaattggc cagaattttc acgagaaaaa   1740

ctcacaacgg ctatgattgc tcaccacttt agaatgttca cgattagagc ttggcattta   1800

actgatggat tcaatgaaaa aattgaaaat gccgtagact atgacatgtt cctcaaactc   1860

agtgaagttg gaaaatttaa acatcttaat aaaatctgct ataaccgtgt attacatggt   1920

gataacacat caattaagaa acttggcatt caaaagaaaa accattttgt tgtagtcaat   1980

cagtcattaa atagacaagg cataacttat tataattatg acgaatttga tgatttagat   2040

gaaagtagaa agtatatttt caataaaacc gctgaatatc aagaagagat tgatatctta   2100

aaagatattt aa                                                       2112
```

<210> SEQ ID NO 42
<211> LENGTH: 2112
<212> TYPE: DNA
<213> ORGANISM: Pasteurella multocida

<400> SEQUENCE: 42

```
atgaatacat tatcacaagc aataaaagca tataacagca atgactatca attagcactc     60

aaattatttg aaaagtcggc ggaaatctat ggacggaaaa ttgttgaatt tcaaattacc    120

aaatgcaaag aaaaactctc agcacatcct tctgttaatt cagcacatct ttctgtaaat    180

aaagaagaaa aagtcaatgt ttgcgatagt ccgttagata ttgcaacaca actgttactt    240

tccaacgtaa aaaaattagt actttctgac tcggaaaaaa acacgttaaa aaataaatgg    300

aaattgctca ctgagaagaa atctgaaaat gcggaggtaa gagcggtcgc ccttgtacca    360

aaagatttc ccaaagatct ggttttagcg cctttacctg atcatgttaa tgattttaca    420
```

-continued tggtacaaaa agcgaaagaa aagacttggc ataaaacctg aacatcaaca tgttggtctt 480
tctattatcg ttacaacatt caatcgacca gcaattttat cgattacatt agcctgttta 540
gtaaaccaaa aaacacatta cccgtttgaa gttatcgtga cagatgatgg tagtcaggaa 600
gatctatcac cgatcattcg ccaatatgaa aataaattgg atattcgcta cgtcagacaa 660
aaagataacg gttttcaagc cagtgccgct cggaatatgg gattacgctt agcaaaatat 720
gactttattg gcttactcga ctgtgatatg gcgccaaatc cattatgggt tcattcttat 780
gttgcagagc tattagaaga tgatgattta acaatcattg gtccaagaaa atacatcgat 840
acacaacata ttgacccaaa agacttctta aataacgcga gtttgcttga atcattacca 900
gaagtgaaaa ccaataatag tgttgccgca aaaggggaag gaacagtttc tctggattgg 960
cgcttagaac aattcgaaaa aacagaaaat ctccgcttat ccgattcgcc tttccgtttt 1020
tttgcggcgg gtaatgttgc tttcgctaaa aaatggctaa ataaatccgg tttctttgat 1080
gaggaattta atcactgggg tggagaagat gtggaatttg gatatcgctt attccgttac 1140
ggtagtttct ttaaaactat tgatggcatt atggcctacc atcaagagcc accaggtaaa 1200
gaaaatgaaa ccgatcgtga agcgggaaaa aatattacgc tcgatattat gagagaaaag 1260
gtcccttata tctatagaaa acttttacca atagaagatt cgcatatcaa tagagtacct 1320
ttagtttcaa tttatatccc agcttataac tgtgcaaact atattcaacg ttgcgtagat 1380
agtgcactga atcagactgt tgttgatctc gaggtttgta tttgtaacga tggttcaaca 1440
gataatacct tagaagtgat caataagctt tatggtaata atcctagggt acgcatcatg 1500
tctaaaccaa atggcggaat agcctcagca tcaaatgcag ccgtttcttt tgctaaaggt 1560
tattacattg ggcagttaga ttcagaagat tatcttgagc ctgatgcagt tgaactgtgt 1620
ttaaaagaat ttttaaaaga taaaacgcta gcttgtgttt ataccactaa tagaaacgtc 1680
aatccggatg gtagcttaat cgctaatggt tacaattggc cagaattttc acgagaaaaa 1740
ctcacaacgg ctatgattgc tcaccacttt agaatgttca cgattagagc ttggcattta 1800
actgatggat tcaatgaaaa aattgaaaat gccgtagact atgacatgtt cctcaaactc 1860
agtgaagttg gaaaatttaa acatcttaat aaaatctgct ataaccgtgt attacatggt 1920
gataacacat caattaagaa acttggcatt caaaagaaaa accattttgt tgtagtcaat 1980
cagtcattaa atagacaagg cataacttat tataattatg acgaatttga tgatttagat 2040
gaaagtagaa agtatatttt caataaaacc gctgaatatc aagaagagat tgatatctta 2100
aaagatattt aa 2112

<210> SEQ ID NO 43
<211> LENGTH: 2112
<212> TYPE: DNA
<213> ORGANISM: Pasteurella multocida

<400> SEQUENCE: 43
atgaatacat tatcacaagc aataaaagca tataacagca atgactatca attagcactc 60
aaattatttg aaaagtcggc ggaaatctat ggacggaaaa ttgttgaatt tcaaattacc 120
aaatgcaaag aaaaactctc agcacatcct tctgttaatt cagcacatct ttctgtaaat 180
aaagaagaaa aagtcaatgt ttgcgatagt ccgttagata ttgcaacaca actgttactt 240
tccaacgtaa aaaaattagt actttctgac tcggaaaaaa acacgttaaa aaataaatgg 300
aaattgctca ctgagaagaa atctgaaaat gcggaggtaa gagcggtcgc ccttgtacca 360

-continued

```
aaagattttc ccaaagatct ggttttagcg cctttacctg atcatgttaa tgattttaca    420

tggtacaaaa agcgaaagaa aagacttggc ataaaacctg aacatcaaca tgttggtctt    480

tctattatcg ttacaacatt caatcgacca gcaattttat cgattacatt agcctgttta    540

gtaaaccaaa aaacacatta cccgtttgaa gttatcgtga cagatgatgg tagtcaggaa    600

gatctatcac cgatcattcg ccaatatgaa aataaattgg atattcgcta cgtcagacaa    660

aaagataacg gttttcaagc cagtgccgct cggaatatgg gattacgctt agcaaaatat    720

gactttattg gcttactcga ctgtgatatg gcgccaaatc cattatgggt tcattcttat    780

gttgcagagc tattagaaga tgatgattta acaatcattg gtccaagaaa atacatcgat    840

acacaacata ttgacccaaa agacttctta aataacgcga gtttgcttga atcattacca    900

gaagtgaaaa ccaataatag tgttgccgca aaaggggaag gaacagtttc tctggattgg    960

cgcttagaac aattcgaaaa aacagaaaat ctccgcttat ccgattcgcc tttccgtttt   1020

tttgcggcgg gtaatgttgc tttcgctaaa aaatggctaa ataaatccgg tttctttgat   1080

gaggaattta atcactgggg tggagaagat gtggaatttg gatatcgctt attccgttac   1140

ggtagtttct ttaaaactat tgatggcatt atggcctacc atcaagagcc accaggtaaa   1200

gaaaatgaaa ccgatcgtga agcgggaaaa aatattacgc tcgatattat gagagaaaag   1260

gtcccttata tctatagaaa acttttacca atagaagatt cgcatatcaa tagagtacct   1320

ttagtttcaa tttatatccc agcttataac tgtgcaaact atattcaacg ttgcgtagat   1380

agtgcactga atcagactgt tgttgatctc gaggtttgta tttgtaacga tggttcaaca   1440

gataatacct tagaagtgat caataagctt tatggtaata atcctagggt acgcatcatg   1500

tctaaaccaa atggcggaat agcctcagca tcaaatgcag ccgtttcttt tgctaaaggt   1560

tattacattg ggcagttaga ttcaaatgat tatcttgagc ctgatgcagt tgaactgtgt   1620

ttaaaagaat tttaaaaaga taaaacgcta gcttgtgttt ataccactaa tagaaacgtc   1680

aatccggatg gtagcttaat cgctaatggt tacaattggc cagaattttc acgagaaaaa   1740

ctcacaacgg ctatgattgc tcaccacttt agaatgttca cgattagagc ttggcattta   1800

actgatggat tcaatgaaaa aattgaaaat gccgtagact atgacatgtt cctcaaactc   1860

agtgaagttg gaaaatttaa acatcttaat aaaatctgct ataaccgtgt attacatggt   1920

gataacacat caattaagaa acttggcatt caaaagaaaa accattttgt tgtagtcaat   1980

cagtcattaa atagacaagg cataacttat tataattatg acgaatttga tgatttagat   2040

gaaagtagaa agtatatttt caataaaacc gctgaatatc aagaagagat tgatatctta   2100

aaagatattt aa                                                       2112
```

<210> SEQ ID NO 44
<211> LENGTH: 2112
<212> TYPE: DNA
<213> ORGANISM: Pasteurella multocida

<400> SEQUENCE: 44

```
atgaatacat tatcacaagc aataaaagca tataacagca atgactatca attagcactc     60

aaattatttg aaaagtcggc ggaaatctat ggacggaaaa ttgttgaatt tcaaattacc    120

aaatgcaaag aaaaactctc agcacatcct tctgttaatt cagcacatct ttctgtaaat    180

aaagaagaaa aagtcaatgt ttgcgatagt ccgttagata ttgcaacaca actgttactt    240

tccaacgtaa aaaaattagt actttctgac tcggaaaaaa acacgttaaa aaataaatgg    300

aaattgctca ctgagaagaa atctgaaaat gcggaggtaa gagcggtcgc ccttgtacca    360
```

-continued

```
aaagattttc ccaaagatct ggttttagcg cctttacctg atcatgttaa tgattttaca    420
tggtacaaaa agcgaaagaa aagacttggc ataaaacctg aacatcaaca tgttggtctt    480
tctattatcg ttacaacatt caatcgacca gcaattttat cgattacatt agcctgttta    540
gtaaaccaaa aacacatta cccgtttgaa gttatcgtga cagatgatgg tagtcaggaa    600
gatctatcac cgatcattcg ccaatatgaa aataaattgg atattcgcta cgtcagacaa    660
aaagataacg gttttcaagc cagtgccgct cggaatatgg gattacgctt agcaaaatat    720
gactttattg gcttactcga ctgtgatatg gcgccaaatc cattatgggt tcattcttat    780
gttgcagagc tattagaaga tgatgattta acaatcattg gtccaagaaa atacatcgat    840
acacaacata ttgacccaaa agacttctta aataacgcga gtttgcttga atcattacca    900
gaagtgaaaa ccaataatag tgttgccgca aaaggggaag gaacagtttc tctggattgg    960
cgcttagaac aattcgaaaa aacagaaaat ctccgcttat ccgattcgcc tttccgtttt   1020
tttgcggcgg gtaatgttgc tttcgctaaa aaatggctaa ataaatccgg tttctttgat   1080
gaggaattta atcactgggg tggagaagat gtggaatttg gatatcgctt attccgttac   1140
ggtagtttct ttaaaactat tgatggcatt atggcctacc atcaagagcc accaggtaaa   1200
gaaaatgaaa ccgatcgtga agcgggaaaa aatattacgc tcgatattat gagagaaaag   1260
gtcccttata tctatagaaa acttttacca atagaagatt cgcatatcaa tagagtacct   1320
ttagtttcaa tttatatccc agcttataac tgtgcaaact atattcaacg ttgcgtagat   1380
agtgcactga atcagactgt tgttgatctc gaggtttgta tttgtaacga tggttcaaca   1440
gataatacct tagaagtgat caataagctt tatggtaata atcctagggt acgcatcatg   1500
tctaaaccaa atggcggaat agcctcagca tcaaatgcag ccgtttcttt tgctaaaggt   1560
tattacattg ggcagttaga ttcaaaagat tatcttgagc ctgatgcagt tgaactgtgt   1620
ttaaaagaat ttttaaaaga taaaacgcta gcttgtgttt ataccactaa tagaaacgtc   1680
aatccggatg gtagcttaat cgctaatggt tacaattggc cagaattttc acgagaaaaa   1740
ctcacaacgg ctatgattgc tcaccacttt agaatgttca cgattagagc ttggcattta   1800
actgatggat tcaatgaaaa aattgaaaat gccgtagact atgacatgtt cctcaaactc   1860
agtgaagttg gaaaatttaa acatcttaat aaaatctgct ataaccgtgt attacatggt   1920
gataacacat caattaagaa acttggcatt caaaagaaaa accattttgt tgtagtcaat   1980
cagtcattaa atagacaagg cataacttat tataattatg acgaatttga tgatttagat   2040
gaaagtagaa agtatatttt caataaaacc gctgaatatc aagaagagat tgatatctta   2100
aaagatattt aa                                                       2112
```

<210> SEQ ID NO 45
<211> LENGTH: 2112
<212> TYPE: DNA
<213> ORGANISM: Pasteurella multocida

<400> SEQUENCE: 45

```
atgaatacat tatcacaagc aataaaagca tataacagca atgactatca attagcactc     60
aaattatttg aaaagtcggc ggaaatctat ggacggaaaa ttgttgaatt tcaaattacc    120
aaatgcaaag aaaaactctc agcacatcct tctgttaatt cagcacatct ttctgtaaat    180
aaagaagaaa aagtcaatgt ttgcgatagt ccgttagata ttgcaacaca actgttactt    240
tccaacgtaa aaaaattagt actttctgac tcggaaaaaa acacgttaaa aaataaatgg    300
```

-continued

```
aaattgctca ctgagaagaa atctgaaaat gcggaggtaa gagcggtcgc ccttgtacca    360

aaagatttc ccaaagatct ggttttagcg cctttacctg atcatgttaa tgattttaca    420

tggtacaaaa agcgaaagaa aagacttggc ataaaacctg aacatcaaca tgttggtctt    480

tctattatcg ttacaacatt caatcgacca gcaattttat cgattacatt agcctgttta    540

gtaaaccaaa aaacacatta cccgtttgaa gttatcgtga cagatgatgg tagtcaggaa    600

gatctatcac cgatcattcg ccaatatgaa aataaattgg atattcgcta cgtcagacaa    660

aaagataacg gttttcaagc cagtgccgct cggaatatgg gattacgctt agcaaaatat    720

gactttattg gcttactcga ctgtgatatg gcgccaaatc cattatgggt tcattcttat    780

gttgcagagc tattagaaga tgatgattta acaatcattg gtccaagaaa atacatcgat    840

acacaacata ttgacccaaa agacttctta aataacgcga gtttgcttga atcattacca    900

gaagtgaaaa ccaataatag tgttgccgca aaaggggaag gaacagtttc tctggattgg    960

cgcttagaac aattcgaaaa aacagaaaat ctccgcttat ccgattcgcc tttccgtttt   1020

tttgcggcgg gtaatgttgc tttcgctaaa aaatggctaa ataaatccgg tttctttgat   1080

gaggaattta atcactgggg tggagacgat gtggaatttg gatatcgctt attccgttac   1140

ggtagtttct ttaaaactat tgatggcatt atggcctacc atcaagagcc accaggtaaa   1200

gaaaatgaaa ccgatcgtga agcgggaaaa aatattacgc tcgatattat gagagaaaag   1260

gtcccttata tctatagaaa acttttacca atagaagatt cgcatatcaa tagagtacct   1320

ttagtttcaa tttatatccc agcttataac tgtgcaaact atattcaacg ttgcgtagat   1380

agtgcactga atcagactgt tgttgatctc gaggtttgta tttgtaacga tggttcaaca   1440

gataatacct tagaagtgat caataagctt tatggtaata atcctagggt acgcatcatg   1500

tctaaaccaa atggcggaat agcctcagca tcaaatgcag ccgtttcttt tgctaaaggt   1560

tattacattg ggcagttaga ttcagatgat tatcttgagc ctgatgcagt tgaactgtgt   1620

ttaaaagaat ttttaaaaga taaaacgcta gcttgtgttt ataccactaa tagaaacgtc   1680

aatccggatg gtagcttaat cgctaatggt tacaattggc cagaattttc acgagaaaaa   1740

ctcacaacgg ctatgattgc tcaccacttt agaatgttca cgattagagc ttggcattta   1800

actgatggat tcaatgaaaa aattgaaaat gccgtagact atgacatgtt cctcaaactc   1860

agtgaagttg gaaaatttaa acatcttaat aaaatctgct ataaccgtgt attacatggt   1920

gataacacat caattaagaa acttggcatt caaaagaaaa accattttgt tgtagtcaat   1980

cagtcattaa atagacaagg cataacttat tataattatg acgaatttga tgatttagat   2040

gaaagtagaa agtatatttt caataaaacc gctgaatatc aagaagagat tgatatctta   2100

aaagatattt aa                                                       2112
```

<210> SEQ ID NO 46
<211> LENGTH: 2112
<212> TYPE: DNA
<213> ORGANISM: Pasteurella multocida

<400> SEQUENCE: 46

```
atgaatacat tatcacaagc aataaaagca tataacagca atgactatca attagcactc     60

aaattatttg aaaagtcggc ggaaatctat ggacggaaaa ttgttgaatt tcaaattacc    120

aaatgcaaag aaaaactctc agcacatcct tctgttaatt cagcacatct ttctgtaaat    180

aaagaagaaa aagtcaatgt ttgcgatagt ccgttagata ttgcaacaca actgttactt    240

tccaacgtaa aaaaattagt actttctgac tcggaaaaaa acacgttaaa aaataaatgg    300
```

-continued

```
aaattgctca ctgagaagaa atctgaaaat gcggaggtaa gagcggtcgc ccttgtacca    360
aaagatttc ccaaagatct ggttttagcg cctttacctg atcatgttaa tgattttaca    420
tggtacaaaa agcgaaagaa aagacttggc ataaaacctg aacatcaaca tgttggtctt    480
tctattatcg ttacaacatt caatcgacca gcaattttat cgattacatt agcctgttta    540
gtaaaccaaa aaacacatta cccgtttgaa gttatcgtga cagatgatgg tagtcaggaa    600
gatctatcac cgatcattcg ccaatatgaa aataaattgg atattcgcta cgtcagacaa    660
aaagataacg gttttcaagc cagtgccgct cggaatatgg gattacgctt agcaaaatat    720
gactttattg gcttactcga ctgtgatatg gcgccaaatc cattatgggt tcattcttat    780
gttgcagagc tattagaaga tgatgattta acaatcattg gtccaagaaa atacatcgat    840
acacaacata ttgacccaaa agacttctta aataacgcga gtttgcttga atcattacca    900
gaagtgaaaa ccaataatag tgttgccgca aaaggggaag gaacagtttc tctggattgg    960
cgcttagaac aattcgaaaa aacagaaaat ctccgcttat ccgattcgcc tttccgtttt   1020
tttgcggcgg gtaatgttgc tttcgctaaa aaatggctaa ataaatccgg tttctttgat   1080
gaggaattta atcactgggg tggacaagat gtggaatttg gatatcgctt attccgttac   1140
ggtagtttct ttaaaactat tgatggcatt atggcctacc atcaagagcc accaggtaaa   1200
gaaaatgaaa ccgatcgtga agcgggaaaa aatattacgc tcgatattat gagagaaaag   1260
gtcccttata tctatagaaa acttttacca atagaagatt cgcatatcaa tagagtacct   1320
ttagtttcaa tttatatccc agcttataac tgtgcaaact atattcaacg ttgcgtagat   1380
agtgcactga atcagactgt tgttgatctc gaggtttgta tttgtaacga tggttcaaca   1440
gataatacct tagaagtgat caataagctt tatggtaata atcctagggt acgcatcatg   1500
tctaaaccaa atggcggaat agcctcagca tcaaatgcag ccgtttcttt tgctaaaggt   1560
tattacattg ggcagttaga ttcagatgat tatcttgagc ctgatgcagt tgaactgtgt   1620
ttaaaagaat ttttaaaaga taaaacgcta gcttgtgttt ataccactaa tagaaacgtc   1680
aatccggatg gtagcttaat cgctaatggt tacaattggc cagaattttc acgagaaaaa   1740
ctcacaacgg ctatgattgc tcaccacttt agaatgttca cgattagagc ttggcattta   1800
actgatggat tcaatgaaaa aattgaaaat gccgtagact atgacatgtt cctcaaactc   1860
agtgaagttg gaaaatttaa acatcttaat aaaatctgct ataaccgtgt attacatggt   1920
gataacacat caattaagaa acttggcatt caaaagaaaa accattttgt tgtagtcaat   1980
cagtcattaa atagacaagg cataacttat tataattatg acgaatttga tgatttagat   2040
gaaagtagaa agtatatttt caataaaacc gctgaatatc aagaagagat tgatatctta   2100
aaagatattt aa                                                       2112
```

<210> SEQ ID NO 47
<211> LENGTH: 2112
<212> TYPE: DNA
<213> ORGANISM: Pasteurella multocida

<400> SEQUENCE: 47

```
atgaatacat tatcacaagc aataaaagca tataacagca atgactatca attagcactc     60
aaattatttg aaaagtcggc ggaaatctat ggacggaaaa ttgttgaatt tcaaattacc    120
aaatgcaaag aaaaactctc agcacatcct tctgttaatt cagcacatct ttctgtaaat    180
aaagaagaaa aagtcaatgt ttgcgatagt ccgttagata ttgcaacaca actgttactt    240
```

-continued

```
tccaacgtaa aaaaattagt actttctgac tcggaaaaaa acacgttaaa aaataaatgg    300

aaattgctca ctgagaagaa atctgaaaat gcggaggtaa gagcggtcgc ccttgtacca    360

aaagattttc ccaaagatct ggttttagcg cctttacctg atcatgttaa tgattttaca    420

tggtacaaaa agcgaaagaa aagacttggc ataaaacctg aacatcaaca tgttggtctt    480

tctattatcg ttacaacatt caatcgacca gcaattttat cgattacatt agcctgttta    540

gtaaaccaaa aaacacatta cccgtttgaa gttatcgtga cagatgatgg tagtcaggaa    600

gatctatcac cgatcattcg ccaatatgaa aataaattgg atattcgcta cgtcagacaa    660

aaagataacg gttttcaagc cagtgccgct cggaatatgg gattacgctt agcaaaatat    720

gactttattg gcttactcga ctgtgatatg gcgccaaatc cattatgggt tcattcttat    780

gttgcagagc tattagaaga tgatgattta acaatcattg gtccaagaaa atacatcgat    840

acacaacata ttgacccaaa agacttctta aataacgcga gtttgcttga atcattacca    900

gaagtgaaaa ccaataatag tgttgccgca aaaggggaag gaacagtttc tctggattgg    960

cgcttagaac aattcgaaaa aacagaaaat ctccgcttat ccgattcgcc tttccgtttt   1020

tttgcggcgg gtaatgttgc tttcgctaaa aaatggctaa ataaatccgg tttctttgat   1080

gaggaattta atcactgggg tggacacgat gtggaatttg gatatcgctt attccgttac   1140

ggtagtttct ttaaaactat tgatggcatt atggcctacc atcaagagcc accaggtaaa   1200

gaaaatgaaa ccgatcgtga agcgggaaaa aatattacgc tcgatattat gagagaaaag   1260

gtcccttata tctatagaaa acttttacca atagaagatt cgcatatcaa tagagtacct   1320

ttagtttcaa tttatatccc agcttataac tgtgcaaact atattcaacg ttgcgtagat   1380

agtgcactga atcagactgt tgttgatctc gaggtttgta tttgtaacga tggttcaaca   1440

gataatacct tagaagtgat caataagctt tatggtaata atcctagggt acgcatcatg   1500

tctaaaccaa atggcggaat agcctcagca tcaaatgcag ccgtttcttt tgctaaaggt   1560

tattacattg ggcagttaga ttcagatgat tatcttgagc ctgatgcagt tgaactgtgt   1620

ttaaaagaat ttttaaaaga taaaacgcta gcttgtgttt ataccactaa tagaaacgtc   1680

aatccggatg gtagcttaat cgctaatggt tacaattggc cagaattttc acgagaaaaa   1740

ctcacaacgg ctatgattgc tcaccacttt agaatgttca cgattagagc ttggcattta   1800

actgatggat tcaatgaaaa aattgaaaat gccgtagact atgacatgtt cctcaaactc   1860

agtgaagttg gaaaatttaa acatcttaat aaaatctgct ataaccgtgt attacatggt   1920

gataacacat caattaagaa acttggcatt caaaagaaaa accattttgt tgtagtcaat   1980

cagtcattaa atagacaagg cataacttat tataattatg acgaatttga tgatttagat   2040

gaaagtagaa agtatatttt caataaaacc gctgaatatc aagaagagat tgatatctta   2100

aaagatattt aa                                                       2112
```

```
<210> SEQ ID NO 48
<211> LENGTH: 2112
<212> TYPE: DNA
<213> ORGANISM: Pasteurella multocida

<400> SEQUENCE: 48

atgaatacat tatcacaagc aataaaagca tataacagca atgactatca attagcactc     60

aaattatttg aaaagtcggc ggaaatctat ggacggaaaa ttgttgaatt tcaaattacc    120

aaatgcaaag aaaaactctc agcacatcct tctgttaatt cagcacatct ttctgtaaat    180

aaagaagaaa aagtcaatgt ttgcgatagt ccgttagata ttgcaacaca actgttactt    240
```

```
tccaacgtaa aaaaattagt actttctgac tcggaaaaaa acacgttaaa aaataaatgg    300
aaattgctca ctgagaagaa atctgaaaat gcggaggtaa gagcggtcgc ccttgtacca    360
aaagattttc ccaaagatct ggttttagcg cctttacctg atcatgttaa tgattttaca    420
tggtacaaaa agcgaaagaa aagacttggc ataaaacctg aacatcaaca tgttggtctt    480
tctattatcg ttacaacatt caatcgacca gcaattttat cgattacatt agcctgttta    540
gtaaaccaaa aaacacatta cccgtttgaa gttatcgtga cagatgatgg tagtcaggaa    600
gatctatcac cgatcattcg ccaatatgaa aataaattgg atattcgcta cgtcagacaa    660
aaagataacg gttttcaagc cagtgccgct cggaatatgg gattacgctt agcaaaatat    720
gactttattg gcttactcga ctgtgatatg gcgccaaatc cattatgggt tcattcttat    780
gttgcagagc tattagaaga tgatgattta acaatcattg gtccaagaaa atacatcgat    840
acacaacata ttgacccaaa agacttctta aataacgcga gtttgcttga atcattacca    900
gaagtgaaaa ccaataatag tgttgccgca aaaggggaag gaacagtttc tctggattgg    960
cgcttagaac aattcgaaaa aacagaaaat ctccgcttat ccgattcgcc tttccgtttt   1020
tttgcggcgg gtaatgttgc tttcgctaaa aaatggctaa ataaatccgg tttctttgat   1080
gaggaattta atcactgggg tggagaagaa gtggaatttg gatatcgctt attccgttac   1140
ggtagtttct ttaaaactat tgatggcatt atggcctacc atcaagagcc accaggtaaa   1200
gaaaatgaaa ccgatcgtga agcgggaaaa aatattacgc tcgatattat gagagaaaag   1260
gtcccttata tctatagaaa acttttacca atagaagatt cgcatatcaa tagagtacct   1320
ttagtttcaa tttatatccc agcttataac tgtgcaaact atattcaacg ttgcgtagat   1380
agtgcactga atcagactgt tgttgatctc gaggtttgta tttgtaacga tggttcaaca   1440
gataatacct tagaagtgat caataagctt tatggtaata atcctagggt acgcatcatg   1500
tctaaaccaa atggcggaat agcctcagca tcaaatgcag ccgtttcttt tgctaaaggt   1560
tattacattg ggcagttaga ttcagatgat tatcttgagc ctgatgcagt tgaactgtgt   1620
ttaaaagaat ttttaaaaga taaaacgcta gcttgtgttt ataccactaa tagaaacgtc   1680
aatccggatg gtagcttaat cgctaatggt tacaattggc cagaattttc acgagaaaaa   1740
ctcacaacgg ctatgattgc tcaccacttt agaatgttca cgattagagc ttggcattta   1800
actgatggat tcaatgaaaa aattgaaaat gccgtagact atgacatgtt cctcaaactc   1860
agtgaagttg gaaaatttaa acatcttaat aaaatctgct ataaccgtgt attacatggt   1920
gataacacat caattaagaa acttggcatt caaaagaaaa accattttgt tgtagtcaat   1980
cagtcattaa atagacaagg cataacttat tataattatg acgaatttga tgatttagat   2040
gaaagtagaa agtatatttt caataaaacc gctgaatatc aagaagagat tgatatctta   2100
aaagatattt aa                                                       2112
```

<210> SEQ ID NO 49
<211> LENGTH: 2112
<212> TYPE: DNA
<213> ORGANISM: Pasteurella multocida

<400> SEQUENCE: 49

```
atgaatacat tatcacaagc aataaaagca tataacagca atgactatca attagcactc     60
aaattatttg aaaagtcggc ggaaatctat ggacggaaaa ttgttgaatt tcaaattacc    120
aaatgcaaag aaaaactctc agcacatcct tctgttaatt cagcacatct ttctgtaaat    180
```

-continued

```
aaagaagaaa aagtcaatgt ttgcgatagt ccgttagata ttgcaacaca actgttactt    240

tccaacgtaa aaaaattagt actttctgac tcggaaaaaa acacgttaaa aaataaatgg    300

aaattgctca ctgagaagaa atctgaaaat gcggaggtaa gagcggtcgc ccttgtacca    360

aaagattttc ccaaagatct ggttttagcg cctttacctg atcatgttaa tgattttaca    420

tggtacaaaa agcgaaagaa aagacttggc ataaaacctg aacatcaaca tgttggtctt    480

tctattatcg ttacaacatt caatcgacca gcaattttat cgattacatt agcctgttta    540

gtaaaccaaa aaacacatta cccgtttgaa gttatcgtga cagatgatgg tagtcaggaa    600

gatctatcac cgatcattcg ccaatatgaa aataaattgg atattcgcta cgtcagacaa    660

aaagataacg gttttcaagc cagtgccgct cggaatatgg gattacgctt agcaaaatat    720

gactttattg gcttactcga ctgtgatatg gcgccaaatc cattatgggt tcattcttat    780

gttgcagagc tattagaaga tgatgattta acaatcattg gtccaagaaa atacatcgat    840

acacaacata ttgacccaaa agacttctta aataacgcga gtttgcttga atcattacca    900

gaagtgaaaa ccaataatag tgttgccgca aaaggggaag gaacagtttc tctggattgg    960

cgcttagaac aattcgaaaa aacagaaaat ctccgcttat ccgattcgcc tttccgtttt   1020

tttgcggcgg gtaatgttgc tttcgctaaa aaatggctaa ataaatccgg tttctttgat   1080

gaggaattta atcactgggg tggagaaaat gtggaatttg gatatcgctt attccgttac   1140

ggtagtttct ttaaaactat tgatggcatt atggcctacc atcaagagcc accaggtaaa   1200

gaaaatgaaa ccgatcgtga agcgggaaaa aatattacgc tcgatattat gagagaaaag   1260

gtcccttata tctatagaaa acttttacca atagaagatt cgcatatcaa tagagtacct   1320

ttagtttcaa tttatatccc agcttataac tgtgcaaact atattcaacg ttgcgtagat   1380

agtgcactga atcagactgt tgttgatctc gaggtttgta tttgtaacga tggttcaaca   1440

gataatacct tagaagtgat caataagctt tatggtaata atcctagggt acgcatcatg   1500

tctaaaccaa atggcggaat agcctcagca tcaaatgcag ccgtttcttt tgctaaaggt   1560

tattacattg ggcagttaga ttcagatgat tatcttgagc ctgatgcagt tgaactgtgt   1620

ttaaaagaat ttttaaaaga taaaacgcta gcttgtgttt ataccactaa tagaaacgtc   1680

aatccggatg gtagcttaat cgctaatggt tacaattggc cagaattttc acgagaaaaa   1740

ctcacaacgg ctatgattgc tcaccacttt agaatgttca cgattagagc ttggcattta   1800

actgatggat tcaatgaaaa aattgaaaat gccgtagact atgacatgtt cctcaaactc   1860

agtgaagttg gaaaatttaa acatcttaat aaaatctgct ataaccgtgt attacatggt   1920

gataacacat caattaagaa acttggcatt caaaagaaaa accattttgt tgtagtcaat   1980

cagtcattaa atagacaagg cataacttat tataattatg acgaatttga tgatttagat   2040

gaaagtagaa agtatatttt caataaaacc gctgaatatc aagaagagat tgatatctta   2100

aaagatattt aa                                                       2112
```

<210> SEQ ID NO 50
<211> LENGTH: 2112
<212> TYPE: DNA
<213> ORGANISM: Pasteurella multocida

<400> SEQUENCE: 50

```
atgaatacat tatcacaagc aataaaagca tataacagca atgactatca attagcactc     60

aaattatttg aaaagtcggc ggaaatctat ggacggaaaa ttgttgaatt tcaaattacc    120

aaatgcaaag aaaaactctc agcacatcct tctgttaatt cagcacatct ttctgtaaat    180
```

-continued aaagaagaaa aagtcaatgt ttgcgatagt ccgttagata ttgcaacaca actgttactt 240
tccaacgtaa aaaaattagt actttctgac tcggaaaaaa acacgttaaa aaataaatgg 300
aaattgctca ctgagaagaa atctgaaaat gcggaggtaa gagcggtcgc ccttgtacca 360 aaagatttc ccaaagatct ggttttagcg cctttacctg atcatgttaa tgattttaca 420
tggtacaaaa agcgaaagaa aagacttggc ataaaacctg aacatcaaca tgttggtctt 480
tctattatcg ttacaacatt caatcgacca gcaattttat cgattacatt agcctgttta 540
gtaaaccaaa aaacacatta cccgtttgaa gttatcgtga cagatgatgg tagtcaggaa 600
gatctatcac cgatcattcg ccaatatgaa aataaattgg atattcgcta cgtcagacaa 660
aaagataacg gttttcaagc cagtgccgct cggaatatgg gattacgctt agcaaaatat 720
gactttattg gcttactcga ctgtgatatg gcgccaaatc cattatgggt tcattcttat 780
gttgcagagc tattagaaga tgatgattta acaatcattg gtccaagaaa atacatcgat 840
acacaacata ttgacccaaa agacttctta aataacgcga gtttgcttga atcattacca 900
gaagtgaaaa ccaataatag tgttgccgca aaaggggaag gaacagtttc tctggattgg 960
cgcttagaac aattcgaaaa aacagaaaat ctccgcttat ccgattcgcc tttccgtttt 1020
tttgcggcgg gtaatgttgc tttcgctaaa aaatggctaa ataaatccgg tttctttgat 1080
gaggaattta atcactgggg tggagaaaaa gtggaatttg gatatcgctt attccgttac 1140
ggtagtttct ttaaaactat tgatggcatt atggcctacc atcaagagcc accaggtaaa 1200
gaaaatgaaa ccgatcgtga agcgggaaaa aatattacgc tcgatattat gagagaaaag 1260
gtcccttata tctatagaaa acttttacca atagaagatt cgcatatcaa tagagtacct 1320
ttagtttcaa tttatatccc agcttataac tgtgcaaact atattcaacg ttgcgtagat 1380
agtgcactga atcagactgt tgttgatctc gaggtttgta tttgtaacga tggttcaaca 1440
gataatacct tagaagtgat caataagctt tatggtaata atcctagggt acgcatcatg 1500
tctaaaccaa atggcggaat agcctcagca tcaaatgcag ccgtttcttt tgctaaaggt 1560
tattacattg ggcagttaga ttcagatgat tatcttgagc ctgatgcagt tgaactgtgt 1620
ttaaaagaat ttttaaaaga taaaacgcta gcttgtgttt ataccactaa tagaaacgtc 1680
aatccggatg gtagcttaat cgctaatggt tacaattggc cagaattttc acgagaaaaa 1740
ctcacaacgg ctatgattgc tcaccacttt agaatgttca cgattagagc ttggcattta 1800
actgatggat tcaatgaaaa aattgaaaat gccgtagact atgacatgtt cctcaaactc 1860
agtgaagttg gaaaatttaa acatcttaat aaaatctgct ataaccgtgt attacatggt 1920
gataacacat caattaagaa acttggcatt caaaagaaaa accattttgt tgtagtcaat 1980
cagtcattaa atagacaagg cataacttat tataattatg acgaatttga tgatttagat 2040
gaaagtagaa agtatatttt caataaaacc gctgaatatc aagaagagat tgatatctta 2100
aaagatattt aa 2112

<210> SEQ ID NO 51
<211> LENGTH: 2136
<212> TYPE: DNA
<213> ORGANISM: Pasteurella multocida

<400> SEQUENCE: 51
atgaacacat tatcacaagc aataaaagca tataacagca atgactatca attagcactc 60
aaattatttg aaaagtcggc ggaaatctat ggacggaaaa ttgttgaatt tcaaattacc 120

-continued

```
aaatgccaag aaaaactctc agcacatcct tctgttaatt cagcacatct ttctgtaaat    180

aaagaagaaa aagtcaatgt ttgcgatagt ccgttagata ttgcaacaca actgttactt    240

tccaacgtaa aaaaattagt actttctgac tcggaaaaaa acacgttaaa aaataaatgg    300

aaattgctca ctgagaagaa atctgaaaat gcggaggtaa gagcggtcgc ccttgtacca    360

aaagattttc ccaaagatct ggttttagcg cctttacctg atcatgttaa tgattttaca    420

tggtacaaaa agcgaaagaa aagacttggc ataaaacctg aacatcaaca tgttggtctt    480

tctattatcg ttacaacatt caatcgacca gcaattttat cgattacatt agcctgttta    540

gtaaaccaaa aacacatta cccgtttgaa gttatcgtga cagatgatgg tagtcaggaa     600

gatctatcac cgatcattcg ccaatatgaa aataaattgg atattcgcta cgtcagacaa    660

aaagataacg gttttcaagc cagtgccgct cggaatatgg gattacgctt agcaaaatat    720

gactttattg gcttactcga ctgtgatatg gcgccaaatc cattatgggt tcattcttat    780

gttgcagagc tattagaaga tgatgattta acaatcattg gtccaagaaa atacatcgat    840

acacaacata ttgacccaaa agacttctta aataacgcga gtttgcttga atcattacca    900

gaagtgaaaa ccaataatag tgttgccgca aaaggggaag gaacagtttc tctggattgg    960

cgcttagaac aattcgaaaa aacagaaaat ctccgcttat ccgattcgcc tttccgtttt   1020

tttgcggcgg gtaatgttgc tttcgctaaa aaatggctaa ataaatccgg tttctttgat   1080

gaggaattta atcactgggg tggagaagat gtggaatttg gatatcgctt attccgttac   1140

ggtagtttct ttaaaactat tgatggcatt atggcctacc atcaagagcc accaggtaaa   1200

gaaaatgaaa ccgatcgtga agcgggaaaa aatattacgc tcgatattat gagagaaaag   1260

gtcccttata tctatagaaa acttttacca atagaagatt cgcatattca tagaatacct   1320

ttagtttcta tttatatccc cgcttataac tgtgcaaatt atattcaaag atgtgtagat   1380

agtgctctta atcaaactgt tgtcgatctc gaggtttgta tttgtaacga tggttcaaca   1440

gataatacct tagaagtgat caataagctt tatggtaata atcctagggt acgcatcatg   1500

tctaaaccaa atggcggaat agcctcagca tcaaatgcag ccgtttcttt tgctaaaggt   1560

tattacattg ggcagttaga ttcagatgat tatcttgagc ctgatgcagt tgaactgtgt   1620

ttaaaagaat ttttaaaaga taaaacgcta gcttgtgttt ataccactaa tagaaacgtc   1680

aatccggatg gtagcttaat cgctaatggt tacaattggc cagaattttc acgagaaaaa   1740

ctcacaacgg ctatgattgc tcaccatttt agaatgttta cgattagagc ttggcattta   1800

acggatggat ttaacgaaaa tattgaaaac gccgtggatt atgacatgtt ccttaaactc   1860

agtgaagttg gaaaatttaa acatcttaat aaaatctgct ataaccgcgt attacatggt   1920

gataacacat ccattaagaa actcggcatt caaaagaaaa accattttgt tgtagtcaat   1980

cagtcattaa atagacaagg catcaattat tataattatg acaaatttga tgatttagat   2040

gaaagtagaa agtatatctt caataaaacc gctgaatatc aagaagaaat ggatatttta   2100

aaagatctta aactcattca gaataaagat gcctaa                             2136
```

<210> SEQ ID NO 52
<211> LENGTH: 2091
<212> TYPE: DNA
<213> ORGANISM: Pasteurella multocida

<400> SEQUENCE: 52

```
atgaatacat tatcacaagc aataaaagca tataacagca atgactatga attagcactc     60

aaattatttg agaagtctgc tgaaacctac gggcgaaaaa tcgttgaatt ccaaattatc    120
```

-continued aaatgtaaag aaaaactctc gaccaattct tatgtaagtg aagataaaaa aaacagtgtt 180
tgcgatagct cattagatat cgcaacacag ctcttacttt ccaacgtaaa aaaattaact 240
ctatccgaat cagaaaaaaa cagtttaaaa aataaatgga aatctatcac tgggaaaaaa 300
tcggagaacg cagaaatcag aaaggtggaa ctagtaccca aagattttcc taaagatctt 360
gttcttgctc cattgccaga tcatgttaat gattttacat ggtacaaaaa tcgaaaaaaa 420
agcttaggta taaagcctgt aaataagaat atcggtcttt ctattattat tcctacattt 480
aatcgtagcc gtattttaga tataacgtta gcctgtttgg tcaatcagaa aacaaactac 540
ccatttgaag tcgttgttgc agatgatggt agtaaggaaa acttacttac cattgtgcaa 600
aaatacgaac aaaaacttga cataaagtat gtaagacaaa aagattatgg atatcaattg 660
tgtgcagtca gaaacttagg tttacgtaca gcaaagtatg attttgtctc gattctagac 720
tgcgatatgg caccacaaca attatgggtt cattcttatc ttacagaact attagaagac 780
aatgatattg ttttaattgg acctagaaaa tatgtggata ctcataatat taccgcagaa 840
caattcctta acgatccata tttaatagaa tcactacctg aaaccgctac aaataacaat 900
ccttcgatta catcaaaagg aaatatatcg ttggattgga gattagaaca tttcaaaaaa 960
accgataatc tacgtctatg tgattcaccg tttcgttatt ttagttgcgg taatgttgca 1020
ttttctaaag aatggctaaa taaagtaggt tggttcgatg aagaatttaa tcattggggg 1080
ggcgaagatg tagaatttgg ttacagatta tttgccaaag gctgtttttt cagagtaatt 1140
gacggcggaa tggcatacca tcaagaacca cctggtaaag aaaatgaaac agaccgcgaa 1200
gctggtaaaa gtattacgct taaaattgtg aaagaaaagg taccttacat ctatagaaaa 1260
cttttaccaa tagaagattc gcatatcaat agagtacctt tagtttcaat ttatatccca 1320
gcttataact gtgcaaacta tattcaacgt tgcgtagata gtgcactgaa tcagactgtt 1380
gttgatctcg aggtttgtat ttgtaacgat ggttcaacag ataatacctt agaagtgatc 1440
aataagcttt atggtaataa tcctagggta cgcatcatgt ctaaaccaaa tggcggaata 1500
gcctcagcat caaatgcagc cgtttctttt gctaaaggtt attacattgg gcagttagat 1560
tcagatgatt atcttgagcc tgatgcagtt gaactgtgtt taaaagaatt tttaaaagat 1620
aaaacgctag cttgtgttta taccactaat agaaacgtca atccggatgg tagcttaatc 1680
gctaatggtt acaattggcc agaattttca cgagaaaaac tcacaacggc tatgattgct 1740
caccacttta gaatgttcac gattagagct tggcatttaa ctgatggatt caatgaaaaa 1800
attgaaaatg ccgtagacta tgacatgttc ctcaaactca gtgaagttgg aaaatttaaa 1860
catcttaata aaatctgcta taaccgtgta ttacatggtg ataacacatc aattaagaaa 1920
cttggcattc aaaagaaaaa ccattttgtt gtagtcaatc agtcattaaa tagacaaggc 1980
ataacttatt ataattatga cgaatttgat gatttagatg aaagtagaaa gtatattttc 2040
aataaaaccg ctgaatatca agaagagatt gatatcttaa aagatattta a 2091

<210> SEQ ID NO 53
<211> LENGTH: 29
<212> TYPE: DNA
<213> ORGANISM: artificial sequence
<220> FEATURE:
<223> OTHER INFORMATION: primer P1

<400> SEQUENCE: 53
atgaacacat tatcacaagc aataaaagc 29

-continued

<210> SEQ ID NO 54
<211> LENGTH: 27
<212> TYPE: DNA
<213> ORGANISM: artificial sequence
<220> FEATURE:
<223> OTHER INFORMATION: primer P2
<220> FEATURE:
<221> NAME/KEY: misc_feature
<222> LOCATION: (23)..(23)
<223> OTHER INFORMATION: Y = C/T

<400> SEQUENCE: 54
gcgaatcttc tattggtaaa agytttc 27

<210> SEQ ID NO 55
<211> LENGTH: 26
<212> TYPE: DNA
<213> ORGANISM: artificial sequence
<220> FEATURE:
<223> OTHER INFORMATION: primer P3

<400> SEQUENCE: 55
cttttaccaa tagaagattc gcatat 26

<210> SEQ ID NO 56
<211> LENGTH: 33
<212> TYPE: DNA
<213> ORGANISM: artificial sequence
<220> FEATURE:
<223> OTHER INFORMATION: primer P4

<400> SEQUENCE: 56
gaagacgtct taggcatctt tattctgaat gag 33

<210> SEQ ID NO 57
<211> LENGTH: 43
<212> TYPE: DNA
<213> ORGANISM: artificial sequence
<220> FEATURE:
<223> OTHER INFORMATION: primer P5

<400> SEQUENCE: 57
gggaattctg cagttaaata tcttttaaga tatcaatctc ttc 43

<210> SEQ ID NO 58
<211> LENGTH: 33
<212> TYPE: DNA
<213> ORGANISM: artificial sequence
<220> FEATURE:
<223> OTHER INFORMATION: sense primer
<220> FEATURE:
<221> NAME/KEY: misc_feature
<222> LOCATION: (9)..(9)
<223> OTHER INFORMATION: inosine
<220> FEATURE:
<221> NAME/KEY: misc_feature
<222> LOCATION: (12)..(12)
<223> OTHER INFORMATION: inosine
<220> FEATURE:
<221> NAME/KEY: misc_feature
<222> LOCATION: (18)..(18)
<223> OTHER INFORMATION: inosine
<220> FEATURE:
<221> NAME/KEY: misc_feature
<222> LOCATION: (24)..(24)
<223> OTHER INFORMATION: inosine
<220> FEATURE:
<221> NAME/KEY: misc_feature
<222> LOCATION: (27)..(27)
<223> OTHER INFORMATION: inosine

<400> SEQUENCE: 58
garttybtnm rngarggnaa rgcnytntay gay 33

<210> SEQ ID NO 59
<211> LENGTH: 39
<212> TYPE: DNA
<213> ORGANISM: artificial sequence
<220> FEATURE:
<223> OTHER INFORMATION: antisense primer
<220> FEATURE:
<221> NAME/KEY: misc_feature
<222> LOCATION: (7)..(7)
<223> OTHER INFORMATION: inosine
<220> FEATURE:
<221> NAME/KEY: misc_feature
<222> LOCATION: (10)..(10)
<223> OTHER INFORMATION: inosine
<220> FEATURE:
<221> NAME/KEY: misc_feature
<222> LOCATION: (16)..(16)
<223> OTHER INFORMATION: inosine
<220> FEATURE:
<221> NAME/KEY: misc_feature
<222> LOCATION: (22)..(22)
<223> OTHER INFORMATION: inosine
<220> FEATURE:
<221> NAME/KEY: misc_feature
<222> LOCATION: (25)..(25)
<223> OTHER INFORMATION: A, G, C or T

<400> SEQUENCE: 59
rcartanccn ccrtanccra answnggrtt rttrtartg 39

<210> SEQ ID NO 60
<211> LENGTH: 30
<212> TYPE: DNA
<213> ORGANISM: artificial sequence
<220> FEATURE:
<223> OTHER INFORMATION: 2nd antisense primer

<400> SEQUENCE: 60
tatatttaca gcagtatcat tttctaaagg 30

<210> SEQ ID NO 61
<211> LENGTH: 501
<212> TYPE: PRT
<213> ORGANISM: Pasteurella multocida

<400> SEQUENCE: 61

Met Ser Leu Phe Lys Arg Ala Thr Glu Leu Phe Lys Ser Gly Asn Tyr
1 5 10 15

Lys Asp Ala Leu Thr Leu Tyr Glu Asn Ile Ala Lys Ile Tyr Gly Ser
20 25 30

Glu Ser Leu Val Lys Tyr Asn Ile Asp Ile Cys Lys Lys Asn Ile Thr
35 40 45

Gln Ser Lys Ser Asn Lys Ile Glu Glu Asp Asn Ile Ser Gly Glu Asn
50 55 60

Glu Phe Ser Val Ser Ile Lys Asp Leu Tyr Asn Glu Ile Ser Asn Ser
65 70 75 80

Glu Leu Gly Ile Thr Lys Glu Arg Leu Gly Ala Pro Pro Leu Val Ser
85 90 95

Ile Ile Met Thr Ser His Asn Thr Glu Lys Phe Ile Glu Ala Ser Ile
100 105 110

Asn Ser Leu Leu Leu Gln Thr Tyr Asn Asn Leu Glu Val Ile Val Val

-continued

```
        115                 120                 125

Asp Asp Tyr Ser Thr Asp Lys Thr Phe Gln Ile Ala Ser Arg Ile Ala
    130                 135                 140

Asn Ser Thr Ser Lys Val Lys Thr Phe Arg Leu Asn Ser Asn Leu Gly
145                 150                 155                 160

Thr Tyr Phe Ala Lys Asn Thr Gly Ile Leu Lys Ser Lys Gly Asp Ile
                165                 170                 175

Ile Phe Phe Gln Asp Ser Asp Asp Val Cys His His Glu Arg Ile Glu
            180                 185                 190

Arg Cys Val Asn Ala Leu Leu Ser Asn Lys Asp Asn Ile Ala Val Arg
        195                 200                 205

Cys Ala Tyr Ser Arg Ile Asn Leu Glu Thr Gln Asn Ile Ile Lys Val
    210                 215                 220

Asn Asp Asn Lys Tyr Lys Leu Gly Leu Ile Thr Leu Gly Val Tyr Arg
225                 230                 235                 240

Lys Val Phe Asn Glu Ile Gly Phe Phe Asn Cys Thr Thr Lys Ala Ser
                245                 250                 255

Asp Asp Glu Phe Tyr His Arg Ile Ile Lys Tyr Tyr Gly Lys Asn Arg
            260                 265                 270

Ile Asn Asn Leu Phe Leu Pro Leu Tyr Tyr Asn Thr Met Arg Glu Asp
        275                 280                 285

Ser Leu Phe Ser Asp Met Val Glu Trp Val Asp Glu Asn Asn Ile Lys
    290                 295                 300

Gln Lys Thr Ser Asp Ala Arg Gln Asn Tyr Leu His Glu Phe Gln Lys
305                 310                 315                 320

Ile His Asn Glu Arg Lys Phe Asn Glu Leu Lys Glu Ile Phe Ser Phe
                325                 330                 335

Pro Arg Ile His Asp Ala Leu Pro Ile Ser Lys Glu Met Ser Lys Leu
            340                 345                 350

Ser Asn Pro Lys Ile Pro Val Tyr Ile Asn Ile Cys Ser Ile Pro Ser
        355                 360                 365

Arg Ile Lys Gln Leu Gln Tyr Thr Ile Gly Val Leu Lys Asn Gln Cys
    370                 375                 380

Asp His Phe His Ile Tyr Leu Asp Gly Tyr Pro Glu Val Pro Asp Phe
385                 390                 395                 400

Ile Lys Lys Leu Gly Asn Lys Ala Thr Val Ile Asn Cys Gln Asn Lys
                405                 410                 415

Asn Glu Ser Ile Arg Asp Asn Gly Lys Phe Ile Leu Leu Glu Lys Leu
            420                 425                 430

Ile Lys Glu Asn Lys Asp Gly Tyr Tyr Ile Thr Cys Asp Asp Asp Ile
        435                 440                 445

Arg Tyr Pro Ala Asp Tyr Ile Asn Thr Met Ile Lys Lys Ile Asn Lys
    450                 455                 460

Tyr Asn Asp Lys Ala Ala Ile Gly Leu His Gly Val Ile Phe Pro Ser
465                 470                 475                 480

Arg Val Asn Lys Tyr Phe Ser Ser Asp Arg Ile Val Tyr Asn Phe Gln
                485                 490                 495

Lys Thr Phe Arg Lys
            500
```

<210> SEQ ID NO 62
<211> LENGTH: 1510
<212> TYPE: DNA
<213> ORGANISM: Pasteurella multocida -continued

<400> SEQUENCE: 62
aatgagctta tttaaacgtg ctactgagct atttaagtca ggaaactata aagatgcact 60
aactctatat gaaaatatag ctaaaattta tggttcagaa agccttgtta aatataatat 120
tgatatatgt aaaaaaaata taacacaatc aaaaagtaat aaaatagaag aagataatat 180
ttctggagaa aacgaatttt cagtatcaat aaaagatcta tataacgaaa taagcaatag 240
tgaattaggg attacaaaag aaagactagg agcccccccct ctagtcagta ttataatgac 300
ttctcataat acagaaaaat tcattgaagc ctcaattaat tcactattat tgcaaacata 360
caataactta gaagttatcg ttgtagatga ttatagcaca gataaaacat ttcagatcgc 420
atccagaata gcaaactcta caagtaaagt aaaaacattc cgattaaact caaatctagg 480
gacatacttt gcgaaaaata caggaatttt aaagtctaaa ggagatatta ttttctttca 540
ggatagcgat gatgtatgtc accatgaaag aatcgaaaga tgtgttaatg cattattatc 600
gaataaagat aatatagctg ttagatgtgc atattctaga ataaatctag aaacacaaaa 660
tataataaaa gttaatgata ataaatacaa attaggatta ataactttag gcgtttatag 720
aaaagtattt aatgaaattg gtttttttaa ctgcacaacc aaagcatcgg atgatgaatt 780
ttatcataga ataattaaat actatggtaa aaataggata aataacttat ttctaccact 840
gtattataac acaatgcgtg aagattcatt attttctgat atggttgagt gggtagatga 900
aaataatata aagcaaaaaa cctctgatgc tagacaaaat tatctccatg aattccaaaa 960
aatacacaat gaaaggaaat ttaatgaatt aaaagagatt tttagctttc ctagaattca 1020
tgacgcctta cctatatcaa aagaaatgag taagctcagc aaccctaaaa ttcctgttta 1080
tataaatata tgctcaatac cttcaagaat aaaacaactt caatacacta ttggagtact 1140
aaaaaaccaa tgcgatcatt ttcatattta tcttgatgga tatccagaag tacctgattt 1200
tataaaaaaa ctagggaata aagcgaccgt tattaattgt caaaacaaaa atgagtctat 1260
tagagataat ggaaagttta ttctattaga aaaacttata aaggaaaata aagatggata 1320
ttatataact tgtgatgatg atatccggta tcctgctgac tacataaaca ctatgataaa 1380
aaaaattaat aaatacaatg ataaagcagc aattggatta catggtgtta tattcccaag 1440
tagagtcaac aagtattttt catcagacag aattgtctat aattttcaaa aaacctttag 1500
aaaatgatac 1510

<210> SEQ ID NO 63
<211> LENGTH: 238
<212> TYPE: PRT
<213> ORGANISM: Escherichia coli

<400> SEQUENCE: 63

Met Ile Val Ala Asn Met Ser Ser Tyr Pro Pro Arg Lys Lys Glu Leu
1 5 10 15

Val His Ser Ile Gln Ser Leu His Ala Gln Val Asp Lys Ile Asn Leu
20 25 30

Cys Leu Asn Glu Phe Glu Glu Ile Pro Glu Glu Leu Asp Gly Phe Ser
35 40 45

Lys Leu Asn Pro Val Ile Pro Asp Lys Asp Tyr Lys Asp Val Gly Lys
50 55 60

Phe Ile Phe Pro Cys Ala Lys Asn Asp Met Ile Val Leu Thr Asp Asp
65 70 75 80

Asp Ile Ile Tyr Pro Pro Asp Tyr Val Glu Lys Met Leu Asn Phe Tyr

-continued

```
                85                  90                  95

Asn Ser Phe Ala Ile Phe Asn Cys Ile Val Gly Ile His Gly Cys Ile
            100                 105                 110

Tyr Ile Asp Ala Phe Asp Gly Asp Gln Ser Lys Arg Lys Val Phe Ser
        115                 120                 125

Phe Thr Gln Gly Leu Leu Arg Pro Arg Val Val Asn Gln Leu Gly Thr
    130                 135                 140

Gly Thr Val Phe Leu Lys Ala Asp Gln Leu Pro Ser Leu Lys Tyr Met
145                 150                 155                 160

Asp Gly Ser Gln Arg Phe Val Asp Val Arg Phe Ser Arg Tyr Met Leu
                165                 170                 175

Glu Asn Glu Ile Gly Met Ile Cys Val Pro Arg Glu Lys Asn Trp Leu
            180                 185                 190

Arg Glu Val Ser Ser Gly Ser Met Glu Gly Leu Trp Asn Thr Phe Thr
        195                 200                 205

Lys Lys Trp Pro Leu Asp Ile Ile Lys Glu Thr Gln Ala Ile Ala Gly
    210                 215                 220

Tyr Ser Lys Leu Asn Leu Glu Leu Val Tyr Asn Val Glu Gly
225                 230                 235


<210> SEQ ID NO 64
<211> LENGTH: 520
<212> TYPE: PRT
<213> ORGANISM: Escherichia coli

<400> SEQUENCE: 64

Met Asn Ala Glu Tyr Ile Asn Leu Val Glu Arg Lys Lys Lys Leu Gly
1               5                   10                  15

Thr Asn Ile Gly Ala Leu Asp Phe Leu Leu Ser Ile His Lys Glu Lys
            20                  25                  30

Val Asp Leu Gln His Lys Asn Ser Pro Leu Lys Gly Asn Asp Asn Leu
        35                  40                  45

Ile His Lys Arg Ile Asn Glu Tyr Asp Asn Val Leu Glu Leu Ser Lys
    50                  55                  60

Asn Val Ser Ala Gln Asn Ser Gly Asn Glu Phe Ser Tyr Leu Leu Gly
65                  70                  75                  80

Tyr Ala Asp Ser Leu Arg Lys Val Gly Met Leu Asp Thr Tyr Ile Lys
                85                  90                  95

Ile Val Cys Tyr Leu Thr Ile Gln Ser Arg Tyr Phe Lys Asn Gly Glu
            100                 105                 110

Arg Val Lys Leu Phe Glu His Ile Ser Asn Ala Leu Arg Tyr Ser Arg
        115                 120                 125

Ser Asp Phe Leu Ile Asn Leu Ile Phe Glu Arg Tyr Ile Glu Tyr Ile
    130                 135                 140

Asn His Leu Lys Leu Ser Pro Lys Gln Lys Asp Phe Tyr Phe Cys Thr
145                 150                 155                 160

Lys Phe Ser Lys Phe His Asp Tyr Thr Lys Asn Gly Tyr Lys Tyr Leu
                165                 170                 175

Ala Phe Asp Asn Gln Ala Asp Ala Gly Tyr Gly Leu Thr Leu Leu Leu
            180                 185                 190

Asn Ala Asn Asp Asp Met Gln Asp Ser Tyr Asn Leu Leu Pro Glu Gln
        195                 200                 205

Glu Leu Phe Ile Cys Asn Ala Val Ile Asp Asn Met Asn Ile Tyr Arg
    210                 215                 220
```

-continued

Ser Gln Phe Asn Lys Cys Leu Arg Lys Tyr Asp Leu Ser Glu Ile Thr
225 230 235 240

Asp Ile Tyr Pro Asn Lys Ile Ile Leu Gln Gly Ile Lys Phe Asp Lys
245 250 255

Lys Lys Asn Val Tyr Gly Lys Asp Leu Val Ser Ile Ile Met Ser Val
260 265 270

Phe Asn Ser Glu Asp Thr Ile Ala Tyr Ser Leu His Ser Leu Leu Asn
275 280 285

Gln Thr Tyr Glu Asn Ile Glu Ile Leu Val Cys Asp Asp Cys Ser Ser
290 295 300

Asp Lys Ser Leu Glu Ile Ile Lys Ser Ile Ala Tyr Ser Ser Ser Arg
305 310 315 320

Val Lys Val Tyr Ser Ser Arg Lys Asn Gln Gly Pro Tyr Asn Ile Arg
325 330 335

Asn Glu Leu Ile Lys Lys Ala His Gly Asn Phe Ile Thr Phe Gln Asp
340 345 350

Ala Asp Asp Leu Ser His Pro Glu Arg Ile Gln Arg Gln Val Glu Val
355 360 365

Leu Arg Asn Asn Lys Ala Val Ile Cys Met Ala Asn Trp Ile Arg Val
370 375 380

Ala Ser Asn Gly Lys Ile Gln Phe Phe Tyr Asp Asp Lys Ala Thr Arg
385 390 395 400

Met Ser Val Val Ser Ser Met Ile Lys Lys Asp Ile Phe Ala Thr Val
405 410 415

Gly Gly Tyr Arg Gln Ser Leu Ile Gly Ala Asp Thr Glu Phe Tyr Glu
420 425 430

Thr Val Ile Met Arg Tyr Gly Arg Glu Ser Ile Val Arg Leu Leu Gln
435 440 445

Pro Leu Ile Leu Gly Leu Trp Gly Asp Ser Gly Leu Thr Arg Asn Lys
450 455 460

Gly Thr Glu Ala Leu Pro Asp Gly Tyr Ile Ser Gln Ser Arg Arg Glu
465 470 475 480

Tyr Ser Asp Ile Ala Ala Arg Gln Arg Val Leu Gly Lys Ser Ile Val
485 490 495

Ser Asp Lys Asp Val Arg Gly Leu Leu Ser Arg Tyr Gly Leu Phe Lys
500 505 510

Asp Val Ser Gly Ile Ile Glu Gln
515 520

<210> SEQ ID NO 65
<211> LENGTH: 746
<212> TYPE: PRT
<213> ORGANISM: Mus musculus

<400> SEQUENCE: 65

Met Gln Ala Lys Lys Arg Tyr Phe Ile Leu Leu Ser Ala Gly Ser Cys
1 5 10 15

Leu Ala Leu Leu Phe Tyr Phe Gly Gly Val Gln Phe Arg Ala Ser Arg
20 25 30

Ser His Ser Arg Arg Glu Glu His Ser Gly Arg Asn Gly Leu His Gln
35 40 45

Pro Ser Pro Asp His Phe Trp Pro Arg Phe Pro Asp Ala Leu Arg Pro
50 55 60

Phe Phe Pro Trp Asp Gln Leu Glu Asn Glu Asp Ser Ser Val His Ile
65 70 75 80

-continued

```
Ser Pro Arg Gln Lys Arg Asp Ala Asn Ser Ser Ile Tyr Lys Gly Lys
                85                  90                  95

Lys Cys Arg Met Glu Ser Cys Phe Asp Phe Thr Leu Cys Lys Lys Asn
            100                 105                 110

Gly Phe Lys Val Tyr Val Tyr Pro Gln Gln Lys Gly Glu Lys Ile Ala
        115                 120                 125

Glu Ser Tyr Gln Asn Ile Leu Ala Ala Ile Glu Gly Ser Arg Phe Tyr
    130                 135                 140

Thr Ser Asp Pro Ser Gln Ala Cys Leu Phe Val Leu Ser Leu Asp Thr
145                 150                 155                 160

Leu Asp Arg Asp Gln Leu Ser Pro Gln Tyr Val His Asn Leu Arg Ser
                165                 170                 175

Lys Val Gln Ser Leu His Leu Trp Asn Asn Gly Arg Asn His Leu Ile
            180                 185                 190

Phe Asn Leu Tyr Ser Gly Thr Trp Pro Asp Tyr Thr Glu Asp Val Gly
        195                 200                 205

Phe Asp Ile Gly Gln Ala Met Leu Ala Lys Ala Ser Ile Ser Thr Glu
    210                 215                 220

Asn Phe Arg Pro Asn Phe Asp Val Ser Ile Pro Leu Phe Ser Lys Asp
225                 230                 235                 240

His Pro Arg Thr Gly Gly Glu Arg Gly Phe Leu Lys Phe Asn Thr Ile
                245                 250                 255

Pro Pro Leu Arg Lys Tyr Met Leu Val Phe Lys Gly Lys Arg Tyr Leu
            260                 265                 270

Thr Gly Ile Gly Ser Asp Thr Arg Asn Ala Leu Tyr His Val His Asn
        275                 280                 285

Gly Glu Asp Val Leu Leu Leu Thr Thr Cys Lys His Gly Lys Asp Trp
    290                 295                 300

Gln Lys His Lys Asp Ser Arg Cys Asp Arg Asp Asn Thr Glu Tyr Glu
305                 310                 315                 320

Lys Tyr Asp Tyr Arg Glu Met Leu His Asn Ala Thr Phe Cys Leu Val
                325                 330                 335

Pro Arg Gly Arg Arg Leu Gly Ser Phe Arg Phe Leu Glu Ala Leu Gln
            340                 345                 350

Ala Ala Cys Val Pro Val Met Leu Ser Asn Gly Trp Glu Leu Pro Phe
        355                 360                 365

Ser Glu Val Ile Asn Trp Asn Gln Ala Ala Val Ile Gly Asp Glu Arg
    370                 375                 380

Leu Leu Leu Gln Ile Pro Ser Thr Ile Arg Ser Ile His Gln Asp Lys
385                 390                 395                 400

Ile Leu Ala Leu Arg Gln Gln Thr Gln Phe Leu Trp Glu Ala Tyr Phe
                405                 410                 415

Ser Ser Val Glu Lys Ile Val Leu Thr Thr Leu Glu Ile Ile Gln Asp
            420                 425                 430

Arg Ile Phe Lys His Ile Ser Arg Asn Ser Leu Ile Trp Asn Lys His
        435                 440                 445

Pro Gly Gly Leu Phe Val Leu Pro Gln Tyr Ser Ser Tyr Leu Gly Asp
    450                 455                 460

Phe Pro Tyr Tyr Tyr Ala Asn Leu Gly Leu Lys Pro Pro Ser Lys Phe
465                 470                 475                 480

Thr Ala Val Ile His Ala Val Thr Pro Leu Val Ser Gln Ser Gln Pro
                485                 490                 495
```

-continued

```
Val Leu Lys Leu Leu Val Ala Ala Ala Lys Ser Gln Tyr Cys Ala Gln
            500                 505                 510

Ile Ile Val Leu Trp Asn Cys Asp Lys Pro Leu Pro Ala Lys His Arg
        515                 520                 525

Trp Pro Ala Thr Ala Val Pro Val Ile Val Ile Glu Gly Glu Ser Lys
    530                 535                 540

Val Met Ser Ser Arg Phe Leu Pro Tyr Asp Asn Ile Ile Thr Asp Ala
545                 550                 555                 560

Val Leu Ser Leu Asp Glu Asp Thr Val Leu Ser Thr Thr Glu Val Asp
                565                 570                 575

Phe Ala Phe Thr Val Trp Gln Ser Phe Pro Glu Arg Ile Val Gly Tyr
            580                 585                 590

Pro Ala Arg Ser His Phe Trp Asp Asn Ser Lys Glu Arg Trp Gly Tyr
        595                 600                 605

Thr Ser Lys Trp Thr Asn Asp Tyr Ser Met Val Leu Thr Gly Ala Ala
    610                 615                 620

Ile Tyr His Lys Tyr Tyr His Tyr Leu Tyr Ser His Tyr Leu Pro Ala
625                 630                 635                 640

Ser Leu Lys Asn Met Val Asp Gln Leu Ala Asn Cys Glu Asp Ile Leu
                645                 650                 655

Met Asn Phe Leu Val Ser Ala Val Thr Lys Leu Pro Pro Ile Lys Val
            660                 665                 670

Thr Gln Lys Lys Gln Tyr Lys Glu Thr Met Met Gly Gln Thr Ser Arg
        675                 680                 685

Ala Ser Arg Trp Ala Asp Pro Asp His Phe Ala Gln Arg Gln Ser Cys
    690                 695                 700

Met Asn Thr Phe Ala Ser Trp Phe Gly Tyr Met Pro Leu Ile His Ser
705                 710                 715                 720

Gln Met Arg Leu Asp Pro Val Leu Phe Lys Asp Gln Val Ser Ile Leu
                725                 730                 735

Arg Lys Lys Tyr Arg Asp Ile Glu Arg Leu
            740                 745


<210> SEQ ID NO 66
<211> LENGTH: 718
<212> TYPE: PRT
<213> ORGANISM: Mus musculus

<400> SEQUENCE: 66

Met Cys Ala Ser Val Lys Ser Asn Ile Arg Gly Pro Ala Leu Ile Pro
1               5                   10                  15

Arg Met Lys Thr Lys His Arg Ile Tyr Tyr Val Thr Leu Phe Ser Ile
            20                  25                  30

Val Leu Leu Gly Leu Ile Ala Thr Gly Met Phe Gln Phe Trp Pro His
        35                  40                  45

Ser Ile Glu Ser Ser Ser Asp Gly Gly Val Glu Lys Arg Ser Ile Arg
    50                  55                  60

Glu Val Pro Val Val Arg Leu Pro Thr Asp Ser Pro Ile Pro Glu Arg
65                  70                  75                  80

Gly Asp Leu Ser Cys Arg Met His Thr Cys Phe Asp Val Tyr Arg Cys
                85                  90                  95

Gly Phe Asn Pro Lys Asn Lys Ile Lys Val Tyr Ile Tyr Pro Leu Lys
            100                 105                 110

Lys Tyr Val Asp Asp Ala Gly Val Pro Val Ser Ser Ala Ile Ser Arg
        115                 120                 125
```

-continued

```
Glu Tyr Asn Glu Leu Leu Thr Ala Ile Ser Asp Ser Asp Tyr Tyr Thr
    130                 135                 140

Asp Asp Ile Asn Arg Ala Cys Leu Phe Val Pro Ser Ile Asp Val Leu
145                 150                 155                 160

Asn Gln Asn Pro Leu Arg Ile Lys Glu Thr Ala Gln Ala Leu Ala Gln
                165                 170                 175

Leu Ser Arg Trp Asp Arg Gly Thr Asn His Leu Leu Phe Asn Met Leu
            180                 185                 190

Pro Gly Ala Pro Pro Asp Tyr Asn Thr Ala Leu Asp Val Pro Arg Asp
        195                 200                 205

Arg Ala Leu Leu Ala Gly Gly Gly Phe Ser Thr Trp Thr Tyr Arg Gln
    210                 215                 220

Gly Tyr Asp Val Ser Ile Pro Val Phe Ser Pro Leu Ser Ala Glu Met
225                 230                 235                 240

Ala Leu Pro Glu Lys Ala Pro Gly Pro Arg Arg Tyr Phe Leu Leu Ser
                245                 250                 255

Ser Gln Met Ala Ile His Pro Glu Tyr Arg Glu Glu Leu Glu Ala Leu
            260                 265                 270

Gln Ala Lys His Gln Glu Ser Val Leu Val Leu Asp Lys Cys Thr Asn
        275                 280                 285

Leu Ser Glu Gly Val Leu Ser Val Arg Lys Arg Cys His Gln His Gln
    290                 295                 300

Val Phe Asp Tyr Pro Gln Val Leu Gln Glu Ala Thr Phe Cys Thr Val
305                 310                 315                 320

Leu Arg Arg Ala Arg Leu Gly Gln Ala Val Leu Ser Asp Val Leu Gln
                325                 330                 335

Ala Gly Cys Val Pro Val Val Ile Ala Asp Ser Tyr Ile Leu Pro Phe
            340                 345                 350

Ser Glu Val Leu Asp Trp Lys Lys Ala Ser Val Val Val Pro Glu Glu
        355                 360                 365

Lys Met Ser Asp Val Tyr Ser Ile Leu Gln Asn Ile Pro Gln Arg Gln
    370                 375                 380

Ile Glu Glu Met Gln Arg Gln Ala Arg Trp Phe Trp Glu Ala Tyr Phe
385                 390                 395                 400

Gln Ser Ile Lys Ala Ile Ala Leu Ala Thr Leu Gln Ile Ile Asn Asp
                405                 410                 415

Arg Ile Tyr Pro Tyr Ala Ala Ile Ser Tyr Glu Glu Trp Asn Asp Pro
            420                 425                 430

Pro Ala Val Lys Trp Ala Ser Val Ser Asn Pro Leu Phe Leu Pro Leu
        435                 440                 445

Ile Pro Pro Gln Ser Gln Gly Phe Thr Ala Ile Val Leu Thr Tyr Asp
    450                 455                 460

Arg Val Glu Ser Leu Phe Arg Val Ile Thr Glu Val Ser Lys Val Pro
465                 470                 475                 480

Ser Leu Ser Lys Leu Leu Val Val Trp Asn Asn Gln Asn Lys Asn Pro
                485                 490                 495

Pro Glu Glu Ser Leu Trp Pro Lys Ile Arg Val Pro Leu Lys Val Val
            500                 505                 510

Arg Thr Ala Glu Asn Lys Leu Ser Asn Arg Phe Phe Pro Tyr Asp Glu
        515                 520                 525

Ile Glu Thr Glu Ala Val Leu Ala Ile Asp Asp Asp Ile Ile Met Leu
    530                 535                 540
```

-continued

```
Thr Ser Asp Glu Leu Gln Phe Gly Tyr Glu Val Trp Arg Glu Phe Pro
545                 550                 555                 560

Asp Arg Leu Val Gly Tyr Pro Gly Arg Leu His Leu Trp Asp His Glu
                565                 570                 575

Met Asn Lys Trp Lys Tyr Glu Ser Glu Trp Thr Asn Glu Val Ser Met
            580                 585                 590

Val Leu Thr Gly Ala Ala Phe Tyr His Lys Tyr Phe Asn Tyr Leu Tyr
        595                 600                 605

Thr Tyr Lys Met Pro Gly Asp Ile Lys Asn Trp Val Asp Ala His Met
    610                 615                 620

Asn Cys Glu Asp Ile Ala Met Asn Phe Leu Val Ala Asn Val Thr Gly
625                 630                 635                 640

Lys Ala Val Ile Lys Val Thr Pro Arg Lys Lys Phe Lys Cys Pro Glu
                645                 650                 655

Cys Thr Ala Ile Asp Gly Leu Ser Leu Asp Gln Thr His Met Val Glu
            660                 665                 670

Arg Ser Glu Cys Ile Asn Lys Phe Ala Ser Val Phe Gly Thr Met Pro
        675                 680                 685

Leu Lys Val Val Glu His Arg Ala Asp Pro Val Leu Tyr Lys Asp Asp
    690                 695                 700

Phe Pro Glu Lys Leu Lys Ser Phe Pro Asn Ile Gly Ser Leu
705                 710                 715
```

<210> SEQ ID NO 67
<211> LENGTH: 76
<212> TYPE: PRT
<213> ORGANISM: Artificial Sequence
<220> FEATURE:
<223> OTHER INFORMATION: motif
<220> FEATURE:
<221> NAME/KEY: MISC_FEATURE
<222> LOCATION: (4)..(4)
<223> OTHER INFORMATION: ANY AMINO ACID
<220> FEATURE:
<221> NAME/KEY: MISC_FEATURE
<222> LOCATION: (6)..(6)
<223> OTHER INFORMATION: Leu or Ile
<220> FEATURE:
<221> NAME/KEY: MISC_FEATURE
<222> LOCATION: (8)..(11)
<223> OTHER INFORMATION: any amino acid
<220> FEATURE:
<221> NAME/KEY: MISC_FEATURE
<222> LOCATION: (14)..(14)
<223> OTHER INFORMATION: any amino acid
<220> FEATURE:
<221> NAME/KEY: MISC_FEATURE
<222> LOCATION: (15)..(15)
<223> OTHER INFORMATION: Ser or Thr
<220> FEATURE:
<221> NAME/KEY: MISC_FEATURE
<222> LOCATION: (16)..(16)
<223> OTHER INFORMATION: Ser or Thr
<220> FEATURE:
<221> NAME/KEY: MISC_FEATURE
<222> LOCATION: (18)..(18)
<223> OTHER INFORMATION: Lys or Asn
<220> FEATURE:
<221> NAME/KEY: MISC_FEATURE
<222> LOCATION: (19)..(19)
<223> OTHER INFORMATION: Thr or Ser
<220> FEATURE:
<221> NAME/KEY: MISC_FEATURE
<222> LOCATION: (20)..(25)
<223> OTHER INFORMATION: any amino acid
<220> FEATURE:
<221> NAME/KEY: MISC_FEATURE
<222> LOCATION: (28)..(28)

-continued

<223> OTHER INFORMATION: any amino acid
<220> FEATURE:
<221> NAME/KEY: MISC_FEATURE
<222> LOCATION: (29)..(31)
<223> OTHER INFORMATION: Ser or Thr
<220> FEATURE:
<221> NAME/KEY: MISC_FEATURE
<222> LOCATION: (32)..(32)
<223> OTHER INFORMATION: Lys or Arg
<220> FEATURE:
<221> NAME/KEY: MISC_FEATURE
<222> LOCATION: (34)..(34)
<223> OTHER INFORMATION: Lys or Arg
<220> FEATURE:
<221> NAME/KEY: MISC_FEATURE
<222> LOCATION: (35)..(40)
<223> OTHER INFORMATION: any amino acid
<220> FEATURE:
<221> NAME/KEY: MISC_FEATURE
<222> LOCATION: (42)..(42)
<223> OTHER INFORMATION: any amino acid
<220> FEATURE:
<221> NAME/KEY: MISC_FEATURE
<222> LOCATION: (44)..(44)
<223> OTHER INFORMATION: any amino acid
<220> FEATURE:
<221> NAME/KEY: MISC_FEATURE
<222> LOCATION: (46)..(61)
<223> OTHER INFORMATION: any amino acid
<220> FEATURE:
<221> NAME/KEY: MISC_FEATURE
<222> LOCATION: (65)..(65)
<223> OTHER INFORMATION: any amino acid
<220> FEATURE:
<221> NAME/KEY: MISC_FEATURE
<222> LOCATION: (68)..(68)
<223> OTHER INFORMATION: any amino acid
<220> FEATURE:
<221> NAME/KEY: MISC_FEATURE
<222> LOCATION: (69)..(69)
<223> OTHER INFORMATION: Cys or Ser
<220> FEATURE:
<221> NAME/KEY: MISC_FEATURE
<222> LOCATION: (71)..(71)
<223> OTHER INFORMATION: His or Pro
<220> FEATURE:
<221> NAME/KEY: MISC_FEATURE
<222> LOCATION: (75)..(75)
<223> OTHER INFORMATION: any amino acid

<400> SEQUENCE: 67

```
Gln Thr Tyr Xaa Asn Xaa Glu Xaa Xaa Xaa Xaa Asp Asp Xaa Xaa Xaa
1               5                   10                  15

Asp Xaa Xaa Xaa Xaa Xaa Xaa Xaa Xaa Ile Ala Xaa Xaa Xaa Xaa Xaa
            20                  25                  30

Val Xaa Xaa Xaa Xaa Xaa Xaa Xaa Asn Xaa Gly Xaa Tyr Xaa Xaa Xaa
        35                  40                  45

Xaa Xaa Xaa Xaa Xaa Xaa Xaa Xaa Xaa Xaa Xaa Xaa Xaa Phe Gln Asp
    50                  55                  60

Xaa Asp Asp Xaa Xaa His Xaa Glu Arg Ile Xaa Arg
65                  70                  75
```

<210> SEQ ID NO 68
<211> LENGTH: 102
<212> TYPE: PRT
<213> ORGANISM: Artificial Sequence
<220> FEATURE:
<223> OTHER INFORMATION: motif
<220> FEATURE:
<221> NAME/KEY: MISC_FEATURE
<222> LOCATION: (1)..(1)
<223> OTHER INFORMATION: Lys or Arg
<220> FEATURE:

-continued

<221> NAME/KEY: MISC_FEATURE
<222> LOCATION: (3)..(3)
<223> OTHER INFORMATION: any amino acid
<220> FEATURE:
<221> NAME/KEY: MISC_FEATURE
<222> LOCATION: (8)..(19)
<223> OTHER INFORMATION: each position may be any amino acid
<220> FEATURE:
<221> NAME/KEY: MISC_FEATURE
<222> LOCATION: (20)..(24)
<223> OTHER INFORMATION: may be missing from sequence; each position may
be any amino acid
<220> FEATURE:
<221> NAME/KEY: MISC_FEATURE
<222> LOCATION: (20)..(24)
<223> OTHER INFORMATION: all or part of sequence comprising residues 20-
24 may be missing; each position may be any amino acid
<220> FEATURE:
<221> NAME/KEY: MISC_FEATURE
<222> LOCATION: (29)..(29)
<223> OTHER INFORMATION: Arg or Ile
<220> FEATURE:
<221> NAME/KEY: MISC_FEATURE
<222> LOCATION: (32)..(32)
<223> OTHER INFORMATION: amy amino acid
<220> FEATURE:
<221> NAME/KEY: MISC_FEATURE
<222> LOCATION: (35)..(37)
<223> OTHER INFORMATION: any amino acid
<220> FEATURE:
<221> NAME/KEY: MISC_FEATURE
<222> LOCATION: (39)..(84)
<223> OTHER INFORMATION: each position may be any amino acid
<220> FEATURE:
<221> NAME/KEY: MISC_FEATURE
<222> LOCATION: (85)..(94)
<223> OTHER INFORMATION: all or part of sequence comprising residues 85-
94 may be missing; each position may be any amino acid
<220> FEATURE:
<221> NAME/KEY: MISC_FEATURE
<222> LOCATION: (96)..(96)
<223> OTHER INFORMATION: any amino acid

<400> SEQUENCE: 68

```
Xaa Asp Xaa Gly Lys Phe Ile Xaa Xaa Xaa Xaa Xaa Xaa Xaa Xaa Xaa
1               5                   10                  15

Xaa Xaa Xaa Xaa Xaa Xaa Xaa Xaa Asp Asp Asp Ile Xaa Tyr Pro Xaa
            20                  25                  30

Asp Tyr Xaa Xaa Xaa Met Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Val Asn Xaa
                85                  90                  95

Leu Gly Thr Gly Thr Val
            100
```

<210> SEQ ID NO 69
<211> LENGTH: 1854
<212> TYPE: DNA
<213> ORGANISM: Pasteurella multocida

<400> SEQUENCE: 69

```
atgagcttat ttaaacgtgc tactgagcta tttaagtcag gaaactataa agatgcacta      60

actctatatg aaaatatagc taaaatttat ggttcagaaa gccttgttaa atataatatt     120

gatatatgta aaaaaaatat aacacaatca aaaagtaata aaatagaaga agataatatt     180
```

-continued

```
tctggagaaa acaaattttc agtatcaata aaagatctat ataacgaaat aagcaatagt    240
gaattaggga ttacaaaaga aagactagga gcccccccctc tagtcagtat tataatgact    300
tctcataata cagaaaaatt cattgaagcc tcaattaatt cactattatt gcaaacatac    360
aataacttag aagttatcgt tgtagatgat tatagcacag ataaaacatt tcagatcgca    420
tccagaatag caaactctac aagtaaagta aaaacattcc gattaaactc aaatctaggg    480
acatactttg cgaaaaatac aggaatttta aagtctaaag gagatattat tttctttcag    540
gatagcgatg atgtatgtca ccatgaaaga atcgaaagat gtgttaatgc attattatcg    600
aataaagata atatagctgt tagatgtgca tattctagaa taaatctaga aacacaaaat    660
ataataaaag ttaatgataa taaatacaaa ttaggattaa taactttagg cgtttataga    720
aaagtattta atgaaattgg tttttttaac tgcacaacca aagcatcgga tgatgaattt    780
tatcatagaa taattaaata ctatggtaaa aataggataa ataacttatt tctaccactg    840
tattataaca caatgcgtga agattcatta ttttctgata tggttgagtg ggtagatgaa    900
aataatataa agcaaaaaac ctctgatgct agacaaaatt atctccatga attccaaaaa    960
atacacaatg aaaggaaatt aaatgaatta aaagagattt ttagctttcc tagaattcat   1020
gacgccttac ctatatcaaa agaaatgagt aagctcagca accctaaaat tcctgtttat   1080
ataaatatat gctcaatacc ttcaagaata aaacaacttc aatacactat tggagtacta   1140
aaaaaccaat gcgatcattt tcatatttat cttgatggat atccagaagt acctgatttt   1200
ataaaaaaac tagggaataa agcgaccgtt attaattgtc aaaacaaaaa tgagtctatt   1260
agagataatg gaaagtttat tctattagaa aaacttataa aggaaaataa agatggatat   1320
tatataactt gtgatgatga tatccggtat cctgctgact acataaacac tatgataaaa   1380
aaaattaata aatacaatga taaagcagca attggattac atggtgttat attcccaagt   1440
agagtcaaca agtatttttc atcagacaga attgtctata attttcaaaa acctttagaa   1500
aatgatactg ctgtaaatat attaggaact ggaactgttg cctttagagt atctattttt   1560
aataaatttt ctctatctga ttttgagcat cctggcatgg tagatatcta tttttctata   1620
ctatgtaaga aaaacaatat actccaagtt tgtatatcac gaccatcgaa ttggctaaca   1680
gaagataaca aaaacactga gaccttattt catgaattcc aaaatagaga tgaaatacaa   1740
agtaaactca ttatttcaaa caacccttgg ggatactcaa gtatatatcc attattaaat   1800
aataatgcta attattctga acttattccg tgtttatctt tttataacga gtaa         1854
```

<210> SEQ ID NO 70
<211> LENGTH: 617
<212> TYPE: PRT
<213> ORGANISM: Pasteurella multocida

<400> SEQUENCE: 70

```
Met Ser Leu Phe Lys Arg Ala Thr Glu Leu Phe Lys Ser Gly Asn Tyr
1               5                   10                  15

Lys Asp Ala Leu Thr Leu Tyr Glu Asn Ile Ala Lys Ile Tyr Gly Ser
            20                  25                  30

Glu Ser Leu Val Lys Tyr Asn Ile Asp Ile Cys Lys Lys Asn Ile Thr
        35                  40                  45

Gln Ser Lys Ser Asn Lys Ile Glu Glu Asp Asn Ile Ser Gly Glu Asn
    50                  55                  60

Lys Phe Ser Val Ser Ile Lys Asp Leu Tyr Asn Glu Ile Ser Asn Ser
65                  70                  75                  80
```

-continued

```
Glu Leu Gly Ile Thr Lys Glu Arg Leu Gly Ala Pro Pro Leu Val Ser
                85                  90                  95

Ile Ile Met Thr Ser His Asn Thr Glu Lys Phe Ile Glu Ala Ser Ile
            100                 105                 110

Asn Ser Leu Leu Leu Gln Thr Tyr Asn Asn Leu Glu Val Ile Val Val
        115                 120                 125

Asp Asp Tyr Ser Thr Asp Lys Thr Phe Gln Ile Ala Ser Arg Ile Ala
    130                 135                 140

Asn Ser Thr Ser Lys Val Lys Thr Phe Arg Leu Asn Ser Asn Leu Gly
145                 150                 155                 160

Thr Tyr Phe Ala Lys Asn Thr Gly Ile Leu Lys Ser Lys Gly Asp Ile
                165                 170                 175

Ile Phe Phe Gln Asp Ser Asp Asp Val Cys His His Glu Arg Ile Glu
            180                 185                 190

Arg Cys Val Asn Ala Leu Leu Ser Asn Lys Asp Asn Ile Ala Val Arg
        195                 200                 205

Cys Ala Tyr Ser Arg Ile Asn Leu Glu Thr Gln Asn Ile Ile Lys Val
    210                 215                 220

Asn Asp Asn Lys Tyr Lys Leu Gly Leu Ile Thr Leu Gly Val Tyr Arg
225                 230                 235                 240

Lys Val Phe Asn Glu Ile Gly Phe Phe Asn Cys Thr Thr Lys Ala Ser
                245                 250                 255

Asp Asp Glu Phe Tyr His Arg Ile Ile Lys Tyr Tyr Gly Lys Asn Arg
            260                 265                 270

Ile Asn Asn Leu Phe Leu Pro Leu Tyr Tyr Asn Thr Met Arg Glu Asp
        275                 280                 285

Ser Leu Phe Ser Asp Met Val Glu Trp Val Asp Glu Asn Asn Ile Lys
    290                 295                 300

Gln Lys Thr Ser Asp Ala Arg Gln Asn Tyr Leu His Glu Phe Gln Lys
305                 310                 315                 320

Ile His Asn Glu Arg Lys Leu Asn Glu Leu Lys Glu Ile Phe Ser Phe
                325                 330                 335

Pro Arg Ile His Asp Ala Leu Pro Ile Ser Lys Glu Met Ser Lys Leu
            340                 345                 350

Ser Asn Pro Lys Ile Pro Val Tyr Ile Asn Ile Cys Ser Ile Pro Ser
        355                 360                 365

Arg Ile Lys Gln Leu Gln Tyr Thr Ile Gly Val Leu Lys Asn Gln Cys
    370                 375                 380

Asp His Phe His Ile Tyr Leu Asp Gly Tyr Pro Glu Val Pro Asp Phe
385                 390                 395                 400

Ile Lys Lys Leu Gly Asn Lys Ala Thr Val Ile Asn Cys Gln Asn Lys
                405                 410                 415

Asn Glu Ser Ile Arg Asp Asn Gly Lys Phe Ile Leu Leu Glu Lys Leu
            420                 425                 430

Ile Lys Glu Asn Lys Asp Gly Tyr Tyr Ile Thr Cys Asp Asp Asp Ile
        435                 440                 445

Arg Tyr Pro Ala Asp Tyr Ile Asn Thr Met Ile Lys Lys Ile Asn Lys
    450                 455                 460

Tyr Asn Asp Lys Ala Ala Ile Gly Leu His Gly Val Ile Phe Pro Ser
465                 470                 475                 480

Arg Val Asn Lys Tyr Phe Ser Ser Asp Arg Ile Val Tyr Asn Phe Gln
                485                 490                 495
```

-continued

```
Lys Pro Leu Glu Asn Asp Thr Ala Val Asn Ile Leu Gly Thr Gly Thr
            500                 505                 510

Val Ala Phe Arg Val Ser Ile Phe Asn Lys Phe Ser Leu Ser Asp Phe
        515                 520                 525

Glu His Pro Gly Met Val Asp Ile Tyr Phe Ser Ile Leu Cys Lys Lys
    530                 535                 540

Asn Asn Ile Leu Gln Val Cys Ile Ser Arg Pro Ser Asn Trp Leu Thr
545                 550                 555                 560

Glu Asp Asn Lys Asn Thr Glu Thr Leu Phe His Glu Phe Gln Asn Arg
                565                 570                 575

Asp Glu Ile Gln Ser Lys Leu Ile Ile Ser Asn Asn Pro Trp Gly Tyr
            580                 585                 590

Ser Ser Ile Tyr Pro Leu Leu Asn Asn Asn Ala Asn Tyr Ser Glu Leu
        595                 600                 605

Ile Pro Cys Leu Ser Phe Tyr Asn Glu
    610                 615


<210> SEQ ID NO 71
<211> LENGTH: 2112
<212> TYPE: DNA
<213> ORGANISM: Pasteurella multocida

<400> SEQUENCE: 71

atgaatacat tatcacaagc aataaaagca tataacagca atgactatca attagcactc      60

aaattatttg aaaagtcggc ggaaatctat ggacggaaaa ttgttgaatt tcaaattacc     120

aaatgcaaag aaaaactctc agcacatcct tctgttaatt cagcacatct ttctgtaaat     180

aaagaagaaa aagtcaatgt ttgcgatagt ccgttagata ttgcaacaca actgttactt     240

tccaacgtaa aaaaattagt actttctgac tcggaaaaaa acacgttaaa aaataaatgg     300

aaattgctca ctgagaagaa atctgaaaat gcggaggtaa gagcggtcgc ccttgtacca     360

aaagattttc ccaaagatct ggttttagcg cctttacctg atcatgttaa tgattttaca     420

tggtacaaaa agcgaaagaa aagacttggc ataaaacctg aacatcaaca tgttggtctt     480

tctattatcg ttacaacatt caatcgacca gcaattttat cgattacatt agcctgttta     540

gtaaaccaaa aaacacatta cccgtttgaa gttatcgtga cagatgatgg tagtcaggaa     600

gatctatcac cgatcattcg ccaatatgaa aataaattgg atattcgcta cgtcagacaa     660

aaagataacg gttttcaagc cagtgccgct cggaatatgg gattacgctt agcaaaatat     720

gactttattg gcttactcga ctgtgatatg gcgccaaatc cattatgggt tcattcttat     780

gttgcagagc tattagaaga tgatgattta acaatcattg gtccaagaaa atacatcgat     840

acacaacata ttgacccaaa agacttctta aataacgcga gtttgcttga atcattacca     900

gaagtgaaaa ccaataatag tgttgccgca aaaggggaag gaacagtttc tctggattgg     960

cgcttagaac aattcgaaaa aacagaaaat ctccgcttat ccgattcgcc tttccgtttt    1020

tttgcggcgg gtaatgttgc tttcgctaaa aaatggctaa ataaatccgg tttctttgat    1080

gaggaattta atcactgggg tggagaagat gtggaatttg gatatcgctt attccgttac    1140

ggtagtttct ttaaaactat tgatggcatt atggcctacc atcaagagcc accaggtaaa    1200

gaaaatgaaa ccgatcgtga agcgggaaaa aatattacgc tcgatattat gagagaaaag    1260

gtcccttata tctatagaaa acttttacca atagaagatt cgcatatcaa tagagtacct    1320

ttagtttcaa tttatatccc agcttataac tgtgcaaact atattcaacg ttgcgtagat    1380

agtgcactga atcagactgt tgttgatctc gaggtttgta tttgtaacga tggttcaaca    1440
```

-continued

```
gataatacct tagaagtgat caataagctt tatggtaata atcctagggt acgcatcatg   1500

tctaaaccaa atggcggaat agcctcagca tcaaatgcag ccgtttcttt tgctaaaggt   1560

tattacattg ggcagttaga ttcagatgat tatcttgagc ctgatgcagt tgaactgtgt   1620

ttaaaagaat ttttaaaaga taaaacgcta gcttgtgttt ataccactaa tagaaacgtc   1680

aatccggatg gtagcttaat cgctaatggt tacaattggc cagaattttc acgagaaaaa   1740

ctcacaacgg ctatgattgc tcaccacttt agaatgttca cgattagagc ttggcattta   1800

actgatggat tcaatgaaaa aattgaaaat gccgtagact atgacatgtt cctcaaactc   1860

agtgaagttg gaaaatttaa acatcttaat aaaatctgct ataaccgtgt attacatggt   1920

gataacacat caattaagaa acttggcatt caaaagaaaa accattttgt tgtagtcaat   1980

cagtcattaa atagacaagg cataacttat tataattatg acgaatttga tgatttagat   2040

gaaagtagaa agtatatttt caataaaacc gctgaatatc aagaagagat tgatatctta   2100

aaagatattt aa                                                        2112
```

What is claimed is:

1. A method for enzymatically producing defined glycosaminoglycan polymers comprising the steps of:

providing at least one functional acceptor, wherein the functional acceptor has at least two sugar units selected from the group consisting of uronic acid and hexosamine;

providing at least one recombinant glycosaminoglycan transferase having an empty acceptor site and being capable of elongating the at least one functional acceptor in a controlled and/or repetitive fashion to form extended glycosaminoglycan molecules, and wherein the at least one recombinant glycosaminoglycan transferase is selected from the group consisting of:

(a) a recombinant glycosaminoglycan transferase having the amino acid sequence as set forth in SEQ ID NO: 4;

(b) a recombinant glycosaminoglycan transferase encoded by a nucleotide sequence selected from the group consisting of SEQ ID NOs: 3 and 26;

(c) a recombinant glycosaminoglycan transferase having an amino acid sequence encoded by a nucleotide sequence capable of hybridizing to the complement of at least one of SEQ ID NOS: 3 and 26 under hybridization conditions comprising hybridization at a temperature of 68° C. in 5x SSC/5x Denhardt's solution/1.0% SDS, followed with washing in 3x SSC at 42°;

(d) a chimeric recombinant glycosaminoglycan transferase having an amino acid sequence selected from the group consisting of SEQ ID NOs: 74-76 and 85;

(e) a recombinant glycosaminoglycan transferase having an amino acid sequence that is at least 90% identical to SEQ ID NO: 4; and (f) a recombinant glycosaminoglycan transferase encoded by a nucleotide sequence that is at least 90% identical to at least one of SEQ ID NOS: 3 and 26; and providing at least one UDP-sugar selected from the group consisting of UDP-GlcUA, UDP-GlcNAc, UDP-Glc, UDP-GalNAc, UDP-GlcN and UDP-GalN in a stoichiometric ratio to the at least one functional acceptor such that the at least one recombinant glycosaminoglycan transferase elongates the at least one functional acceptor to provide glycosaminoglycan polymers wherein the glycosaminoglycan polymers have a desired size distribution such that the glycosaminoglycan polymers are substantially monodisperse in size such that the glycosaminoglycan polymers have a polydispersity value in a range of from 1.0 to 1.5, and wherein the desired size distribution is obtained by controlling the stoichiometric ratio of UDP-sugar to functional acceptor.

2. The method of claim 1 wherein, in the step of providing at least one functional acceptor, uronic acid is further defined as a uronic acid selected from the group consisting of GlcUA, iduronic acid (IdoUA), and GalUA, and wherein hexosamine is further defined as a hexosamine selected from the group consisting of GlcNAc, GalNAc, GlcN, and GalN.

3. The method of claim 1 wherein, in the step of providing at least one functional acceptor, the functional acceptor is at least one of:

(a) an HA oligosaccharide having between three sugar units and a molecular weight of about 4.2 kDa;

(b) an HA polymer having a mass in a range of from about 3.5 kDa to about 2 MDa;

(c) a chondroitin oligosaccharide comprising at least three sugar units;

(d) a chondroitin polymer;

(e) a chondroitin sulfate polymer;

(f) a heparin polymer;

(g) a heparan polymer;

(h) a heparosan polymer; and (i) an extended acceptor selected from the group consisting of HA chains, chondroitin chains, heparosan chains, mixed glycosaminoglycan chains, analog containing chains, and combinations thereof.

4. The method of claim 1 wherein, in the step of providing at least one recombinant glycosaminoglycan transferase, the at least one recombinant glycosaminoglycan transferase is a recombinant chondroitin synthase.

5. The method of claim 1 wherein, in the step of providing at least one recombinant glycosaminoglycan transferase, the at least one recombinant glycosaminoglycan transferase comprises a recombinant single action glycosyltransferase capable of adding only one of GlcUA, GlcNAc, Glc, GalNAc, GlcN, and GalN.

6. The method of claim 1 wherein, in the step of providing at least one recombinant glycosaminoglycan transferase, the at least one recombinant glycosaminoglycan transferase comprises a recombinant synthetic chimeric glycosaminoglycan transferase capable of adding two or more of GlcUA, GlcNAc, Glc, GalNAc, GlcN, and GalN.

7. The method of claim 1, further comprising the step of providing a divalent metal ion, wherein the divalent metal ion is selected from the group consisting of manganese, magnesium, cobalt, nickel and combinations thereof.

8. The method of claim 1, wherein the method occurs in a buffer having a pH from about 6 to about 8.

9. The method of claim 1 wherein the substantially monodisperse glycosaminoglycan polymers have a molecular weight in a range of from about 3.5 kDa to about 0.5 MDa, and have a polydispersity value in a range of from about 1.0 to about 1.1.

10. The method of claim 1 wherein the substantially monodisperse glycosaminoglycan polymers have a molecular weight in a range of from about 0.5 MDa to about 4.5 MDa, and have a polydispersity value in a range of from about 1.0 to about 1.5.

11. The method of claim 10 wherein the substantially monodisperse glycosaminoglycan polymers have a polydispersity value in a range of from about 1.0 to about 1.2.

12. The method of claim 1 wherein, in the step of providing at least one functional acceptor, the at least one functional acceptor further comprises a moiety selected from the group consisting of a fluorescent tag, a radioactive tag, an affinity tag, a detection probe, a medicant, and combinations thereof.

13. The method of claim 1 wherein, in the step of providing at least one UDP-sugar, at least one UDP-sugar is radioactively labeled.

14. The method of claim 1 wherein the glycosaminoglycan polymers are chimeric or hybrid glycosaminoglycan polymers.

15. The method of claim 1 wherein, in the step of providing at least one functional acceptor, the at least one functional acceptor is sulfated or is a modified oligosaccharide.

16. A method for enzymatically producing defined glycosaminoglycan polymers comprising the steps of:

providing at least one functional acceptor, wherein the functional acceptor is selected from the group consisting of an HA polymer, a chondroitin polymer, a chondroitin sulfate polymer, a heparosan polymer, mixed GAG chains, analog containing chains and combinations thereof;

providing at least one recombinant glycosaminoglycan transferase having an empty acceptor site and being capable of elongating the at least one functional acceptor in a controlled and/or repetitive fashion to form extended glycosaminoglycan molecules, and wherein the at least one recombinant glycosaminoglycan transferase is selected from the group consisting of:

(a) a recombinant glycosaminoglycan transferase having the amino acid sequence as set forth in SEQ ID NO: 4;

(b) a recombinant glycosaminoglycan transferase encoded by a nucleotide sequence selected from the group consisting of SEQ ID NOs: 3 and 26;

(c) a recombinant glycosaminoglycan transferase having an amino acid sequence encoded by a nucleotide sequence capable of hybridizing to the complement of at least one of SEQ ID NOs: 3 and 26 under hybridization conditions comprising hybridization at a temperature of 68° C. in 5x SSC/5x Denhardt's solution/1.0% SDS, followed with washing in 3x SSC at 42° C.;

(d) a chimeric recombinant glycosaminoglycan transferase having an amino acid sequence selected from the group consisting of SEQ ID NOs: 74-76 and 85;

(e) a recombinant glycosaminoglycan transferase having an amino acid sequence that is at least 90% identical to SEQ ID NO: 4; and (f) a recombinant glycosaminoglycan transferase encoded by a nucleotide sequence that is at least 90% identical to at least one of SEQ ID NOS:3 and 26; and providing at least one UDP-sugar selected from the group consisting of UDP-GlcUA, UDP-GlcNAc, UDP-Glc, UDP-GalNAc, UDP-GlcN, and UDP-GalN in a stoichiometric ratio to the at least one functional acceptor such that the at least one recombinant glycosaminoglycan transferase elongates the at least one functional acceptor to provide glycosaminoglycan polymers wherein the glycosaminoglycan polymers have a desired size distribution greater than 1 MDa, and wherein the desired size distribution is obtained by controlling the stoichiometric ratio of UDP-sugar to functional acceptor.

17. The method of claim 16 wherein, in the step of providing at least one functional acceptor, the functional acceptor is an HA polymer having a mass in a range of from about 3.5 kDa to about 2 MDa.

18. The method of claim 16 wherein, in the step of providing at least one recombinant glycosaminoglycan transferase, the at least one recombinant glycosaminoglycan transferase is a recombinant chondroitin synthase.

19. The method of claim 16 wherein, in the step of providing at least one recombinant glycosaminoglycan transferase, the at least one recombinant glycosaminoglycan transferase comprises a recombinant single action glycosyltransferase capable of adding only one of GlcUA, GlcNAc, Glc, GalNAc, GlcN and GalN.

20. The method of claim 16 wherein, in the step of providing at least one recombinant glycosaminoglycan transferase, the at least one recombinant glycosaminoglycan transferase comprises a recombinant synthetic chimeric glycosaminoglycan transferase capable of adding two or more of GlcUA, GlcNAc, Glc, GalNAc, GlcN, and GalN.

21. The method of claim 16, further comprising the step of providing a divalent metal ion selected from the group consisting of manganese, magnesium, cobalt, nickel and combinations thereof.

22. The method of claim 16, wherein the method occurs in a buffer having a pH from about 6 to about 8.

23. The method of claim 16 wherein, in the step of providing at least one functional acceptor, the at least one functional acceptor further comprises a moiety selected from the group consisting of a fluorescent tag, a radioactive tag, an affinity tag, a detection probe, a medicant, and combinations thereof.

24. The method of claim 16 wherein, in the step of providing at least one UDP-sugar, at least one UDP-sugar is radioactively labeled.

25. The method of claim 16 wherein the glycosaminoglycan polymers are chimeric or hybrid glycosaminoglycans.

26. The method of claim 16 wherein, in the step of providing at least one functional acceptor, the at least one functional acceptor is sulfated or is a modified oligosaccharide.

27. A method for producing a polysaccharide biomaterial containing a medicament delivery assembly, comprising the steps of:

providing at least one functional acceptor, wherein the functional acceptor has at least two sugar units selected from the group consisting of uronic acid and hexosamine;

providing at least one recombinant glycosaminoglycan transferase having an empty acceptor site and being capable of elongating the at least one functional acceptor in a controlled and/or repetitive fashion to form extended glycosaminoglycan molecules, and wherein the at least one recombinant glycosaminoglycan transferase is selected from the group consisting of:

(a) recombinant glycosaminoglycan transferase having the amino acid sequence as set forth in SEQ ID NO: 4;

(b) a recombinant glycosaminoglycan transferase encoded by a nucleotide sequence selected from the group consisting of SEQ ID NOs: 3 and 26;

(c) a recombinant glycosaminoglycan transferase having an amino acid sequence encoded by a nucleotide sequence capable of hybridizing to the complement of at least one of SEQ ID NOs: 3 and 26 under hybridization conditions comprising hybridization at a temperature of 68° C. in 5x SSC/5x Denhardt's solution/ 1.0% SDS, followed with washing in 3x SSC at 42° C.;

(d) a chimeric recombinant glycosaminoglycan transferase having an amino acid sequence selected from the group consisting of SEQ ID NOs: 74-76 and 85;

(e) a recombinant glycosaminoglycan transferase having an amino acid sequence that is at least 90% identical to SEQ ID NO: 4; and (f) a recombinant glycosaminoglycan transferase encoded by a nucleotide sequence that is at least 90% identical to at least one of SEQ ID NOS: 3 and 26; and providing at least one UDP-sugar selected from the group consisting of UDP-GlcUA, UDP-GlcNAc, UDP-Glc, UDP-GalNAc, UDP-GlcN, and UDP-GalN in a stoichiometric ratio to the at least one functional acceptor such that the at least one recombinant glycosaminoglycan transferase elongates the at least one functional acceptor to provide glycosaminoglycan polymers wherein the glycosaminoglycan polymers have a desired size distribution such that the glycosaminoglycan polymers are substantially monodisperse in size such that the glycosaminoglycan polymers have a polydispersity value in a range of from 1.0 to 1.5, and wherein the desired size distribution is obtained by controlling the stoichiometric ratio of UDP-sugar to functional acceptor, and whereby the glycosaminoglycan polymers are capable of acting as a polysaccharide bioadhesive; providing at least one medicament delivery assembly containing one or more medicaments entrapped therein and deliverable within a wound site or a surgical site; and mixing the prepared polysaccharide bioadhesive with the at least one medicament delivery assembly, wherein the prepared polysaccharide bioadhesive entraps the at least one medicament delivery assembly to produce a polysaccharide biomaterial containing a medicament delivery system.

28. The method of claim 1, wherein the defined glycosaminoglycan polymers are capable of acting as a bioadhesive sealant, a tissue engineering aid, a cell matrix mimetic, a cell behavior or growth modulator, a drug delivery agent, or combinations thereof.

* * * * *

UNITED STATES PATENT AND TRADEMARK OFFICE
CERTIFICATE OF CORRECTION

PATENT NO. : 7,579,173 B2
APPLICATION NO. : 11/651379
DATED : August 25, 2009
INVENTOR(S) : Paul L. DeAngelis and Wei Jing It is certified that error appears in the above-identified patent and that said Letters Patent is hereby corrected as shown below:

Column 50, line 25: Delete "300" and replace with -- 30° --.

Column 55, line 57: Delete "$pMCS^{1-214}$" and replace with -- $pmCS^{1-214}$ --.

Column 56, line 7: Delete "$pMCS^{1-214}$" and replace with -- $pmCS^{1-214}$ --.

Column 71, line 18: Delete "(bper" and replace with -- (bPer --.

Column 74, line 59: Delete "Seizer," and replace with -- Selzer, --.

Column 78, line 63: Delete "Elten." and replace with -- Etten. --.

Column 80, line 14: Delete "Rijn, l." and replace with -- Rijn, I. --.

IN THE SEQUENCE LISTING:

Column 79, line 1 beginning of Sequence Listing: After "NUMBER OF SEQ ID NOS:" delete "71" and replace with -- 85 --.

Column 217, line 24 in the Sequence listing: After "aaagatattt aa 2112" insert the entire missing sequence listing for SEQ ID NOS 72-85:

--

<210> 72
<211> 107
<212> PRT
<213> Pasteurella multocida

<400> 72

```
Ser Ile Ile Val Thr Thr Phe Asn Arg Pro Ala Ile Leu Ser Ile Thr
1               5                   10                  15

Leu Ala Cys Leu Val Asn Gln Lys Thr His Tyr Pro Phe Glu Val Ile
            20                  25                  30

Val Thr Asp Asp Gly Ser Gln Glu Asp Leu Ser Pro Ile Ile Arg Gln
        35                  40                  45

Tyr Glu Asn Lys Leu Asp Ile Arg Tyr Val Arg Gln Lys Asp Asn Gly
    50                  55                  60

Phe Gln Ala Ser Ala Ala Arg Asn Met Gly Leu Arg Leu Ala Lys Tyr
65                  70                  75                  80

Asp Phe Ile Gly Leu Leu Asp Cys Asp Met Ala Pro Asn Pro Leu Trp
                85                  90                  95

Val His Ser Tyr Val Ala Glu Leu Leu Glu Asp
            100                 105
```

<210> 73
<211> 105
<212> PRT
<213> Pasteurella multocida

<400> 73

```
Ser Ile Tyr Ile Pro Ala Tyr Asn Cys Ala Asn Tyr Ile Gln Arg Cys
1               5                   10                  15

Val Asp Ser Ala Leu Asn Gln Thr Thr Val Asp Leu Glu Val Cys Ile
            20                  25                  30

Cys Asn Asp Gly Ser Thr Asp Asn Thr Leu Glu Val Ile Asn Lys Leu
        35                  40                  45

Tyr Gly Asn Asn Pro Arg Val Arg Ile Met Ser Lys Pro Asn Gly Gly
    50                  55                  60

Ile Ala Ser Ala Ser Asn Ala Ala Val Ser Phe Ala Lys Gly Tyr Tyr
65                  70                  75                  80

Ile Gly Gln Leu Asp Ser Asp Asp Tyr Leu Glu Pro Asp Ala Val Glu
                85                  90                  95

Leu Cys Leu Lys Glu Phe Leu Lys Asp
            100                 105
```

<210> 74
<211> 771
<212> PRT
<213> Pasteurella multocida

<400> 74

Met Asn Thr Leu Ser Gln Ala Ile Lys Ala Tyr Asn Ser Asn Asp Tyr
1 5 10 15

Gln Leu Ala Leu Lys Leu Phe Glu Lys Ser Ala Glu Ile Tyr Gly Arg
20 25 30

Lys Ile Val Glu Phe Gln Ile Thr Lys Cys Lys Glu Lys Leu Ser Ala
35 40 45

His Pro Ser Val Asn Ser Ala His Leu Ser Val Asn Lys Glu Glu Lys
50 55 60

Val Asn Val Cys Asp Ser Pro Leu Asp Ile Ala Thr Gln Leu Leu Leu
65 70 75 80

Ser Asn Val Lys Lys Leu Val Leu Ser Asp Ser Glu Lys Asn Thr Leu
85 90 95

Lys Asn Lys Trp Lys Leu Leu Thr Glu Lys Lys Ser Glu Asn Ala Glu
100 105 110

Val Arg Ala Val Ala Leu Val Pro Lys Asp Phe Pro Lys Asp Leu Val
115 120 125

Leu Ala Pro Leu Pro Asp His Val Asn Asp Phe Thr Trp Tyr Lys Lys
130 135 140

Arg Lys Lys Arg Leu Gly Ile Lys Pro Glu His Gln His Val Gly Leu
145 150 155 160

Ser Ile Ile Val Thr Thr Phe Asn Arg Pro Ala Ile Leu Ser Ile Thr
165 170 175

Leu Ala Cys Leu Val Asn Gln Lys Thr His Tyr Pro Phe Glu Val Ile
180 185 190

Val Thr Asp Asp Gly Ser Gln Glu Asp Leu Ser Pro Ile Ile Arg Gln
195 200 205

Tyr Glu Asn Lys Leu Asp Ile Arg Tyr Val Arg Gln Lys Asp Asn Gly
210 215 220

Phe Gln Ala Ser Ala Ala Arg Asn Met Gly Leu Arg Leu Ala Lys Tyr
225 230 235 240

Asp Phe Ile Gly Leu Leu Asp Cys Asp Met Ala Pro Asn Pro Leu Trp
245 250 255

Val His Ser Tyr Val Ala Glu Leu Leu Val Gln Lys Tyr Glu Gln Lys
260 265 270

Leu Asp Ile Lys Tyr Val Arg Gln Lys Asp Tyr Gly Tyr Gln Leu Cys
275 280 285

Ala Val Arg Asn Leu Gly Leu Arg Thr Ala Lys Tyr Asp Phe Val Ser
290 295 300

Ile Leu Asp Cys Asp Met Ala Pro Gln Gln Leu Trp Val His Ser Tyr
305 310 315 320

Leu Thr Glu Leu Leu Glu Asp Asn Asp Ile Val Leu Ile Gly Pro Arg
325 330 335

Lys Tyr Val Asp Thr His Asn Ile Thr Ala Glu Gln Phe Leu Asn Asp
340 345 350

Pro Tyr Leu Ile Glu Ser Leu Pro Glu Thr Ala Thr Asn Asn Asn Pro
355 360 365

Ser Ile Thr Ser Lys Gly Asn Ile Ser Leu Asp Trp Arg Leu Glu His
370 375 380

Phe Lys Lys Thr Asp Asn Leu Arg Leu Cys Asp Ser Pro Phe Arg Tyr
385 390 395 400

Phe Ser Cys Gly Asn Val Ala Phe Ser Lys Glu Trp Leu Asn Lys Val
405 410 415

Gly Trp Phe Asp Glu Glu Phe Asn His Trp Gly Gly Glu Asp Val Glu
420 425 430

Phe Gly Tyr Arg Leu Phe Ala Lys Gly Cys Phe Phe Arg Val Ile Asp
435 440 445

Gly Gly Met Ala Tyr His Gln Glu Pro Pro Gly Lys Glu Asn Glu Thr
450 455 460

Asp Arg Glu Ala Gly Lys Ser Ile Thr Leu Lys Ile Val Lys Glu Lys
465 470 475 480

Val Pro Tyr Ile Tyr Arg Lys Leu Leu Pro Ile Glu Asp Ser His Ile
485 490 495

His Arg Ile Pro Leu Val Ser Ile Tyr Ile Pro Ala Tyr Asn Cys Ala
500 505 510

Asn Tyr Ile Gln Arg Cys Val Asp Ser Ala Leu Asn Gln Thr Val Val
515 520 525

Asp Leu Glu Val Cys Ile Cys Asn Asp Gly Ser Thr Asp Asn Thr Leu
530 535 540

Glu Val Ile Asn Lys Leu Tyr Gly Asn Asn Pro Arg Val Arg Ile Met
545 550 555 560

Ser Lys Pro Asn Gly Gly Ile Ala Ser Ala Ser Asn Ala Ala Val Ser
565 570 575

Phe Ala Lys Gly Tyr Tyr Ile Gly Gln Leu Asp Ser Asp Asp Tyr Leu
580 585 590

Glu Pro Asp Ala Val Glu Leu Cys Leu Lys Glu Phe Leu Lys Asp Lys
595 600 605

Thr Leu Ala Cys Val Tyr Thr Thr Asn Arg Asn Val Asn Pro Asp Gly
610 615 620

Ser Leu Ile Ala Asn Gly Tyr Asn Trp Pro Glu Phe Ser Arg Glu Lys
625 630 635 640

Leu Thr Thr Ala Met Ile Ala His His Phe Arg Met Phe Thr Ile Arg
645 650 655

Ala Trp His Leu Thr Asp Gly Phe Asn Glu Asn Ile Glu Asn Ala Val
660 665 670

Asp Tyr Asp Met Phe Leu Lys Leu Ser Glu Val Gly Lys Phe Lys His
675 680 685

Leu Asn Lys Ile Cys Tyr Asn Arg Val Leu His Gly Asp Asn Thr Ser
690 695 700

Ile Lys Lys Leu Gly Ile Gln Lys Lys Asn His Phe Val Val Val Asn
705 710 715 720

Gln Ser Leu Asn Arg Gln Gly Ile Asn Tyr Tyr Asn Tyr Asp Lys Phe
725 730 735

Asp Asp Leu Asp Glu Ser Arg Lys Tyr Ile Phe Asn Lys Thr Ala Glu
740 745 750

Tyr Gln Glu Glu Met Asp Ile Leu Lys Asp Leu Lys Leu Ile Gln Asn
755 760 765

Lys Asp Ala
770

<210> 75
<211> 696
<212> PRT
<213> Pasteurella multocida

<400> 75

Met Asn Thr Leu Ser Gln Ala Ile Lys Ala Tyr Asn Ser Asn Asp Tyr
1 5 10 15

Glu Leu Ala Leu Lys Leu Phe Glu Lys Ser Ala Glu Thr Tyr Gly Arg
20 25 30

Lys Ile Val Glu Phe Gln Ile Ile Lys Cys Lys Glu Lys Leu Ser Thr
35 40 45

Asn Ser Tyr Val Ser Glu Asp Lys Lys Asn Ser Val Cys Asp Ser Ser
50 55 60

Leu Asp Ile Ala Thr Gln Leu Leu Leu Ser Asn Val Lys Lys Leu Thr
65 70 75 80

Leu Ser Glu Ser Glu Lys Asn Ser Leu Lys Asn Lys Trp Lys Ser Ile
85 90 95

Thr Gly Lys Lys Ser Glu Asn Ala Glu Ile Arg Lys Val Glu Leu Val
100 105 110

Pro Lys Asp Phe Pro Lys Asp Leu Val Leu Ala Pro Leu Pro Asp His
115 120 125

Val Asn Asp Phe Thr Trp Tyr Lys Asn Arg Lys Lys Ser Leu Gly Ile
130 135 140

```
Lys Pro Val Asn Lys Asn Ile Gly Leu Ser Ile Ile Ile Pro Thr Phe
145                 150                 155                 160

Asn Arg Ser Arg Ile Leu Asp Ile Thr Leu Ala Cys Leu Val Asn Gln
                165                 170                 175

Lys Thr Asn Tyr Pro Phe Glu Val Val Val Ala Asp Asp Gly Ser Lys
            180                 185                 190

Glu Asn Leu Leu Thr Ile Ile Arg Gln Tyr Glu Asn Lys Leu Asp Ile
        195                 200                 205

Arg Tyr Val Arg Gln Lys Asp Asn Gly Phe Gln Ala Ser Ala Ala Arg
    210                 215                 220

Asn Met Gly Leu Arg Leu Ala Lys Tyr Asp Phe Ile Gly Leu Leu Asp
225                 230                 235                 240

Cys Asp Met Ala Pro Asn Pro Leu Trp Val His Ser Tyr Val Ala Glu
                245                 250                 255

Leu Leu Glu Asp Asp Asp Leu Thr Ile Ile Gly Pro Arg Lys Tyr Ile
            260                 265                 270

Asp Thr Gln His Ile Asp Pro Lys Asp Phe Leu Asn Asn Ala Ser Leu
        275                 280                 285

Leu Glu Ser Leu Pro Glu Val Lys Thr Asn Asn Ser Val Ala Ala Lys
    290                 295                 300

Gly Glu Gly Thr Val Ser Leu Asp Trp Arg Leu Glu Gln Phe Glu Lys
305                 310                 315                 320

Thr Glu Asn Leu Arg Leu Ser Asp Ser Pro Phe Arg Phe Phe Ala Ala
                325                 330                 335

Gly Asn Val Ala Phe Ala Lys Lys Trp Leu Asn Lys Ser Gly Phe Phe
            340                 345                 350

Asp Glu Glu Phe Asn His Trp Gly Gly Glu Asp Val Glu Phe Gly Tyr
        355                 360                 365

Arg Leu Phe Arg Tyr Gly Ser Phe Phe Lys Thr Ile Asp Gly Ile Met
    370                 375                 380

Ala Tyr His Gln Glu Pro Pro Gly Lys Glu Asn Glu Thr Asp Arg Glu
385                 390                 395                 400

Ala Gly Lys Asn Ile Thr Leu Asp Ile Met Arg Glu Lys Val Pro Tyr
                405                 410                 415

Ile Tyr Arg Lys Leu Leu Pro Ile Glu Asp Ser His Ile Asn Arg Val
            420                 425                 430

Pro Leu Val Ser Ile Tyr Ile Pro Ala Tyr Asn Cys Ala Asn Tyr Ile
        435                 440                 445

Gln Arg Cys Val Asp Ser Ala Leu Asn Gln Thr Val Val Asp Leu Glu
    450                 455                 460
```

Val Cys Ile Cys Asn Asp Gly Ser Thr Asp Asn Thr Leu Glu Val Ile
465 470 475 480

Asn Lys Leu Tyr Gly Asn Asn Pro Arg Val Arg Ile Met Ser Lys Pro
485 490 495

Asn Gly Gly Ile Ala Ser Ala Ser Asn Ala Ala Val Ser Phe Ala Lys
500 505 510

Gly Tyr Tyr Ile Gly Gln Leu Asp Ser Asp Asp Tyr Leu Glu Pro Asp
515 520 525

Ala Val Glu Leu Cys Leu Lys Glu Phe Leu Lys Asp Lys Thr Leu Ala
530 535 540

Cys Val Tyr Thr Thr Asn Arg Asn Val Asn Pro Asp Gly Ser Leu Ile
545 550 555 560

Ala Asn Gly Tyr Asn Trp Pro Glu Phe Ser Arg Glu Lys Leu Thr Thr
565 570 575

Ala Met Ile Ala His His Phe Arg Met Phe Thr Ile Arg Ala Trp His
580 585 590

Leu Thr Asp Gly Phe Asn Glu Lys Ile Glu Asn Ala Val Asp Tyr Asp
595 600 605

Met Phe Leu Lys Leu Ser Glu Val Gly Lys Phe Lys His Leu Asn Lys
610 615 620

Ile Cys Tyr Asn Arg Val Leu His Gly Asp Asn Thr Ser Ile Lys Lys
625 630 635 640

Leu Gly Ile Gln Lys Lys Asn His Phe Val Val Val Asn Gln Ser Leu
645 650 655

Asn Arg Gln Gly Ile Thr Tyr Tyr Asn Tyr Asp Glu Phe Asp Asp Leu
660 665 670

Asp Glu Ser Arg Lys Tyr Ile Phe Asn Lys Thr Ala Glu Tyr Gln Glu
675 680 685

Glu Ile Asp Ile Leu Lys Asp Ile
690 695

<210> 76
<211> 711
<212> PRT
<213> Pasteurella multocida

<400> 76

Met Asn Thr Leu Ser Gln Ala Ile Lys Ala Tyr Asn Ser Asn Asp Tyr
1 5 10 15

Gln Leu Ala Leu Lys Leu Phe Glu Lys Ser Ala Glu Ile Tyr Gly Arg
20 25 30

Lys Ile Val Glu Phe Gln Ile Thr Lys Cys Lys Glu Lys Leu Ser Ala
35 40 45

```
His Pro Ser Val Asn Ser Ala His Leu Ser Val Asn Lys Glu Glu Lys
    50                  55                  60

Val Asn Val Cys Asp Ser Pro Leu Asp Ile Ala Thr Gln Leu Leu Leu
65                  70                  75                  80

Ser Asn Val Lys Lys Leu Val Leu Ser Asp Ser Glu Lys Asn Thr Leu
                85                  90                  95

Lys Asn Lys Trp Lys Leu Leu Thr Glu Lys Lys Ser Glu Asn Ala Glu
            100                 105                 110

Val Arg Ala Val Ala Leu Val Pro Lys Asp Phe Pro Lys Asp Leu Val
        115                 120                 125

Leu Ala Pro Leu Pro Asp His Val Asn Asp Phe Thr Trp Tyr Lys Lys
    130                 135                 140

Arg Lys Lys Arg Leu Gly Ile Lys Pro Glu His Gln His Val Gly Leu
145                 150                 155                 160

Ser Ile Ile Val Thr Thr Phe Asn Arg Pro Ala Ile Leu Ser Ile Thr
                165                 170                 175

Leu Ala Cys Leu Val Asn Gln Lys Thr His Tyr Pro Phe Glu Val Ile
            180                 185                 190

Val Thr Asp Asp Gly Ser Gln Glu Asp Leu Ser Pro Ile Ile Arg Gln
        195                 200                 205

Tyr Glu Asn Lys Leu Asp Ile Arg Tyr Val Arg Gln Lys Asp Tyr Gly
    210                 215                 220

Tyr Gln Leu Cys Ala Val Arg Asn Leu Gly Leu Arg Thr Ala Lys Tyr
225                 230                 235                 240

Asp Phe Val Ser Ile Leu Asp Cys Asp Met Ala Pro Gln Gln Leu Trp
                245                 250                 255

Val His Ser Tyr Leu Thr Glu Leu Leu Glu Asp Asn Asp Ile Val Leu
            260                 265                 270

Ile Gly Pro Arg Lys Tyr Val Asp Thr His Asn Ile Thr Ala Glu Gln
        275                 280                 285

Phe Leu Asn Asp Pro Tyr Leu Ile Glu Ser Leu Pro Glu Thr Ala Thr
    290                 295                 300

Asn Asn Asn Pro Ser Ile Thr Ser Lys Gly Asn Ile Ser Leu Asp Trp
305                 310                 315                 320

Arg Leu Glu His Phe Lys Lys Thr Asp Asn Leu Arg Leu Cys Asp Ser
                325                 330                 335

Pro Phe Arg Tyr Phe Ser Cys Gly Asn Val Ala Phe Ser Lys Glu Trp
            340                 345                 350

Leu Asn Lys Val Gly Trp Phe Asp Glu Glu Phe Asn His Trp Gly Gly
        355                 360                 365
```

Glu Asp Val Glu Phe Gly Tyr Arg Leu Phe Ala Lys Gly Cys Phe Phe
370 375 380

Arg Val Ile Asp Gly Gly Met Ala Tyr His Gln Glu Pro Pro Gly Lys
385 390 395 400

Glu Asn Glu Thr Asp Arg Glu Ala Gly Lys Ser Ile Thr Leu Lys Ile
405 410 415

Val Lys Glu Lys Val Pro Tyr Ile Tyr Arg Lys Leu Leu Pro Ile Glu
420 425 430

Asp Ser His Ile His Arg Ile Pro Leu Val Ser Ile Tyr Ile Pro Ala
435 440 445

Tyr Asn Cys Ala Asn Tyr Ile Gln Arg Cys Val Asp Ser Ala Leu Asn
450 455 460

Gln Thr Val Val Asp Leu Glu Val Cys Ile Cys Asn Asp Gly Ser Thr
465 470 475 480

Asp Asn Thr Leu Glu Val Ile Asn Lys Leu Tyr Gly Asn Asn Pro Arg
485 490 495

Val Arg Ile Met Ser Lys Pro Asn Gly Gly Ile Ala Ser Ala Ser Asn
500 505 510

Ala Ala Val Ser Phe Ala Lys Gly Tyr Tyr Ile Gly Gln Leu Asp Ser
515 520 525

Asp Asp Tyr Leu Glu Pro Asp Ala Val Glu Leu Cys Leu Lys Glu Phe
530 535 540

Leu Lys Asp Lys Thr Leu Ala Cys Val Tyr Thr Thr Asn Arg Asn Val
545 550 555 560

Asn Pro Asp Gly Ser Leu Ile Ala Asn Gly Tyr Asn Trp Pro Glu Phe
565 570 575

Ser Arg Glu Lys Leu Thr Thr Ala Met Ile Ala His His Phe Arg Met
580 585 590

Phe Thr Ile Arg Ala Trp His Leu Thr Asp Gly Phe Asn Glu Asn Ile
595 600 605

Glu Asn Ala Val Asp Tyr Asp Met Phe Leu Lys Leu Ser Glu Val Gly
610 615 620

Lys Phe Lys His Leu Asn Lys Ile Cys Tyr Asn Arg Val Leu His Gly
625 630 635 640

Asp Asn Thr Ser Ile Lys Lys Leu Gly Ile Gln Lys Lys Asn His Phe
645 650 655

Val Val Val Asn Gln Ser Leu Asn Arg Gln Gly Ile Asn Tyr Tyr Asn
660 665 670

Tyr Asp Lys Phe Asp Asp Leu Asp Glu Ser Arg Lys Tyr Ile Phe Asn
675 680 685

Lys Thr Ala Glu Tyr Gln Glu Glu Met Asp Ile Leu Lys Asp Leu Lys
690 695 700

Leu Ile Gln Asn Lys Asp Ala
705 710

<210> 77
<211> 696
<212> PRT
<213> Pasteurella multocida

<400> 77

Met Asn Thr Leu Ser Gln Ala Ile Lys Ala Tyr Asn Ser Asn Asp Tyr
1 5 10 15

Glu Leu Ala Leu Lys Leu Phe Glu Lys Ser Ala Glu Thr Tyr Gly Arg
20 25 30

Lys Ile Val Glu Phe Gln Ile Ile Lys Cys Lys Glu Lys Leu Ser Thr
35 40 45

Asn Ser Tyr Val Ser Glu Asp Lys Lys Asn Ser Val Cys Asp Ser Ser
50 55 60

Leu Asp Ile Ala Thr Gln Leu Leu Leu Ser Asn Val Lys Lys Leu Thr
65 70 75 80

Leu Ser Glu Ser Glu Lys Asn Ser Leu Lys Asn Lys Trp Lys Ser Ile
85 90 95

Thr Gly Lys Lys Ser Glu Asn Ala Glu Ile Arg Lys Val Glu Leu Val
100 105 110

Pro Lys Asp Phe Pro Lys Asp Leu Val Leu Ala Pro Leu Pro Asp His
115 120 125

Val Asn Asp Phe Thr Trp Tyr Lys Asn Arg Lys Lys Ser Leu Gly Ile
130 135 140

Lys Pro Val Asn Lys Asn Ile Gly Leu Ser Ile Ile Ile Pro Thr Phe
145 150 155 160

Asn Arg Ser Arg Ile Leu Asp Ile Thr Leu Ala Cys Leu Val Asn Gln
165 170 175

Lys Thr Asn Tyr Pro Phe Glu Val Val Val Ala Asp Asp Gly Ser Lys
180 185 190

Glu Asn Leu Leu Thr Ile Val Gln Lys Tyr Glu Gln Lys Leu Asp Ile
195 200 205

Lys Tyr Val Arg Gln Lys Asp Asn Gly Phe Gln Ala Ser Ala Ala Arg
210 215 220

Asn Met Gly Leu Arg Leu Ala Lys Tyr Asp Phe Ile Gly Leu Leu Asp
225 230 235 240

Cys Asp Met Ala Pro Asn Pro Leu Trp Val His Ser Tyr Val Ala Glu
245 250 255

Leu Leu Glu Asp Asp Asp Leu Thr Ile Ile Gly Pro Arg Lys Tyr Ile
260 265 270

```
Asp Thr Gln His Ile Asp Pro Lys Asp Phe Leu Asn Asn Ala Ser Leu
        275                 280                 285

Leu Glu Ser Leu Pro Glu Val Lys Thr Asn Asn Ser Val Ala Ala Lys
    290                 295                 300

Gly Glu Gly Thr Val Ser Leu Asp Trp Arg Leu Glu Gln Phe Glu Lys
305                 310                 315                     320

Thr Glu Asn Leu Arg Leu Ser Asp Ser Pro Phe Arg Phe Phe Ala Ala
                325                 330                 335

Gly Asn Val Ala Phe Ala Lys Lys Trp Leu Asn Lys Ser Gly Phe Phe
            340                 345                 350

Asp Glu Glu Phe Asn His Trp Gly Gly Glu Asp Val Glu Phe Gly Tyr
        355                 360                 365

Arg Leu Phe Arg Tyr Gly Ser Phe Phe Lys Thr Ile Asp Gly Ile Met
    370                 375                 380

Ala Tyr His Gln Glu Pro Pro Gly Lys Glu Asn Glu Thr Asp Arg Glu
385                 390                 395                     400

Ala Gly Lys Asn Ile Thr Leu Asp Ile Met Arg Glu Lys Val Pro Tyr
                405                 410                 415

Ile Tyr Arg Lys Leu Leu Pro Ile Glu Asp Ser His Ile Asn Arg Val
            420                 425                 430

Pro Leu Val Ser Ile Tyr Ile Pro Ala Tyr Asn Cys Ala Asn Tyr Ile
        435                 440                 445

Gln Arg Cys Val Asp Ser Ala Leu Asn Gln Thr Val Val Asp Leu Glu
    450                 455                 460

Val Cys Ile Cys Asn Asp Gly Ser Thr Asp Asn Thr Leu Glu Val Ile
465                 470                 475                     480

Asn Lys Leu Tyr Gly Asn Asn Pro Arg Val Arg Ile Met Ser Lys Pro
                485                 490                 495

Asn Gly Gly Ile Ala Ser Ala Ser Asn Ala Ala Val Ser Phe Ala Lys
            500                 505                 510

Gly Tyr Tyr Ile Gly Gln Leu Asp Ser Asp Asp Tyr Leu Glu Pro Asp
        515                 520                 525

Ala Val Glu Leu Cys Leu Lys Glu Phe Leu Lys Asp Lys Thr Leu Ala
    530                 535                 540

Cys Val Tyr Thr Thr Asn Arg Asn Val Asn Pro Asp Gly Ser Leu Ile
545                 550                 555                     560
```

Ala Asn Gly Tyr Asn Trp Pro Glu Phe Ser Arg Glu Lys Leu Thr Thr
565 570 575

Ala Met Ile Ala His His Phe Arg Met Phe Thr Ile Arg Ala Trp His
580 585 590

Leu Thr Asp Gly Phe Asn Glu Lys Ile Glu Asn Ala Val Asp Tyr Asp
595 600 605

Met Phe Leu Lys Leu Ser Glu Val Gly Lys Phe Lys His Leu Asn Lys
610 615 620

Ile Cys Tyr Asn Arg Val Leu His Gly Asp Asn Thr Ser Ile Lys Lys
625 630 635 640

Leu Gly Ile Gln Lys Lys Asn His Phe Val Val Val Asn Gln Ser Leu
645 650 655

Asn Arg Gln Gly Ile Thr Tyr Tyr Asn Tyr Asp Glu Phe Asp Asp Leu
660 665 670

Asp Glu Ser Arg Lys Tyr Ile Phe Asn Lys Thr Ala Glu Tyr Gln Glu
675 680 685

Glu Ile Asp Ile Leu Lys Asp Ile
690 695

<210> 78
<211> 40
<212> PRT
<213> Pasteurella multocida

<400> 78

Asn Lys Leu Asp Ile Arg Tyr Val Arg Gln Lys Asp Asn Gly Phe Gln
1 5 10 15

Ala Ser Ala Ala Arg Asn Met Gly Leu Arg Leu Ala Lys Tyr Asp Phe
20 25 30

Ile Gly Leu Leu Asp Cys Asp Met
35 40

<210> 79
<211> 40
<212> PRT
<213> Pasteurella multocida

<400> 79

Gln Lys Leu Asp Ile Lys Tyr Val Arg Gln Lys Asp Tyr Gly Tyr Gln
1 5 10 15

Leu Cys Ala Val Arg Asn Leu Gly Leu Arg Thr Ala Lys Tyr Asp Phe
20 25 30

Val Ser Ile Leu Asp Cys Asp Met
35 40

<210> 80
<211> 40
<212> PRT
<213> Meleagris gallopavo

<400> 80

Glu Lys Leu Asp Ile Lys Tyr Val Arg Gln Lys Asp Tyr Gly Tyr Gln
1 5 10 15

Leu Cys Ala Val Arg Asn Leu Gly Leu Arg Thr Ala Lys Tyr Asp Phe
20 25 30

Val Ser Ile Leu Asp Cys Asp Met
35 40

<210> 81
<211> 36
<212> PRT
<213> Goose

<400> 81

Val Asp Ile Lys Tyr Val Arg Gln Lys Asp Tyr Gly Tyr Gln Leu Cys
1 5 10 15

Ala Val Arg Asn Leu Gly Leu Arg Thr Ala Lys Tyr Asp Phe Val Ser
20 25 30

Ile Leu Asp Cys
35

<210> 82
<211> 33
<212> PRT
<213> sea lion

<400> 82

Lys Tyr Val Arg Gln Lys Asp Tyr Gly Tyr Gln Leu Cys Ala Val Arg
1 5 10 15

Asn Leu Gly Leu Arg Thr Ala Lys Tyr Asp Phe Val Ser Ile Leu Asp
20 25 30

Cys

<210> 83
<211> 35
<212> PRT
<213> Artificial sequence

<220>
<223> Consensus of SEQ ID NOS:78-82

<220>
<221> misc_feature
<222> (12)..(12)
<223> Xaa can be any naturally occurring amino acid <220>
<221> misc_feature
<222> (20)..(20)
<223> Xaa can be any naturally occurring amino acid <220>
<221> misc_feature
<222> (30)..(30)
<223> Xaa can be any naturally occurring amino acid

<400> 83

Asp Ile Lys Tyr Val Arg Gln Lys Asp Tyr Gly Xaa Gln Leu Cys Ala
1 5 10 15

```
Val Arg Asn Xaa Gly Leu Arg Thr Ala Lys Tyr Asp Phe Xaa Ser Ile
            20                  25                  30

Leu Asp Cys
        35

<210>  84
<211>  703
<212>  PRT
<213>  Pasteurella multocida

<400>  84

Met Asn Thr Leu Ser Gln Ala Ile Lys Ala Tyr Asn Ser Asn Asp Tyr
1               5                   10                  15

Gln Leu Ala Leu Lys Leu Phe Glu Lys Ser Ala Glu Ile Tyr Gly Arg
            20                  25                  30

Lys Ile Val Glu Phe Gln Ile Thr Lys Cys Lys Glu Lys Leu Ser Ala
        35                  40                  45

His Pro Ser Val Asn Ser Ala His Leu Ser Val Asn Lys Glu Glu Lys
    50                  55                  60

Val Asn Val Cys Asp Ser Pro Leu Asp Ile Ala Thr Gln Leu Leu Leu
65                  70                  75                  80

Ser Asn Val Lys Lys Leu Val Leu Ser Asp Ser Glu Lys Asn Thr Leu
                85                  90                  95

Lys Asn Lys Trp Lys Leu Leu Thr Glu Lys Lys Ser Glu Asn Ala Glu
            100                 105                 110

Val Arg Ala Val Ala Leu Val Pro Lys Asp Phe Pro Lys Asp Leu Val
        115                 120                 125

Leu Ala Pro Leu Pro Asp His Val Asn Asp Phe Thr Trp Tyr Lys Lys
    130                 135                 140

Arg Lys Lys Arg Leu Gly Ile Lys Pro Glu His Gln His Val Gly Leu
145                 150                 155                 160

Ser Ile Ile Val Thr Thr Phe Asn Arg Pro Ala Ile Leu Ser Ile Thr
                165                 170                 175

Leu Ala Cys Leu Val Asn Gln Lys Thr His Tyr Pro Phe Glu Val Ile
            180                 185                 190

Val Thr Asp Asp Gly Ser Gln Glu Asp Leu Ser Pro Ile Ile Arg Gln
        195                 200                 205

Tyr Glu Asn Lys Leu Asp Ile Arg Tyr Val Arg Gln Lys Asp Tyr Gly
    210                 215                 220

Tyr Gln Leu Cys Ala Val Arg Asn Leu Gly Leu Arg Thr Ala Lys Tyr
225                 230                 235                 240

Asp Phe Val Ser Ile Leu Asp Cys Asp Met Ala Pro Gln Gln Leu Trp
                245                 250                 255

Val His Ser Tyr Leu Thr Glu Leu Leu Glu Asp Asp Asp Leu Thr Ile
            260                 265                 270
```

```
Ile Gly Pro Arg Lys Tyr Ile Asp Thr Gln His Ile Asp Pro Lys Asp
        275                 280                 285

Phe Leu Asn Asn Ala Ser Leu Leu Glu Ser Leu Pro Glu Val Lys Thr
    290                 295                 300

Asn Asn Ser Val Ala Ala Lys Gly Glu Gly Thr Val Ser Leu Asp Trp
305                 310                 315                 320

Arg Leu Glu Gln Phe Glu Lys Thr Glu Asn Leu Arg Leu Ser Asp Ser
                325                 330                 335

Pro Phe Arg Phe Phe Ala Ala Gly Asn Val Ala Phe Ala Lys Lys Trp
            340                 345                 350

Leu Asn Lys Ser Gly Phe Phe Asp Glu Glu Phe Asn His Trp Gly Gly
        355                 360                 365

Glu Asp Val Glu Phe Gly Tyr Arg Leu Phe Arg Tyr Gly Ser Phe Phe
    370                 375                 380

Lys Thr Ile Asp Gly Ile Met Ala Tyr His Gln Glu Pro Pro Gly Lys
385                 390                 395                 400

Glu Asn Glu Thr Asp Arg Glu Ala Gly Lys Asn Ile Thr Leu Asp Ile
                405                 410                 415

Met Arg Glu Lys Val Pro Tyr Ile Tyr Arg Lys Leu Leu Pro Ile Glu
            420                 425                 430

Asp Ser His Ile Asn Arg Val Pro Leu Val Ser Ile Tyr Ile Pro Ala
        435                 440                 445

Tyr Asn Cys Ala Asn Tyr Ile Gln Arg Cys Val Asp Ser Ala Leu Asn
    450                 455                 460

Gln Thr Val Val Asp Leu Glu Val Cys Ile Cys Asn Asp Gly Ser Thr
465                 470                 475                 480

Asp Asn Thr Leu Glu Val Ile Asn Lys Leu Tyr Gly Asn Asn Pro Arg
                485                 490                 495

Val Arg Ile Met Ser Lys Pro Asn Gly Gly Ile Ala Ser Ala Ser Asn
            500                 505                 510

Ala Ala Val Ser Phe Ala Lys Gly Tyr Tyr Ile Gly Gln Leu Asp Ser
        515                 520                 525

Asp Asp Tyr Leu Glu Pro Asp Ala Val Glu Leu Cys Leu Lys Glu Phe
    530                 535                 540

Leu Lys Asp Lys Thr Leu Ala Cys Val Tyr Thr Thr Asn Arg Asn Val
545                 550                 555                 560
```

```
Asn Pro Asp Gly Ser Leu Ile Ala Asn Gly Tyr Asn Trp Pro Glu Phe
                565                 570                 575

Ser Arg Glu Lys Leu Thr Thr Ala Met Ile Ala His His Phe Arg Met
            580                 585                 590

Phe Thr Ile Arg Ala Trp His Leu Thr Asp Gly Phe Asn Glu Lys Ile
        595                 600                 605

Glu Asn Ala Val Asp Tyr Asp Met Phe Leu Lys Leu Ser Glu Val Gly
    610                 615                 620

Lys Phe Lys His Leu Asn Lys Ile Cys Tyr Asn Arg Val Leu His Gly
625                 630                 635                 640

Asp Asn Thr Ser Ile Lys Lys Leu Gly Ile Gln Lys Lys Asn His Phe
                645                 650                 655

Val Val Val Asn Gln Ser Leu Asn Arg Gln Gly Ile Thr Tyr Tyr Asn
            660                 665                 670

Tyr Asp Glu Phe Asp Asp Leu Asp Glu Ser Arg Lys Tyr Ile Phe Asn
        675                 680                 685

Lys Thr Ala Glu Tyr Gln Glu Glu Ile Asp Ile Leu Lys Asp Ile
    690                 695                 700
```

<210> 85
<211> 705
<212> PRT
<213> Pasteurella multocida

<400> 85

```
Met Asn Thr Leu Ser Gln Ala Ile Lys Ala Tyr Asn Ser Asn Asp Tyr
1               5                   10                  15

Glu Leu Ala Leu Lys Leu Phe Glu Lys Ser Ala Glu Thr Tyr Gly Arg
            20                  25                  30

Lys Ile Val Glu Phe Gln Ile Ile Lys Cys Lys Glu Lys Leu Ser Thr
        35                  40                  45

Asn Ser Tyr Val Ser Glu Asp Lys Lys Asn Ser Val Cys Asp Ser Ser
    50                  55                  60

Leu Asp Ile Ala Thr Gln Leu Leu Leu Ser Asn Val Lys Lys Leu Thr
65                  70                  75                  80

Leu Ser Glu Ser Glu Lys Asn Ser Leu Lys Asn Lys Trp Lys Ser Ile
                85                  90                  95

Thr Gly Lys Lys Ser Glu Asn Ala Glu Ile Arg Lys Val Glu Leu Val
            100                 105                 110

Pro Lys Asp Phe Pro Lys Asp Leu Val Leu Ala Pro Leu Pro Asp His
        115                 120                 125

Val Asn Asp Phe Thr Trp Tyr Lys Asn Arg Lys Lys Ser Leu Gly Ile
    130                 135                 140
```

```
Lys Pro Val Asn Lys Asn Ile Gly Leu Ser Ile Ile Ile Pro Thr Phe
145                 150                 155                 160

Asn Arg Ser Arg Ile Leu Asp Ile Thr Leu Ala Cys Leu Val Asn Gln
                165                 170                 175

Lys Thr Asn Tyr Pro Phe Glu Val Val Val Ala Asp Asp Gly Ser Lys
            180                 185                 190

Glu Asn Leu Leu Thr Ile Val Gln Lys Tyr Glu Gln Lys Leu Asp Ile
        195                 200                 205

Lys Tyr Val Arg Gln Lys Asp Asn Gly Phe Gln Ala Ser Ala Ala Arg
    210                 215                 220

Asn Met Gly Leu Arg Leu Ala Lys Tyr Asp Phe Ile Gly Leu Leu Asp
225                 230                 235                 240

Cys Asp Met Ala Pro Asn Pro Leu Trp Val His Ser Tyr Val Ala Glu
                245                 250                 255

Leu Leu Leu Glu Asp Asn Asp Ile Val Leu Ile Gly Pro Arg Lys Tyr
            260                 265                 270

Val Asp Thr His Asn Ile Thr Ala Glu Gln Phe Leu Asn Asp Pro Tyr
        275                 280                 285

Leu Ile Glu Ser Leu Pro Glu Thr Ala Thr Asn Asn Asn Pro Ser Ile
    290                 295                 300

Thr Ser Lys Gly Asn Ile Ser Leu Asp Trp Arg Leu Glu His Phe Lys
305                 310                 315                 320

Lys Thr Asp Asn Leu Arg Leu Cys Asp Ser Pro Phe Arg Tyr Phe Ser
                325                 330                 335

Cys Gly Asn Val Ala Phe Ser Lys Glu Trp Leu Asn Lys Val Gly Trp
            340                 345                 350

Phe Asp Glu Glu Phe Asn His Trp Gly Gly Glu Asp Val Glu Phe Gly
        355                 360                 365

Tyr Arg Leu Phe Ala Lys Gly Cys Phe Phe Arg Val Ile Asp Gly Gly
    370                 375                 380

Met Ala Tyr His Gln Glu Pro Pro Gly Lys Glu Asn Glu Thr Asp Arg
385                 390                 395                 400

Glu Ala Gly Lys Ser Ile Thr Leu Lys Ile Val Lys Glu Lys Val Pro
                405                 410                 415

Tyr Ile Tyr Arg Lys Leu Leu Pro Ile Glu Asp Ser His Ile His Arg
            420                 425                 430

Ile Pro Leu Val Ser Ile Tyr Ile Pro Ala Tyr Asn Cys Ala Asn Tyr
        435                 440                 445

Ile Gln Arg Cys Val Asp Ser Ala Leu Asn Gln Thr Val Val Asp Leu
    450                 455                 460
```

```
Glu Val Cys Ile Cys Asn Asp Gly Ser Thr Asp Asn Thr Leu Glu Val
465                 470                 475                 480

Ile Asn Lys Leu Tyr Gly Asn Asn Pro Arg Val Arg Ile Met Ser Lys
                485                 490                 495

Pro Asn Gly Gly Ile Ala Ser Ala Ser Asn Ala Ala Val Ser Phe Ala
            500                 505                 510

Lys Gly Tyr Tyr Ile Gly Gln Leu Asp Ser Asp Asp Tyr Leu Glu Pro
        515                 520                 525

Asp Ala Val Glu Leu Cys Leu Lys Glu Phe Leu Lys Asp Lys Thr Leu
    530                 535                 540

Ala Cys Val Tyr Thr Thr Asn Arg Asn Val Asn Pro Asp Gly Ser Leu
545                 550                 555                 560

Ile Ala Asn Gly Tyr Asn Trp Pro Glu Phe Ser Arg Glu Lys Leu Thr
                565                 570                 575

Thr Ala Met Ile Ala His His Phe Arg Met Phe Thr Ile Arg Ala Trp
            580                 585                 590

His Leu Thr Asp Gly Phe Asn Glu Asn Ile Glu Asn Ala Val Asp Tyr
        595                 600                 605

Asp Met Phe Leu Lys Leu Ser Glu Val Gly Lys Phe Lys His Leu Asn
    610                 615                 620

Lys Ile Cys Tyr Asn Arg Val Leu His Gly Asp Asn Thr Ser Ile Lys
625                 630                 635                 640

Lys Leu Gly Ile Gln Lys Lys Asn His Phe Val Val Val Asn Gln Ser
                645                 650                 655

Leu Asn Arg Gln Gly Ile Asn Tyr Tyr Asn Tyr Asp Lys Phe Asp Asp
            660                 665                 670

Leu Asp Glu Ser Arg Lys Tyr Ile Phe Asn Lys Thr Ala Glu Tyr Gln
        675                 680                 685

Glu Glu Met Asp Ile Leu Lys Asp Leu Lys Leu Ile Gln Asn Lys Asp
    690                 695                 700

Ala
705
```

--.

Column 217, line 63 claim 1: Delete "UDP-GIcUA, UDP-GIcNAc, UDP-GIc," and replace with -- UDP-GlcUA, UDP-GlcNAc, UDP-Glc, --.

Column 217, line 64 claim 1: Delete "UDP-GaINAc, UDP-GIcN and UDP-GaIN" and replace with -- UDP-GalNAc, UDP-GlcN and UDP-GalN --.

Column 218, line 37 claim 2: Delete "GIcUA," and replace with -- GlcUA, --.

Column 218, line 38 claim 2: Delete "GaIUA," and replace with -- GalUA, --.

Column 218, line 40 claim 2: Delete "GIcNAc, GaINAc, GIcN, and GaIN." and replace with -- GlcNAc, GalNAc, GlcN, and GalN. --.

Column 219, line 2 claim 5: Delete "GIcUA, GIcNAc, GIc," and replace with -- GlcUA, GlcNAc, Glc, --.

Column 219, line 3 claim 5: Delete "GaINAc, GIcN, and GaIN." and replace with -- GalNAc, GlcN, and GalN. --.

Column 219, line 9 claim 6: Delete "GIcUA, GIcNAc, GIc, GaINAc, GIcN, and GaIN." and replace with -- GlcUA, GlcNAc, Glc, GalNAc, GlcN, and GalN. --.

Column 220, line 15 claim 16: Delete "UDP-GIcUA, UDP-GIcNAc, UDP-GIc," and replace with -- UDP-GlcUA, UDP-GlcNAc, UDP-Glc, --.

Column 220, line 16 claim 16: Delete "UDP-GaINAc, UDP-GIcN and UDP-GaIN" and replace with -- UDP-GalNAc, UDP-GlcN and UDP-GalN --.

Column 220, line 38 claim 19: Delete "GIcUA, GIcNAc, GIc," and replace with -- GlcUA, GlcNAc, Glc, --.

Column 220, line 39 claim 19: Delete "GaINAc, GIcN and GaIN." and replace with -- GalNAc, GlcN and GalN. --.

Column 220, line 45 claim 20: Delete "GIcUA, GIcNAc, GIc, GaINAc, GIcN, and GaIN." and replace with -- GlcUA, GlcNAc, Glc, GalNAc, GlcN, and GalN. --.

Column 222, line 2 claim 27: Delete "UDP-GIcUA, UDP-GIcNAc, UDP-GIc," and replace with -- UDP-GlcUA, UDP-GlcNAc, UDP-Glc, --.

Column 222, line 3 claim 27: Delete "UDP-GaINAc, UDP-GIcN, and UDP-GaIN" and replace with -- UDP-GalNAc, UDP-GlcN, and UDP-GalN --.

Signed and Sealed this

Sixteenth Day of March, 2010

David J. Kappos
*Director of the United States Patent and Trademark Office*